US012623988B2

(12) United States Patent
Burkart et al.

(10) Patent No.: US 12,623,988 B2
(45) Date of Patent: May 12, 2026

(54) SCALEABLE PREPARATION OF POLYKETIDES

(71) Applicant: The Regents of the University of California, Oakland, CA (US)

(72) Inventors: Michael D. Burkart, San Diego, CA (US); Warren C. Chan, San Diego, CA (US); Brian Leon, San Diego, CA (US); James J. La Clair, San Diego, CA (US); Kelsey A. Trieger, San Diego, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 17/632,764

(22) PCT Filed: Aug. 5, 2020

(86) PCT No.: PCT/US2020/045066

§ 371 (c)(1),
(2) Date: Feb. 3, 2022

(87) PCT Pub. No.: WO2021/026273

PCT Pub. Date: Feb. 11, 2021

(65) Prior Publication Data

US 2023/0029301 A1 Jan. 26, 2023

Related U.S. Application Data

(60) Provisional application No. 62/883,491, filed on Aug. 6, 2019.

(51) Int. Cl.

| | |
|---|---|
| ***C07D 313/00*** | (2006.01) |
| ***C07C 43/178*** | (2006.01) |
| ***C07D 317/22*** | (2006.01) |
| ***C07D 493/04*** | (2006.01) |

(52) U.S. Cl.

CPC .......... *C07C 43/178* (2013.01); *C07D 313/00* (2013.01); *C07D 317/22* (2013.01); *C07D 493/04* (2013.01)

(58) Field of Classification Search

CPC ............................ C07D 313/00; A61K 31/336

See application file for complete search history.

(56) References Cited

U.S. PATENT DOCUMENTS

| | | | |
|---|---|---|---|
| 4,861,856 | A | 8/1989 | Darnell et al. |
| 2007/0065920 | A1 | 3/2007 | Salas |
| 2007/0173541 | A1 | 7/2007 | Ini et al. |
| 2009/0312316 | A1 | 12/2009 | Wilkinson et al. |
| 2015/0133535 | A1 | 5/2015 | Burkart et al. |

FOREIGN PATENT DOCUMENTS

| | | | | |
|---|---|---|---|---|
| CN | 85105643 A | | 5/1987 | |
| WO | WO2017/053887 | * | 3/2017 | ............ C12N 5/074 |
| WO | WO-2017/156454 A1 | | 9/2017 | |

OTHER PUBLICATIONS

Villa et al., Org. Lett. 2012, 14, 21, 5396-5399; Publication Date: Oct. 16, 2012.*

Chan, W.C. et al., (Oct. 29, 2018). "Daedal Facets of Splice Modulator Optimization," *ACS Med. Chem. Lett.* 9(11):1070-1072.

Chan, W.C. et al. (Dec. 23, 2020). "Scalable Synthesis of 17S-FD-895 Expands the Structural Understanding of Splice Modulatory Activity," *Cell Reports Physical Science* 1(12):100277.

Chan, W.C. et al. (May 25, 2023, e-published May 8, 2023). "Stereochemical Control of Splice Modulation in FD-895 Analogues," *J Med Chem* 66(10):6577-6590.

Cretu, C. et al. (Oct. 20, 2016, e-published Oct. 6, 2016). "Molecular Architecture of SF3b and Structural Consequences of Its Cancer-Related Mutations," Mol. Cell 64(2):307-319.

Crews, L.A. et al. (Nov. 3, 2016). "RNA Splicing Modulation Selectively Impairs Leukemia Stem Cell Maintenance in Secondary Human AML," Cell Stem Cell. 19(5):599-612.

Effenberger, K.A. et al. (Mar. 2016, e-published Jan. 7, 2016). "Interchangeable SF3B1 inhibitors interfere with pre-mRNA splicing at multiple stages," RNA 22(3):350-359.

Effenberger, K.A. et al. (Mar. 2017, e-published Jul. 21, 2016). "Modulating splicing with small molecular inhibitors of the spliceosome," Wiley Interdiscip. Rev. RNA 8(2):10.1002/wrna.1381.

Extended European Search Report mailed on Nov. 10, 2023, for European Patent Application No. 20849507.7, 10 pages.

Gao, Y. et al. (May 17, 2013). "Chemical perturbation of Mcl-1 pre-mRNA splicing to induce apoptosis in cancer cells," ACS Chem. Biol. 8(5):895-900.

International Search Report mailed on Dec. 31, 2020, for PCT Application No. PCT/US2020/045066, filed Aug. 5, 2020, 4 pages.

Lagisetti, C. et al. (Dec. 2013, e-published Dec. 11, 2013). "Optimization of antitumor modulators of pre-mRNA splicing," *J. Med. Chem.* 56(24):10033-10044.

Meng, F. et al. (Sep. 18, 2014). "Multifunctional organoboron compounds for scalable natural product synthesis," Nature 513(7518):367-374.

Partial Supplementary European Search Report mailed on Aug. 9, 2023, for European Patent Application No. 20849507.7, 13 pages.

Schellenberg, M. J. et al. (Jan. 2011, e-published Nov. 9, 2010). "Structural model of the p14/SF3b155 • branch duplex complex," *RNA*, 17(1):155-165.

Villa, R. et al. (Nov. 2, 2012, e-published Oct. 16, 2012). "Structure of FD-895 revealed through total synthesis," Org. Lett. 14(21):5396-5399; with supporting information pp. S1-S54.

Villa, R. et al. (Sep. 12, 2013, e-published Aug. 21, 2013). "Stabilized cyclopropane analogs of the splicing inhibitor FD-895," *J. Med. Chem.* 56(17):6576-6582.

(Continued)

*Primary Examiner* — Alicia L Otton

(74) *Attorney, Agent, or Firm* — Mintz, Levin, Cohn, Ferris Glovsky and Popeo, P.C.

(57) ABSTRACT

Disclosed herein, inter alia, are methods of making polyketide compounds.

21 Claims, 22 Drawing Sheets

(56) References Cited

OTHER PUBLICATIONS

Written Opinion mailed on Dec. 31, 2020, for PCT Application No. PCT/US2020/045066, filed Aug. 5, 2020, 6 pages.

* cited by examiner

6d

3

6e

6c

2

6b

6a

17S-FD-895 (1)

| | st | ch | %y | g |
|---|---|---|---|---|
| 6a | 4 | 2 | 24 | ### |
| 6b | 2 | 2 | 40 | ### |
| 6c | 7 | 3 | ## | ### |
| 6d | 7 | 5 | 29 | ### |
| 6e | 2 | # | ## | ### |
| 2 | # | # | ## | ### |
| 3 | # | # | ## | ### |
| 1 | 1 | 1 | ## | ### |
| T | # | # | ## | |

6a 7

7 11 iso-11 6c6 6c7

16 17 + 18

17 19 20 iso-14 iso-1a 5 17S-FD-895 (1)

17S-FD-895 (1)

2

3 pladienolide B

4

5a

5b

2

3

17*S*-FD-895 (1)

$^{13}$C1-17*S*-FD-895

$^{13}$C30-17*S*-FD-895

1c

GI50 value = 0.71 nM
95% CI = 0.40-1.2 nM pladienolide B

FD-895

CYP-B

1

FD-895

1a

1b

35

36b

37b

38b

3b

2

1b

SCALEABLE PREPARATION OF POLYKETIDES

CROSS-REFERENCES TO RELATED APPLICATIONS

This application claims the benefit of U.S. Provisional Application No. 62/883,491, filed Aug. 6, 2019, which is incorporated herein by reference in its entirety and for all purposes.

BACKGROUND

While initial efforts suggested the rapid translation of small molecule splice modulators to the clinic for patients suffering from cancers, the inability to practically access gram scale lead molecules with viable pharmacological properties continues to stall their clinical application. Here, we report a gram-scalable approach to prepare 17S-FD-895, a highly potent and pharmacologically stable splice modulator, an observation that is supported by parallel, synthetically enabled structure activity relationship (SAR) validation efforts.

BRIEF SUMMARY

In an aspect is provided a compound having the formula:

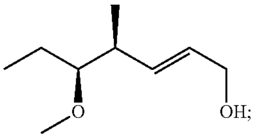

wherein, the compound is at least 95% enantiomerically pure.

In an aspect is provided a compound having the formula:

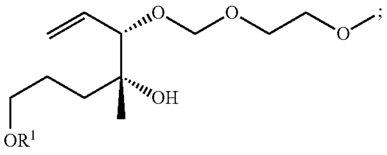

wherein, $R^1$ is a silyl protecting group and wherein the compound is at least 95% enantiomerically pure.

In an aspect is provided a compound having the formula:

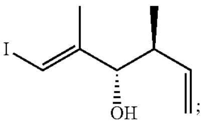

wherein, the compound is at least 95% enantiomerically pure.

In an aspect is provided a compound having the formula:

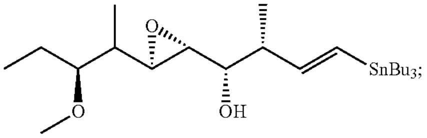

wherein, the compound is at least 95% enantiomerically pure.

In an aspect is provided a compound having the formula:

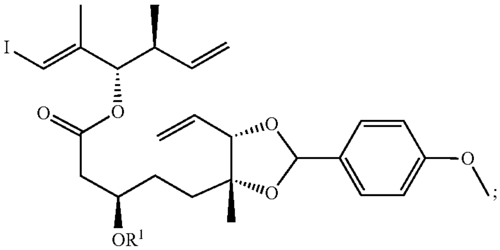

wherein, $R^1$ is a silyl protecting group and wherein the compound is at least 95% enantiomerically pure.

In an aspect is provided a compound having the formula:

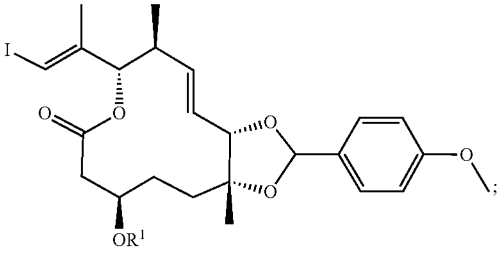

wherein, $R^1$ is a silyl protecting group and wherein the compound is at least 95% enantiomerically pure.

In an aspect is provided a compound having the formula:

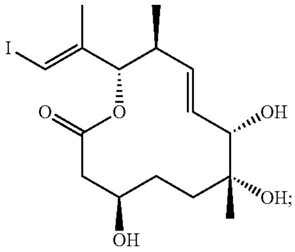

wherein, the compound is at least 95% enantiomerically pure.

In an aspect is provided a compound having the formula:

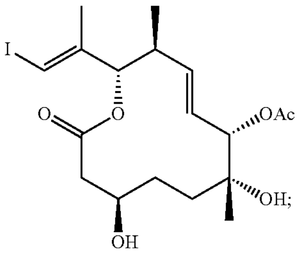

wherein, the compound is at least 95% enantiomerically pure.

In an aspect is provided a compound having the formula:

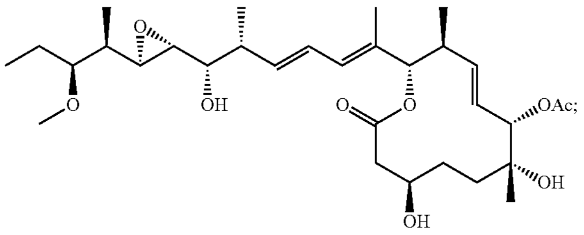

wherein, the compound is at least 95% enantiomerically pure.

In an aspect is provided a pharmaceutical composition including a compound having the formula:

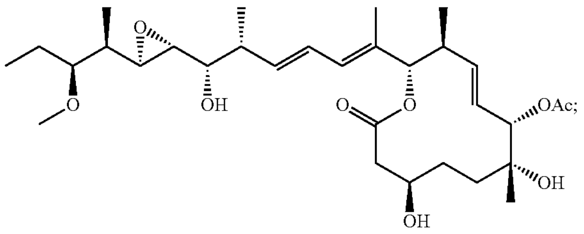 [SMILES: CC[C@H](OC)[C@@H](C)[C@H]1O[C@@H]1[C@@H](O)[C@H](C)/C=C/C=C(\C)[C@H]1OC(=O)C[C@H](O)CC[C@@](C)(O)[C@@H](OC(C)=O)/C=C/[C@@H]1C]

and a pharmaceutically acceptable excipient, wherein the compound is at least 95% enantiomerically pure.

In an aspect is provided a method of making a compound having the formula:

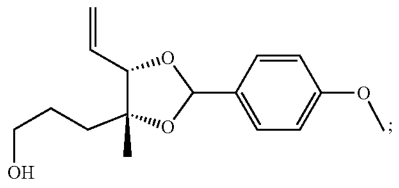

comprising reacting a compound having the formula:

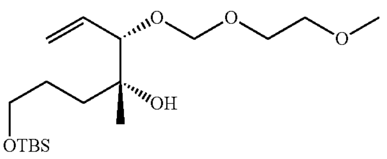 [SMILES: C=C[C@H](OCOCCOC)[C@](C)(O)CCCO[Si](C)(C)C(C)(C)C]

with 1-(dimethoxymethyl)-4-methoxybenzene in the presence of $CBr_4$, an alcohol, a base, and one or more organic solvents.

In an aspect is provided a method of making a compound having the formula:

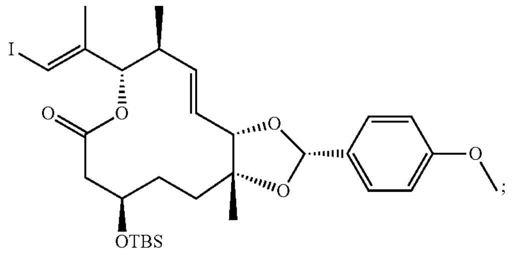 [SMILES: COc1ccc([C@H]2O[C@H]3/C=C/[C@H](C)[C@@H](/C(C)=C/I)OC(=O)C[C@H](O[Si](C)(C)C(C)(C)C)CC[C@@]3(C)O2)cc1]

comprising reacting a compound having the formula:

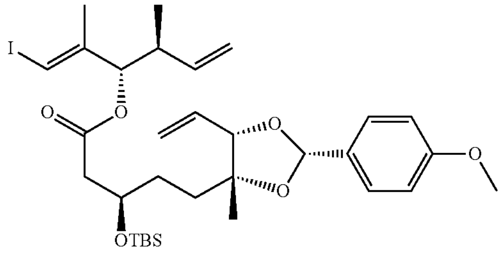 [SMILES: C=C[C@@H]1O[C@H](c2ccc(OC)cc2)O[C@]1(C)CC[C@H](CC(=O)O[C@H](/C(C)=C/I)[C@@H](C)C=C)O[Si](C)(C)C(C)(C)C]

with a transition metal catalyst for olefin metathesis in the presence of one or more organic solvents.

In an aspect is provided a method of making a compound having the formula:

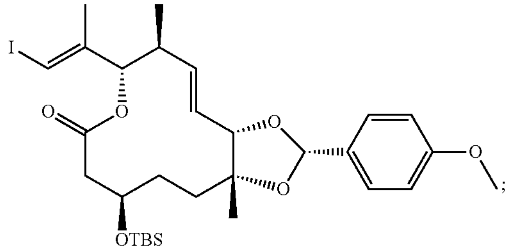 [SMILES: COc1ccc([C@H]2O[C@H]3/C=C/[C@H](C)[C@@H](/C(C)=C/I)OC(=O)C[C@H](O[Si](C)(C)C(C)(C)C)CC[C@@]3(C)O2)cc1]

comprising reacting a compound having the formula:

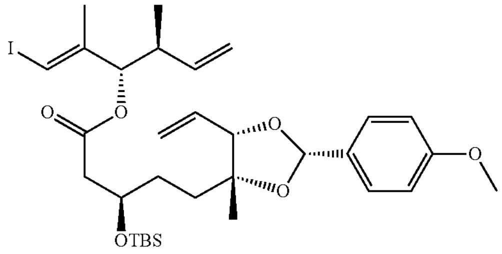 [SMILES: C=C[C@@H]1O[C@H](c2ccc(OC)cc2)O[C@]1(C)CC[C@H](CC(=O)O[C@H](/C(C)=C/I)[C@@H](C)C=C)O[Si](C)(C)C(C)(C)C]

with Hoveyda-Grubbs $2^{nd}$ generation catalyst in the presence of toluene.

In an aspect is provided a method of making a compound having the formula:

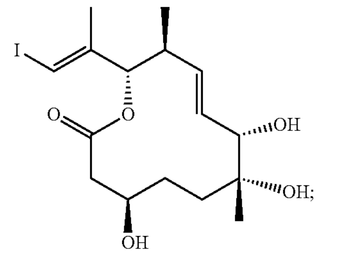 [SMILES: C/C(=C\I)[C@H]1OC(=O)C[C@H](O)CC[C@@](C)(O)[C@@H](O)/C=C/[C@@H]1C]

comprising reacting a compound having the formula:

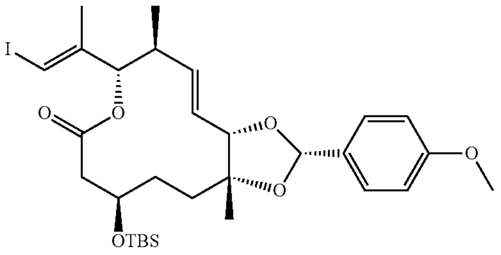 [SMILES: COc1ccc([C@H]2O[C@H]3/C=C/[C@H](C)[C@@H](/C(C)=C/I)OC(=O)C[C@H](O[Si](C)(C)C(C)(C)C)CC[C@@]3(C)O2)cc1]

with a strong acid, in the presence of an alcohol and one or more organic solvents.

In an aspect is provided a method of making a compound having the formula:

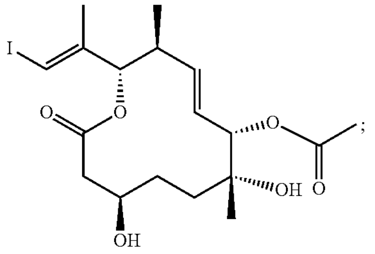 [SMILES: CC(=O)O[C@H]1/C=C/[C@H](C)[C@@H](/C(C)=C/I)OC(=O)C[C@H](O)CC[C@@]1(C)O]

comprising reacting a compound having the formula:

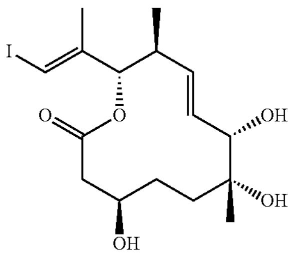 [SMILES: C/C(=C\I)[C@H]1OC(=O)C[C@H](O)CC[C@@](C)(O)[C@@H](O)/C=C/[C@@H]1C]

with an acetylating agent in the presence of a strong acid and one or more organic solvents.

In embodiments, is provided a method of making a compound having the formula:

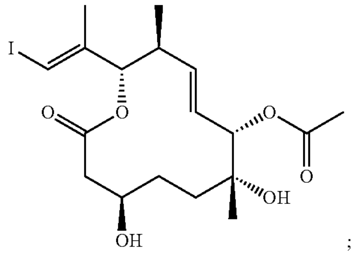 [SMILES: CC(=O)O[C@H]1/C=C/[C@H](C)[C@@H](/C(C)=C/I)OC(=O)C[C@H](O)CC[C@@]1(C)O]

comprising reacting a compound having the formula:

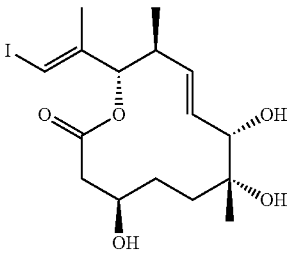 [SMILES: C/C(=C\I)[C@H]1OC(=O)C[C@H](O)CC[C@@](C)(O)[C@@H](O)/C=C/[C@@H]1C]

with acetic anhydride, in the presence of 4-dimethylamino-pyridine and pyridine.

In an aspect is provided a method of making a linear polyketide compound.

In an aspect is provided a method of treating cancer, the method including administering to a subject in need thereof an effective amount of the polyketide compound made using the method as described herein.

In an aspect is provided a method of making a 17S-FD-895, the method including the use of compounds 6a, 6b, 6c, 6d and 6e, as described herein.

BRIEF DESCRIPTION OF THE DRAWINGS

(FIG. 2A) The conversion of 6a to 7 required significant reaction tuning. The solution arose from a process that enabled the in situ conversion of the corresponding triol into selectively-protected pro-C6-C7 acetal 7. (FIG. 2B) A two-day 5 step process was developed to convert 7 to 11 using a single chromatographic purification. This streamline process could be conducted was conducted at the decagram scale effective yields of 11 obtained as a single stereomeric material. (FIG. 2C) One issue with the transformation of 7 to b arose due to the lack of enantiopurity of component 6c, which resulted in iso-11. Resolution of 6c by formation by esterification with (S)-mandelic acid affording 6c6 and 6c7, which could be separated chromatographically and subsequent hydrolysis afforded enantiopure 6a. (FIG. 2D) While operable at milligram scales, RCM on 16 afforded mixtures of the desired product 18 with associated rearrangement product 17. (FIG. 2E) While removal of the C7 alcohol by oxidation to 17 enabled the RCM to enone 19, reduction led to the formation the formation of 20 in a 4:1 mixture with desired 18. (FIG. 2F) An impurity was observed at the stage of compound 14.

(FIG. 3A) The synthesis of 17S-FD-895 (1) arises through the coupling of side chain 2 and core 3. The 11 $sp^3$ stereocenters and stereochemistry of the 3 olefins of 1 arose from 12 precursors (inset) that are available on the kg scale. The key steps used to prepare each component are noted. (FIG. 3B) The retro-analysis of the related macrolide, pladienolide B, as developed by Ghosh (25) from core 5a and Kotake (27) from core 5b. Colored highlights denote the sourced components as shown in grey inset.

(FIG. 4A) Stille coupling of side chain 2 and core 3 yield 1 with an effective mass balance. (FIG. 4B) Synthesis of $^{13}$C1-17S-FD-895 (Scheme AS1 (FIG. 10)) and $^{13}$C30-17S-FD-895 (Scheme AS2) were prepared by installing $^{13}$C-containing precursors into the routes in Schemes A1-A2. $^{13}$C-NMR returned a single peak, suggestive that a single isomeric material was present within these batches. (FIG. 4C) SARs identified through analogue development. Red spheres indicate unexplored stereoisomers. (FIG. 4D-4F) Analogues 1a-1c were synthesized and $GI_{50}$ values were evaluated in HCT-116 cells. Select regions of $^1$H NMR spectra are provided to illustrate chemical shift modifications. (FIG. 4D) Replacing dichlorophenylborane and (−)-sparteine in the Sammakia aldol addition with $TiCl_4$ and diisopropylamine afforded the inverted C3 stereocenter in 1a (Scheme AS3). (FIG. 4E) C7 core isomer 1b was synthesized from 34 in 6 steps (Scheme AS4). (FIG. 4F) C18-C19 epoxide isomer 1d was prepared by isolation of the minor Sharpless epoxide during preparation of 2.

FIG. 5B: FD-895, and FIG. 5C: CYPB are shown in grey corresponding to SF3B1 and PHF5A. Van der Waals surfaces rendered to depict the core of FIG. 5D: pladienolide B, FIG. 5E: FD-895, and FIG. 5F: CYPB and side chain of FIG. 5G: pladienolide B, FIG. 5H: FD-895, and FIG. 5I: CYPB are shown. Surface renderings depicting pladienolide B, FD-895 or CYPB. The structures of pladienolide B bound to the SF3B core are described in (14). A discussion on the structures of FD-895 and the cyclopropane analog CYPB are provided in (18).

FIG. 7A: 17S-FD-895 (1), FIG. 7B: 3S,17S-FD-895 (1a) or FIG. 7C: 7R,17S-FD-895 (1b).

DETAILED DESCRIPTION

I. Definitions

Figure 1:
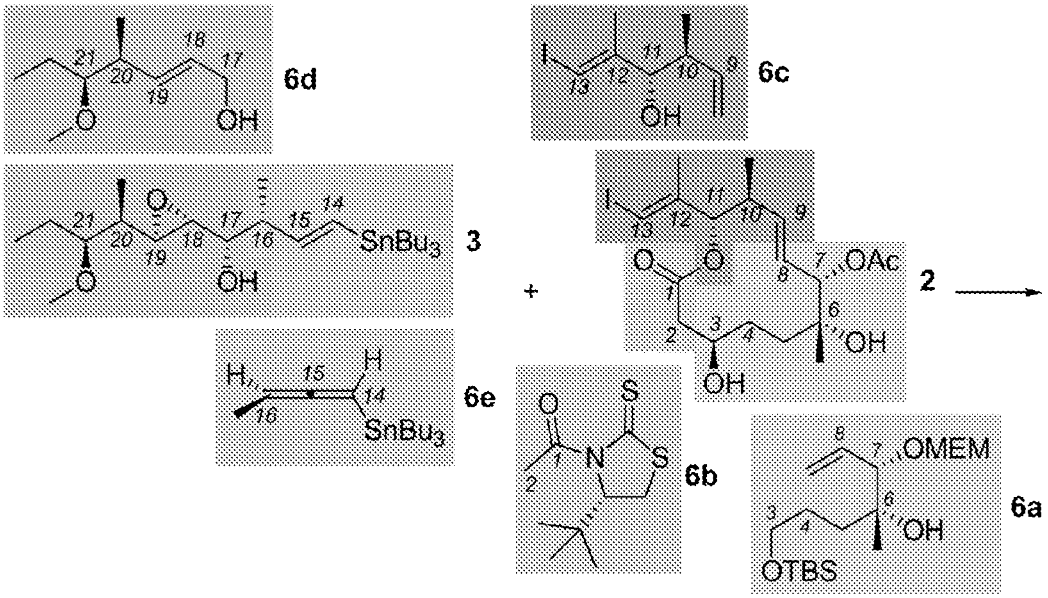
FIG. 1. Synthetic design. The synthesis of 17S-FD-895 arises through the coupling of two fragments as given by side chain 3 and its associated components 6e and 6d, and core 2 and its three associated components 6a-6c. The 11 $sp^3$ stereocenters and stereochemistry of the 3 olefins of 1 are distributed between components 6a (contains the C6 and C7 stereodiad), 6b (induces the C3 stereocenter and influences the C8-C9 olefin), 6c (C10, C11 stereocenters, contains the C12-C13 olefin and induces the C13-C14 stereochemistry and C8-C9 olefin), 6d (contains the C20-C21 stereodiad, contains functionality to install the C18-C19 epoxide) and 6e (induces the C16-C17 stereodiad). A tabulation of the number of steps to prepare (st), number chromatographic purifications (ch), % yield (% y) and amount of material (in g) prepared to date. Color-coded shading is used to highlight the assembly process.
Figure 1:
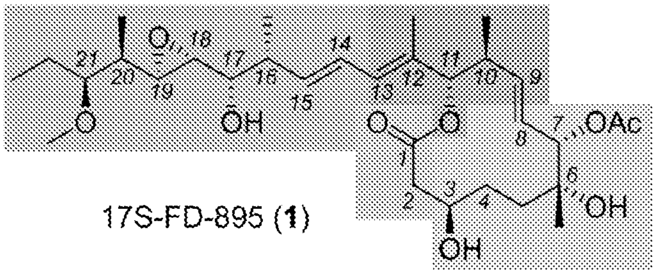

The abbreviations used herein have their conventional meaning within the chemical and biological arts. The chemical structures and formulae set forth herein are constructed according to the standard rules of chemical valency known in the chemical arts.

Where substituent groups are specified by their conventional chemical formulae, written from left to right, they equally encompass the chemically identical substituents that would result from writing the structure from right to left, e.g., $—CH_2O—$ is equivalent to $—OCH_2—$.

The term "allyl," by itself or as part of another substituent, means, unless otherwise stated, a straight (i.e., unbranched) or branched carbon chain (or carbon), or combination thereof, which may be fully saturated, mono- or polyunsaturated and can include mono-, di- and multivalent radicals. The alkyl may include a designated number of carbons (e.g., $C_1$-$C_{10}$ means one to ten carbons). In embodiments, the allyl is fully saturated. In embodiments, the alkyl is monounsaturated. In embodiments, the allyl is polyunsaturated. Alkyl is an uncyclized chain. Examples of saturated hydrocarbon radicals include, but are not limited to, groups such as methyl, ethyl, n-propyl, isopropyl, n-butyl, t-butyl, isobutyl, sec-butyl, methyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. An alkoxy is an allyl attached to the remainder of the molecule via an oxygen linker (—O—). An alkyl moiety may be an alkenyl moiety. An alkyl moiety may be an alkynyl moiety. An alkenyl includes one or more double bonds. An alkynyl includes one or more triple bonds. An alkyl moiety may be fully saturated. An alkenyl may include more than one double bond and/or one or more triple bonds in addition to the one or more double bonds. An alkynyl may include more than one triple bond and/or one or more double bonds in addition to the one or more triple bonds.

The term "allylene," by itself or as part of another substituent, means, unless otherwise stated, a divalent radical derived from an alkyl, as exemplified, but not limited by, $—CH_2CH_2CH_2CH_2—$. Typically, an alkyl (or allylene) group will have from 1 to 24 carbon atoms, with those groups having 10 or fewer carbon atoms being preferred herein. A "lower alkyl" or "lower alkylene" is a shorter chain alkyl or alkylene group, generally having eight or fewer carbon atoms. The term "alkenylene," by itself or as part of another substituent, means, unless otherwise stated, a divalent radical derived from an allene. The term "alkynylene" by itself or as part of another substituent, means, unless otherwise stated, a divalent radical derived from an alkyne. In embodiments, the alkylene is fully saturated. In embodiments, the alkylene is monounsaturated. In embodiments, the allylene is polyunsaturated. An allenylene includes one or more double bonds. An alkynylene includes one or more triple bonds.

The term "heteroalkyl," by itself or in combination with another term, means, unless otherwise stated, a stable straight or branched chain, or combinations thereof, including at least one carbon atom and at least one heteroatom (e.g., O, N, P, Si, and S), and wherein the nitrogen and sulfur atoms may optionally be oxidized, and the nitrogen heteroatom may optionally be quaternized. The heteroatom(s) (e.g., O, N, S, Si, or P) may be placed at any interior position of the heteroalkyl group or at the position at which the alkyl group is attached to the remainder of the molecule. Heteroalkyl is an uncyclized chain. Examples include, but are not limited to: $—CH_2—CH_2—O—CH_3$, $—CH_2—CH_2—NH—CH_3$, $—CH_2—CH_2—N(CH_3)—CH_3$, $—CH_2—S—CH_2—CH_3$, $—CH_2—S—CH_2$, $—S(O)—CH_3$, $—CH_2—CH_2—S(O)_2—CH_3$, $—CH{=}CHO—CH_3$, $—Si(CH_3)_3$, $—CH_2—CH{=}N—OCH_3$, $—CH{=}CH—N(CH_3)—CH_3$, $—O—CH_3$, $—O—CH_2—CH_3$, and —CN. Up to two or three heteroatoms may be consecutive, such as, for example, $—CH_2—NH—OCH_3$ and $—CH_2—O—Si(CH_3)_3$. A heteroalkyl moiety may include one heteroatom (e.g., O, N, S, Si, or P). A heteroalkyl moiety may include two optionally different heteroatoms (e.g., O, N, S, Si, or P). A heteroalkyl moiety may include three optionally different heteroatoms (e.g., O, N, S, Si, or P). A heteroalkyl moiety may include four optionally different heteroatoms (e.g., O, N, S, Si, or P). A heteroalkyl moiety may include five optionally different heteroatoms (e.g., O, N, S, Si, or P). A heteroalkyl moiety may include up to 8 optionally different heteroatoms (e.g., O, N, S, Si, or P). The term "heteroalkenyl," by itself or in combination with another term, means, unless otherwise stated, a heteroalkyl including at least one double bond. A heteroalkenyl may optionally include more than one double bond and/or one or more triple bonds in additional to the one or more double bonds. The term "heteroalkynyl," by itself or in combination with another term, means, unless otherwise stated, a heteroalkyl including at least one triple bond. A heteroalkynyl may optionally include more than one triple bond and/or one or more double bonds in additional to the one or more triple bonds. In embodiments, the heteroalkyl is fully saturated. In embodiments, the heteroallyl is monounsaturated. In embodiments, the heteroallyl is polyunsaturated.

Similarly, the term "heteroalkylene," by itself or as part of another substituent, means, unless otherwise stated, a divalent radical derived from heteroalkyl, as exemplified, but not limited by, $—CH_2—CH_2—S—CH_2—CH_2—$ and $—CH_2—S—CH_2—CH_2—NH—CH_2—$. For heteroallylene groups, heteroatoms can also occupy either or both of the chain termini (e.g., allyleneoxy, alkylenedioxy, alkyleneamino, alkylenediamino, and the like). Still further, for alkylene and heteroalkylene linking groups, no orientation of the linking group is implied by the direction in which the formula of the linking group is written. For example, the formula $—C(O)_2R'—$ represents both $—C(O)_2R'—$ and $—R'C(O)_2—$. As described above, heteroalkyl groups, as used herein, include those groups that are attached to the remainder of the molecule through a heteroatom, such as —C(O)R', —C(O)NR', —NR'R", —OR', —SR', and/or $—SO_2R'$. Where "heteroalkyl" is recited, followed by recitations of specific heteroalkyl groups, such as —NR'R" or the like, it will be understood that the terms heteroalkyl and —NR'R" are not redundant or mutually exclusive. Rather, the specific heteroalkyl groups are recited to add clarity. Thus, the term "heteroalkyl" should not be interpreted herein as excluding specific heteroalkyl groups, such as —NR'R" or the like. The term "heteroalkenylene," by itself or as part of another substituent, means, unless otherwise stated, a divalent radical derived from a heteroalkene. The term "heteroalkynylene" by itself or as part of another substituent, means, unless otherwise stated, a divalent radical derived from an heteroalkyne. In embodiments, the heteroalkylene is fully saturated. In embodiments, the heteroalkylene is monounsaturated. In embodiments, the heteroalkylene is polyunsaturated. A heteroalkenylene includes one or more double bonds. A heteroalkynylene includes one or more triple bonds.

The terms "cycloalkyl" and "heterocycloalkyl," by themselves or in combination with other terms, mean, unless otherwise stated, cyclic versions of "alkyl" and "heteroalkyl," respectively. Cycloalkyl and heterocycloalkyl are not aromatic. Additionally, for heterocycloallyl, a heteroatom can occupy the position at which the heterocycle is attached to the remainder of the molecule. Examples of cycloalkyl include, but are not limited to, cyclopropyl, cyclobutyl, cyclopentyl, cyclohexyl, 1-cyclohexenyl, 3-cyclohexenyl, cycloheptyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like. A "cycloalkylene" and a "heterocycloalkylene," alone or as part of another substituent, means a divalent radical derived from a cycloalkyl and heterocycloallyl, respectively. In embodiments, the cycloalkyl is fully saturated. In embodiments, the cycloalkyl is monounsaturated. In embodiments, the cycloalkyl is polyunsaturated. In embodiments, the heterocycloallyl is fully saturated. In embodiments, the heterocycloallyl is monounsaturated. In embodiments, the heterocycloalkyl is polyunsaturated.

In embodiments, the term "cycloalkyl" means a monocyclic, bicyclic, or a multicyclic cycloalkyl ring system. In embodiments, monocyclic ring systems are cyclic hydrocarbon groups containing from 3 to 8 carbon atoms, where such groups can be saturated or unsaturated, but not aromatic. In embodiments, cycloalkyl groups are fully saturated. Examples of monocyclic cycloalkyls include cyclopropyl, cyclobutyl, cyclopentyl, cyclopentenyl, cyclohexyl, cyclohexenyl, cycloheptyl, and cyclooctyl. Bicyclic cycloalkyl ring systems are bridged monocyclic rings or fused bicyclic rings. In embodiments, bridged monocyclic rings contain a monocyclic cycloalkyl ring where two non adjacent carbon atoms of the monocyclic ring are linked by an alkylene bridge of between one and three additional carbon atoms (i.e., a bridging group of the form $(CH_2)_w$, where w is 1, 2, or 3). Representative examples of bicyclic ring systems include, but are not limited to, bicyclo[3.1.1]heptane, bicyclo[2.2.1]heptane, bicyclo[2.2.2]octane, bicyclo[3.2.2]nonane, bicyclo[3.3.1]nonane, and bicyclo[4.2.1]nonane. In embodiments, fused bicyclic cycloalkyl ring systems contain a monocyclic cycloallyl ring fused to either a phenyl, a monocyclic cycloallyl, a monocyclic cycloalkenyl, a monocyclic heterocyclyl, or a monocyclic heteroaryl. In embodiments, the bridged or fused bicyclic cycloalkyl is attached to the parent molecular moiety through any carbon atom contained within the monocyclic cycloalkyl ring. In embodiments, cycloalkyl groups are optionally substituted with one or two groups which are independently oxo or thia. In embodiments, the fused bicyclic cycloalkyl is a 5 or 6 membered monocyclic cycloalkyl ring fused to either a phenyl ring, a 5 or 6 membered monocyclic cycloalkyl, a 5 or 6 membered monocyclic cycloalkenyl, a 5 or 6 membered monocyclic heterocyclyl, or a 5 or 6 membered monocyclic heteroaryl, wherein the fused bicyclic cycloallyl is optionally substituted by one or two groups which are independently oxo or thia. In embodiments, multicyclic cycloallyl ring systems are a monocyclic cycloalkyl ring (base ring) fused to either (i) one ring system selected from the group consisting of a bicyclic aryl, a bicyclic heteroaryl, a bicyclic cycloalkyl, a bicyclic cycloallenyl, and a bicyclic heterocyclyl; or (ii) two other ring systems independently selected from the group consisting of a phenyl, a bicyclic aryl, a monocyclic or bicyclic heteroaryl, a monocyclic or bicyclic cycloalkyl, a monocyclic or bicyclic cycloalkenyl, and a monocyclic or bicyclic heterocyclyl. In embodiments, the multicyclic cycloalkyl is attached to the parent molecular moiety through any carbon atom contained within the base ring. In embodiments, multicyclic cycloallyl ring systems are a monocyclic cycloallyl ring (base ring) fused to either (i) one ring system selected from the group consisting of a bicyclic aryl, a bicyclic heteroaryl, a bicyclic cycloalkyl, a bicyclic cycloalkenyl, and a bicyclic heterocyclyl; or (ii) two other ring systems independently selected from the group consisting of a phenyl, a monocyclic heteroaryl, a monocyclic cycloalkyl, a monocyclic cycloalkenyl, and a monocyclic heterocyclyl. Examples of multicyclic cycloalkyl groups include, but are not limited to tetradecahydrophenanthrenyl, perhydrophenothiazin-1-yl, and perhydrophenoxazin-1-yl. A bicyclic or multicyclic cycloalkyl ring system refers to multiple rings fused together wherein at least one of the fused rings is a cycloalkyl ring and wherein the multiple rings are attached to the parent molecular moiety through any carbon atom contained within a cycloalkyl ring of the multiple rings.

In embodiments, a cycloalkyl is a cycloalkenyl. The term "cycloalkenyl" is used in accordance with its plain ordinary meaning. In embodiments, a cycloalkenyl is a monocyclic, bicyclic, or a multicyclic cycloalkenyl ring system. In embodiments, monocyclic cycloalkenyl ring systems are cyclic hydrocarbon groups containing from 3 to 8 carbon atoms, where such groups are unsaturated (i.e., containing at least one annular carbon carbon double bond), but not aromatic. Examples of monocyclic cycloallenyl ring systems include cyclopentenyl and cyclohexenyl. In embodiments, bicyclic cycloalkenyl rings are bridged monocyclic rings or a fused bicyclic rings. In embodiments, bridged monocyclic rings contain a monocyclic cycloalkenyl ring where two non adjacent carbon atoms of the monocyclic ring are linked by an alkylene bridge of between one and three additional carbon atoms (i.e., a bridging group of the form $(CH_2)_w$, where w is 1, 2, or 3). Representative examples of bicyclic cycloalkenyls include, but are not limited to, norbornenyl and bicyclo[2.2.2]oct 2 enyl. In embodiments, fused bicyclic cycloalkenyl ring systems contain a monocyclic cycloalkenyl ring fused to either a phenyl, a monocyclic cycloalkyl, a monocyclic cycloalkenyl, a monocyclic heterocyclyl, or a monocyclic heteroaryl. In embodiments, the bridged or fused bicyclic cycloalkenyl is attached to the parent molecular moiety through any carbon atom contained within the monocyclic cycloallenyl ring. In embodiments, cycloallenyl groups are optionally substituted with one or two groups which are independently oxo or thia. In embodiments, multicyclic cycloalkenyl rings contain a monocyclic cycloalkenyl ring (base ring) fused to either (i) one ring system selected from the group consisting of a bicyclic aryl, a bicyclic heteroaryl, a bicyclic cycloallyl, a bicyclic cycloalkenyl, and a bicyclic heterocyclyl; or (ii) two ring systems independently selected from the group consisting of a phenyl, a bicyclic aryl, a monocyclic or bicyclic heteroaryl, a monocyclic or bicyclic cycloallyl, a monocyclic or bicyclic cycloalkenyl, and a monocyclic or bicyclic heterocyclyl. In embodiments, the multicyclic cycloalkenyl is attached to the parent molecular moiety through any carbon atom contained within the base ring. In embodiments, multicyclic cycloallenyl rings contain a monocyclic cycloalkenyl ring (base ring) fused to either (i) one ring system selected from the group consisting of a bicyclic aryl, a bicyclic heteroaryl, a bicyclic cycloalkyl, a bicyclic cycloalkenyl, and a bicyclic heterocyclyl; or (ii) two ring systems independently selected from the group consisting of a phenyl, a monocyclic heteroaryl, a monocyclic cycloalkyl, a monocyclic cycloalkenyl, and a monocyclic heterocyclyl. A bicyclic or multicyclic cycloallenyl ring system refers to multiple rings fused together wherein at least one of the fused rings is a cycloalkenyl ring and wherein the multiple rings are attached to the parent molecular moiety through any carbon atom contained within a cycloalkenyl ring of the multiple rings.

In embodiments, the term "heterocycloallyl" means a monocyclic, bicyclic, or a multicyclic heterocycloallyl ring system. In embodiments, heterocycloalkyl groups are fully saturated. A bicyclic or multicyclic heterocycloallyl ring system refers to multiple rings fused together wherein at least one of the fused rings is a heterocycloalkyl ring and wherein the multiple rings are attached to the parent molecular moiety through any atom contained within a heterocycloallyl ring of the multiple rings.

In embodiments, a heterocycloalkyl is a heterocyclyl. The term "heterocyclyl" as used herein, means a monocyclic, bicyclic, or multicyclic heterocycle. The heterocyclyl monocyclic heterocycle is a 3, 4, 5, 6 or 7 membered ring containing at least one heteroatom independently selected from the group consisting of O, N, and S where the ring is saturated or unsaturated, but not aromatic. The 3 or 4 membered ring contains 1 heteroatom selected from the group consisting of O, N and S. The 5 membered ring can contain zero or one double bond and one, two or three heteroatoms selected from the group consisting of O, N and S. The 6 or 7 membered ring contains zero, one or two double bonds and one, two or three heteroatoms selected from the group consisting of O, N and S. The heterocyclyl monocyclic heterocycle is connected to the parent molecular moiety through any carbon atom or any nitrogen atom contained within the heterocyclyl monocyclic heterocycle. Representative examples of heterocyclyl monocyclic heterocycles include, but are not limited to, azetidinyl, azepanyl, aziridinyl, diazepanyl, 1,3-dioxanyl, 1,3-dioxolanyl, 1,3-dithiolanyl, 1,3-dithianyl, imidazolinyl, imidazolidinyl, isothiazolinyl, isothiazolidinyl, isoxazolinyl, isoxazolidinyl, morpholinyl, oxadiazolinyl, oxadiazolidinyl, oxazolinyl, oxazolidinyl, piperazinyl, piperidinyl, pyranyl, pyrazolinyl, pyrazolidinyl, pyrrolinyl, pyrrolidinyl, tetrahydrofuranyl, tetrahydrothienyl, thiadiazolinyl, thiadiazolidinyl, thiazolinyl, thiazolidinyl, thiomorpholinyl, 1,1-dioxidothiomorpholinyl (thiomorpholine sulfone), thiopyranyl, and trithianyl. The heterocyclyl bicyclic heterocycle is a monocyclic heterocycle fused to either a phenyl, a monocyclic cycloalkyl, a monocyclic cycloalkenyl, a monocyclic heterocycle, or a monocyclic heteroaryl. The heterocyclyl bicyclic heterocycle is connected to the parent molecular moiety through any carbon atom or any nitrogen atom contained within the monocyclic heterocycle portion of the bicyclic ring system. Representative examples of bicyclic heterocyclyls include, but are not limited to, 2,3-dihydrobenzofuran-2-yl, 2,3-dihydrobenzofuran-3-yl, indolin-1-yl, indolin-2-yl, indolin-3-yl, 2,3-dihydrobenzothien-2-yl, decahydroquinolinyl, decahydroisoquinolinyl, octahydro-1H-indolyl, and octahydrobenzofuranyl. In embodiments, heterocyclyl groups are optionally substituted with one or two groups which are independently oxo or thia. In certain embodiments, the bicyclic heterocyclyl is a 5 or 6 membered monocyclic heterocyclyl ring fused to a phenyl ring, a 5 or 6 membered monocyclic cycloalkyl, a 5 or 6 membered monocyclic cycloalkenyl, a 5 or 6 membered monocyclic heterocyclyl, or a 5 or 6 membered monocyclic heteroaryl, wherein the bicyclic heterocyclyl is optionally substituted by one or two groups which are independently oxo or thia. Multicyclic heterocyclyl ring systems are a monocyclic heterocyclyl ring (base ring) fused to either (i) one ring system selected from the group consisting of a bicyclic aryl, a bicyclic heteroaryl, a bicyclic cycloalkyl, a bicyclic cycloalkenyl, and a bicyclic heterocyclyl; or (ii) two other ring systems independently selected from the group consisting of a phenyl, a bicyclic aryl, a monocyclic or bicyclic heteroaryl, a monocyclic or bicyclic cycloalkyl, a monocyclic or bicyclic cycloalkenyl, and a monocyclic or bicyclic heterocyclyl. The multicyclic heterocyclyl is attached to the parent molecular moiety through any carbon atom or nitrogen atom contained within the base ring. In embodiments, multicyclic heterocyclyl ring systems are a monocyclic heterocyclyl ring (base ring) fused to either (i) one ring system selected from the group consisting of a bicyclic aryl, a bicyclic heteroaryl, a bicyclic cycloallyl, a bicyclic cycloalkenyl, and a bicyclic heterocyclyl; or (ii) two other ring systems independently selected from the group consisting of a phenyl, a monocyclic heteroaryl, a monocyclic cycloalkyl, a monocyclic cycloalkenyl, and a monocyclic heterocyclyl. Examples of multicyclic heterocyclyl groups include, but are not limited to 10H-phenothiazin-10-yl, 9,10-dihydroacridin-9-yl, 9,10-dihydroacridin-10-yl, 10H-phenoxazin-10-yl, 10,11-dihydro-5H-dibenzo[b,f]azepin-5-yl, 1,2,3,4-tetrahydropyrido[4,3-g]isoquinolin-2-yl, 12H-benzo[b]phenoxazin-12-yl, and dodecahydro-1H-carbazol-9-yl.

The terms "halo" or "halogen," by themselves or as part of another substituent, mean, unless otherwise stated, a fluorine, chlorine, bromine, or iodine atom. Additionally, terms such as "haloalkyl" are meant to include monohaloalkyl and polyhaloalkyl. For example, the term "halo($C_1$-$C_4$) alkyl" includes, but is not limited to, fluoromethyl, difluoromethyl, trifluoromethyl, 2,2,2-trifluoroethyl, 4-chlorobutyl, 3-bromopropyl, and the like.

The term "acyl" means, unless otherwise stated, —C(O)R where R is a substituted or unsubstituted alkyl, substituted or unsubstituted cycloalkyl, substituted or unsubstituted heteroalkyl, substituted or unsubstituted heterocycloalkyl, substituted or unsubstituted aryl, or substituted or unsubstituted heteroaryl.

The term "aryl" means, unless otherwise stated, a polyunsaturated, aromatic, hydrocarbon substituent, which can be a single ring or multiple rings (preferably from 1 to 3 rings) that are fused together (i.e., a fused ring aryl) or linked covalently. A fused ring aryl refers to multiple rings fused together wherein at least one of the fused rings is an aryl ring and wherein the multiple rings are attached to the parent molecular moiety through any carbon atom contained within an aryl ring of the multiple rings. The term "heteroaryl" refers to aryl groups (or rings) that contain at least one heteroatom such as N, O, or S, wherein the nitrogen and sulfur atoms are optionally oxidized, and the nitrogen atom(s) are optionally quaternized. Thus, the term "heteroaryl" includes fused ring heteroaryl groups (i.e., multiple rings fused together wherein at least one of the fused rings is a heteroaromatic ring and wherein the multiple rings are attached to the parent molecular moiety through any atom contained within a heteroaromatic ring of the multiple rings). A 5,6-fused ring heteroarylene refers to two rings fused together, wherein one ring has 5 members and the other ring has 6 members, and wherein at least one ring is a heteroaryl ring. Likewise, a 6,6-fused ring heteroarylene refers to two rings fused together, wherein one ring has 6 members and the other ring has 6 members, and wherein at least one ring is a heteroaryl ring. And a 6,5-fused ring heteroarylene refers to two rings fused together, wherein one ring has 6 members and the other ring has 5 members, and wherein at least one ring is a heteroaryl ring. A heteroaryl group can be attached to the remainder of the molecule through a carbon or heteroatom. Non-limiting examples of aryl and heteroaryl groups include phenyl, naphthyl, pyrrolyl, pyrazolyl, pyridazinyl, triazinyl, pyrimidinyl, imidazolyl, pyrazinyl, purinyl, oxazolyl, isoxazolyl, thiazolyl, furyl, thienyl, pyridyl, pyrimidyl, benzothiazolyl, benzoxazoyl benzimidazolyl, benzofuran, isobenzofuranyl, indolyl, isoindolyl, benzothiophenyl, isoquinolyl, quinoxalinyl, quinolyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl and heteroaryl ring systems are selected from the group of acceptable substituents described below. An "arylene" and a "heteroarylene," alone or as part of another substituent, mean a divalent radical derived from an aryl and heteroaryl, respectively. A heteroaryl group substituent may be —O— bonded to a ring heteroatom nitrogen.

A fused ring heterocyloallyl-aryl is an aryl fused to a heterocycloalkyl. A fused ring heterocycloallyl-heteroaryl is a heteroaryl fused to a heterocycloalkyl. A fused ring heterocycloallyl-cycloallyl is a heterocycloallyl fused to a cycloallyl. A fused ring heterocycloallyl-heterocycloalkyl is a heterocycloalkyl fused to another heterocycloalkyl. Fused ring heterocycloallyl-aryl, fused ring heterocycloalkyl-heteroaryl, fused ring heterocycloalkyl-cycloalkyl, or fused ring heterocycloalkyl-heterocycloallyl may each independently be unsubstituted or substituted with one or more of the substituents described herein.

Spirocyclic rings are two or more rings wherein adjacent rings are attached through a single atom. The individual rings within spirocyclic rings may be identical or different. Individual rings in spirocyclic rings may be substituted or unsubstituted and may have different substituents from other individual rings within a set of spirocyclic rings. Possible substituents for individual rings within spirocyclic rings are the possible substituents for the same ring when not part of spirocyclic rings (e.g. substituents for cycloallyl or heterocycloalkyl rings). Spirocylic rings may be substituted or unsubstituted cycloallyl, substituted or unsubstituted cycloalkylene, substituted or unsubstituted heterocycloalkyl or substituted or unsubstituted heterocycloallylene and individual rings within a spirocyclic ring group may be any of the immediately previous list, including having all rings of one type (e.g. all rings being substituted heterocycloallylene wherein each ring may be the same or different substituted heterocycloalkylene). When referring to a spirocyclic ring system, heterocyclic spirocyclic rings means a spirocyclic rings wherein at least one ring is a heterocyclic ring and wherein each ring may be a different ring. When referring to a spirocyclic ring system, substituted spirocyclic rings means that at least one ring is substituted and each substituent may optionally be different.

The symbol "  " denotes the point of attachment of a chemical moiety to the remainder of a molecule or chemical formula.

The term "oxo," as used herein, means an oxygen that is double bonded to a carbon atom.

The term "allylsulfonyl," as used herein, means a moiety having the formula —$S(O_2)$—R', where R' is a substituted or unsubstituted allyl group as defined above. R' may have a specified number of carbons (e.g., "$C_1$-$C_4$ alkylsulfonyl").

The term "allylarylene" as an arylene moiety covalently bonded to an alkylene moiety (also referred to herein as an allylene linker). In embodiments, the alkylarylene group has the formula:

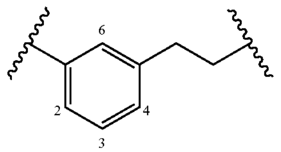

or

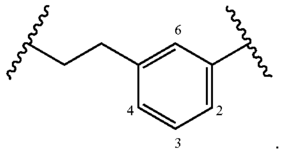

.

An alkylarylene moiety may be substituted (e.g. with a substituent group) on the alkylene moiety or the arylene linker (e.g. at carbons 2, 3, 4, or 6) with halogen, oxo, —$N_3$, —$CF_3$, —$CCl_3$, —$CBr_3$, —$Cl_3$, —CN, —CHO, —OH, —$NH_2$, —COOH, —$CONH_2$, —$NO_2$, —SH, —$SO_2CH_3$— $SO_3H$, —$OSO_3H$, —$SO_2NH_2$, —$NHNH_2$, —$ONH_2$, —$NHC(O)NHNH_2$, substituted or unsubstituted $C_1$-$C_5$ alkyl or substituted or unsubstituted 2 to 5 membered heteroalkyl). In embodiments, the alkylarylene is unsubstituted.

Each of the above terms (e.g., "alkyl," "heteroalkyl," "cycloallyl," "heterocycloalkyl," "aryl," and "heteroaryl") includes both substituted and unsubstituted forms of the indicated radical. Preferred substituents for each type of radical are provided below.

Substituents for the alkyl and heteroalkyl radicals (including those groups often referred to as alkylene, alkenyl, heteroalkylene, heteroalkenyl, alkynyl, cycloalkyl, heterocycloallyl, cycloallenyl, and heterocycloalkenyl) can be one or more of a variety of groups selected from, but not limited to, —OR', ═O, ═NR', ═N—OR', —NR'R", —SR', -halogen, —SiR'R"R'", —OC(O)R', —C(O)R', —$CO_2$R', —CONR'R", —OC(O)NR'R", —NR"C(O)R', —NR'—C(O)NR"R'", —NR"C$(O)_2$R', —NR—C(NR'R"R'")═NR"", —NR—C(NR'R")═NR'", —S(O)R', —$S(O)_2$R', —$S(O)_2$NR'R", —$NRSO_2$R', —NR'NR"R'", —ONR'R", —NR'C(O)NR"NR'"R"", —CN, —$NO_2$, —NR'$SO_2$R", —NR'C(O)R", —NR'C(O)—OR", —NR'OR", in a number ranging from zero to (2m'+1), where m' is the total number of carbon atoms in such radical. R, R', R", R'", and R"" each preferably independently refer to hydrogen, substituted or unsubstituted heteroalkyl, substituted or unsubstituted cycloallyl, substituted or unsubstituted heterocycloallyl, substituted or unsubstituted aryl (e.g., aryl substituted with 1-3 halogens), substituted or unsubstituted heteroaryl, substituted or unsubstituted alkyl, alkoxy, or thioalkoxy groups, or arylalkyl groups. When a compound described herein includes more than one R group, for example, each of the R groups is independently selected as are each R', R", R'", and R"" group when more than one of these groups is present. When R' and R" are attached to the same nitrogen atom, they can be combined with the nitrogen atom to form a 4-, 5-, 6-, or 7-membered ring. For example, —NR'R" includes, but is not limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —$CF_3$ and —$CH_2CF_3$) and acyl (e.g., —$C(O)CH_3$, —$C(O)CF_3$, —$C(O)CH_2OCH_3$, and the like).

Similar to the substituents described for the alkyl radical, substituents for the aryl and heteroaryl groups are varied and are selected from, for example: —OR', —NR'R", —SR', -halogen, —SiR'R"R'", —OC(O)R', —C(O)R', —$CO_2$R', —CONR'R", —OC(O)NR'R", —NR"C(O)R', —NR'—C(O)NR"R'", —NR"C$(O)_2$R', —NR—C(NR'R"R'")═NR"", —NR—C(NR'R")═NR'", —S(O)R', —$S(O)_2$R', —$S(O)_2$NR'R", —$NRSO_2$R', —NR'NR"R'", —ONR'R", —NR'C(O)NR"NR'"R"", —CN, —$NO_2$, —R', —$N_3$, —$CH(Ph)_2$, fluoro($C_1$-$C_4$)alkoxy, and fluoro($C_1$-$C_4$)alkyl, —NR'$SO_2$R", —NR'C(O)R", —NR'C(O)—OR", —NR'OR", in a number ranging from zero to the total number of open valences on the aromatic ring system; and where R', R", R'", and R"" are preferably independently selected from hydrogen, substituted or unsubstituted alkyl, substituted or unsubstituted heteroalkyl, substituted or unsubstituted cycloallyl, substituted or unsubstituted heterocycloallyl, substituted or unsubstituted aryl, and substituted or unsubstituted heteroaryl.

When a compound described herein includes more than one R group, for example, each of the R groups is independently selected as are each R', R", R''', and R'''' groups when more than one of these groups is present.

Substituents for rings (e.g. cycloalkyl, heterocycloalkyl, aryl, heteroaryl, cycloalkylene, heterocycloalkylene, arylene, or heteroarylene) may be depicted as substituents on the ring rather than on a specific atom of a ring (commonly referred to as a floating substituent). In such a case, the substituent may be attached to any of the ring atoms (obeying the rules of chemical valency) and in the case of fused rings or spirocyclic rings, a substituent depicted as associated with one member of the fused rings or spirocyclic rings (a floating substituent on a single ring), may be a substituent on any of the fused rings or spirocyclic rings (a floating substituent on multiple rings). When a substituent is attached to a ring, but not a specific atom (a floating substituent), and a subscript for the substituent is an integer greater than one, the multiple substituents may be on the same atom, same ring, different atoms, different fused rings, different spirocyclic rings, and each substituent may optionally be different. Where a point of attachment of a ring to the remainder of a molecule is not limited to a single atom (a floating substituent), the attachment point may be any atom of the ring and in the case of a fused ring or spirocyclic ring, any atom of any of the fused rings or spirocyclic rings while obeying the rules of chemical valency. Where a ring, fused rings, or spirocyclic rings contain one or more ring heteroatoms and the ring, fused rings, or spirocyclic rings are shown with one more floating substituents (including, but not limited to, points of attachment to the remainder of the molecule), the floating substituents may be bonded to the heteroatoms. Where the ring heteroatoms are shown bound to one or more hydrogens (e.g. a ring nitrogen with two bonds to ring atoms and a third bond to a hydrogen) in the structure or formula with the floating substituent, when the heteroatom is bonded to the floating substituent, the substituent will be understood to replace the hydrogen, while obeying the rules of chemical valency.

Two or more substituents may optionally be joined to form aryl, heteroaryl, cycloallyl, or heterocycloalkyl groups. Such so-called ring-forming substituents are typically, though not necessarily, found attached to a cyclic base structure. In one embodiment, the ring-forming substituents are attached to adjacent members of the base structure. For example, two ring-forming substituents attached to adjacent members of a cyclic base structure create a fused ring structure. In another embodiment, the ring-forming substituents are attached to a single member of the base structure. For example, two ring-forming substituents attached to a single member of a cyclic base structure create a spirocyclic structure. In yet another embodiment, the ring-forming substituents are attached to non-adjacent members of the base structure.

Two of the substituents on adjacent atoms of the aryl or heteroaryl ring may optionally form a ring of the formula -T-C(O)—(CRR')$_q$U—, wherein T and U are independently —NR—, —O—, —CRR'—, or a single bond, and q is an integer of from 0 to 3. Alternatively, two of the substituents on adjacent atoms of the aryl or heteroaryl ring may optionally be replaced with a substituent of the formula -A-(CH$_2$)$_r$—B—, wherein A and B are independently —CRR'—, —O—, —NR—, —S—, —S(O)—, —S(O)$_2$—, —S(O)$_2$NR'—, or a single bond, and r is an integer of from 1 to 4. One of the single bonds of the new ring so formed may optionally be replaced with a double bond. Alternatively, two of the substituents on adjacent atoms of the aryl or heteroaryl ring may optionally be replaced with a substituent of the formula —(CRR')$_s$—X'— (C"R"R''')$_d$—, where s and d are independently integers of from 0 to 3, and X is —O—, —NR'—, —S—, —S(O)—, —S(O)$_2$—, or —S(O)$_2$NR'—. The substituents R, R', R", and R''' are preferably independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl.

As used herein, the terms "heteroatom" or "ring heteroatom" are meant to include oxygen (O), nitrogen (N), sulfur (S), phosphorus (P), and silicon (Si).

A "substituent group," as used herein, means a group selected from the following moieties:

(A) oxo, halogen, —CCl$_3$, —CBr$_3$, —CF$_3$, —Cl$_3$, CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —C(O)OH, —C(O)NH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCl$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$, unsubstituted alkyl (e.g., $C_1$-$C_8$ allyl, $C_1$-$C_6$ alkyl, or $C_1$-$C_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., $C_3$-$C_8$ cycloalkyl, $C_3$-$C_6$ cycloallyl, or $C_5$-$C_6$ cycloalkyl), unsubstituted heterocycloallyl (e.g., 3 to 8 membered heterocycloallyl, 3 to 6 membered heterocycloallyl, or 5 to 6 membered heterocycloalkyl), unsubstituted aryl (e.g., $C_6$-$C_{10}$ aryl, $C_{10}$ aryl, or phenyl), or unsubstituted heteroaryl (e.g., 5 to 10 membered heteroaryl, 5 to 9 membered heteroaryl, or 5 to 6 membered heteroaryl), and (B) allyl, heteroalkyl, cycloallyl, heterocycloalkyl, aryl, heteroaryl, substituted with at least one substituent selected from:

(i) oxo, halogen, —CCl$_3$, —CBr$_3$, —CF$_3$, —Cl$_3$, CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —C(O)OH, —C(O)NH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCl$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$, unsubstituted alkyl (e.g., $C_1$-$C_8$ alkyl, $C_1$-$C_6$ allyl, or $C_1$-$C_4$ alkyl), unsubstituted heteroalkyl (e.g., 2 to 8 membered heteroalkyl, 2 to 6 membered heteroallyl, or 2 to 4 membered heteroalkyl), unsubstituted cycloallyl (e.g., $C_3$-$C_8$ cycloalkyl, $C_3$-$C_6$ cycloalkyl, or $C_5$-$C_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., $C_6$-$C_{10}$ aryl, $C_{10}$ aryl, or phenyl), or unsubstituted heteroaryl (e.g., 5 to 10 membered heteroaryl, 5 to 9 membered heteroaryl, or 5 to 6 membered heteroaryl), and (ii) allyl, heteroalkyl, cycloalkyl, heterocycloalkyl, aryl, heteroaryl, substituted with at least one substituent selected from:

(a) oxo, halogen, —CCl$_3$, —CBr$_3$, —CF$_3$, —Cl$_3$, CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —C(O)OH, —C(O)NH$_2$, —NO$_2$, —SH, —SO$_3$H, $—SO_4H$, $—SO_2NH_2$, $—NHNH_2$, $—ONH_2$, $—NHC(O)NHNH_2$, $—NHC(O)NH_2$, $—NHSO_2H$, —NHC(O)H, —NHC(O)OH, —NHOH, $—OCCl_3$, $—OCF_3$, $—OCBr_3$, $—OCI_3$, $—OCHCl_2$, $—OCHBr_2$, $—OCHI_2$, $—OCHF_2$, $—OCH_2Cl$, $—OCH_2Br$, $—OCH_2I$, $—OCH_2F$, $—N_3$, unsubstituted allyl (e.g., $C_1$-$C_8$ alkyl, $C_1$-$C_6$ alkyl, or $C_1$-$C_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., $C_3$-$C_8$ cycloalkyl, $C_3$-$C_6$ cycloalkyl, or $C_5$-$C_6$ cycloallyl), unsubstituted heterocycloallyl (e.g., 3 to 8 membered heterocycloalkyl, 3 to 6 membered heterocycloalkyl, or 5 to 6 membered heterocycloalkyl), unsubstituted aryl (e.g., $C_6$-$C_{10}$ aryl, $C_{10}$ aryl, or phenyl), or unsubstituted heteroaryl (e.g., 5 to 10 membered heteroaryl, 5 to 9 membered heteroaryl, or 5 to 6 membered heteroaryl), and (b) alkyl, heteroalkyl, cycloalkyl, heterocycloallyl, aryl, heteroaryl, substituted with at least one substituent selected from: oxo, halogen, $—CCl_3$, $—CBr_3$, $—CF_3$, $—CI_3$, $—CHCl_2$, $—CHBr_2$, $—CHF_2$, $—CHI_2$, $—CH_2Cl$, $—CH_2Br$, $—CH_2F$, $—CH_2I$, —CN, —OH, $—NH_2$, —C(O)OH, $—C(O)NH_2$, $—NO_2$, —SH, $—SO_3H$, $—SO_4H$, $—SO_2NH_2$, $—NHNH_2$, $—ONH_2$, $—NHC(O)NHNH_2$, $—NHC(O)NH_2$, $—NHSO_2H$, —NHC(O)H, —NHC(O)OH, —NHOH, $—OCCl_3$, $—OCF_3$, $—OCBr_3$, $—OCI_3$, $—OCHCl_2$, $—OCHBr_2$, $—OCHI_2$, $—OCHF_2$, $—OCH_2Cl$, $—OCH_2Br$, $—OCH_2I$, $—OCH_2F$, $—N_3$, unsubstituted allyl (e.g., $C_1$-$C_8$ allyl, $C_1$-$C_6$ alkyl, or $C_1$-$C_4$ allyl), unsubstituted heteroallyl (e.g., 2 to 8 membered heteroalkyl, 2 to 6 membered heteroalkyl, or 2 to 4 membered heteroallyl), unsubstituted cycloallyl (e.g., $C_3$-$C_8$ cycloalkyl, $C_3$-$C_6$ cycloallyl, or $C_5$-$C_6$ cycloalkyl), unsubstituted heterocycloalkyl (e.g., 3 to 8 membered heterocycloallyl, 3 to 6 membered heterocycloalkyl, or 5 to 6 membered heterocycloalkyl), unsubstituted aryl (e.g., $C_6$-$C_{10}$ aryl, $C_{10}$ aryl, or phenyl), or unsubstituted heteroaryl (e.g., 5 to 10 membered heteroaryl, 5 to 9 membered heteroaryl, or 5 to 6 membered heteroaryl).

A "size-limited substituent" or "size-limited substituent group," as used herein, means a group selected from all of the substituents described above for a "substituent group," wherein each substituted or unsubstituted allyl is a substituted or unsubstituted $C_1$-$C_{20}$ alkyl, each substituted or unsubstituted heteroallyl is a substituted or unsubstituted 2 to 20 membered heteroalkyl, each substituted or unsubstituted cycloallyl is a substituted or unsubstituted $C_3$-$C_8$ cycloalkyl, each substituted or unsubstituted heterocycloalkyl is a substituted or unsubstituted 3 to 8 membered heterocycloalkyl, each substituted or unsubstituted aryl is a substituted or unsubstituted $C_6$-$C_{10}$ aryl, and each substituted or unsubstituted heteroaryl is a substituted or unsubstituted 5 to 10 membered heteroaryl.

A "lower substituent" or "lower substituent group," as used herein, means a group selected from all of the substituents described above for a "substituent group," wherein each substituted or unsubstituted alkyl is a substituted or unsubstituted $C_1$-$C_8$ alkyl, each substituted or unsubstituted heteroallyl is a substituted or unsubstituted 2 to 8 membered heteroalkyl, each substituted or unsubstituted cycloallyl is a substituted or unsubstituted $C_3$-$C_7$ cycloalkyl, each substituted or unsubstituted heterocycloalkyl is a substituted or unsubstituted 3 to 7 membered heterocycloallyl, each substituted or unsubstituted aryl is a substituted or unsubstituted $C_6$-$C_{10}$ aryl, and each substituted or unsubstituted heteroaryl is a substituted or unsubstituted 5 to 9 membered heteroaryl.

In some embodiments, each substituted group described in the compounds herein is substituted with at least one substituent group. More specifically, in some embodiments, each substituted alkyl, substituted heteroallyl, substituted cycloallyl, substituted heterocycloallyl, substituted aryl, substituted heteroaryl, substituted allylene, substituted heteroalkylene, substituted cycloallylene, substituted heterocycloallylene, substituted arylene, and/or substituted heteroarylene described in the compounds herein are substituted with at least one substituent group. In other embodiments, at least one or all of these groups are substituted with at least one size-limited substituent group. In other embodiments, at least one or all of these groups are substituted with at least one lower substituent group.

In other embodiments of the compounds herein, each substituted or unsubstituted alkyl may be a substituted or unsubstituted $C_1$-$C_{20}$ alkyl, each substituted or unsubstituted heteroallyl is a substituted or unsubstituted 2 to 20 membered heteroalkyl, each substituted or unsubstituted cycloalkyl is a substituted or unsubstituted $C_3$-$C_8$ cycloalkyl, each substituted or unsubstituted heterocycloallyl is a substituted or unsubstituted 3 to 8 membered heterocycloallyl, each substituted or unsubstituted aryl is a substituted or unsubstituted $C_6$-$C_{10}$ aryl, and/or each substituted or unsubstituted heteroaryl is a substituted or unsubstituted 5 to 10 membered heteroaryl. In some embodiments of the compounds herein, each substituted or unsubstituted alkylene is a substituted or unsubstituted $C_1$-$C_{20}$ allylene, each substituted or unsubstituted heteroalkylene is a substituted or unsubstituted 2 to 20 membered heteroalkylene, each substituted or unsubstituted cycloallylene is a substituted or unsubstituted $C_3$-$C_8$ cycloallylene, each substituted or unsubstituted heterocycloallylene is a substituted or unsubstituted 3 to 8 membered heterocycloallylene, each substituted or unsubstituted arylene is a substituted or unsubstituted $C_6$-$C_{10}$ arylene, and/or each substituted or unsubstituted heteroarylene is a substituted or unsubstituted 5 to 10 membered heteroarylene.

In some embodiments, each substituted or unsubstituted alkyl is a substituted or unsubstituted $C_1$-$C_8$ alkyl, each substituted or unsubstituted heteroallyl is a substituted or unsubstituted 2 to 8 membered heteroallyl, each substituted or unsubstituted cycloalkyl is a substituted or unsubstituted $C_3$-$C_7$ cycloalkyl, each substituted or unsubstituted heterocycloalkyl is a substituted or unsubstituted 3 to 7 membered heterocycloalkyl, each substituted or unsubstituted aryl is a substituted or unsubstituted $C_6$-$C_{10}$ aryl, and/or each substituted or unsubstituted heteroaryl is a substituted or unsubstituted 5 to 9 membered heteroaryl. In some embodiments, each substituted or unsubstituted allylene is a substituted or unsubstituted $C_1$-$C_8$ alkylene, each substituted or unsubstituted heteroallylene is a substituted or unsubstituted 2 to 8 membered heteroalkylene, each substituted or unsubstituted cycloalkylene is a substituted or unsubstituted $C_3$-$C_7$ cycloalkylene, each substituted or unsubstituted heterocycloalkylene is a substituted or unsubstituted 3 to 7 membered heterocycloalkylene, each substituted or unsubstituted arylene is a substituted or unsubstituted $C_6$-$C_{10}$ arylene, and/or each substituted or unsubstituted heteroarylene is a substituted or unsubstituted 5 to 9 membered heteroarylene. In some embodiments, the compound is a chemical species set forth in the Examples section, figures, or tables below.

In embodiments, a substituted or unsubstituted moiety (e.g., substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, substituted or unsubstituted allylene, substituted or unsubstituted heteroalkylene, substituted or unsubstituted cycloalkylene, substituted or unsubstituted heterocycloallylene, substituted or unsubstituted arylene, and/or substituted or unsubstituted heteroarylene) is unsubstituted (e.g., is an unsubstituted allyl, unsubstituted heteroalkyl, unsubstituted cycloallyl, unsubstituted heterocycloalkyl, unsubstituted aryl, unsubstituted heteroaryl, unsubstituted alkylene, unsubstituted heteroalkylene, unsubstituted cycloalkylene, unsubstituted heterocycloalkylene, unsubstituted arylene, and/or unsubstituted heteroarylene, respectively). In embodiments, a substituted or unsubstituted moiety (e.g., substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, substituted or unsubstituted alkylene, substituted or unsubstituted heteroallylene, substituted or unsubstituted cycloalkylene, substituted or unsubstituted heterocycloalkylene, substituted or unsubstituted arylene, and/or substituted or unsubstituted heteroarylene) is substituted (e.g., is a substituted alkyl, substituted heteroalkyl, substituted cycloallyl, substituted heterocycloallyl, substituted aryl, substituted heteroaryl, substituted alkylene, substituted heteroalkylene, substituted cycloalkylene, substituted heterocycloallylene, substituted arylene, and/or substituted heteroarylene, respectively).

In embodiments, a substituted moiety (e.g., substituted allyl, substituted heteroalkyl, substituted cycloallyl, substituted heterocycloallyl, substituted aryl, substituted heteroaryl, substituted alkylene, substituted heteroalkylene, substituted cycloalkylene, substituted heterocycloallylene, substituted arylene, and/or substituted heteroarylene) is substituted with at least one substituent group, wherein if the substituted moiety is substituted with a plurality of substituent groups, each substituent group may optionally be different. In embodiments, if the substituted moiety is substituted with a plurality of substituent groups, each substituent group is different.

In embodiments, a substituted moiety (e.g., substituted allyl, substituted heteroalkyl, substituted cycloallyl, substituted heterocycloallyl, substituted aryl, substituted heteroaryl, substituted alkylene, substituted heteroalkylene, substituted cycloalkylene, substituted heterocycloallylene, substituted arylene, and/or substituted heteroarylene) is substituted with at least one size-limited substituent group, wherein if the substituted moiety is substituted with a plurality of size-limited substituent groups, each size-limited substituent group may optionally be different. In embodiments, if the substituted moiety is substituted with a plurality of size-limited substituent groups, each size-limited substituent group is different.

In embodiments, a substituted moiety (e.g., substituted allyl, substituted heteroalkyl, substituted cycloallyl, substituted heterocycloallyl, substituted aryl, substituted heteroaryl, substituted alkylene, substituted heteroalkylene, substituted cycloalkylene, substituted heterocycloallylene, substituted arylene, and/or substituted heteroarylene) is substituted with at least one lower substituent group, wherein if the substituted moiety is substituted with a plurality of lower substituent groups, each lower substituent group may optionally be different. In embodiments, if the substituted moiety is substituted with a plurality of lower substituent groups, each lower substituent group is different.

In embodiments, a substituted moiety (e.g., substituted allyl, substituted heteroalkyl, substituted cycloallyl, substituted heterocycloallyl, substituted aryl, substituted heteroaryl, substituted alkylene, substituted heteroalkylene, substituted cycloalkylene, substituted heterocycloallylene, substituted arylene, and/or substituted heteroarylene) is substituted with at least one substituent group, size-limited substituent group, or lower substituent group; wherein if the substituted moiety is substituted with a plurality of groups selected from substituent groups, size-limited substituent groups, and lower substituent groups; each substituent group, size-limited substituent group, and/or lower substituent group may optionally be different. In embodiments, if the substituted moiety is substituted with a plurality of groups selected from substituent groups, size-limited substituent groups, and lower substituent groups; each substituent group, size-limited substituent group, and/or lower substituent group is different.

Certain compounds of the present disclosure possess asymmetric carbon atoms (optical or chiral centers) or double bonds; the enantiomers, racemates, diastereomers, tautomers, geometric isomers, stereoisometric forms that may be defined, in terms of absolute stereochemistry, as (R)- or (S)- or, as (D)- or (L)- for amino acids, and individual isomers are encompassed within the scope of the present disclosure. The compounds of the present disclosure do not include those that are known in art to be too unstable to synthesize and/or isolate. The present disclosure is meant to include compounds in racemic and optically pure forms. Optically active (R)- and (S)-, or (D)- and (L)-isomers may be prepared using chiral synthons or chiral reagents, or resolved using conventional techniques. When the compounds described herein contain olefinic bonds or other centers of geometric asymmetry, and unless specified otherwise, it is intended that the compounds include both E and Z geometric isomers.

As used herein, the term "isomers" refers to compounds having the same number and kind of atoms, and hence the same molecular weight, but differing in respect to the structural arrangement or configuration of the atoms.

The term "tautomer," as used herein, refers to one of two or more structural isomers which exist in equilibrium and which are readily converted from one isomeric form to another.

It will be apparent to one skilled in the art that certain compounds of this disclosure may exist in tautomeric forms, all such tautomeric forms of the compounds being within the scope of the disclosure.

Unless otherwise stated, structures depicted herein are also meant to include all stereochemical forms of the structure; i.e., the R and S configurations for each asymmetric center. Therefore, single stereochemical isomers as well as enantiomeric and diastereomeric mixtures of the present compounds are within the scope of the disclosure.

Unless otherwise stated, structures depicted herein are also meant to include compounds which differ only in the presence of one or more isotopically enriched atoms. For example, compounds having the present structures except for the replacement of a hydrogen by a deuterium or tritium, or the replacement of a carbon by $^{13}C$- or $^{14}C$-enriched carbon are within the scope of this disclosure.

The compounds of the present disclosure may also contain unnatural proportions of atomic isotopes at one or more of the atoms that constitute such compounds. For example, the compounds may be radiolabeled with radioactive isotopes, such as for example tritium (3H), iodine-125 ($^{125}I$), or carbon-14 ($^{14}C$). All isotopic variations of the compounds of the present disclosure, whether radioactive or not, are encompassed within the scope of the present disclosure.

It should be noted that throughout the application that alternatives are written in Markush groups, for example, each amino acid position that contains more than one possible amino acid. It is specifically contemplated that each member of the Markush group should be considered separately, thereby comprising another embodiment, and the Markush group is not to be read as a single unit.

As used herein, the terms "bioconjugate" and "bioconjugate linker" refers to the resulting association between atoms or molecules of "bioconjugate reactive groups" or "bioconjugate moieties". The association can be direct or indirect. For example, a conjugate between a first bioconjugate reactive group (e.g., —$NH_2$, —C(O)OH, —N-hydroxysuccinimide, or -maleimide) and a second bioconjugate reactive group (e.g., sulfhydryl, sulfur-containing amino acid, amine, amine sidechain containing amino acid, or carboxylate) provided herein can be direct, e.g., by covalent bond or linker (e.g. a first linker of second linker), or indirect, e.g., by non-covalent bond (e.g. electrostatic interactions (e.g. ionic bond, hydrogen bond, halogen bond), van der Waals interactions (e.g. dipole-dipole, dipole-induced dipole, London dispersion), ring stacking (pi effects), hydrophobic interactions and the like). In embodiments, bioconjugates or bioconjugate linkers are formed using bioconjugate chemistry (i.e. the association of two bioconjugate reactive groups) including, but are not limited to nucleophilic substitutions (e.g., reactions of amines and alcohols with acyl halides, active esters), electrophilic substitutions (e.g., enamine reactions) and additions to carbon-carbon and carbon-heteroatom multiple bonds (e.g., Michael reaction, Diels-Alder addition). These and other useful reactions are discussed in, for example, March, ADVANCED ORGANIC CHEMISTRY, 3rd Ed., John Wiley & Sons, New York, 1985; Hermanson, BIOCONJUGATE TECHNIQUES, Academic Press, San Diego, 1996; and Feeney et al., MODIFICATION OF PROTEINS; Advances in Chemistry Series, Vol. 198, American Chemical Society, Washington, D.C., 1982. In embodiments, the first bioconjugate reactive group (e.g., maleimide moiety) is covalently attached to the second bioconjugate reactive group (e.g. a sulfhydryl). In embodiments, the first bioconjugate reactive group (e.g., haloacetyl moiety) is covalently attached to the second bioconjugate reactive group (e.g. a sulfhydryl). In embodiments, the first bioconjugate reactive group (e.g., pyridyl moiety) is covalently attached to the second bioconjugate reactive group (e.g. a sulfhydryl). In embodiments, the first bioconjugate reactive group (e.g., —N-hydroxysuccinimide moiety) is covalently attached to the second bioconjugate reactive group (e.g. an amine). In embodiments, the first bioconjugate reactive group (e.g., maleimide moiety) is covalently attached to the second bioconjugate reactive group (e.g. a sulfhydryl). In embodiments, the first bioconjugate reactive group (e.g., -sulfo-N-hydroxysuccinimide moiety) is covalently attached to the second bioconjugate reactive group (e.g. an amine).

Useful bioconjugate reactive moieties used for bioconjugate chemistries herein include, for example:

(a) carboxyl groups and various derivatives thereof including, but not limited to, N-hydroxysuccinimide esters, N-hydroxybenztriazole esters, acid halides, acyl imidazoles, thioesters, p-nitrophenyl esters, allyl, alkenyl, alkynyl and aromatic esters;

(b) hydroxyl groups which can be converted to esters, ethers, aldehydes, etc.

(c) haloalkyl groups wherein the halide can be later displaced with a nucleophilic group such as, for example, an amine, a carboxylate anion, thiol anion, carbanion, or an alkoxide ion, thereby resulting in the covalent attachment of a new group at the site of the halogen atom;

(d) dienophile groups which are capable of participating in Diels-Alder reactions such as, for example, maleimido or maleimide groups;

(e) aldehyde or ketone groups such that subsequent derivatization is possible via formation of carbonyl derivatives such as, for example, imines, hydrazones, semicarbazones or oximes, or via such mechanisms as Grignard addition or alkyllithium addition;

(f) sulfonyl halide groups for subsequent reaction with amines, for example, to form sulfonamides;

(g) thiol groups, which can be converted to disulfides, reacted with acyl halides, or bonded to metals such as gold, or react with maleimides;

(h) amine or sulfhydryl groups (e.g., present in cysteine), which can be, for example, acylated, alkylated or oxidized;

(i) alkenes, which can undergo, for example, cycloadditions, acylation, Michael addition, etc;

(j) epoxides, which can react with, for example, amines and hydroxyl compounds;

(k) phosphoramidites and other standard functional groups useful in nucleic acid synthesis;

(l) metal silicon oxide bonding; and (m) metal bonding to reactive phosphorus groups (e.g. phosphines) to form, for example, phosphate diester bonds.

(n) azides coupled to alkynes using copper catalyzed cycloaddition click chemistry.

(o) biotin conjugate can react with avidin or strepavidin to form an avidin-biotin complex or streptavidin-biotin complex.

The bioconjugate reactive groups can be chosen such that they do not participate in, or interfere with, the chemical stability of the conjugate described herein. Alternatively, a reactive functional group can be protected from participating in the crosslinking reaction by the presence of a protecting group. In embodiments, the bioconjugate comprises a molecular entity derived from the reaction of an unsaturated bond, such as a maleimide, and a sulfhydryl group.

"Analog," or "analogue" is used in accordance with its plain ordinary meaning within Chemistry and Biology and refers to a chemical compound that is structurally similar to another compound (i.e., a so-called "reference" compound) but differs in composition, e.g., in the replacement of one atom by an atom of a different element, or in the presence of a particular functional group, or the replacement of one functional group by another functional group, or the absolute stereochemistry of one or more chiral centers of the reference compound. Accordingly, an analog is a compound that is similar or comparable in function and appearance but not in structure or origin to a reference compound.

The terms "a" or "an," as used in herein means one or more. In addition, the phrase "substituted with a[n]," as used herein, means the specified group may be substituted with one or more of any or all of the named substituents. For example, where a group, such as an alkyl or heteroaryl group, is "substituted with an unsubstituted $C_1$-$C_{20}$ alkyl, or unsubstituted 2 to 20 membered heteroalkyl," the group may contain one or more unsubstituted $C_1$-$C_{20}$ alkyls, and/or one or more unsubstituted 2 to 20 membered heteroalkyls.

Moreover, where a moiety is substituted with an R substituent, the group may be referred to as "R-substituted." Where a moiety is R-substituted, the moiety is substituted with at least one R substituent and each R substituent is optionally different. Where a particular R group is present in the description of a chemical genus (such as Formula (I)), a Roman alphabetic symbol may be used to distinguish each appearance of that particular R group. For example, where multiple $R^{13}$ substituents are present, each $R^{13}$ substituent may be distinguished as $R^{13.A}$, $R^{13.B}$, $R^{13.C}$, $R^{13.D}$, etc., wherein each of $R^{13.A}$, $R^{13.B}$, $R^{13.C}$, $R^{13.D}$, etc. is defined within the scope of the definition of $R^{13}$ and optionally differently.

"Oxidizing agent" is used in accordance with its ordinary plain meaning within chemistry and biology and refers to a substance that has the ability to oxidize other substances (i.e. removes electrons from the substance). The term "oxidizing agent" is a substance that, in the course of a chemical redox reaction, removes one or more electrons from a substance (e.g., the reactant), wherein the oxidizing agent gains one or more electrons from the substrate. In embodiments, an oxidizing agent is a chemical species that transfers electronegative atoms to another substrate (e.g., a reactant). In embodiments, the oxidizing agent is analogous to the term "electron acceptor" and may be used herein interchangeably. Non-limiting examples of oxidizing agents include oxygen ($O_2$), ozone ($O_3$), hydrogen peroxide ($H_2O_2$), nitric acid ($HNO_3$), sulfuric acid ($H_2SO_4$), hexavalent chromium, pyridinium chlorochromate (PCC), N-methylmorpholine-N-oxide (NMO), chromium trioxide ($CrO_3$, Jones reagent), potassium permanganate ($K_2MnO_4$), potassium nitrate ($KNO_3$), Dess-Martin periodinane (DMP), 2-iodoxybenzoic acid (IBX), 2,2,6,6-tetramethylpiperidinyloxy (TEMPO), and Selectfluor® (F-TEDA-$BF_4$, chloromethyl-4-fluoro-1,4-diazoniabicyclo[2.2.2]octane bis(tetrafluoroborate), potassium perchlorate, or ammonium persulfate.

The term "halogenating agent" is used in accordance with its ordinary plain meaning within chemistry and refers to a substance (e.g., compound or composition) that has the ability to incorporate one or more halogen atoms (e.g. bromination, dibromination, tribromination, chlorination, dichlorination, trichlorination, iodination, diiodination, triiodination, fluorination, difluorination, trifluorination, etc.) into another substance (e.g., compound or composition). Halogenating agents include chlorinating agents, brominating agents, iodinating agents and fluorinating agents, wherein a chlorinating agent incorporates a chlorine atom, a brominating agent incorporates a bromine atom, an iodinating agent incorporates an iodine atom, or a fluorinating agent incorporates a fluorine atom. Brominating agents include, but are not limited to, N-bromosuccinimide (NBS), dibromoisocyanuric acid (DBI), bromine, bromotrichloromethane, 1,2-dibromo-1,1,2,2-tetrachloroethane, carbon tetrabromide, tetrabutylammonium tribromide, trimethylphenylammonium tribromide, benzyltrimethylammonium tribromide, pyridinium bromide perbromide, 4-dimethylaminopyridinium bromide perbromide, 1-butyl-3-methylimidazolium tribromide, 1,8-diazabicyclo[5.4.0]-7-undecene, hydrogen tribromide, N-bromophthalimide, N-bromosaccharin, N-bromoacetamide, 2-bromo-2-cyano-N,N-dimethylacetamide, 1,3-dibromo-5,5-dimethylhydantoin, monosodium bromoisocyanurate hydrate, boron tribromide, phosphorus tribromide, bromodimethylsulfonium bromide, 5,5-dibromomeldrum's acid, 2,4,4,6-tetrabromo-2,5-cyclohexadienone, or bis(2,4,6-trimethylpyridine)-bromonium hexafluorophosphate. Chlorinating agents include, but are not limited to, N-chlorosuccinimide (NCS), thionyl chloride, methanesulfonyl chloride, trichloromethanesulfonyl chloride, tert-butyl hypochlorite, chloromethyl methyl ether, dichloromethyl methyl ether, methoxyacetyl chloride, oxalyl chloride, cyanuric chloride, N-chlorophthalimide, sodium dichloroisocyanurate, trichloroisocyanuric acid, chloramine B hydrate, o-chloramine T dihydrate, chloramine T trihydrate, dichloramine B, dichloramine T, benzyltrimethylammonium, tetrachloroiodate. Iodinating agents include, but are not limited to, N-iodosuccinimide (NIS), 1,3-diodo-5,5'-dimethylhidantoin (DIH), iodine, hydriodic acid, diiodomethane, 1-chloro-2-iodoethane, carbon tetraiodide, tetramethylammonium dichloroiodate, benzyltrimethylammonium dichloroiodate, pyridine iodine monochloride, N,N-dimethyl-N-(methylsulfanylmethylene)-ammonium iodide, N-iodosaccharin, trimethylsilyl iodide, bis(pyridine) iodonium tetrafluoroborate, bis(2,4,6-trimethylpyridine)-iodonium hexafluorophosphate. In embodiments, the halogenating agent is not a fluorinating agent.

A "metal source" is used in accordance with its ordinary plain meaning within chemistry and biology and refers to a compound, salt or complex that includes a transition metal (e.g., as found in the periodic table of the elements). In embodiments, the metal source is a transition metal element (i.e., an element whose atom has a partially filled d sub-shell, or which can give rise to cations with an incomplete d sub-shell). The metal source may be a compound, salt, or complex and may contain one or more transition metals. In one embodiment, the metal source can be a "silver source", wherein the transition metal is silver. Non-limiting examples of a silver source include silver(I) tetrafluoroborate ($AgBF_4$), silver(I) nitrate ($AgNO_3$), silver(II) fluoride ($AgF_2$), silver(I) fluoride (AgF), silver trifluoromethanesulfonate (AgOTf), silver bis(trifluoromethanesulfonyl)imide ($AgNTf_2$), silver carbonate ($Ag_2CO_3$), silver(I) oxide ($Ag_2O$), silver(I) acetate (AgOAc), silver(I) sulfate ($Ag_2SO_4$), silver methanesulfonate (AgOMs), silver hexafluoroantimonate(V) ($AgSbF_6$), silver p-toluenesulfonate (AgOTs), silver(I) trifluoromethanethiolate ($AgSCF_3$), and silver(I) bromide (AgBr). In one embodiment, the metal source can be a "copper source", wherein the transition metal is copper. Non-limiting examples of a copper source include copper(II) sulfate ($CuSO_4$). In one embodiment, the metal source can be an "iron source", wherein the transition metal is iron. Non-limiting examples of an iron source include iron(III) chloride ($FeCl_3$) and iron(I) nitrate ($FeNO_3$) In one embodiment, the metal source can be a "manganese source", wherein the transition metal is manganese. Non-limiting examples of a manganese source include manganese(II) chloride ($MnCl_2$), manganese (III) acetate ($Mn(OAc)_3$), manganese(III) acetylacetonate ($Mn(acac)_3$), and manganese(III) 2-pyridinecarboxylate ($Mn(pic)_3$). See, *Chem. Lett.* 2017, 46, 1692, which is incorporated herein by reference in its entirety.

A "detectable agent" or "detectable moiety" is a composition, substance, element, or compound or moiety thereof detectable by appropriate means such as spectroscopic, photochemical, biochemical, immunochemical, chemical, magnetic resonance imaging, or other physical means. For example, useful detectable agents include $^{18}$F, $^{32}$P, $^{33}$P, $^{45}$Ti, $^{47}$Sc, $^{52}$Fe, $^{59}$Fe, $^{62}$Cu, $^{64}$Cu, $^{67}$Cu, $^{67}$Ga, $^{68}$Ga, $^{77}$As, $^{86}$Y, $^{90}$Y, $^{89}$Sr, $^{89}$Zr, $^{94}$Tc, $^{94}$Tc, $^{99m}$Tc, $^{99}$Mo, $^{105}$Pd, $^{105}$Rh, $^{111}$Ag, $^{111}$In, $^{123}$I, $^{124}$I, $^{125}$I, $^{131}$I, $^{142}$Pr, $^{143}$Pr, $^{149}$Pm, $^{153}$Sm, $^{154-1581}$Gd, $^{161}$Tb, $^{166}$Dy, $^{166}$Ho, $^{169}$Er, $^{175}$Lu, $^{177}$Lu, $^{186}$Re, $^{188}$Re, $^{189}$Re, $^{194}$Ir, $^{198}$Au, $^{199}$Au, $^{211}$At, $^{211}$Pb, $^{212}$Bi, $^{212}$Pb, $^{213}$Bi, $^{223}$Ra, $^{225}$Ac, Cr, V, Mn, Fe, Co, Ni, Cu, La, Ce, Pr, Nd, Pm, Sm, Eu, Gd, Tb, Dy, Ho, Er, Tm, Yb, Lu, $^{32}$P, fluorophore (e.g. fluorescent dyes), electron-dense reagents, enzymes (e.g., as commonly used in an ELISA), biotin, digoxigenin, paramagnetic molecules, paramagnetic nanoparticles, ultrasmall superparamagnetic iron oxide ("USPIO") nanoparticles, USPIO nanoparticle aggregates, superparamagnetic iron oxide ("SPIO") nanoparticles, SPIO nanoparticle aggregates, monocrystalline iron oxide nanoparticles, monocrystalline iron oxide, nanoparticle contrast agents, liposomes or other delivery vehicles containing Gadolinium chelate ("Gd-chelate") molecules, Gadolinium, radioisotopes, radionuclides (e.g. carbon-11, nitrogen-13, oxygen-15, fluorine-18, rubidium-82), fluorodeoxyglucose (e.g. fluorine-18 labeled), any gamma ray emitting radionuclides, positron-emitting radionuclide, radiolabeled glucose, radiolabeled water, radiolabeled ammonia, biocolloids, microbubbles (e.g. including microbubble shells including albumin, galactose, lipid, and/or polymers; microbubble gas core including air, heavy gas(es), perfluorocarbon, nitrogen, octafluoropropane, perflexane lipid microsphere, perflutren, etc.), iodinated contrast agents (e.g. iohexol, iodixanol, ioversol, iopamidol, ioxilan, iopromide, diatrizoate, metrizoate, ioxaglate), barium sulfate, thorium dioxide, gold, gold nanoparticles, gold nanoparticle aggregates, fluorophores, two-photon fluorophores, or haptens and proteins or other entities which can be made detectable, e.g., by incorporating a radiolabel into a peptide or antibody specifically reactive with a target peptide. A detectable moiety is a monovalent detectable agent or a detectable agent capable of forming a bond with another composition.

Radioactive substances (e.g., radioisotopes) that may be used as imaging and/or labeling agents in accordance with the embodiments of the disclosure include, but are not limited to, $^{18}F$, $^{32}P$, $^{33}P$, $^{45}Ti$, $^{47}Sc$, $^{52}Fe$, $^{59}Fe$, $^{62}Cu$, $^{64}Cu$, $^{67}Cu$, $^{67}Ga$, $^{68}Ga$, $^{77}As$, $^{86}Y$ $^{90}Y$, $^{89}Sr$, $^{89}Zr$, $^{94}Tc$, $^{94}Tc$, $^{99m}Tc$, $^{99}Mo$, $^{105}Pd$, $^{105}Rh$, $^{111}Ag$, $^{111}In$, $^{123}I$, $^{124}I$, $^{125}I$, $^{131}I$, $^{142}Pr$, $^{143}Pr$, $^{149}Pm$, $^{153}Sm$, $^{154-1581}Gd$, $^{161}Tb$, $^{166}Dy$, $^{166}Ho$, $^{169}Er$, $^{175}Lu$, $^{177}Lu$, $^{186}Re$, $^{188}Re$, $^{189}Re$, $^{194}I$, $^{198}Au$, $^{199}Au$, $^{211}At$, $^{211}Pb$, $^{212}Bi$, $^{212}Pb$, $^{213}Bi$, $^{223}Ra$ and $^{225}Ac$. Paramagnetic ions that may be used as additional imaging agents in accordance with the embodiments of the disclosure include, but are not limited to, ions of transition and lanthanide metals (e.g. metals having atomic numbers of 21-29, 42, 43, 44, or 57-71). These metals include ions of Cr, V, Mn, Fe, Co, Ni, Cu, La, Ce, Pr, Nd, Pm, Sm, Eu, Gd, Tb, Dy, Ho, Er, Tm, Yb and Lu.

Descriptions of compounds of the present disclosure are limited by principles of chemical bonding known to those skilled in the art. Accordingly, where a group may be substituted by one or more of a number of substituents, such substitutions are selected so as to comply with principles of chemical bonding and to give compounds which are not inherently unstable and/or would be known to one of ordinary skill in the art as likely to be unstable under ambient conditions, such as aqueous, neutral, and several known physiological conditions. For example, a heterocycloalkyl or heteroaryl is attached to the remainder of the molecule via a ring heteroatom in compliance with principles of chemical bonding known to those skilled in the art thereby avoiding inherently unstable compounds.

The term "leaving group" is used in accordance with its ordinary meaning in chemistry and refers to a moiety (e.g., atom, functional group, molecule) that separates from the molecule following a chemical reaction (e.g., bond formation, reductive elimination, condensation, cross-coupling reaction) involving an atom or chemical moiety to which the leaving group is attached, also referred to herein as the "leaving group reactive moiety", and a complementary reactive moiety (i.e. a chemical moiety that reacts with the leaving group reactive moiety) to form a new bond between the remnants of the leaving groups reactive moiety and the complementary reactive moiety. Thus, the leaving group reactive moiety and the complementary reactive moiety form a complementary reactive group pair. Non limiting examples of leaving groups include hydrogen, hydroxide, organotin moieties (e.g., organotin heteroalkyl), halogen (e.g., Br), perfluoroalkylsulfonates (e.g. triflate), tosylates, mesylates, water, alcohols, nitrate, phosphate, thioether, amines, ammonia, fluoride, carboxylate, phenoxides, boronic acid, boronate esters, and alkoxides. In embodiments, two molecules with leaving groups are allowed to contact, and upon a reaction and/or bond formation (e.g., acyloin condensation, aldol condensation, Claisen condensation, Stille reaction) the leaving groups separates from the respective molecule. In embodiments, a leaving group is a bioconjugate reactive moiety. In embodiments, at least two leaving groups (e.g., $R^1$ and $R^{13}$) are allowed to contact such that the leaving groups are sufficiently proximal to react, interact or physically touch. In embodiments, the leaving group is designed to facilitate the reaction.

The term "protecting group" is used in accordance with its ordinary meaning in organic chemistry and refers to a moiety covalently bound to a heteroatom, heterocycloallyl, or heteroaryl to prevent reactivity of the heteroatom, heterocycloalkyl, or heteroaryl during one or more chemical reactions performed prior to removal of the protecting group. In embodiments, the protecting group is covalently bound to a heteroatom that is part of a heteroalkyl, heterocycloallyl or heteroaryl moiety. Typically a protecting group is bound to a heteroatom (e.g., O) during a part of a multistep synthesis wherein it is not desired to have the heteroatom react (e.g., a chemical reduction) with the reagent. Following protection the protecting group may be removed (e.g., by modulating the pH). In embodiments the protecting group is an alcohol protecting group. Non-limiting examples of alcohol protecting groups include acetyl, benzoyl, benzyl, methoxymethyl ether (MOM), tetrahydropyranyl (THP), and silyl ether (e.g., trimethylsilyl (TMS), tert-butyl dimethylsilyl (TBS)). In embodiments the protecting group is an amine protecting group. Non-limiting examples of amine protecting groups include carbobenzyloxy (Cbz), p-methoxybenzyl carbonyl (Moz or MeOZ), tert-butyloxycarbonyl (BOC), 9-fluorenylmethyloxycarbonyl (FMOC), acetyl (Ac), benzoyl (Bz), benzyl (Bn), carbamate, p-methoxybenzyl ether (PMB), 3,4-dimethoxybenzyl (DMPM), p-methoxyphenyl (PMP), pivaloyl (Piv), tosyl (Ts), and phthalimide.

The term "silyl protecting group" is used in accordance with its ordinary meaning in organic chemistry and refers to a protecting group that contains a silicon atom covalently bonded to a heteroatom to prevent reactivity of the heteroatom. In embodiments, the silyl protecting group is covalently bound to an alloxy group to form a silyl ether. Non-limiting examples of silyl protecting groups include trimethylsilyl (TMS), triethylsilyl (TES), tert-butyl dimethylsilyl (TBS/TBDMS), tert-butyldiphenylsilyl (TBDPS), and triisopropylsilyl (TIPS).

The term "transition metal catalyst for olefin metathesis" is used in accordance with its ordinary meaning in organic chemistry and refers to a transition metal catalyst that catalyzes a reaction that entails the redistribution of fragments of alkenes (e.g., olefins) by the scission and regeneration of carbon-carbon double bonds. In embodiments, the olefin metathesis is a cross metathesis. In embodiments, the olefin metathesis involves ring closure between two terminal vinyl groups (ring closing metathesis). In embodiments, the transition metal catalyst is a heterogenous catalyst. In embodiments, the transition metal catalyst is a molybdenum-based catalyst. In embodiments, the transition metal catalyst is a molybdenum(VI)-based catalyst. In embodiments, the transition metal catalyst is a tungsten-based catalyst. In embodiments, the transition metal catalyst is a tungsten(VI)-based catalyst. In embodiments, the transition metal catalyst is a ruthenium-based catalyst. In embodiments, the transition metal catalyst is a ruthenium(II)-based catalyst. In embodiments, the transition metal catalyst is a Grubbs catalyst. In embodiments, the transition metal catalyst is a Schrock catalyst. In embodiments, the transition metal catalyst is a Hoveyda-Grubbs catalyst. Non-limiting examples of transition metal catalyst for olefin metathesis include: Grubbs $1^{st}$ generation catalyst [benzylidene-bis(tricyclohexylphosphine)dichlororuthenium, bis(tricyclohexylphosphine)benzylidine ruthenium(IV) dichloride, or dichloro(benzylidene)bis(tricyclohexylphosphine)ruthenium(II)]; Grubbs $2^{nd}$ generation catalyst [(1,3-bis(2,4,6-trimethylphenyl)-2-imidazolidinylidene)dichloro(phenylmethylene)(tricyclohexylphosphine)ruthenium, benzylidene [1,3-bis(2,4,6-trimethylphenyl)-2-imidazolidinylidene] dichloro(tricyclohexylphosphine)ruthenium or dichloro[1,3-bis(2,4,6-trimethylphenyl)-2-imidazolidinylidene] (benzylidene)(tricyclohexylphosphine)ruthenium(II)]; Grubbs $3^{rd}$ generation catalyst [dichloro[1,3-bis(2,4,6-trimethylphenyl)-2-imidazolidinylidene](benzylidene)bis(3-bromopyridine)ruthenium(II), [1,3-bis(2,4,6-trimethylphenyl)-2-imidazolidinylidene]dichloro(phenylmethylene)bis (3-bromopyridine)ruthenium(II), or [1,3-dimesityl-2-imidazolidinylidene]dichloro(phenylmethylene)bis(3-bromopyridine)ruthenium(II)]; Hoveyda-Grubbs $1^{st}$ generation catalyst [dichloro(2-isopropoxyphenylmethylene) (tricyclohexylphosphine)ruthenium(II) or dichloro(o-isopropoxyphenylmethylene)(tricyclohexylphosphine)ruthenium(II)]; Hoveyda-Grubbs $2^{nd}$ generation catalyst [(1, 3-bis-(2,4,6-trimethylphenyl)-2-imidazolidinylidene) dichloro(o-isopropoxyphenylmethylene)ruthenium or dichloro[1,3-bis(2,4,6-trimethylphenyl)-2-imidazolidinylidene](2-isopropoxyphenylmethylene)ruthenium(II)]; NitroGrela [(1,3-dimesitylimidazolidin-2-ylidene)dichloro (2-isopropoxy-5-nitrobenzylidene)ruthenium(II)]; dichloro [1,3-Bis(2-methylphenyl)-2-imidazolidinylidene](benzylidene)(tricyclohexylphosphine)ruthenium(II) [Grubbs Catalyst® M2a SI(o-Tol) (C793)]; dichloro[1,3-bis(2,4,6-trimethylphenyl)-2-imidazolidinylidene](3-methyl-2-butenylidene) (tricyclohexylphosphine)ruthenium(II) [Grubbs Catalyst® M2b (C827)]; dichloro[1,3-bis(2-methylphenyl)-2-imidazolidinylidene](2-isopropoxyphenylmethylene)ruthenium(II) [Hoveyda-Grubbs Catalyst® M72 SI(o-Tol) (C571) or Stewart-Grubbs catalyst]; and dichloro[1,3-bis(2, 4,6-trimethylphenyl)-2-imidazolidinylidene][3-(2-pyridinyl) propylidene]ruthenium(II) (Grubbs Catalyst® C598).

The term "alcohol" is used in accordance with its ordinary meaning in organic chemistry and refers to an organic compound that carries at least one hydroxyl functional group (—OH) bound to a saturated carbon atom. In embodiments, the alcohol is a primary alcohol. In embodiments, the alcohol is a secondary alcohol. In embodiments, the alcohol is a tertiary alcohol. Non-limiting examples of alcohols include: methanol, ethanol, n-propyl alcohol (propan-1-ol or 1-propanol), isopropyl alcohol (propan-2-ol or 2-propanol), cyclohexanol, isobutyl alcohol (2-methylpropan-1-ol or 2-methyl-1-propanol), or tert-amyl alcohol (2-methylbutan-2-ol or 2-methyl-2-butanol).

The term "base" is used in accordance with its ordinary meaning in organic chemistry and refers to a substance that accept protons from any proton donor or contain completely or partially displaceable $OH^-$ ions. In embodiments, the base in an inorganic base. In embodiments, the base is an organic base. Non-limiting examples of inorganic bases include: NaOH, LiOH, $Ca(OH)_2$, magnesium hydroxide, sodium carbonate, sodium bicarbonate, sodium hydrogen carbonate, or ammonium hydroxide. Non-limiting examples of organic bases include: pyridine, alkanamines (such as methylamine), imidazole, benzimidazole, histidine, guanidine, or phosphazene bases.

The compound "17S-FD-895" corresponds to the following structure:

17S-FD-895 (1)

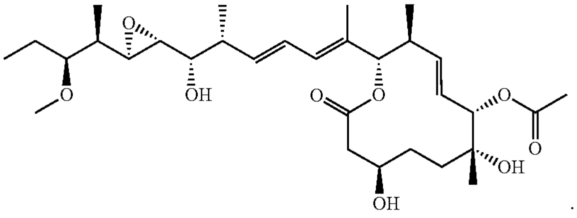

A person of ordinary skill in the art will understand when a variable (e.g., moiety or linker) of a compound or of a compound genus (e.g., a genus described herein) is described by a name or formula of a standalone compound with all valencies filled, the unfilled valence(s) of the variable will be dictated by the context in which the variable is used. For example, when a variable of a compound as described herein is connected (e.g., bonded) to the remainder of the compound through a single bond, that variable is understood to represent a monovalent form (i.e., capable of forming a single bond due to an unfilled valence) of a standalone compound (e.g., if the variable is named "methane" in an embodiment but the variable is known to be attached by a single bond to the remainder of the compound, a person of ordinary skill in the art would understand that the variable is actually a monovalent form of methane, i.e., methyl or $—CH_3$). Likewise, for a linker variable (e.g., $L^1$, $L^2$, or $L^3$ as described herein), a person of ordinary skill in the art will understand that the variable is the divalent form of a standalone compound (e.g., if the variable is assigned to "PEG" or "polyethylene glycol" in an embodiment but the variable is connected by two separate bonds to the remainder of the compound, a person of ordinary skill in the art would understand that the variable is a divalent (i.e., capable of forming two bonds through two unfilled valences) form of PEG instead of the standalone compound PEG).

The term "exogenous" refers to a molecule or substance (e.g., a compound, nucleic acid or protein) that originates from outside a given cell or organism. For example, an "exogenous promoter" as referred to herein is a promoter that does not originate from the plant it is expressed by. Conversely, the term "endogenous" or "endogenous promoter" refers to a molecule or substance that is native to, or originates within, a given cell or organism.

The term "lipid moiety" is used in accordance with its ordinary meaning in chemistry and refers to a hydrophobic molecule which is typically characterized by an aliphatic hydrocarbon chain. In embodiments, the lipid moiety includes a carbon chain of 3 to 100 carbons. In embodiments, the lipid moiety includes a carbon chain of 5 to 50 carbons. In embodiments, the lipid moiety includes a carbon chain of 5 to 25 carbons. In embodiments, the lipid moiety includes a carbon chain of 8 to 25 carbons. Lipid moieties may include saturated or unsaturated carbon chains, and may be optionally substituted. In embodiments, the lipid moiety is optionally substituted with a charged moiety at the terminal end. In embodiments, the lipid moiety is an alkyl or heteroalkyl optionally substituted with a carboxylic acid moiety at the terminal end.

A charged moiety refers to a functional group possessing an abundance of electron density (i.e. electronegative) or is deficient in electron density (i.e. electropositive). Non-limiting examples of a charged moiety includes carboxylic acid, alcohol, phosphate, aldehyde, and sulfonamide. In embodiments, a charged moiety is capable of forming hydrogen bonds.

The term "coupling reagent" is used in accordance with its plain ordinary meaning in the arts and refers to a substance (e.g., a compound or solution) which participates in chemical reaction and results in the formation of a covalent bond (e.g., between bioconjugate reactive moieties, between a bioconjugate reactive moiety and the coupling reagent). In embodiments, the level of reagent is depleted in the course of a chemical reaction. This is in contrast to a solvent, which typically does not get consumed over the course of the chemical reaction. Non-limiting examples of coupling reagents include benzotriazol-1-yl-oxytripyrrolidinophosphonium hexafluorophosphate (PyBOP), 7-Azabenzotriazol-1-yloxy)tripyrrolidinophosphonium hexafluorophosphate (PyAOP), 6-Chloro-benzotriazole-1-yloxy-tris-pyrrolidinophosphonium hexafluorophosphate (PyClock), 1-[Bis(dimethylamino)methylene]-1H-1,2,3-triazolo[4,5-b] pyridinium 3-oxid hexafluorophosphate (HATU), or 2-(1H-benzotriazol-1-yl)-1,1,3,3-tetramethyluronium hexafluorophosphate (HBTU).

The term "solution" is used in accord and refers to a liquid mixture in which the minor component (e.g., a solute or compound) is uniformly distributed within the major component (e.g., a solvent).

The term "organic solvent" as used herein is used in accordance with its ordinary meaning in chemistry and refers to a solvent which includes carbon. Non-limiting examples of organic solvents include acetic acid, acetone, acetonitrile, benzene, 1-butanol, 2-butanol, 2-butanone, t-butyl alcohol, carbon tetrachloride, chlorobenzene, chloroform, cyclohexane, 1,2-dichloroethane, diethylene glycol, diethyl ether, diglyme (diethylene glycol, dimethyl ether), 1,2-dimethoxyethane (glyme, DME), dimethylformamide (DMF), dimethyl sulfoxide (DMSO), 1,4-dioxane, ethanol, ethyl acetate, ethylene glycol, glycerin, heptane, hexamethylphosphoramide (HMPA), hexamethylphosphorous, triamide (HMPT), hexane, methanol, methyl t-butyl ether (MTBE), methylene chloride, N-methyl-2-pyrrolidinone (NMP), nitromethane, pentane, petroleum ether (ligroine), 1-propanol, 2-propanol, pyridine, tetrahydrofuran (THF), toluene, triethyl amine, o-xylene, m-xylene, or p-xylene. In embodiments, the organic solvent is or includes chloroform, dichloromethane, methanol, ethanol, tetrahydrofuran, or dioxane.

As used herein, the term "enantiomerically pure" is used in accordance with its ordinary meaning in organic chemistry and refers to a molecule of indicated chirality with an indicated degree of purity. A sample that is 99% enantiomerically pure, for example, has a molar ratio of 99:1 of the indicated enantiomer relative to one or more alternative enantiomeric configurations. In embodiments, the enantiomeric purity can be measured using NMR, LC-MS, or chiral-HPLC.

As used herein, the term "salt" refers to acid or base salts of the compounds used in the methods provided herein. Illustrative examples of acceptable salts are mineral acid (hydrochloric acid, hydrobromic acid, phosphoric acid, and the like) salts, organic acid (acetic acid, propionic acid, glutamic acid, citric acid and the like) salts, quaternary ammonium (methyl iodide, ethyl iodide, and the like) salts.

The terms "bind" and "bound" as used herein is used in accordance with its plain and ordinary meaning and refers to the association between atoms or molecules. The association can be direct or indirect. For example, bound atoms or molecules may be bound, e.g., by covalent bond, linker (e.g. a first linker or second linker), or non-covalent bond (e.g. electrostatic interactions (e.g. ionic bond, hydrogen bond, halogen bond), van der Waals interactions (e.g. dipole-dipole, dipole-induced dipole, London dispersion), ring stacking (pi effects), hydrophobic interactions and the like).

The term "capable of binding" as used herein refers to a moiety (e.g. a compound as described herein) that is able to measurably bind to a target (e.g., a NF-κB, a Toll-like receptor protein). In embodiments, where a moiety is capable of binding a target, the moiety is capable of binding with a Kd of less than about 10 μM, 5 μM, 1 μM, 500 nM, 250 nM, 100 nM, 75 nM, 50 nM, 25 nM, 15 nM, 10 nM, 5 nM, 1 nM, or about 0.1 nM.

As used herein, the term "conjugated" when referring to two moieties means the two moieties are bonded, wherein the bond or bonds connecting the two moieties may be covalent or non-covalent. In embodiments, the two moieties are covalently bonded to each other (e.g. directly or through a covalently bonded intermediary). In embodiments, the two moieties are non-covalently bonded (e.g. through ionic bond(s), van der waal's bond(s)/interactions, hydrogen bond(s), polar bond(s), or combinations or mixtures thereof).

The term "non-nucleophilic base" as used herein refers to any sterically hindered base that is a poor nucleophile.

The term "nucleophile" as used herein refers to a chemical species that donates an electron pair to an electrophile to form a chemical bond in relation to a reaction. All molecules or ions with a free pair of electrons or at least one pi bond can act as nucleophiles.

The term "strong acid" as used according to its plain and ordinary meaning in the art and includes an acid that is completely dissociated or ionized in an aqueous solution. Examples of common strong acids include hydrochloric acid (HCl), nitric acid ($HNO_3$), sulfuric acid ($H_2SO_4$), hydrobromic acid (HBr), hydroiodic acid (HI), perchloric acid ($HClO_4$), or chloric acid ($HClO_3$). In embodiments, the strong acid is a sulfonic acid, such as p-toluenesulfonic acid (TsOH), pyridinium p-toluenesulfonate, or camphorsulfonic acid (CSA).

The term "carbocation stabilizing solvent" as used herein refers to any polar protic solvent capable of forming dipole-dipole interactions with a carbocation, thereby stabilizing the carbocation.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, i.e., an a carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid. The terms "non-naturally occurring amino acid" and "unnatural amino acid" refer to amino acid analogs, synthetic amino acids, and amino acid mimetics which are not found in nature.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

The terms "polypeptide," "peptide" and "protein" are used interchangeably herein to refer to a polymer of amino acid residues, wherein the polymer may In embodiments be conjugated to a moiety that does not consist of amino acids. The terms apply to amino acid polymers in which one or more amino acid residue is an artificial chemical mimetic of a corresponding naturally occurring amino acid, as well as to naturally occurring amino acid polymers and non-naturally occurring amino acid polymers. A "fusion protein" refers to a chimeric protein encoding two or more separate protein sequences that are recombinantly expressed as a single moiety.

As may be used herein, the terms "nucleic acid," "nucleic acid molecule," "nucleic acid oligomer," "oligonucleotide," "nucleic acid sequence," "nucleic acid fragment" and "polynucleotide" are used interchangeably and are intended to include, but are not limited to, a polymeric form of nucleotides covalently linked together that may have various lengths, either deoxyribonucleotides or ribonucleotides, or analogs, derivatives or modifications thereof. Different polynucleotides may have different three-dimensional structures, and may perform various functions, known or unknown. Non-limiting examples of polynucleotides include a gene, a gene fragment, an exon, an intron, intergenic DNA (including, without limitation, heterochromatic DNA), messenger RNA (mRNA), transfer RNA, ribosomal RNA, a ribozyme, cDNA, a recombinant polynucleotide, a branched polynucleotide, a plasmid, a vector, isolated DNA of a sequence, isolated RNA of a sequence, a nucleic acid probe, and a primer. Polynucleotides useful in the methods of the disclosure may include natural nucleic acid sequences and variants thereof, artificial nucleic acid sequences, or a combination of such sequences.

A polynucleotide is typically composed of a specific sequence of four nucleotide bases: adenine (A); cytosine (C); guanine (G); and thymine (T) (uracil (U) for thymine (T) when the polynucleotide is RNA). Thus, the term "polynucleotide sequence" is the alphabetical representation of a polynucleotide molecule; alternatively, the term may be applied to the polynucleotide molecule itself. This alphabetical representation can be input into databases in a computer having a central processing unit and used for bioinformatics applications such as functional genomics and homology searching. Polynucleotides may optionally include one or more non-standard nucleotide(s), nucleotide analog(s) and/or modified nucleotides.

"Contacting" is used in accordance with its plain ordinary meaning and refers to the process of allowing at least two distinct species (e.g. chemical compounds including biomolecules or cells) to become sufficiently proximal to react, interact or physically touch. It should be appreciated; however, the resulting reaction product can be produced directly from a reaction between the added reagents or from an intermediate from one or more of the added reagents that can be produced in the reaction mixture. The term "contacting" may include allowing two species to react, interact, or physically touch, wherein the two species may be a compound as described herein and a protein or enzyme. In some embodiments contacting includes allowing a compound described herein to interact with a protein or enzyme that is involved in a signaling pathway.

A "therapeutic agent" or "drug agent" as used herein refers to an agent (e.g., compound or composition) that when administered to a subject will have the intended prophylactic effect, e.g., preventing or delaying the onset (or reoccurrence) of an injury, disease, pathology or condition, or reducing the likelihood of the onset (or reoccurrence) of an injury, disease, pathology, or condition, or their symptoms or the intended therapeutic effect, e.g., treatment or amelioration of an injury, disease, pathology or condition, or their symptoms including any objective or subjective parameter of treatment such as abatement; remission; diminishing of symptoms or making the injury, pathology or condition more tolerable to the patient; slowing in the rate of degeneration or decline; making the final point of degeneration less debilitating; or improving a patient's physical or mental well-being. A drug moiety is a monovalent drug. A therapeutic moiety is a monovalent therapeutic agent.

The term "nucleophilic reaction product" as used herein is the product of the reaction between the haloalkyl amine with the nucleophilic agent (e.g., a monovalent nucleophilic agent).

The term "nucleophilic agent" is used in accordance with its plain ordinary chemical meaning and refers to a chemical group (e.g., monovalent chemical group) that is nucleophilic. A nucleophilic agent may be an ion. A nucleophilic agent may be monovalent. A nucleophilic agent may be a moiety (e.g., —OH) attached to the remainder of a compound (e.g., a compound such as methanol, wherein the remainder is —$CH_3$). A nucleophilic agent donates an electron pair to a substance (e.g., an electrophile), which results in the formation of a covalent bond between the nucleophilic agent and the electrophile. Compounds or ions with a free pair of electrons or at least one pi bond can act as a nucleophilic agent. Quantifying relative nucleophilic strength have been devised, referred to as nucleophilicity, via various methods (e.g., the Swain-Scott equation, the Ritchie equation, the Mayr-Patz equation, or the Unified equation). In embodiments, wherein multiple nucleophilic agents are present in the reaction (e.g., —OH or —SH) the nucleophilic agent that participates in the reaction (i.e. the reaction between the haloalkyl amine with the nucleophilic agent) is the stronger nucleophile as determined by one of the methods known in the art (e.g., the Swain-Scott equation, the Ritchie equation, the Mayr-Patz equation, or the Unified equation). In embodiments, the nucleophilic agent includes an enol. In embodiments, the nucleophilic agent is —OH, alcohol, alkoxide anion, hydrogen peroxide, or a carboxylate anion. In embodiments, the nucleophilic agent is hydrogen sulfide, thiols (—SH), thiolate anions, anions of thiolcarboxylic acids (—C(O)—S—), anions of dithiocarbonates (—O—C(S)—S—) or dithiocarbamates (—N—C(S)—S—). In embodiments, the nucleophilic agent is ammonia, azide, amines, nitrites, hydroxylamine, hydrazine, carbazide, phenylhydrazine, semicarbazide, or an amide. In embodiments, the nucleophilic agent includes ammonia, azide, amines, nitrites, hydroxylamine, hydrazine, carbazide, phenylhydrazine, semicarbazide, or an amide. In embodiments, the nucleophilic agent includes —OH, alcohol, alkoxide anion, hydrogen peroxide, or a carboxylate anion. In embodiments, the nucleophilic agent includes hydrogen sulfide, thiols (—SH), thiolate anions, anions of thiolcarboxylic acids (—C(O)—S—), anions of dithiocarbonates (—O—C(S)—S—) or dithiocarbamates (—N—C(S)—S—). In embodiments, the nucleophilic agent is a halo-ester.

The terms "disease" or "condition" refer to a state of being or health status of a patient or subject capable of being treated with the compounds or methods provided herein. The disease may be a cancer. The disease may be an autoimmune disease. The disease may be an inflammatory disease. The disease may be an infectious disease. In some further instances, "cancer" refers to human cancers and carcinomas, sarcomas, adenocarcinomas, lymphomas, leukemias, etc., including solid and lymphoid cancers, kidney, breast, lung, bladder, colon, ovarian, prostate, pancreas, stomach, brain, head and neck, skin, uterine, testicular, glioma, esophagus, and liver cancer, including hepatocarcinoma, lymphoma, including B-acute lymphoblastic lymphoma, non-Hodgkin's lymphomas (e.g., Burkitt's, Small Cell, and Large Cell lymphomas), Hodgkin's lymphoma, leukemia (including AML, ALL, and CML), or multiple myeloma.

The terms "lung disease," "pulmonary disease," "pulmonary disorder," etc. are used interchangeably herein. The term is used to broadly refer to lung disorders characterized by difficulty breathing, coughing, airway discomfort and inflammation, increased mucus, and/or pulmonary fibrosis. Examples of lung diseases include lung cancer, cystic fibrosis, asthma, Chronic Obstructive Pulmonary Disease (COPD), bronchitis, emphysema, bronchiectasis, pulmonary edema, pulmonary fibrosis, sarcoidosis, pulmonary hypertension, pneumonia, tuberculosis, Interstitial Pulmonary Fibrosis (IPF), Interstitial Lung Disease (ILD), Acute Interstitial Pneumonia (AIP), Respiratory Bronchiolitis-associated Interstitial Lung Disease (RBILD), Desquamative Interstitial Pneumonia (DIP), Non-Specific Interstitial Pneumonia (NSIP), Idiopathic Interstitial Pneumonia (IIP), Bronchiolitis obliterans, with Organizing Pneumonia (BOOP), restrictive lung disease, or pleurisy.

As used herein, the term "inflammatory disease" refers to a disease or condition characterized by aberrant inflammation (e.g. an increased level of inflammation compared to a control such as a healthy person not suffering from a disease). Examples of inflammatory diseases include autoimmune diseases, arthritis, rheumatoid arthritis, psoriatic arthritis, juvenile idiopathic arthritis, multiple sclerosis, systemic lupus erythematosus (SLE), myasthenia gravis, juvenile onset diabetes, diabetes mellitus type 1, graft-versus-host disease (GvHD), Guillain-Barre syndrome, Hashimoto's encephalitis, Hashimoto's thyroiditis, ankylosing spondylitis, psoriasis, Sjogren's syndrome, vasculitis, glomerulonephritis, auto-immune thyroiditis, Behcet's disease, Crohn's disease, ulcerative colitis, bullous pemphigoid, sarcoidosis, ichthyosis, Graves ophthalmopathy, inflammatory bowel disease, Addison's disease, Vitiligo, asthma, allergic asthma, acne vulgaris, celiac disease, chronic prostatitis, inflammatory bowel disease, pelvic inflammatory disease, reperfusion injury, ischemia reperfusion injury, stroke, sarcoidosis, transplant rejection, interstitial cystitis, atherosclerosis, scleroderma, and atopic dermatitis.

As used herein, the term "cancer" refers to all types of cancer, neoplasm or malignant tumors found in mammals (e.g. humans), including leukemias, lymphomas, carcinomas and sarcomas. Exemplary cancers that may be treated with a compound or method provided herein include brain cancer, glioma, glioblastoma, neuroblastoma, prostate cancer, colorectal cancer, pancreatic cancer, Medulloblastoma, melanoma, cervical cancer, gastric cancer, ovarian cancer, lung cancer, cancer of the head, Hodgkin's Disease, and Non-Hodgkin's Lymphomas. Exemplary cancers that may be treated with a compound or method provided herein include cancer of the thyroid, endocrine system, brain, breast, cervix, colon, head & neck, liver, kidney, lung, ovary, pancreas, rectum, stomach, and uterus. Additional examples include, thyroid carcinoma, cholangiocarcinoma, pancreatic adenocarcinoma, skin cutaneous melanoma, colon adenocarcinoma, rectum adenocarcinoma, stomach adenocarcinoma, esophageal carcinoma, head and neck squamous cell carcinoma, breast invasive carcinoma, lung adenocarcinoma, lung squamous cell carcinoma, non-small cell lung carcinoma, mesothelioma, multiple myeloma, neuroblastoma, glioma, glioblastoma multiforme, ovarian cancer, rhabdomyosarcoma, primary thrombocytosis, primary macroglobulinemia, primary brain tumors, malignant pancreatic insulanoma, malignant carcinoid, urinary bladder cancer, premalignant skin lesions, testicular cancer, thyroid cancer, neuroblastoma, esophageal cancer, genitourinary tract cancer, malignant hypercalcemia, endometrial cancer, adrenal cortical cancer, neoplasms of the endocrine or exocrine pancreas, medullary thyroid cancer, medullary thyroid carcinoma, melanoma, colorectal cancer, papillary thyroid cancer, hepatocellular carcinoma, or prostate cancer.

The term "leukemia" refers broadly to progressive, malignant diseases of the blood-forming organs and is generally characterized by a distorted proliferation and development of leukocytes and their precursors in the blood and bone marrow. Leukemia is generally clinically classified on the basis of (1) the duration and character of the disease-acute or chronic; (2) the type of cell involved; myeloid (myelogenous), lymphoid (lymphogenous), or monocytic; and (3) the increase or non-increase in the number abnormal cells in the blood-leukemic or aleukemic (subleukemic). Exemplary leukemias that may be treated with a compound or method provided herein include, for example, acute nonlymphocytic leukemia, chronic lymphocytic leukemia, acute granulocytic leukemia, chronic granulocytic leukemia, acute promyelocytic leukemia, adult T-cell leukemia, aleukemic leukemia, a leukocythemic leukemia, basophylic leukemia, blast cell leukemia, bovine leukemia, chronic myelocytic leukemia, leukemia cutis, embryonal leukemia, eosinophilic leukemia, Gross' leukemia, hairy-cell leukemia, hemoblastic leukemia, hemocytoblastic leukemia, histiocytic leukemia, stem cell leukemia, acute monocytic leukemia, leukopenic leukemia, lymphatic leukemia, lymphoblastic leukemia, lymphocytic leukemia, lymphogenous leukemia, lymphoid leukemia, lymphosarcoma cell leukemia, mast cell leukemia, megakaryocytic leukemia, micromyeloblastic leukemia, monocytic leukemia, myeloblastic leukemia, myelocytic leukemia, myeloid granulocytic leukemia, myelomonocytic leukemia, Naegeli leukemia, plasma cell leukemia, multiple myeloma, plasmacytic leukemia, promyelocytic leukemia, Rieder cell leukemia, Schilling's leukemia, stem cell leukemia, subleukemic leukemia, or undifferentiated cell leukemia.

As used herein, the term "lymphoma" refers to a group of cancers affecting hematopoietic and lymphoid tissues. It begins in lymphocytes, the blood cells that are found primarily in lymph nodes, spleen, thymus, and bone marrow. Two main types of lymphoma are non-Hodgkin lymphoma and Hodgkin's disease. Hodgkin's disease represents approximately 15% of all diagnosed lymphomas. This is a cancer associated with Reed-Sternberg malignant B lymphocytes. Non-Hodgkin's lymphomas (NHL) can be classified based on the rate at which cancer grows and the type of cells involved. There are aggressive (high grade) and indolent (low grade) types of NHL. Based on the type of cells involved, there are B-cell and T-cell NHLs. Exemplary B-cell lymphomas that may be treated with a compound or method provided herein include, but are not limited to, small lymphocytic lymphoma, Mantle cell lymphoma, follicular lymphoma, marginal zone lymphoma, extranodal (MALT) lymphoma, nodal (monocytoid B-cell) lymphoma, splenic lymphoma, diffuse large cell B-lymphoma, Burkitt's lymphoma, lymphoblastic lymphoma, immunoblastic large cell lymphoma, or precursor B-lymphoblastic lymphoma. Exemplary T-cell lymphomas that may be treated with a compound or method provided herein include, but are not limited to, cunateous T-cell lymphoma, peripheral T-cell lymphoma, anaplastic large cell lymphoma, mycosis fungoides, and precursor T-lymphoblastic lymphoma.

The term "sarcoma" generally refers to a tumor which is made up of a substance like the embryonic connective tissue and is generally composed of closely packed cells embedded in a fibrillar or homogeneous substance. Sarcomas that may be treated with a compound or method provided herein include a chondrosarcoma, fibrosarcoma, lymphosarcoma, melanosarcoma, myxosarcoma, osteosarcoma, Abemethy's sarcoma, adipose sarcoma, liposarcoma, alveolar soft part sarcoma, ameloblastic sarcoma, botryoid sarcoma, chloroma sarcoma, chorio carcinoma, embryonal sarcoma, Wilms' tumor sarcoma, endometrial sarcoma, stromal sarcoma, Ewing's sarcoma, fascial sarcoma, fibroblastic sarcoma, giant cell sarcoma, granulocytic sarcoma, Hodgkin's sarcoma, idiopathic multiple pigmented hemorrhagic sarcoma, immunoblastic sarcoma of B cells, lymphoma, immunoblastic sarcoma of T-cells, Jensen's sarcoma, Kaposi's sarcoma, Kupffer cell sarcoma, angiosarcoma, leukosarcoma, malignant mesenchymoma sarcoma, parosteal sarcoma, reticulocytic sarcoma, Rous sarcoma, serocystic sarcoma, synovial sarcoma, or telangiectaltic sarcoma.

The term "melanoma" is taken to mean a tumor arising from the melanocytic system of the skin and other organs. Melanomas that may be treated with a compound or method provided herein include, for example, acral-lentiginous melanoma, amelanotic melanoma, benign juvenile melanoma, Cloudman's melanoma, S91 melanoma, Harding-Passey melanoma, juvenile melanoma, lentigo maligna melanoma, malignant melanoma, nodular melanoma, subungal melanoma, or superficial spreading melanoma.

The term "carcinoma" refers to a malignant new growth made up of epithelial cells tending to infiltrate the surrounding tissues and give rise to metastases. Exemplary carcinomas that may be treated with a compound or method provided herein include, for example, medullary thyroid carcinoma, familial medullary thyroid carcinoma, acinar carcinoma, acinous carcinoma, adenocystic carcinoma, adenoid cystic carcinoma, carcinoma adenomatosum, carcinoma of adrenal cortex, alveolar carcinoma, alveolar cell carcinoma, basal cell carcinoma, carcinoma basocellulare, basaloid carcinoma, basosquamous cell carcinoma, bronchioalveolar carcinoma, bronchiolar carcinoma, bronchogenic carcinoma, cerebriform carcinoma, cholangiocellular carcinoma, chorionic carcinoma, colloid carcinoma, comedo carcinoma, corpus carcinoma, cribriform carcinoma, carcinoma en cuirasse, carcinoma cutaneum, cylindrical carcinoma, cylindrical cell carcinoma, duct carcinoma, carcinoma durum, embryonal carcinoma, encephaloid carcinoma, epiermoid carcinoma, carcinoma epitheliale adenoides, exophytic carcinoma, carcinoma ex ulcere, carcinoma fibrosum, gelatiniforni carcinoma, gelatinous carcinoma, giant cell carcinoma, carcinoma gigantocellulare, glandular carcinoma, granulosa cell carcinoma, hair-matrix carcinoma, hematoid carcinoma, hepatocellular carcinoma, Hurthle cell carcinoma, hyaline carcinoma, hypernephroid carcinoma, infantile embryonal carcinoma, carcinoma in situ, intraepidermal carcinoma, intraepithelial carcinoma, Krompecher's carcinoma, Kulchitzky-cell carcinoma, large-cell carcinoma, lenticular carcinoma, carcinoma lenticulare, lipomatous carcinoma, lymphoepithelial carcinoma, carcinoma medullare, medullary carcinoma, melanotic carcinoma, carcinoma molle, mucinous carcinoma, carcinoma muciparum, carcinoma mucocellulare, mucoepidermoid carcinoma, carcinoma mucosum, mucous carcinoma, carcinoma myxomatodes, nasopharyngeal carcinoma, oat cell carcinoma, carcinoma ossificans, osteoid carcinoma, papillary carcinoma, periportal carcinoma, preinvasive carcinoma, prickle cell carcinoma, pultaceous carcinoma, renal cell carcinoma of kidney, reserve cell carcinoma, carcinoma sarcomatodes, schneiderian carcinoma, scirrhous carcinoma, carcinoma scroti, signet-ring cell carcinoma, carcinoma simplex, small-cell carcinoma, solanoid carcinoma, spheroidal cell carcinoma, spindle cell carcinoma, carcinoma spongiosum, squamous carcinoma, squamous cell carcinoma, string carcinoma, carcinoma telangiectaticum, carcinoma telangiectodes, transitional cell carcinoma, carcinoma tuberosum, tuberous carcinoma, verrucous carcinoma, or carcinoma villosum.

As used herein, the terms "metastasis," "metastatic," and "metastatic cancer" can be used interchangeably and refer to the spread of a proliferative disease or disorder, e.g., cancer, from one organ or another non-adjacent organ or body part. "Metastatic cancer" is also called "Stage IV cancer." Cancer occurs at an originating site, e.g., breast, which site is referred to as a primary tumor, e.g., primary breast cancer. Some cancer cells in the primary tumor or originating site acquire the ability to penetrate and infiltrate surrounding normal tissue in the local area and/or the ability to penetrate the walls of the lymphatic system or vascular system circulating through the system to other sites and tissues in the body. A second clinically detectable tumor formed from cancer cells of a primary tumor is referred to as a metastatic or secondary tumor. When cancer cells metastasize, the metastatic tumor and its cells are presumed to be similar to those of the original tumor. Thus, if lung cancer metastasizes to the breast, the secondary tumor at the site of the breast consists of abnormal lung cells and not abnormal breast cells. The secondary tumor in the breast is referred to a metastatic lung cancer. Thus, the phrase metastatic cancer refers to a disease in which a subject has or had a primary tumor and has one or more secondary tumors. The phrases non-metastatic cancer or subjects with cancer that is not metastatic refers to diseases in which subjects have a primary tumor but not one or more secondary tumors. For example, metastatic lung cancer refers to a disease in a subject with or with a history of a primary lung tumor and with one or more secondary tumors at a second location or multiple locations, e.g., in the breast.

The terms "cutaneous metastasis" or "skin metastasis" refer to secondary malignant cell growths in the skin, wherein the malignant cells originate from a primary cancer site (e.g., breast). In cutaneous metastasis, cancerous cells from a primary cancer site may migrate to the skin where they divide and cause lesions. Cutaneous metastasis may result from the migration of cancer cells from breast cancer tumors to the skin.

The term "visceral metastasis" refer to secondary malignant cell growths in the interal organs (e.g., heart, lungs, liver, pancreas, intestines) or body cavities (e.g., pleura, peritoneum), wherein the malignant cells originate from a primary cancer site (e.g., head and neck, liver, breast). In visceral metastasis, cancerous cells from a primary cancer site may migrate to the internal organs where they divide and cause lesions. Visceral metastasis may result from the migration of cancer cells from liver cancer tumors or head and neck tumors to internal organs.

The terms "treating", or "treatment" refers to any indicia of success in the therapy or amelioration of an injury, disease, pathology or condition, including any objective or subjective parameter such as abatement; remission; diminishing of symptoms or making the injury, pathology or condition more tolerable to the patient; slowing in the rate of degeneration or decline; making the final point of degeneration less debilitating; improving a patient's physical or mental well-being. The treatment or amelioration of symptoms can be based on objective or subjective parameters; including the results of a physical examination, neuropsychiatric exams, and/or a psychiatric evaluation. The term "treating" and conjugations thereof, may include prevention of an injury, pathology, condition, or disease. In embodiments, treating is preventing. In embodiments, treating does not include preventing.

"Treating" or "treatment" as used herein (and as well-understood in the art) also broadly includes any approach for obtaining beneficial or desired results in a subject's condition, including clinical results. Beneficial or desired clinical results can include, but are not limited to, alleviation or amelioration of one or more symptoms or conditions, diminishment of the extent of a disease, stabilizing (i.e., not worsening) the state of disease, prevention of a disease's transmission or spread, delay or slowing of disease progression, amelioration or palliation of the disease state, diminishment of the reoccurrence of disease, and remission, whether partial or total and whether detectable or undetectable. In other words, "treatment" as used herein includes any cure, amelioration, or prevention of a disease. Treatment may prevent the disease from occurring; inhibit the disease's spread; relieve the disease's symptoms, fully or partially remove the disease's underlying cause, shorten a disease's duration, or do a combination of these things.

"Treating" and "treatment" as used herein include prophylactic treatment. Treatment methods include administering to a subject a therapeutically effective amount of an active agent. The administering step may consist of a single administration or may include a series of administrations. The length of the treatment period depends on a variety of factors, such as the severity of the condition, the age of the patient, the concentration of active agent, the activity of the compositions used in the treatment, or a combination thereof. It will also be appreciated that the effective dosage of an agent used for the treatment or prophylaxis may increase or decrease over the course of a particular treatment or prophylaxis regime. Changes in dosage may result and become apparent by standard diagnostic assays known in the art. In some instances, chronic administration may be required. For example, the compositions are administered to the subject in an amount and for a duration sufficient to treat the patient. In embodiments, the treating or treatment is no prophylactic treatment.

The term "prevent" refers to a decrease in the occurrence of disease symptoms in a patient. As indicated above, the prevention may be complete (no detectable symptoms) or partial, such that fewer symptoms are observed than would likely occur absent treatment.

"Patient" or "subject in need thereof" refers to a living organism suffering from or prone to a disease or condition that can be treated by administration of a pharmaceutical composition as provided herein. Non-limiting examples include humans, other mammals, bovines, rats, mice, dogs, monkeys, goat, sheep, cows, deer, and other non-mammalian animals. In some embodiments, a patient is human.

A "effective amount" is an amount sufficient for a compound to accomplish a stated purpose relative to the absence of the compound (e.g. achieve the effect for which it is administered, treat a disease, reduce enzyme activity, increase enzyme activity, reduce a signaling pathway, or reduce one or more symptoms of a disease or condition). An example of an "effective amount" is an amount sufficient to contribute to the treatment, prevention, or reduction of a symptom or symptoms of a disease, which could also be referred to as a "therapeutically effective amount." A "reduction" of a symptom or symptoms (and grammatical equivalents of this phrase) means decreasing of the severity or frequency of the symptom(s), or elimination of the symptom(s). A "prophylactically effective amount" of a drug is an amount of a drug that, when administered to a subject, will have the intended prophylactic effect, e.g., preventing or delaying the onset (or reoccurrence) of an injury, disease, pathology or condition, or reducing the likelihood of the onset (or reoccurrence) of an injury, disease, pathology, or condition, or their symptoms. The full prophylactic effect does not necessarily occur by administration of one dose, and may occur only after administration of a series of doses. Thus, a prophylactically effective amount may be administered in one or more administrations. An "activity decreasing amount," as used herein, refers to an amount of antagonist required to decrease the activity of an enzyme relative to the absence of the antagonist. A "function disrupting amount," as used herein, refers to the amount of antagonist required to disrupt the function of an enzyme or protein relative to the absence of the antagonist. The exact amounts will depend on the purpose of the treatment, and will be ascertainable by one skilled in the art using known techniques (see, e.g., Lieberman, *Pharmaceutical Dosage Forms* (vols. 1-3, 1992); Lloyd, *The Art, Science and Technology of Pharmaceutical Compounding* (1999); Pickar, *Dosage Calculations* (1999); and *Remington: The Science and Practice of Pharmacy,* 20th Edition, 2003, Gennaro, Ed., Lippincott, Williams & Wilkins).

For any compound described herein, the therapeutically effective amount can be initially determined from cell culture assays. Target concentrations will be those concentrations of active compound(s) that are capable of achieving the methods described herein, as measured using the methods described herein or known in the art.

As is well known in the art, therapeutically effective amounts for use in humans can also be determined from animal models. For example, a dose for humans can be formulated to achieve a concentration that has been found to be effective in animals. The dosage in humans can be adjusted by monitoring compounds effectiveness and adjusting the dosage upwards or downwards, as described above. Adjusting the dose to achieve maximal efficacy in humans based on the methods described above and other methods is well within the capabilities of the ordinarily skilled artisan.

The term "therapeutically effective amount," as used herein, refers to that amount of the therapeutic agent sufficient to ameliorate the disorder, as described above. For example, for the given parameter, a therapeutically effective amount will show an increase or decrease of at least 5%, 10%, 15%, 20%, 25%, 40% 50%, 60%, 75%, 80%, 90%, or at least 100%. Therapeutic efficacy can also be expressed as "-fold" increase or decrease. For example, a therapeutically effective amount can have at least a 1.2-fold, 1.5-fold, 2-fold, 5-fold, or more effect over a control.

Dosages may be varied depending upon the requirements of the patient and the compound being employed. The dose administered to a patient, in the context of the present disclosure, should be sufficient to effect a beneficial therapeutic response in the patient over time. The size of the dose also will be determined by the existence, nature, and extent of any adverse side-effects. Determination of the proper dosage for a particular situation is within the skill of the practitioner. Generally, treatment is initiated with smaller dosages which are less than the optimum dose of the compound. Thereafter, the dosage is increased by small increments until the optimum effect under circumstances is reached. Dosage amounts and intervals can be adjusted individually to provide levels of the administered compound effective for the particular clinical indication being treated. This will provide a therapeutic regimen that is commensurate with the severity of the individual's disease state.

As used herein, the term "administering" means oral administration, administration as a suppository, topical contact, intravenous, parenteral, intraperitoneal, intramuscular, intralesional, intrathecal, intranasal or subcutaneous administration, or the implantation of a slow-release device, e.g., a mini-osmotic pump, to a subject. Administration is by any route, including parenteral and transmucosal (e.g., buccal, sublingual, palatal, gingival, nasal, vaginal, rectal, or transdermal). Parenteral administration includes, e.g., intravenous, intramuscular, intra-arteriole, intradermal, subcutaneous, intraperitoneal, intraventricular, and intracranial. Other modes of delivery include, but are not limited to, the use of liposomal formulations, intravenous infusion, transdermal patches, etc. In embodiments, the administering does not include administration of any active agent other than the recited active agent.

"Co-administer" it is meant that a composition described herein is administered at the same time, just prior to, or just after the administration of one or more additional therapies. The compounds provided herein can be administered alone or can be coadministered to the patient. Coadministration is meant to include simultaneous or sequential administration of the compounds individually or in combination (more than one compound). Thus, the preparations can also be combined, when desired, with other active substances (e.g. to reduce metabolic degradation). The compositions of the present disclosure can be delivered transdermally, by a topical route, or formulated as applicator sticks, solutions, suspensions, emulsions, gels, creams, ointments, pastes, jellies, paints, powders, and aerosols.

Cancer model organism, as used herein, is an organism exhibiting a phenotype indicative of cancer, or the activity of cancer causing elements, within the organism. The term cancer is defined above. A wide variety of organisms may serve as cancer model organisms, and include for example, cancer cells and mammalian organisms such as rodents (e.g. mouse or rat) and primates (such as humans). Cancer cell lines are widely understood by those skilled in the art as cells exhibiting phenotypes or genotypes similar to in vivo cancers. Cancer cell lines as used herein includes cell lines from animals (e.g. mice) and from humans.

The term "pharmaceutically acceptable salts" is meant to include salts of the active compounds that are prepared with relatively nontoxic acids or bases, depending on the particular substituents found on the compounds described herein. When compounds of the present disclosure contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present disclosure contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, oxalic, methanesulfonic, and the like. Also included are salts of amino acids such as arginate and the like, and salts of organic acids like glucuronic or galactunoric acids and the like (see, for example, Berge et al., "Pharmaceutical Salts", *Journal of Pharmaceutical Science,* 1977, 66, 1-19). Certain specific compounds of the present disclosure contain both basic and acidic functionalities that allow the compounds to be converted into either base or acid addition salts.

Thus, the compounds of the present disclosure may exist as salts, such as with pharmaceutically acceptable acids. The present disclosure includes such salts. Non-limiting examples of such salts include hydrochlorides, hydrobromides, phosphates, sulfates, methanesulfonates, nitrates, maleates, acetates, citrates, fumarates, proprionates, tartrates (e.g., (+)-tartrates, (−)-tartrates, or mixtures thereof including racemic mixtures), succinates, benzoates, and salts with amino acids such as glutamic acid, and quaternary ammonium salts (e.g. methyl iodide, ethyl iodide, and the like). These salts may be prepared by methods known to those skilled in the art.

The neutral forms of the compounds are preferably regenerated by contacting the salt with a base or acid and isolating the parent compound in the conventional manner. The parent form of the compound may differ from the various salt forms in certain physical properties, such as solubility in polar solvents.

In addition to salt forms, the present disclosure provides compounds, which are in a prodrug form. Prodrugs of the compounds described herein are those compounds that readily undergo chemical changes under physiological conditions to provide the compounds of the present disclosure. Prodrugs of the compounds described herein may be converted in vivo after administration. Additionally, prodrugs can be converted to the compounds of the present disclosure by chemical or biochemical methods in an ex vivo environment, such as, for example, when contacted with a suitable enzyme or chemical reagent.

Certain compounds of the present disclosure can exist in unsolvated forms as well as solvated forms, including hydrated forms. In general, the solvated forms are equivalent to unsolvated forms and are encompassed within the scope of the present disclosure. Certain compounds of the present disclosure may exist in multiple crystalline or amorphous forms. In general, all physical forms are equivalent for the uses contemplated by the present disclosure and are intended to be within the scope of the present disclosure.

"Pharmaceutically acceptable excipient" and "pharmaceutically acceptable carrier" refer to a substance that aids the administration of an active agent to and absorption by a subject and can be included in the compositions of the present disclosure without causing a significant adverse toxicological effect on the patient. Non-limiting examples of pharmaceutically acceptable excipients include water, NaCl, normal saline solutions, lactated Ringer's, normal sucrose, normal glucose, binders, fillers, disintegrants, lubricants, coatings, sweeteners, flavors, salt solutions (such as Ringer's solution), alcohols, oils, gelatins, carbohydrates such as lactose, amylose or starch, fatty acid esters, hydroxymethycellulose, polyvinyl pyrrolidine, and colors, and the like. Such preparations can be sterilized and, if desired, mixed with auxiliary agents such as lubricants, preservatives, stabilizers, wetting agents, emulsifiers, salts for influencing osmotic pressure, buffers, coloring, and/or aromatic substances and the like that do not deleteriously react with the compounds of the disclosure. One of skill in the art will recognize that other pharmaceutical excipients are useful in the present disclosure.

The term "preparation" is intended to include the formulation of the active compound with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

As used herein, the term "about" means a range of values including the specified value, which a person of ordinary skill in the art would consider reasonably similar to the specified value. In embodiments, about means within a standard deviation using measurements generally acceptable in the art. In embodiments, about means a range extending to +/−10% of the specified value. In embodiments, about includes the specified value.

II. Compounds

In an aspect is provided a compound having the formula:

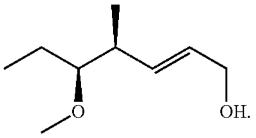

In embodiments, the compound is at least 99% enantiomerically pure. In embodiments, the compound is at least 98% enantiomerically pure. In embodiments, the compound is at least 97% enantiomerically pure. In embodiments, the compound is at least 96% enantiomerically pure. In embodiments, the compound is at least 95% enantiomerically pure. In embodiments, the compound is at least 94% enantiomerically pure. In embodiments, the compound is at least 93% enantiomerically pure. In embodiments, the compound is at least 92% enantiomerically pure. In embodiments, the compound is at least 91% enantiomerically pure. In embodiments, the compound is at least 90% enantiomerically pure.

In an aspect is provided a compound having the formula:

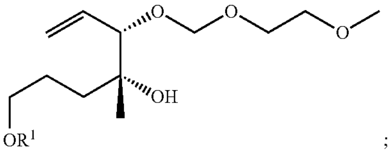

;

$R^1$ is a silyl protecting group. In embodiments, the compound is at least 99% enantiomerically pure. In embodiments, the compound is at least 98% enantiomerically pure. In embodiments, the compound is at least 97% enantiomerically pure. In embodiments, the compound is at least 96% enantiomerically pure. In embodiments, the compound is at least 95% enantiomerically pure. In embodiments, the compound is at least 94% enantiomerically pure. In embodiments, the compound is at least 93% enantiomerically pure. In embodiments, the compound is at least 92% enantiomerically pure. In embodiments, the compound is at least 91% enantiomerically pure. In embodiments, the compound is at least 90% enantiomerically pure. In embodiments, $R^1$ is trimethylsilyl (TMS). In embodiments, $R^1$ is triethylsilyl (TES). In embodiments, $R^1$ is tert-butyl dimethylsilyl (TBS/TBDMS). In embodiments, $R^1$ is tert-butyldiphenylsilyl (TBDPS). In embodiments, $R^1$ is triisopropylsilyl (TIPS).

In embodiments, is provided a compound having the formula:

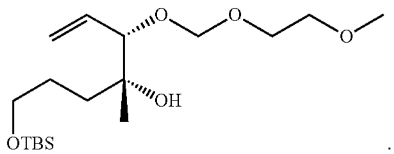 [SMILES: C=C[C@H](OCOCCOC)[C@](C)(O)CCCO[Si](C)(C)C(C)(C)C]

In embodiments, the compound is at least 99% enantiomerically pure. In embodiments, the compound is at least 98% enantiomerically pure. In embodiments, the compound is at least 97% enantiomerically pure. In embodiments, the compound is at least 96% enantiomerically pure. In embodiments, the compound is at least 95% enantiomerically pure. In embodiments, the compound is at least 94% enantiomerically pure. In embodiments, the compound is at least 93% enantiomerically pure. In embodiments, the compound is at least 92% enantiomerically pure. In embodiments, the compound is at least 91% enantiomerically pure. In embodiments, the compound is at least 90% enantiomerically pure.

In an aspect is provided a compound having the formula:

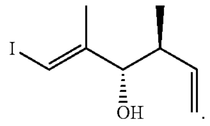

In embodiments, the compound is at least 99% enantiomerically pure. In embodiments, the compound is at least 98% enantiomerically pure. In embodiments, the compound is at least 97% enantiomerically pure. In embodiments, the compound is at least 96% enantiomerically pure. In embodiments, the compound is at least 95% enantiomerically pure. In embodiments, the compound is at least 94% enantiomerically pure. In embodiments, the compound is at least 93% enantiomerically pure. In embodiments, the compound is at least 92% enantiomerically pure. In embodiments, the compound is at least 910% enantiomerically pure. In embodiments, the compound is at least 90% enantiomerically pure.

In an aspect is provided a compound having the formula:

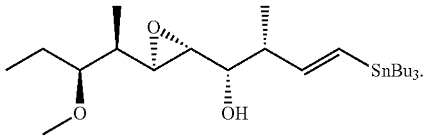

In embodiments, the compound is at least 99% enantiomerically pure. In embodiments, the compound is at least 98% enantiomerically pure. In embodiments, the compound is at least 97% enantiomerically pure. In embodiments, the compound is at least 96% enantiomerically pure. In embodiments, the compound is at least 95% enantiomerically pure. In embodiments, the compound is at least 94% enantiomerically pure. In embodiments, the compound is at least 93% enantiomerically pure. In embodiments, the compound is at least 92% enantiomerically pure. In embodiments, the compound is at least 91% enantiomerically pure. In embodiments, the compound is at least 90% enantiomerically pure.

In an aspect is provided a compound having the formula:

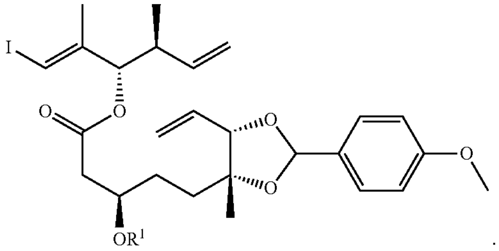

.

$R^1$ is a silyl protecting group. In embodiments, the compound is at least 99% enantiomerically pure. In embodiments, the compound is at least 98% enantiomerically pure. In embodiments, the compound is at least 97% enantiomerically pure. In embodiments, the compound is at least 96% enantiomerically pure. In embodiments, the compound is at least 95% enantiomerically pure. In embodiments, the compound is at least 94% enantiomerically pure. In embodiments, the compound is at least 93% enantiomerically pure. In embodiments, the compound is at least 92% enantiomerically pure. In embodiments, the compound is at least 91% enantiomerically pure. In embodiments, the compound is at least 90% enantiomerically pure. In embodiments, $R^1$ is trimethylsilyl (TMS). In embodiments, $R^1$ is triethylsilyl (TES). In embodiments, $R^1$ is tert-butyl dimethylsilyl (TBS/TBDMS). In embodiments, $R^1$ is tert-butyldiphenylsilyl (TBDPS). In embodiments, $R^1$ is triisopropylsilyl (TIPS).

In embodiments, is provided a compound having the formula:

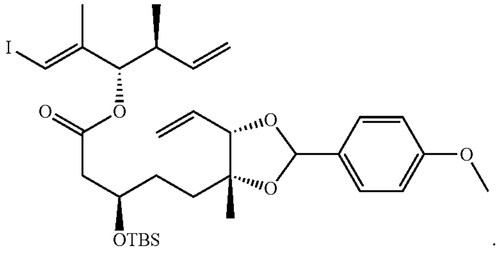

.

In embodiments, the compound is at least 99% enantiomerically pure. In embodiments, the compound is at least 98% enantiomerically pure. In embodiments, the compound is at least 97% enantiomerically pure. In embodiments, the compound is at least 96% enantiomerically pure. In embodiments, the compound is at least 95% enantiomerically pure. In embodiments, the compound is at least 94% enantiomerically pure. In embodiments, the compound is at least 93% enantiomerically pure. In embodiments, the compound is at least 92% enantiomerically pure. In embodiments, the compound is at least 91% enantiomerically pure. In embodiments, the compound is at least 90% enantiomerically pure.

In an aspect is provided a compound having the formula:

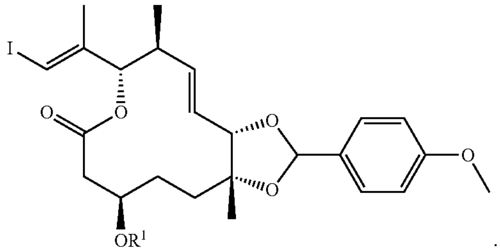

.

In embodiments, $R^1$ is a silyl protecting group and wherein the compound is at least 99% enantiomerically pure. In embodiments, the compound is at least 98% enantiomerically pure. In embodiments, the compound is at least 97% enantiomerically pure. In embodiments, the compound is at least 96% enantiomerically pure. In embodiments, the compound is at least 95% enantiomerically pure. In embodiments, the compound is at least 94% enantiomerically pure. In embodiments, the compound is at least 93% enantiomerically pure. In embodiments, the compound is at least 92% enantiomerically pure. In embodiments, the compound is at least 910% enantiomerically pure. In embodiments, the compound is at least 90% enantiomerically pure. In embodiments, $R^1$ is trimethylsilyl (TMS). In embodiments, $R^1$ is triethylsilyl (TES). In embodiments, $R^1$ is tert-butyl dimethylsilyl (TBS/TBDMS). In embodiments, $R^1$ is tert-butyldiphenylsilyl (TBDPS). In embodiments, $R^1$ is triisopropylsilyl (TIPS).

In embodiments, is provided a compound having the formula:

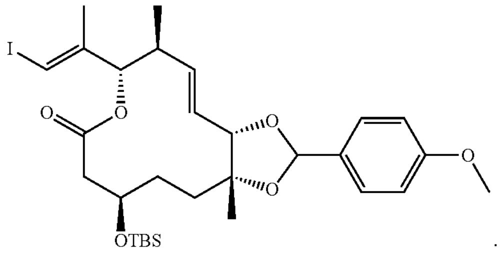

.

In embodiments, the compound is at least 99% enantiomerically pure. In embodiments, the compound is at least 98% enantiomerically pure. In embodiments, the compound is at least 97% enantiomerically pure. In embodiments, the compound is at least 96% enantiomerically pure. In embodiments, the compound is at least 95% enantiomerically pure. In embodiments, the compound is at least 94% enantiomerically pure. In embodiments, the compound is at least 93% enantiomerically pure. In embodiments, the compound is at least 92% enantiomerically pure. In embodiments, the compound is at least 91% enantiomerically pure. In embodiments, the compound is at least 90% enantiomerically pure.

In an aspect is provided a compound having the formula:

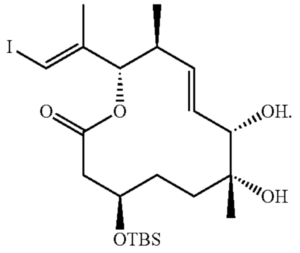

In embodiments, the compound is at least 99% enantiomerically pure. In embodiments, the compound is at least 98% enantiomerically pure. In embodiments, the compound is at least 97% enantiomerically pure. In embodiments, the compound is at least 96% enantiomerically pure. In embodiments, the compound is at least 95% enantiomerically pure. In embodiments, the compound is at least 94% enantiomerically pure. In embodiments, the compound is at least 93% enantiomerically pure. In embodiments, the compound is at least 92% enantiomerically pure. In embodiments, the compound is at least 91% enantiomerically pure. In embodiments, the compound is at least 90% enantiomerically pure.

In an aspect is provided a compound having the formula:

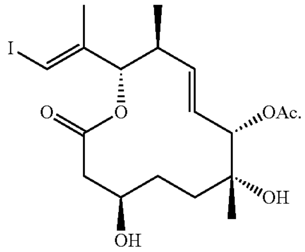 [SMILES: CC(=O)O[C@H]1/C=C/[C@H](C)[C@@H](/C(C)=C/I)OC(=O)C[C@H](O)CC[C@@]1(C)O]

In embodiments, the compound is at least 99% enantiomerically pure. In embodiments, the compound is at least 98% enantiomerically pure. In embodiments, the compound is at least 97% enantiomerically pure. In embodiments, the compound is at least 96% enantiomerically pure. In embodiments, the compound is at least 95% enantiomerically pure. In embodiments, the compound is at least 94% enantiomerically pure. In embodiments, the compound is at least 93% enantiomerically pure. In embodiments, the compound is at least 92% enantiomerically pure. In embodiments, the compound is at least 910% enantiomerically pure. In embodiments, the compound is at least 90% enantiomerically pure.

In an aspect is provided a compound having the formula:

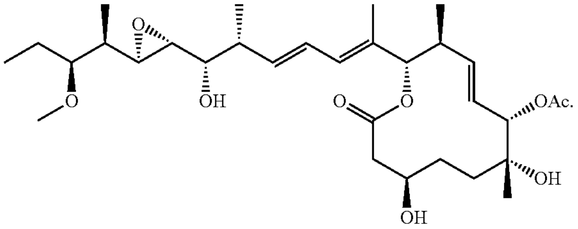 [SMILES: CC[C@H](OC)[C@@H](C)[C@H]1O[C@@H]1[C@@H](O)[C@H](C)/C=C/C=C(\C)[C@H]1OC(=O)C[C@H](O)CC[C@@](C)(O)[C@@H](OC(C)=O)/C=C/[C@@H]1C]

In embodiments, the compound is at least 99% enantiomerically pure. In embodiments, the compound is at least 98% enantiomerically pure. In embodiments, the compound is at least 97% enantiomerically pure. In embodiments, the compound is at least 96% enantiomerically pure. In embodiments, the compound is at least 95% enantiomerically pure. In embodiments, the compound is at least 94% enantiomerically pure. In embodiments, the compound is at least 93% enantiomerically pure. In embodiments, the compound is at least 92% enantiomerically pure. In embodiments, the compound is at least 91% enantiomerically pure. In embodiments, the compound is at least 90% enantiomerically pure.

In embodiments, the compound as described herein, includes at least 5 grams of the compound with or without a pharmaceutically available excipient. In embodiments, the compound is

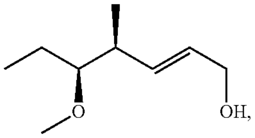

,

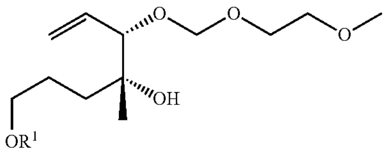

,

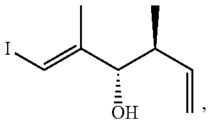

,

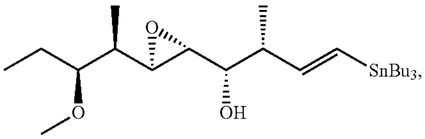

,

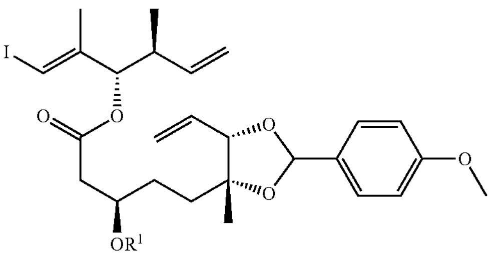

,

-continued
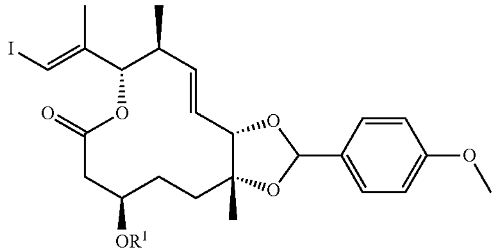
,
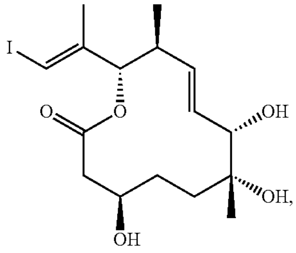
,
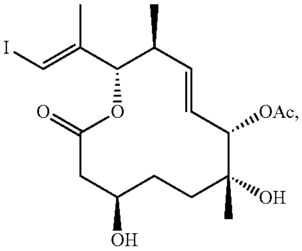
or
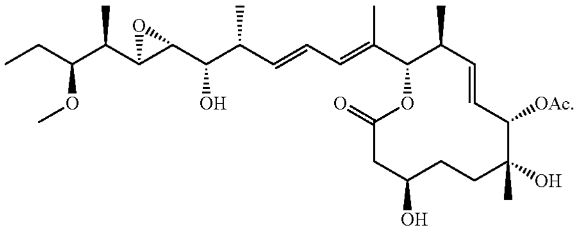
$R^1$ is a silyl protecting group. In embodiments, the compound is
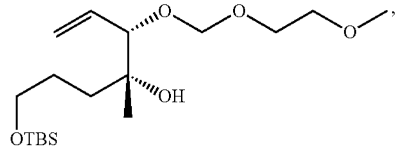
,
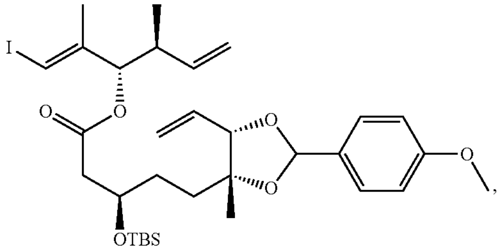
, or
-continued
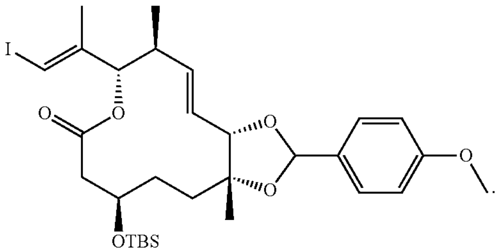
In embodiments, the compound is
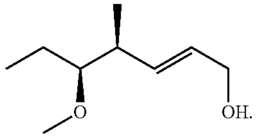
In embodiments, the compound is
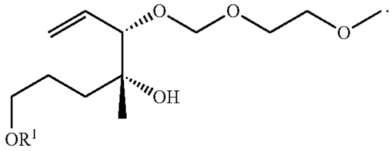
In embodiments, the compound is
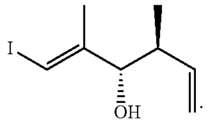
In embodiments, the compound is
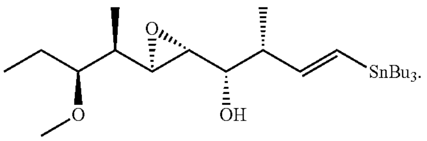
In embodiments, the compound is
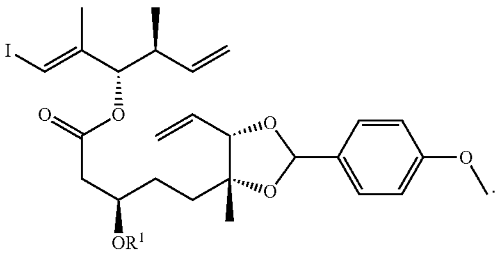

In embodiments, the compound is

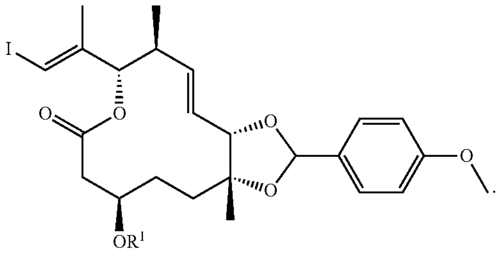

In embodiments, the compound is

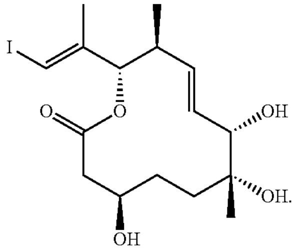 [SMILES: C/C(=C\I)[C@H]1OC(=O)C[C@H](O)CC[C@@](C)(O)[C@@H](O)/C=C/[C@@H]1C]

In embodiments, the compound is

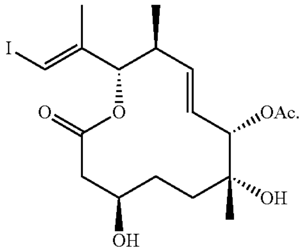 [SMILES: CC(=O)O[C@H]1/C=C/[C@H](C)[C@@H](/C(C)=C/I)OC(=O)C[C@H](O)CC[C@@]1(C)O]

In embodiments, the compound is

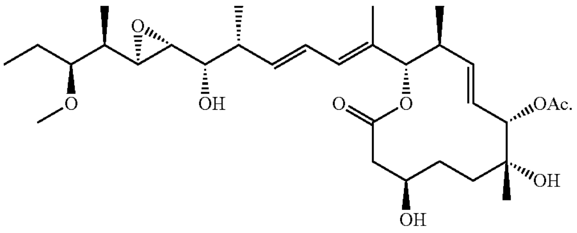 [SMILES: CC[C@H](OC)[C@@H](C)[C@H]1O[C@@H]1[C@@H](O)[C@H](C)/C=C/C=C(\C)[C@H]1OC(=O)C[C@H](O)CC[C@@](C)(O)[C@@H](OC(C)=O)/C=C/[C@@H]1C]

In embodiments, the compound is

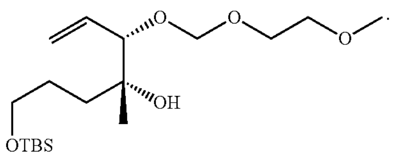 [SMILES: C=C[C@H](OCOCCOC)[C@](C)(O)CCCO[Si](C)(C)C(C)(C)C]

In embodiments, the compound is

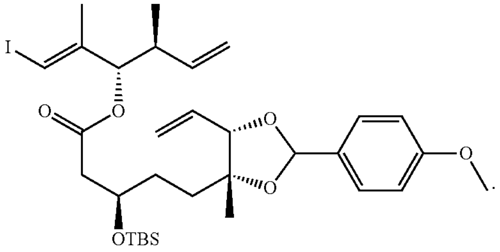

In embodiments, the compound is

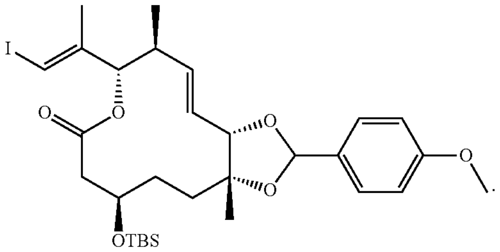

In embodiments, the compound includes at least 10 grams of the compound with or without a pharmaceutically available excipient. In embodiments, the compound includes at least 25 grams of the compound with or without a pharmaceutically available excipient. In embodiments, the compound includes at least 50 grams of the compound with or without a pharmaceutically available excipient. In embodiments, the compound includes at least 100 grams of the compound with or without a pharmaceutically available excipient. In embodiments, the compound includes at least 250 grams of the compound with or without a pharmaceutically available excipient. In embodiments, the compound includes at least 500 grams of the compound with or without a pharmaceutically available excipient. In embodiments, the compound includes at least 1000 grams of the compound with or without a pharmaceutically available excipient. In embodiments, the compound includes at least 2000 grams of the compound with or without a pharmaceutically available excipient. In embodiments, the compound includes at least 3000 grams of the compound with or without a pharmaceutically available excipient. In embodiments, the compound includes at least 4000 grams of the compound with or without a pharmaceutically available excipient. In embodiments, the compound includes at least 5000 grams of the compound with or without a pharmaceutically available excipient. In embodiments, the compound includes at least 10,000 grams of the compound with or without a pharmaceutically available excipient.

III. Pharmaceutical Compositions

In an aspect is provided a pharmaceutical composition including a compound having the formula:

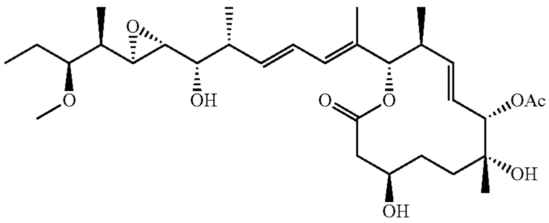 [SMILES: CC[C@H](OC)[C@@H](C)[C@H]1O[C@@H]1[C@@H](O)[C@H](C)/C=C/C=C(\C)[C@H]1OC(=O)C[C@H](O)CC[C@@](C)(O)[C@@H](OC(C)=O)/C=C/[C@@H]1C]

and a pharmaceutically acceptable excipient. In embodiments, the compound is at least 99% enantiomerically pure. In embodiments, the compound is at least 98% enantiomerically pure. In embodiments, the compound is at least 97% enantiomerically pure. In embodiments, the compound is at least 96% enantiomerically pure. In embodiments, the compound is at least 95% enantiomerically pure. In embodiments, the compound is at least 94% enantiomerically pure. In embodiments, the compound is at least 93% enantiomerically pure. In embodiments, the compound is at least 92% enantiomerically pure. In embodiments, the compound is at least 91% enantiomerically pure. In embodiments, the compound is at least 90% enantiomerically pure.

In embodiments, the pharmaceutically acceptable excipient is Kolliphor HS15, Kolliphor EL, Cremaphor RH40, Kolliphor P188, or Kolliphor P407. In embodiments, the pharmaceutically acceptable excipient is Kolliphor HS15. In embodiments, the pharmaceutically acceptable excipient is Kolliphor EL. In embodiments, the pharmaceutically acceptable excipient is Cremaphor RH40, Kolliphor P188. In embodiments, the pharmaceutically acceptable excipient is Kolliphor P407.

IV. Methods of Making Compounds

In an aspect is provided a method of making a compound having the formula:

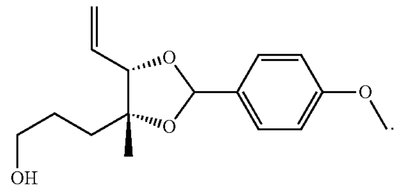

The method includes reacting a compound having the formula:

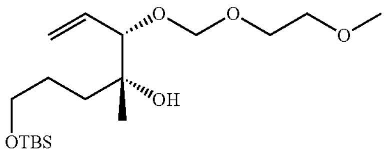 [SMILES: C=C[C@H](OCOCCOC)[C@](C)(O)CCCO[Si](C)(C)C(C)(C)C]

with 1-(dimethoxymethyl)-4-methoxybenzene in the presence of $CBr_4$, an alcohol, a base, and one or more organic solvents. In embodiments, the method includes reacting a compound having the formula:

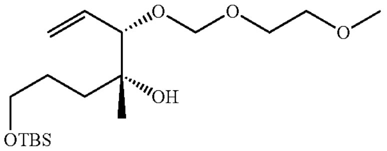 [SMILES: C=C[C@H](OCOCCOC)[C@](C)(O)CCCO[Si](C)(C)C(C)(C)C]

with 1-(dimethoxymethyl)-4-methoxybenzene in the presence of $CBr_4$, isopropanol, imidazole, and dichloromethane.

In embodiments, the alcohol is methanol, ethanol, or isopropanol. In embodiments, the alcohol is methanol. In embodiments, the alcohol is ethanol. In embodiments, the alcohol is isopropanol. In embodiments, the base is imidazole. In embodiments, the organic solvent is dichloromethane or chloroform. In embodiments, the organic solvent is dichloromethane. In embodiments, the organic solvent is chloroform.

In an aspect is provided a method of making a compound having the formula:

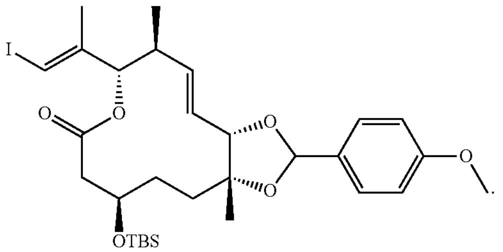

The method includes reacting a compound having the formula:

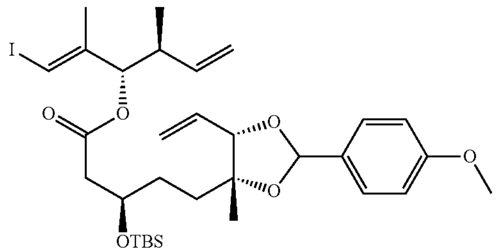

with a transition metal catalyst for olefin metathesis in the presence of one or more organic solvents. In embodiments, the method includes reacting a compound having the formula:

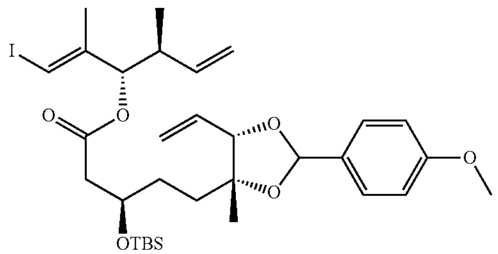

with Hoveyda-Grubbs $2^{nd}$ generation catalyst in the presence of toluene. In embodiments, the method includes reacting a compound having the formula:

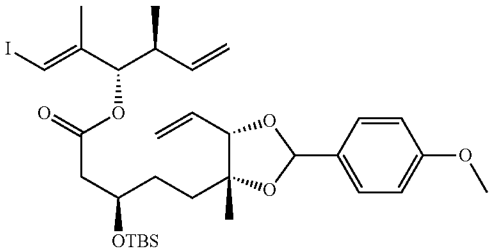

with Hoveyda-Grubbs $2^{nd}$ generation catalyst in the presence of toluene at 120° C.

In embodiments, the transition metal catalyst is a ruthenium-based catalyst. In embodiments, the transition metal catalyst is a Grubbs catalyst. In embodiments, the transition metal catalyst is a Hoveyda-Grubbs catalyst.

In embodiments, the transition metal catalyst is Grubbs $1^{st}$ generation catalyst, Grubbs $2^{nd}$ generation catalyst, Grubbs $3^{rd}$ generation catalyst, Hoveyda-Grubbs $1^{st}$ generation catalyst, Hoveyda-Grubbs $2^{nd}$ generation catalyst, NitroGrela, dichloro[1,3-Bis(2-methylphenyl)-2-imidazolidinylidene](benzylidene)(tricyclohexylphosphine)ruthenium(II) [Grubbs Catalyst® M2a SI(o-Tol) (C793)], dichloro[1,3-bis(2,4,6-trimethylphenyl)-2-imidazolidinylidene](3-methyl-2-butenylidene) (tricyclohexylphosphine)ruthenium(II) [Grubbs Catalyst® M2b (C827)], dichloro[1,3-bis(2-methylphenyl)-2-imidazolidinylidene](2-isopropoxyphenylmethylene)ruthenium(II) [Hoveyda-Grubbs Catalyst® M72 SI(o-Tol) (C571) or Stewart-Grubbs catalyst], or dichloro[1,3-bis(2,4,6-trimethylphenyl)-2-imidazolidinylidene][3-(2-pyridinyl) propylidene]ruthenium(II) (Grubbs Catalyst® C598). In embodiments, the transition metal catalyst is Grubbs $1^{st}$ generation catalyst, Grubbs $2^{nd}$ generation catalyst, Hoveyda-Grubbs $1^{st}$ generation catalyst, Hoveyda-Grubbs $2^{nd}$ generation catalyst, or NitroGrela.

In embodiments, the transition metal catalyst is Grubbs $1^{st}$ generation catalyst. In embodiments, the transition metal catalyst is Grubbs $2^{nd}$ generation catalyst. In embodiments, the transition metal catalyst is Grubbs $3^{rd}$ generation catalyst. In embodiments, the transition metal catalyst is Hoveyda-Grubbs $1^{st}$ generation catalyst. In embodiments, the transition metal catalyst is Hoveyda-Grubbs $2^{nd}$ generation catalyst. In embodiments, the transition metal catalyst is NitroGrela. In embodiments, the transition metal catalyst is dichloro[1,3-Bis(2-methylphenyl)-2-imidazolidinylidene](benzylidene)(tricyclohexylphosphine)ruthenium(II) [Grubbs Catalyst® M2a SI(o-Tol) (C793)]. In embodiments, the transition metal catalyst is dichloro[1,3-bis(2,4,6-trimethylphenyl)-2-imidazolidinylidene](3-methyl-2-butenylidene) (tricyclohexylphosphine)ruthenium(II) [Grubbs Catalyst® M2b (C827)]. In embodiments, the transition metal catalyst is dichloro[1,3-bis(2-methylphenyl)-2-imidazolidinylidene](2-isopropoxyphenylmethylene)ruthenium(II) [Hoveyda-Grubbs Catalyst® M72 SI(o-Tol) (C571) or Stewart-Grubbs catalyst]. In embodiments, the transition metal catalyst is dichloro[1,3-bis(2,4,6-trimethylphenyl)-2-imidazolidinylidene][3-(2-pyridinyl) propylidene]ruthenium(II) (Grubbs Catalyst® C598).

In embodiments, the organic solvent is toluene.

In an aspect is provided a method of making a compound having the formula:

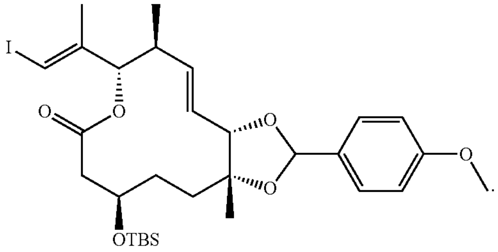

The method includes reacting a compound having the formula:

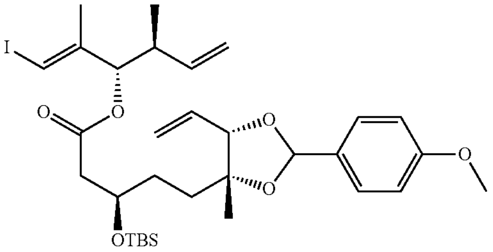

with Hoveyda-Grubbs $2^{nd}$ generation catalyst in the presence of toluene.

In an aspect is provided a method of making a compound having the formula:

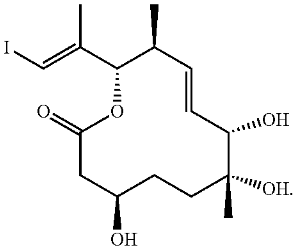 [SMILES: C/C(=C\I)[C@H]1OC(=O)C[C@H](O)CC[C@@](C)(O)[C@@H](O)/C=C/[C@@H]1C]

The method includes reacting a compound having the formula:

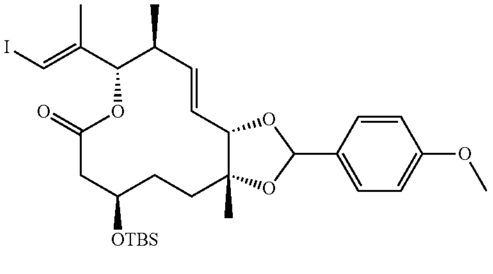

with a strong acid, in the presence of an alcohol and one or more organic solvents. In embodiments, the method includes reacting a compound having the formula:

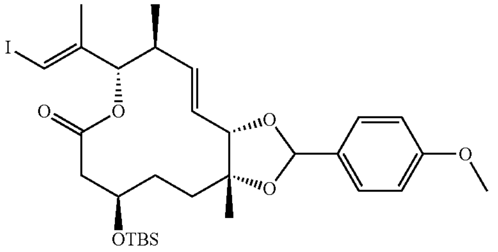

with camphorsulfonic acid, in the presence of methanol and dichloromethane. In embodiments, the strong acid is camphorsulfonic acid, pyridinium p-toluenesulfonate, or p-toluenesulfonic acid. In embodiments, the strong acid is camphorsulfonic acid. In embodiments, the strong acid is pyridinium p-toluenesulfonate. In embodiments, the strong acid is p-toluenesulfonic acid. In embodiments, the organic solvent is dichloromethane or chloroform. In embodiments, the strong acid is camphorsulfonic acid and the solvent is dichloromethane.

In an aspect is provided a method of making a compound having the formula:

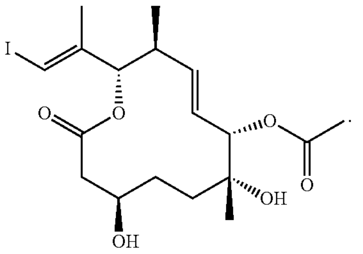 [SMILES: CC(=O)O[C@H]1/C=C/[C@H](C)[C@@H](/C(C)=C/I)OC(=O)C[C@H](O)CC[C@@]1(C)O]

The method includes reacting a compound having the formula:

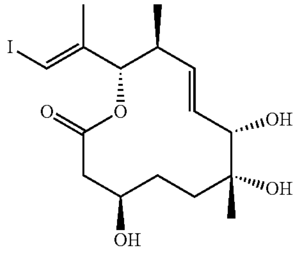 [SMILES: C/C(=C\I)[C@H]1OC(=O)C[C@H](O)CC[C@@](C)(O)[C@@H](O)/C=C/[C@@H]1C]

with an acetylating agent in the presence of a strong acid and one or more organic solvents. The method includes reacting a compound having the formula:

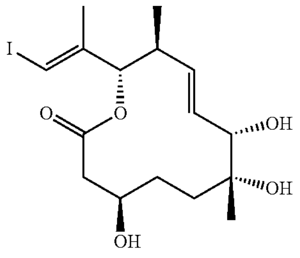 [SMILES: C/C(=C\I)[C@H]1OC(=O)C[C@H](O)CC[C@@](C)(O)[C@@H](O)/C=C/[C@@H]1C]

with 1,1,1-trimethoxyethane in the presence of camphorsulfonic acid and dichloromethane. In embodiments, the acetylating agent is acetic anhydride or 1,1,1-trimethoxyethane. In embodiments, the acetylating agent is acetic anhydride. In embodiments, the acetylating agent is 1,1,1-trimethoxyethane. In embodiments, the strong acid is camphorsulfonic acid, pyridinium p-toluenesulfonate, or p-toluenesulfonic acid. In embodiments, the strong acid is camphorsulfonic acid. In embodiments, the strong acid is pyridinium p-toluenesulfonate. In embodiments, the strong acid is p-toluenesulfonic acid. In embodiments, the organic solvent is dichloromethane or chloroform.

In embodiments, is provided a method of making a compound having the formula:

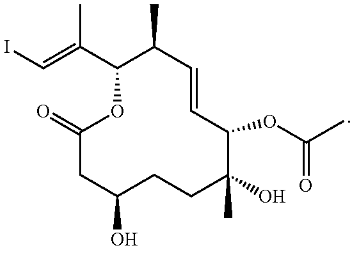 [SMILES: CC(=O)O[C@H]1/C=C/[C@H](C)[C@@H](/C(C)=C/I)OC(=O)C[C@H](O)CC[C@@]1(C)O]

In embodiments, the method includes reacting a compound having the formula:

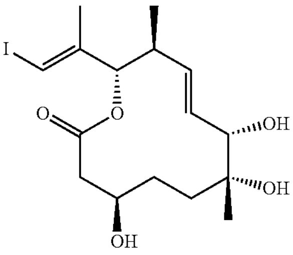 [SMILES: C/C(=C\I)[C@H]1OC(=O)C[C@H](O)CC[C@@](C)(O)[C@@H](O)/C=C/[C@@H]1C]

with acetic anhydride, in the presence of 4-dimethylaminopyridine and pyridine. In embodiments, is provided a method of making a compound having the formula:

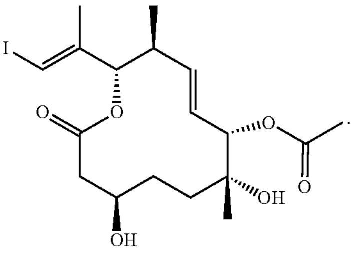 [SMILES: CC(=O)O[C@H]1/C=C/[C@H](C)[C@@H](/C(C)=C/I)OC(=O)C[C@H](O)CC[C@@]1(C)O]

In embodiments, the method includes reacting a compound having the formula:

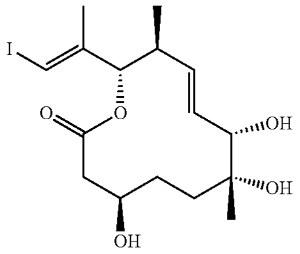 [SMILES: C/C(=C\I)[C@H]1OC(=O)C[C@H](O)CC[C@@](C)(O)[C@@H](O)/C=C/[C@@H]1C]

with acetic anhydride, in the presence of acetylimidazole, 4-dimethylaminopyridine and tetrahydrofuran. In embodiments, is provided a method of making a compound having the formula:

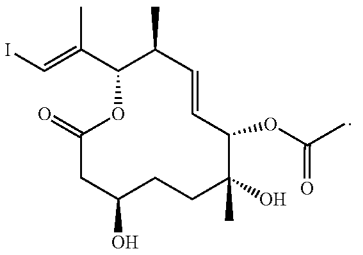 [SMILES: CC(=O)O[C@H]1/C=C/[C@H](C)[C@@H](/C(C)=C/I)OC(=O)C[C@H](O)CC[C@@]1(C)O]

In embodiments, the method includes reacting a compound having the formula:

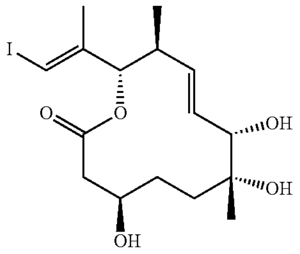 [SMILES: C/C(=C\I)[C@H]1OC(=O)C[C@H](O)CC[C@@](C)(O)[C@@H](O)/C=C/[C@@H]1C]

with acetylchloride, in the presence of triethylamine and dichloromethane at reduced temperature. In embodiments, is provided a method of making a compound having the formula:

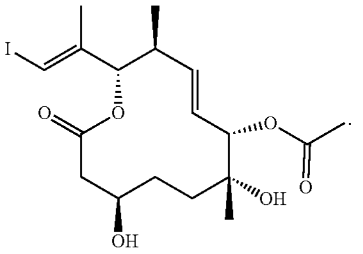 [SMILES: CC(=O)O[C@H]1/C=C/[C@H](C)[C@@H](/C(C)=C/I)OC(=O)C[C@H](O)CC[C@@]1(C)O]

In embodiments, the method includes reacting a compound having the formula:

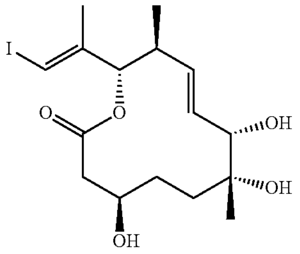 [SMILES: C/C(=C\I)[C@H]1OC(=O)C[C@H](O)CC[C@@](C)(O)[C@@H](O)/C=C/[C@@H]1C]

with S-methylthioacetate in the presence of dichloromethane.

In an aspect is provided a method of making a linear polyketide compound.

In embodiments, the polyketide compound is a splice modulator.

In embodiments, the polyketide compound is 17S-FD-895.

In an aspect is provided a method of making a 17S-FD-895, the method including the use of compounds 6a, 6b, 6c, 6d and 6e, as described herein.

V. Methods of Treatment

In an aspect is provided a method of treating cancer, the method including administering to a subject in need thereof an effective amount of the polyketide compound made using the method as described herein.

In embodiments, the cancer is a blood cancer

VI. Embodiments

Embodiment P1. A method of making a linear polyketide compound.

Embodiment P2. The method of embodiment P1, wherein the polyketide compound is a splice modulator.

Embodiment P3. The method of embodiment P1, wherein the polyketide compound is 17S-FD-895.

Embodiment P4. A method of treating cancer, said method comprising administering to a subject in need thereof an effective amount of the polyketide compound made using the method of any one of embodiments P1 to P3.

Embodiment P5. The method of embodiment P4, wherein the cancer is a blood cancer.

Embodiment P6. A method of making 17S-FD-895, said method comprising the use of compounds 6a, 6b, 6c, 6d and 6e, as shown in Scheme 1.

VII. Additional Embodiments

Embodiment 1. A compound having the formula:

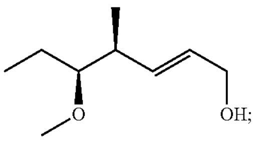

wherein, the compound is at least 95% enantiomerically pure.

Embodiment 2. The compound of embodiment 1, wherein, the compound is at least 98% enantiomerically pure.

Embodiment 3. A compound having the formula:

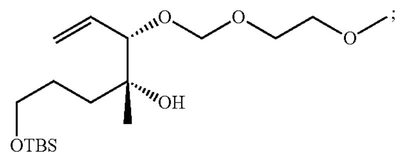

wherein, the compound is at least 95% enantiomerically pure.

Embodiment 4. The compound of embodiment 3, wherein, the compound is at least 98% enantiomerically pure.

Embodiment 5. A compound having the formula:

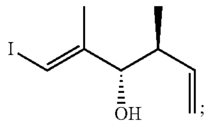

wherein, the compound is at least 95% enantiomerically pure.

Embodiment 6. The compound of embodiment 5, wherein, the compound is at least 98% enantiomerically pure.

Embodiment 7. A compound having the formula:

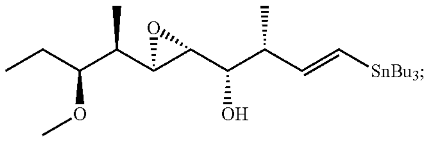

wherein, the compound is at least 95% enantiomerically pure.

Embodiment 8. The compound of embodiment 7, wherein, the compound is at least 98% enantiomerically pure.

Embodiment 9. A compound having the formula:

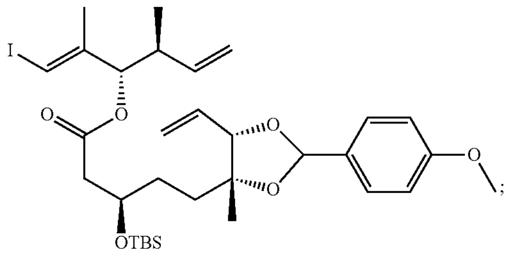

wherein, the compound is at least 95% enantiomerically pure.

Embodiment 10. The compound of embodiment 9, wherein, the compound is at least 98% enantiomerically pure.

Embodiment 11. A compound having the formula:

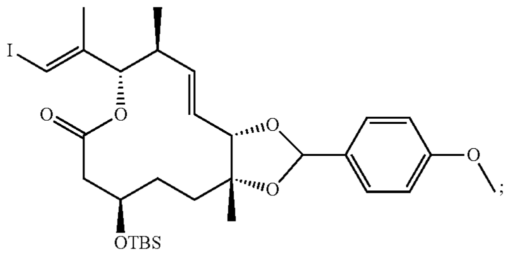

wherein, the compound is at least 95% enantiomerically pure.

Embodiment 12. The compound of embodiment 11, wherein, the compound is at least 98% enantiomerically pure.

Embodiment 13. A compound having the formula:

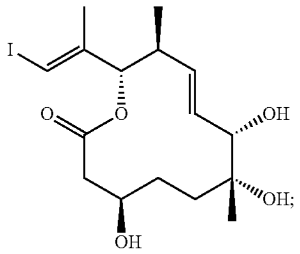

wherein, the compound is at least 95% enantiomerically pure.

Embodiment 14. The compound of embodiment 13, wherein, the compound is at least 98% enantiomerically pure.

Embodiment 15. A compound having the formula:

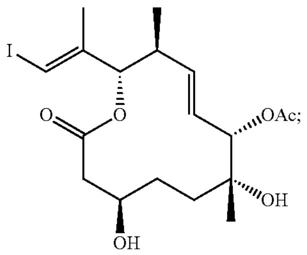

wherein, the compound is at least 95% enantiomerically pure.

Embodiment 16. The compound of embodiment 15, wherein, the compound is at least 98% enantiomerically pure.

Embodiment 17. A compound having the formula:

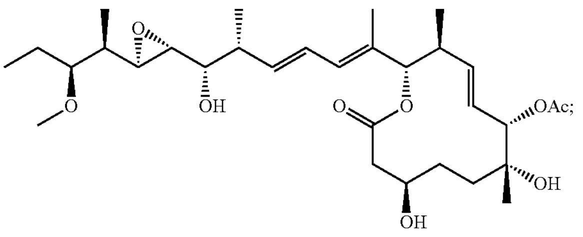

wherein, the compound is at least 95% enantiomerically pure.

Embodiment 18. The compound of embodiment 17, wherein, the compound is at least 98% enantiomerically pure.

Embodiment 19. The compound of embodiments 1 to 18, comprising at least 5 grams of the compound with or without a pharmaceutically available excipient.

Embodiment 20. A pharmaceutical composition comprising a compound having the formula:

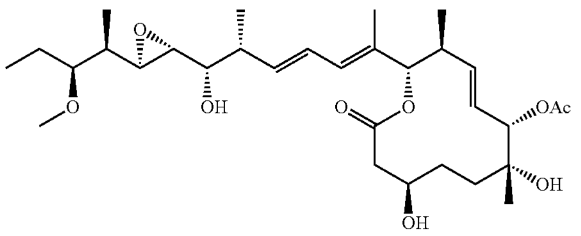

and a pharmaceutically acceptable excipient, wherein the compound is at least 95% enantiomerically pure.

Embodiment 21. The pharmaceutical composition of embodiment 20, wherein, the compound is at least 98% enantiomerically pure.

Embodiment 22. A method of making a compound having the formula:

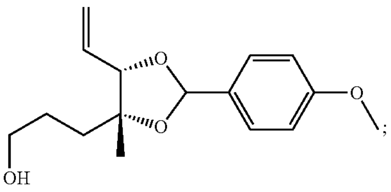

comprising reacting a compound having the formula:

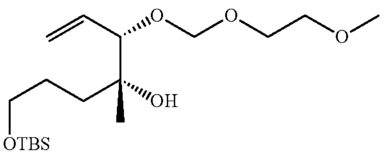 [SMILES: C=C[C@H](OCOCCOC)[C@](C)(O)CCCO[Si](C)(C)C(C)(C)C]

with 1-(dimethoxymethyl)-4-methoxybenzene in the presence of $CBr_4$, an alcohol, a base, and one or more organic solvents.

Embodiment 23. The method of embodiment 22, wherein the alcohol is methanol, ethanol, or isopropanol.

Embodiment 24. The method of embodiment 22, wherein the alcohol is isopropanol.

Embodiment 25. The method of embodiment 22, wherein the base is imidazole.

Embodiment 26. The method of embodiment 22, wherein the organic solvent is dichloromethane or chloroform.

Embodiment 27. A method of making a compound having the formula:

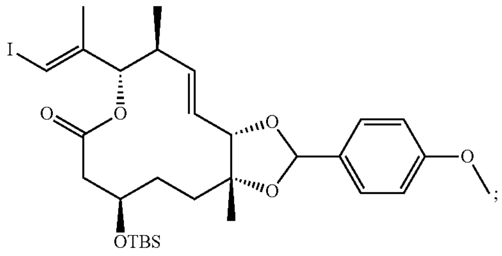

comprising reacting a compound having the formula:

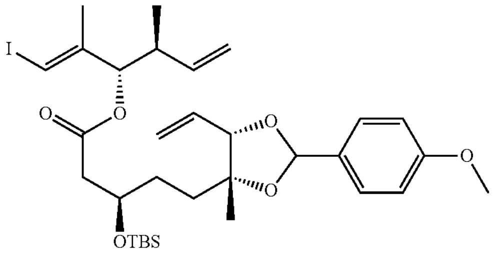

with a transition metal catalyst for olefin metathesis in the presence of one or more organic solvents.

Embodiment 28. The method of embodiment 27, wherein the transition metal catalyst is a ruthenium based catalyst.

Embodiment 29. The method of embodiment 27, wherein the transition metal catalyst is Grubbs $1^{st}$ generation catalyst, Grubbs $2^{nd}$ generation catalyst, Hoveyda-Grubbs $1^{st}$ generation catalyst, Hoveyda-Grubbs $2^{nd}$ generation catalyst, or NitroGrela.

Embodiment 30. The method of embodiment 27, wherein the transition metal catalyst is Hoveyda-Grubbs $2^{nd}$ generation catalyst.

Embodiment 31. The method of embodiment 27, wherein the organic solvent is toluene.

Embodiment 32. A method of making a compound having the formula:

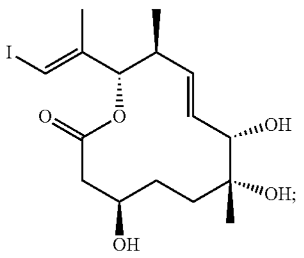 [SMILES: C/C(=C\I)[C@H]1OC(=O)C[C@H](O)CC[C@@](C)(O)[C@@H](O)/C=C/[C@@H]1C]

comprising reacting a compound having the formula:

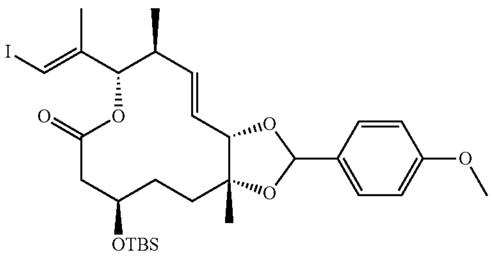

with a strong acid, in the presence of an alcohol and one or more organic solvents.

Embodiment 33. The method of embodiment 32, wherein the strong acid is camphorsulfonic acid.

Embodiment 34. The method of embodiment 32, wherein the organic solvent is dichloromethane or chloroform.

Embodiment 35. A method of making a compound having the formula:

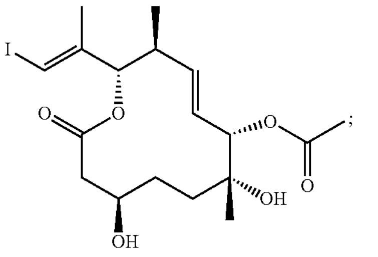 [SMILES: CC(=O)O[C@H]1/C=C/[C@H](C)[C@@H](/C(C)=C/I)OC(=O)C[C@H](O)CC[C@@]1(C)O]

comprising reacting a compound having the formula:

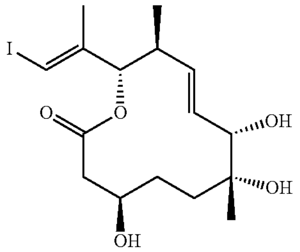 [SMILES: C/C(=C\I)[C@H]1OC(=O)C[C@H](O)CC[C@@](C)(O)[C@@H](O)/C=C/[C@@H]1C]

with an acetylating agent in the presence of a strong acid and one or more organic solvents.

Embodiment 36. The method of embodiment 35, wherein the acetylating agent is acetic anhydride or 1,1,1-trimethoxyethane.

Embodiment 37. The method of embodiment 35, wherein the strong acid is camphorsulfonic acid.

Embodiment 38. The method of embodiment 37, wherein the organic solvent is dichloromethane or chloroform.

EXAMPLES

Example 1. Initial Synthetic Effort

The compound numbers used in Examples 1 and 2 correspond to the compounds described in these examples, as well as the compounds described in FIG. 1, FIGS. 2A-2F, Scheme 1, Schemes S1-S6, and the embodiments.

A practical 14-step assembly process has been developed that enables a cost-effective gram scale production of the potent splice modulator 17S-FD-895, an accomplishment that installs 11 stereocenters, a 12-membered macrolide and complex and dense linear polyketide tail.

Since their first discovery in the mid-1990s, mode of action (MOA) studies a decade later revealed that families of polyketides including FD-895, pladienolides, spliceostatins, herboxadienes, GEX1, FR901464, and the thailanstatins share similar ability to modulate splicing through interactions within the SF3b component of the spliceosome. First suggested as a consensus motif, and later validated by structural biological analyses, these small molecules uniquely position themselves at an interface between SF3B1, PHF5A, and SF3B3. Here, the importance and positioning of the stereochemical centers within these molecules, clearly indicate a unique geometric requirement for functional binding.

While many of the natural products, congeners, and semi-synthetic analogs display the necessary spatial display of functionality to enable facile binding to the SF3B pocket, and hence present potent splice modulation, the high density of their functional groups lends to reduced material stability. Remarkably, many of these natural products are met with very stability in aqueous media with half-lives often less than 30 minutes. Recent studies now indicate that synthetic modifications at C16-C17 are not only tolerated but access a three-dimensional arrangement that profoundly reduce the rate of degradation yet meet the requirements for active binding to the ascribed pocket in SF3B, ultimately leading to the identification of 17S-FD-895 as a potential therapeutic lead.

The level of this problem is in part evident by the first clinical trial on a splicing modulator, E7107. While developed through a remarkable level of diligence and optimization, instability in part was a reason for concern over the results from the first clinical trials on this new class of agent. Advancing on the issues observed with E7107, a subsequent program resulted in the entry of H3B-8800 into Phase 1 clinical trials to evaluate the safety, pharmacokinetics and pharmacodynamics of H3B-8800 for subjects with myelodysplastic syndromes, acute myeloid leukemia (AML), and chronic myelomonocytic leukemia. While access to E7107 and H3B-8800 was achieved synthetically, the ultimate pre-clinical and clinical deliveries arose through semi-synthetic preparations, due in part to the complexities associated with translating the many milligram scaled routes published to date to a gram scaled process. To date, gram scale synthetic approaches have failed to be realized to enable access to all but simpler herboxadiene family. Here, we describe the development of a practical gram scale route to 17S-FD-895 (1) that employs a highly convergent route enabling the preparation of potentially superior derivatives for clinical application.

Developing on a rich forum of synthetic effort, the synthetic challenges of delivering a multi-gram preparation of a molecule that contained 31 carbons of which 11 and 6 occupied respective $sp^3$ and $sp^2$ stereochemistry. Remarkably, only 5 carbons lacked a stereochemical requirement and were functionalized within the entire molecule. On top of this high density of functionality, the molecule contains a 12-membered lactone ring, one of a small class of polyketides including the mycolactones, and other polyketides that display this rare ring size.

Our approach developed from multiple synthetic campaigns that identified the importance in component assembly, and operated through three-faceted strategy. As shown in FIG. 1, the first-facet, component preparation, began by establishing practical methods to synthesize hectogram quantities of six components 6a-6e. Here, the goal of these studies was to engage the efficient preparation of 6a-6e from cost effectively with the overall yield and material accessed tabulated in FIG. 1. With these materials at hand, our focus shifted towards an assembly. Here, the goal was to reach a method that enabled the preparation of grams of 1 from the five components in less than one month.

Furthermore, we targeted a design that delivered bioactive materials only at the last step. As these compounds demonstrate very potent biological activity and the early clinical trials indicate a very low MTD in humans, we opted for a route that had a two faceted assembly beginning with the preparation of two biologically-inactive fragments, as given by core 2 (FIG. 1) and side chain 3 (FIG. 1), followed by a final coupling to afford 17S-FD-895 (1). Supported by structural studies, the lack of the link between the side chain and core should ablate the binding to SF3B, a finding, which was confirmed by activity analyses on the side chain or core intermediates, all of which failed to demonstrate splice modulator activity.

With a safe and convergent approach identified (FIG. 1), we turned our attention towards the assembly of core 2. Our route (Scheme 1) began by developing a method to convert 6a into alcohol 7. After screening a wide array of acidic conditions, we adapted a protocol that was described previously that generated HBr in situ by a slow reaction with iPrOH. While our initial intent was to isolate the corresponding triol (FIG. 2A), the lack of stability of this material, encouraged the development of in situ methods to trap this material as a 5:1 mixture of $\alpha$:$\beta$ acetal isomers 7, (straight line in 7, Scheme 1). After a logical series of reaction optimization steps, we identified an overnight one-pot conversion of 6a to 7 that operated at decagram scale with a single chromatographic purification. As noted, this process involved three operations, removal of the MEM and TBS ethers followed by selective protection of the C6-C7 diol as its PMP acetal.

Figure 2A:
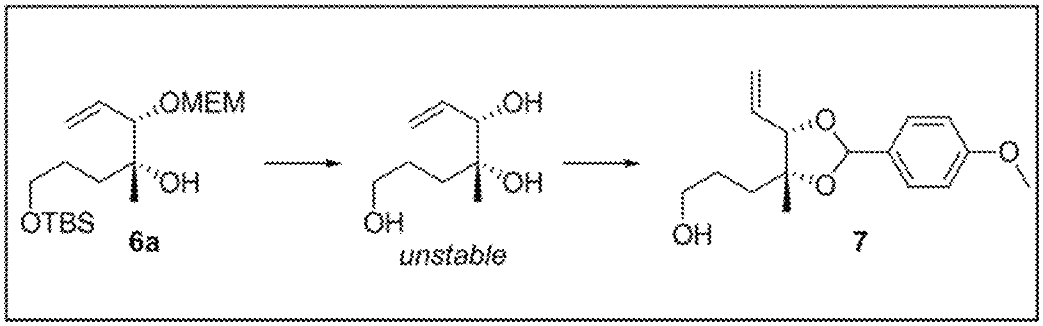
FIGS. 2A-2F. Synthetic issues. A tabulation of the top issues identified and remediated in the development of a gram-scaled synthesis of 1.
Figure 2B:
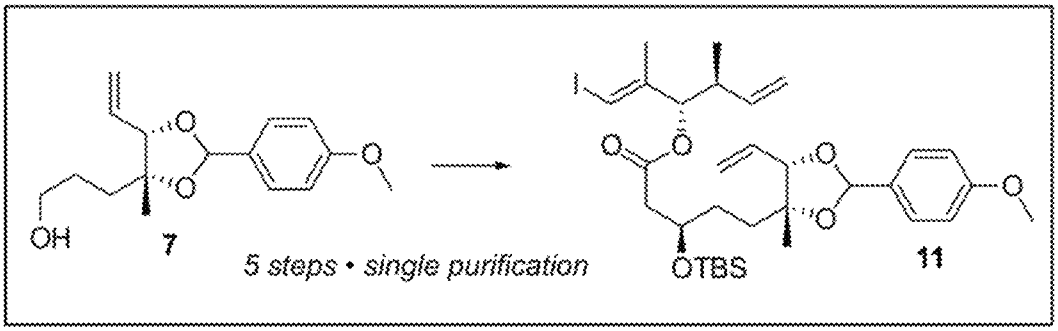
Figure 2C:
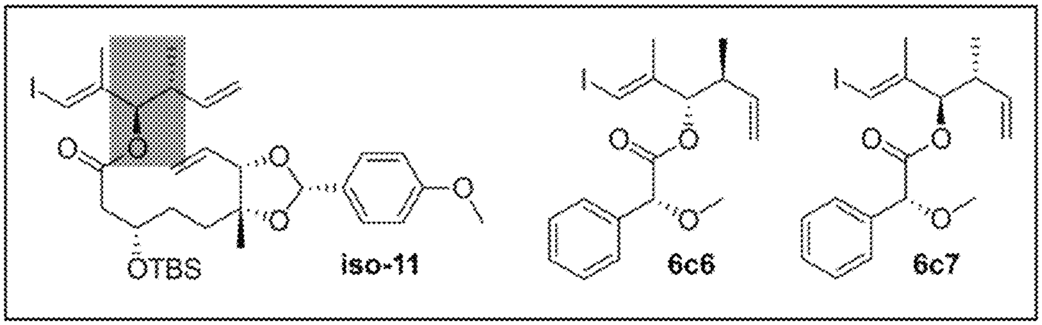
Figure 2D:
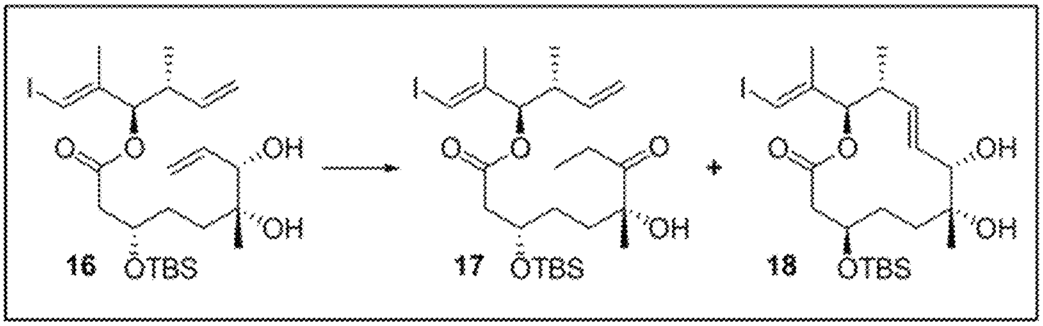
Figure 2E:
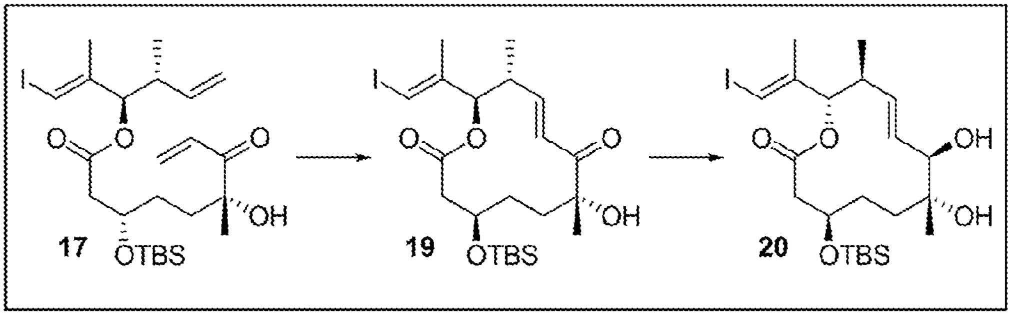
Figure 2F:
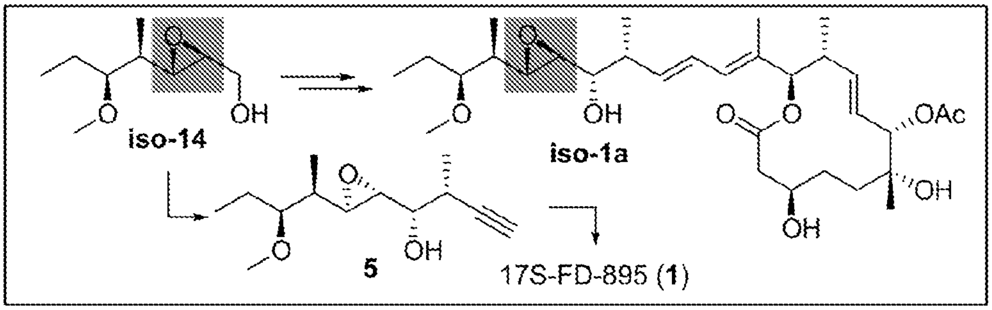
Figure 3A:
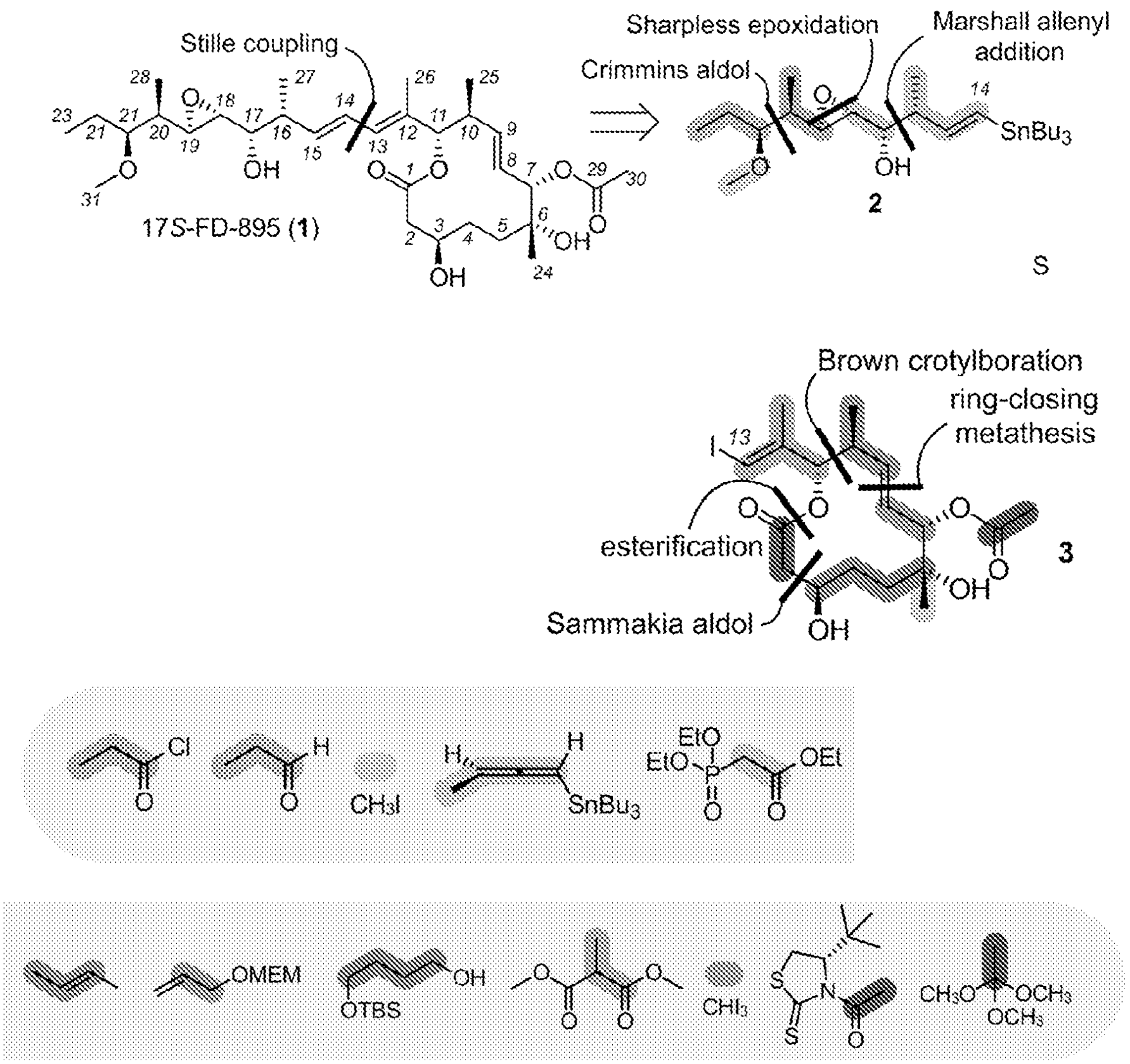
FIGS. 3A-3B. Synthetic design.
Figure 3B:
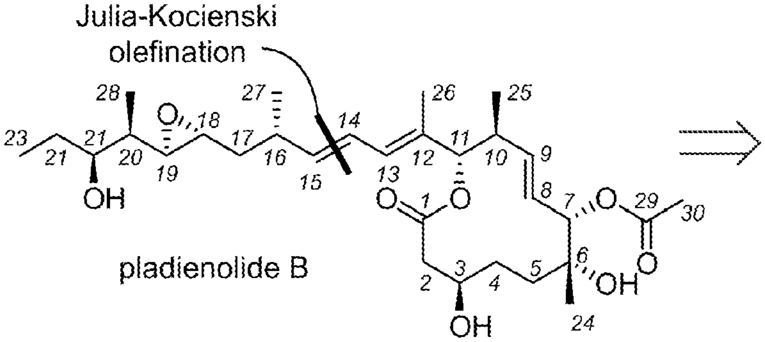
Figure 3B:
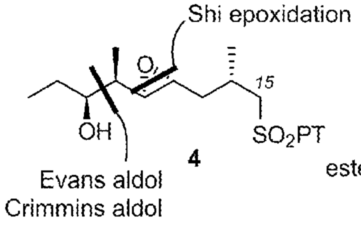
Figure 3B:
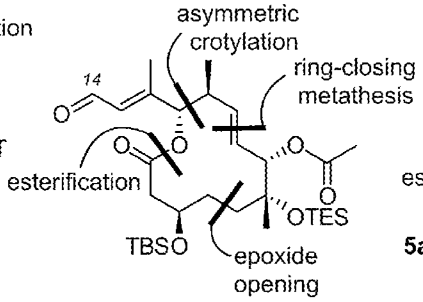
Figure 3B:
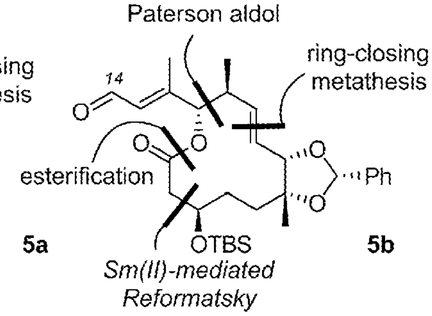

With this transformation secured, our next goal was to develop methods that would facilitate the transformation of 7 to 11. Through detailed evaluation of each step, we were able to identify a process that allowed the five-step conversion of 7 to 11 (Scheme 1) to be conducted in a 48 h process (FIG. 2B). This began by oxidation of alcohol 7 to aldehyde 8, which was readily accomplished using DMSO as a solvent. The resulting aldehyde, was then subjected to acetyl-Crimmins addition using (−)-sparteine as a chiral additive (34). TBS protection followed by mild hydrolysis provided acid 4, which was obtained in high yield and purity after a rapid Dry Column Vacuum Chromatography (DCVC). Advantageously, this method allowed us to successfully recycle the auxiliary 6b1 (see Supporting Information) as well as (−)-sparteine. Overall, we were able to readily carry decagrams of 7 to 4 on a weekly basis.

The next step esterification of 4 with 6c to deliver 7 proved challenging to optimize. While there are many viable conditions for esterification many of these methods resulted in b-elimination of the TBS group at C3 in 4, unwanted opening of the PMP acetal at C6-C7 in 4 as well as dehydration of the alcohol in 6c. After considerable screening, we found that treatment of an equimolar amount of 4 and 6c with 10 mol % of DMAP neat in pivalic anhydride at 70° C. afforded a near quantitative yield of 11, which could be used without purification. While effective, we soon realize that NMR studies on 11, already a mixture of two materials due to them mixture of acetal isomers, suggested the presence of four compounds. Careful analyses revealed that the scaled preparation of 6c delivered a material. If not careful at this stage, the incorporation of this material into the synthetic route would lead to samples of 1 contaminated with 5-10% of the wrong stereochemistry at C10-C11, an observation made in early runs through this route. In response, we developed a method to remove the potential for formation of iso-11 (FIG. 2C) resolving with (S)-mandelic acid. As detailed in the Supporting Information, methods were developed to rapidly prepare 6c6 and 6c7 from lots of 6c, chromatographically purify 6c6 and hydrolyze to deliver enantiopure 6c.

At this point, we were able to access decagram quantities of 11 in about 5-6 days from 6a. Here, removal of the PMP ester followed by the ring closing metathesis of 16 (FIG. 2D) provide direct relay to 2. Unfortunately, this process was not replicable due to the unwanted competing ruthenium-catalyzed isomerization of the allylic alcohol in 16 to a ketone in 17. Although 18 could be accessed, it yield deviated between an unpredictable 25±15%. One solution arose through the oxidation of 16 to 17, accomplished quantitatively using IBX. Here removal of the potential for isomerization by oxidation at C7 provided an efficient RCM to enone 19. Unfortunately, reaction screening efforts using a variety of reducing agents, methods for chiral reduction could not deliver more than 3:1 mixture favoring the undesired 20 over 18. Examination of an X-ray crystal structure of 19 explained this result as the addition of hydride to deliver the desired 18 required a trajectory that would arise from within the macrolide ring. With these options exhausted, we turned our attention back to 11, and conducted a full screen of catalysts (13 tried), temperatures, rates of addition, and found that inverse addition (catalyst to 11) provided an effective means to deliver 11 with minimal by-product formation. Here, we were able to consistently deliver product using a slow addition of the Hoveyda-Grubbs II catalyst to 11 in refluxing toluene, a remarkably simple solution to a decade long issues in the syntheses of these and related 12-membered macrolides.

At this stage, we were now able to transit decagrams of 6a to afford 12 (Scheme 1), a process that required 8 days to complete. At this point, screening efforts enabled us to identify a two-step process that involved global deprotection to stable triol 13 by mild acid hydrolysis followed by acetylation by treatment of 2 with trimethylorthoacetate under acid catalysis from CSA. While flash chromatography was required for each of the last three steps (11 to 12, 12 to 13 and 13 to 2), optimal methods were established that minimized the effort required for efforts at preparative gram scales. To date, we have used this method to prepare core 2. Stability studies on 2 indicate that it was stable over six months at ambient conditions.

The preparation of the side chain 3 was most efficiently conducted in bulk by converting 6d to alkyne 5, a superior point for purification and storage. This began by conducting a Sharpless-epoxidation of 6d followed by oxidation of the corresponding alcohol 14 with IBX in DMSO, a two-step process that can be conducted without flash purification. Alkyne 15 was then prepared at 20 g scale from 6e and 15. While stable for storage at 0° C. under argon, allenyl stannane was optimally prepared by distillation and used within 2-3 months of preparation. Here, the use of methods developed by Marshall provide high selectivity in the installation of the C16-C17 centers, affording a single isomeric 5 from 6d. This process was conducted within 4 days of effort. Like component 2, alkyne 15 was also stable over six months at ambient conditions.

At this stage, we were set for the final coupling. Alkyne 5 was converted to Z-stannane 3 by hydrostannylation using $PdCl_2(PPh_3)$. The yield of this process was further optimized through use of the Figueroa catalyst. Stannane 3 was then purified by flash chromatography and directly subjected to Stille coupling using the Buchwald optimized XPhos G2 (38) catalyst with CuCl, KF in anhydrous tBuOH. Given potent biological activity 1 and potential toxic risk, we conducted this process on small scale with the guideline of handling no more than a gram. Through careful evaluation, we were able to complete this step with a minimal exposure time (2-4 h) through the tandem use of DCVC and Flash chromatography to afford 1. We were able to recover 2 from this process which could be recycled in the conversion of 2 to 1. Unfortunately, this process destroyed the side chain 3, a loss that was limiting as 2 was the limiting reagent within this process.

In our hands, each run through this process can be completed in 16-day period delivering gram quantities of 1.

To date, we applied this route to prepare 1 from 6a (the farthest linear precursor). We have successfully translated a gram scale synthesis of 17S-FD-895 using a process that engages components at a hectagram scale and couples them at a decagram scale using a 14-step, 2-route assembly. We have successfully been able to complete this entire process with two process chemists over three months with eight weeks dedicated to component preparation and four for assembly, a feat that suggests that 5 g of 1 can be prepared at a cost that can be markedly decreased with future pilot efforts.

To further demonstrate the streamlined features of this route, we examine the preparation of analogs of 17S-FD-895 derived from the unwanted, yet collectable, isomeric by-products in this route. We were able to prepare three untested analogs. This effort was readily completed and sets the stage to complete a full SAR study on this class of material.

Scheme 1.
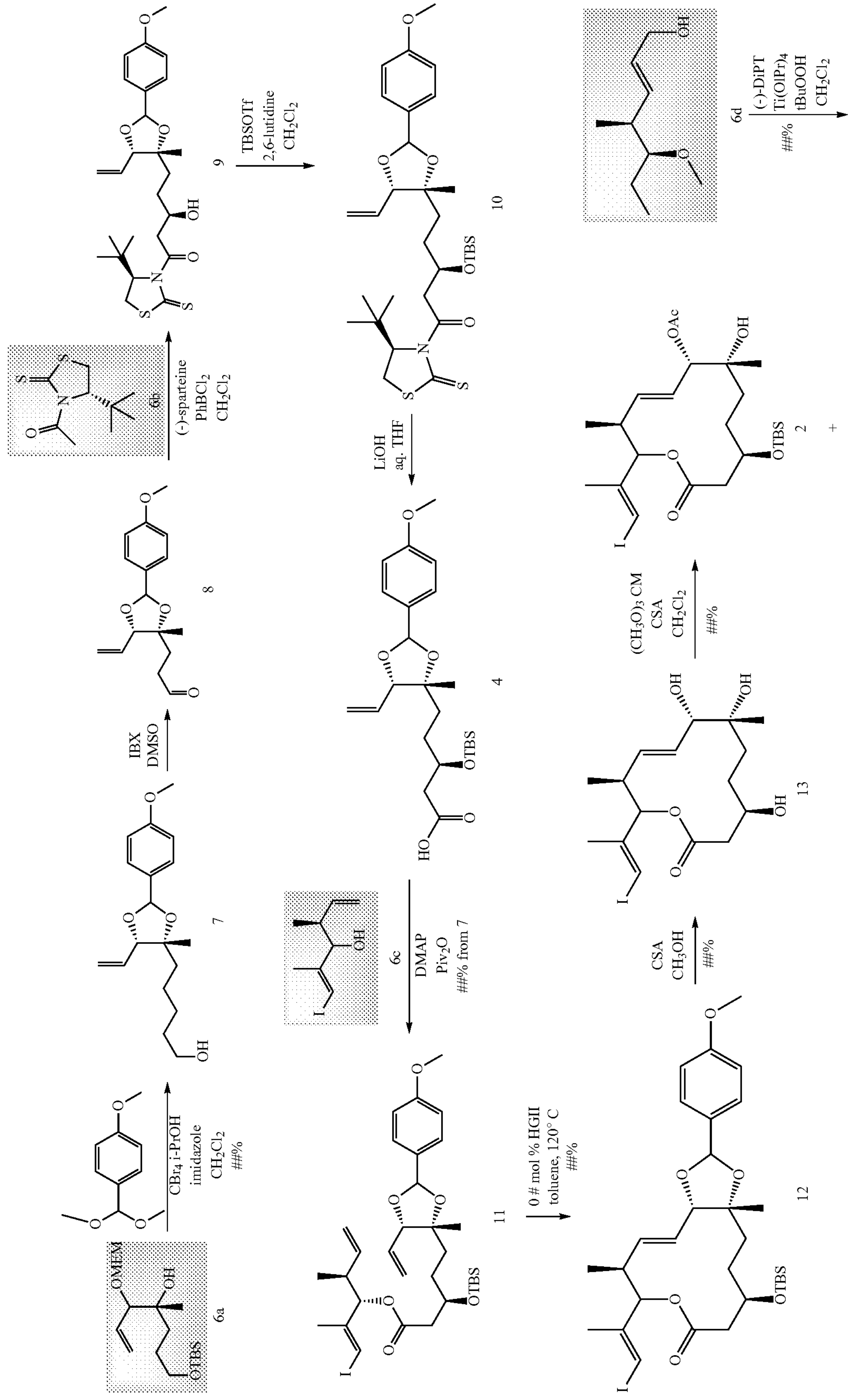

-continued

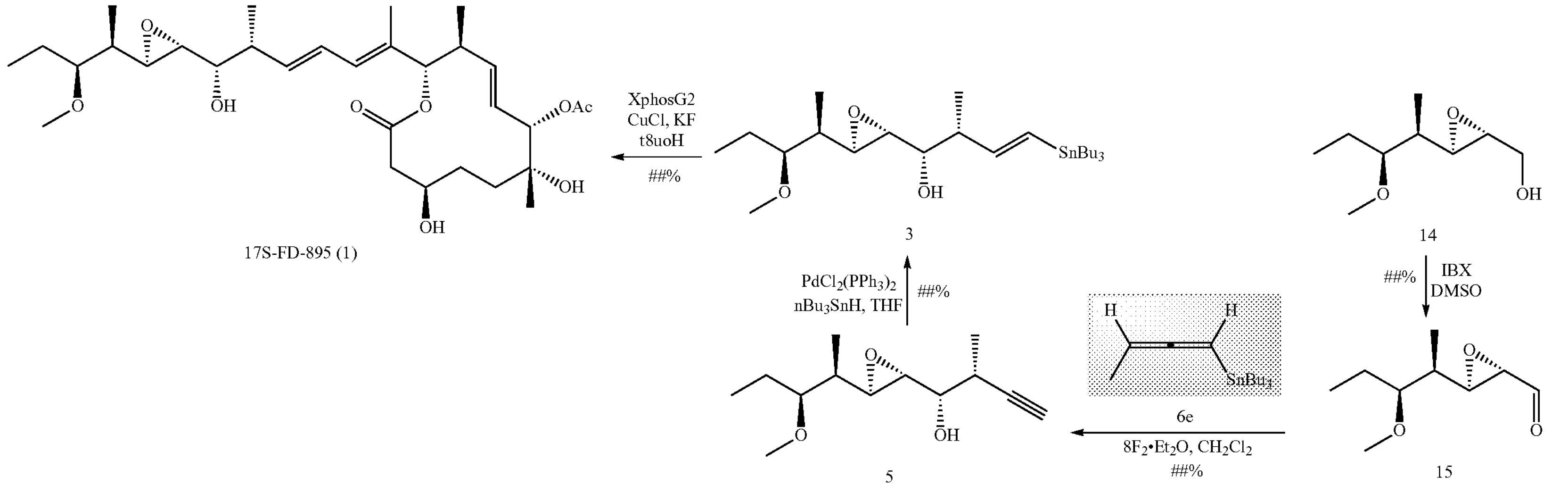

17S-FD-895 (1)

3

14

15

5

Schematic representation of the assembly process developed for the gram-scaled synthesis of 17S-FD-895. Here the five components 6a-6e are processed in a stepwise fashion deliver components, core 2 and side chain 3. A 4-step sequence was developed to prepare 3 beginning with 6d and later applying 6e to install the C16-C17 stereodiad. Preparation of component 2 was achieved in a 9-step sequence from component 6a. This process requited was conducted series of operations that began by conversion of 6a to 7, relay of 7 to 11 using component 6b to install the C3 stereocenter, ring-closing metathesis to 12 and proper adjustment of the functionality in 2. Reagents and conditions are provided along each arrow along with the observed yield.

Example 2. Experimental Data for Initial Synthesis

A. General experimental methods: Chemical reagents were purchased from Acros, Fluka, Sigma-Aldrich, or TCI. Deuterated NMR solvents were purchased from Cambridge Isotope Laboratories. All reactions were conducted with rigorously dried anhydrous solvents that were obtained by passing through a solvent column composed of activated Al alumina. Anhydrous N,N-dimethylformamide was obtained by passage over activated molecular sieves and a subsequent NaOCN column to remove traces of dimethylamine. Triethylamine ($Et_3N$) was dried over Na and freshly distilled. Ethyl-N,N-diisopropylamine ($EtNiPr_2$) was distilled from ninhydrin, then from potassium hydroxide. Anhydrous $CH_3CN$ was obtained by distillation from $CaH_2$. All reactions were performed under positive pressure of Ar in oven-dried glassware sealed with septa, with stirring from a Teflon coated stir bars using an IKAMAG RCT-basic mechanical stirrer (IKA GmbH). Solutions were heated using either a sand or silicon oil bath. Analytical Thin Layer Chromatography (TLC) was performed on Silica Gel 60 F254 precoated glass plates (EM Sciences). Preparative TLC (pTLC) was conducted on Silica Gel 60 plates (EM Sciences). Visualization was achieved with UV light and/or an appropriate stain ($I_2$ on $SiO_2$, $KMnO_4$, bromocresol green, dinitrophenylhydrazine, ninhydrin, and ceric ammonium molybdate). Flash chromatography was carried out Geduran Silica Gel 60 (40-63 mesh) from EM Biosciences. Yields and characterization data correspond to isolated, chromatographically and spectroscopically homogeneous materials. $^1H$ NMR spectra were recorded on Varian Mercury 300, Varian Mercury 400 spectrometers, Varian Mercury Plus 400, a JEOL ECA500, or a Varian VX500 spectrometer. A majority of the $^{13}C$ NMR spectra were recorded at 125 MHz on a Varian VX500 spectrometer equipped with an Xsens Cold probe. The remaining spectra were either collected at 125 MHz on a JEOL ECA 500, 100 MHz on a Varian Mercury 400 or 100 MHz on a Varian Mercury Plus 400 spectrometer. Chemical shifts for $^1H$ NMR and $^{13}C$ NMR analyses were referenced to the reported values of Gottlieb, using the signal from the residual solvent for $^1H$ spectra, or to the $^{13}C$ signal from the deuterated solvent. Chemical shift δ values for $^1H$ and $^{13}C$ spectra are reported in parts per million (ppm) relative to these referenced values, and multiplicities are abbreviated as s=singlet, d=doublet, t=triplet, q=quartet, m=multiplet, br=broad. All $^{13}C$ NMR spectra were recorded with complete proton decoupling. FID files were processed using MestraNova 6.0.2. (MestreLab Research). Electrospray (ESI) mass spectrometric analyses were performed using a ThermoFinnigan LCQ Deca spectrometer, and high-resolution analyses were conducted using a ThermoFinnigan MAT900XL mass spectrometer with electron impact (EI) ionization. A Thermo Scientific LTQ Orbitrap XL mass spectrometer was used for high-resolution electrospray ionization mass spectrometry analysis (HR-ESI-MS). FTIR spectra were obtained on a Nicolet magna 550 series II spectrometer as thin films on either KBr or NaCl discs, and peaks are reported in wavenumbers ($cm^{-1}$). Optical rotations $[\alpha]_D$ were measured using a Perkin-Elmer Model 241 polarimeter with the specified solvent and concentration and are quoted in units of deg $cm^2$ $g^{-1}$. Spectral data and procedures are provided for all new compounds and copies of select spectra have been provided.

B. Synthesis of component 6a. A four-step sequence was developed to prepare component 6a beginning with commercially available 6a1 as shown in Scheme S1.

Scheme S1. Synthesis of side chain component 6a

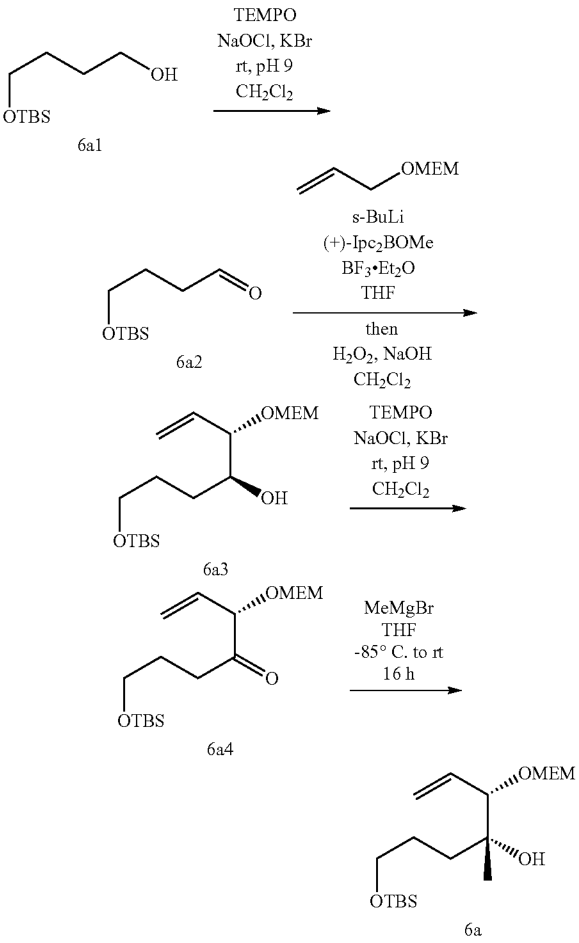

6a1
6a2
6a3
6a4
6a 4-((tert-Butyldimethylsilyl)oxy)butanal (6a2). A solution of KBr (6.99 g, 58.7 mmol) in $H_2O$ (60 mL) was added to a solution of 4-((tert-butyldimethylsilyl)oxy)butan-1-ol (6a1) (100 g, 489 mmol) in $CH_2Cl_2$ (1.0 L) followed by satd. $NaHCO_3$ (100 mL) and 2,2,6,6-tetramethylpiperidin-1-olate (2.29 g, 14.7 mmol). The reaction mixture was cooled to −3° C. and a mixture of NaOCl (0.33 L, 636 mmol) and satd. $NaHCO_3$ (300 mL) was added in a portion wise fashion via a dropping funnel. The mixture was allowed to warm to rt. After stirring at rt for 3 h, the reaction mixture was extracted with $CH_2Cl_2$ (3×250 mL). The combined organic phases were washed with $H_2O$ (500 mL), satd. NaCl (500 mL), dried over $Na_2SO_4$, filtered and concentrated on a rotary evaporator to afford 6a2 (100 g, quant. yield).

Aldehyde 6a2: $^1H$ NMR ($CDCl_3$, 300 MHz) δ 9.79 (t, J=1.7 Hz, 1H), 3.65 (t, J=6.0 Hz, 2H), 2.50 (td, J=7.1, 1.7 Hz, 2H), 1.86 (tt, J=7.1, 5.9 Hz, 2H), 0.94-0.84 (m, 9H), 0.04 (s, 6H); $^{13}C$ NMR ($CDCl_3$, 75 MHz) δ 202.54, 62.06, 40.77, 25.87, 25.49, 18.24, −5.44.

(8S,9S)-14,14,15,15-Tetramethyl-8-vinyl-2,5,7,13-tetraoxa-14-silahexadecan-9-ol (6a3). A solution of s-BuLi (1.4 M in cyclohexane, 353 mL, 494 mmol) was added in a dropwise fashion over a period of 30 min to a solution of 3-((2-methoxyethoxy)methoxy)prop-1-ene (86.7 g, 593 mmol) in anhydrous THF (1 L) a cooled −78° C. under $N_2$ atmosphere. It was critical to maintain the temperature below −70° C. during this addition. After stirring at −78° C.

for 1 h, a solution of methoxybis((1S,2R,3S,5S)-2,6,6-trimethylbicyclo[3.1.1]heptan-3-yl)borane (156 g, 494. mmol) in anhydrous THF (500 mL) was added. The reaction mixture stirred again at −78° C. for 1 h. $BF_3{\cdot}Et_2O$ (79.3 mL, 642 mmol) was added followed by an addition of a solution of 4-((tert-butyldimethylsilyl)oxy)butanal (6a2) (100 g, 494 mmol) in anhydrous THF (200 mL). The reaction mixture was stirred at −78° C. for 3 h and then allowed to warm to rt overnight. After cooling to between −4° C. to 0° C., satd. $NH_4Cl$ (500 mL) was added to the mixture, which was extracted with $CH_2Cl_2$ (3×250 mL). The combined organic phases were washed with $H_2O$ (500 mL), satd. NaCl (500 mL), dried over $Na_2SO_4$, filtered and concentrated on a rotary evaporator. Pure 6a3 (89 g, 52%) was obtained by flash chromatography eluting with a gradient of heptane to EtOAc.

Alcohol 6a3: TLC (5:1 hexanes/EtOAc): $R_f$=0.25; $^1$H NMR ($CDCl_3$, 300 MHz) δ 5.78-5.59 (m, 1H), 5.36-5.23 (m, 2H), 4.78 (d, J=6.9 Hz, 1H), 4.69 (d, J=6.9 Hz, 1H), 3.89 (dt, J=8.2, 7.1 Hz, 1H), 3.85-3.75 (m, 1H), 3.71-3.61 (m, 3H), 3.61-3.47 (m, 4H), 3.38 (s, 3H), 2.94 (s, 1H), 1.79-1.54 (m, 4H), 1.50-1.31 (m, 1H), 0.87 (s, 10H), 0.10 (d, J=0.6 Hz, 5H); $^{13}$C NMR ($CDCl_3$, 75 MHz) δ 134.81, 119.73, 92.99, 81.51, 73.15, 71.75, 67.37, 63.12, 58.96, 29.35, 28.81, 25.91, 18.30, −5.35.

(S)-14,14,15,15-Tetramethyl-8-vinyl-2,5,7,13-tetraoxa-14-silahexadecan-9-one (6a4). A solution of KBr (3.646 g, 30.64 mmol) in $H_2O$ (100 mL) was added to a solution of (8S,9S)-14,14,15,15-tetramethyl-8-vinyl-2,5,7,13-tetraoxa-14-silahexadecan-9-ol (6a3) (89.00 g, 255.3 mmol) in DCM (400 mL) followed by the addition of a satd. $NaHCO_3$ (250 mL) and 2,2,6,6-tetramethylpiperidin-1-olate (3.990 g, 25.53 mmol). The reaction mixture was cooled to 0° C. and a solution of NaOCl (0.32 kg, 510.7 mmol) and satd. $NaHCO_3$ (300 mL) were added in a drop wise fashion via a dropping funnel (20 mL at a time) while maintaining the temperature below 1.5° C. The reaction mixture was allowed to warm to rt and stirred for 2 h. The phases were separated. The aqueous phase was extracted with $CH_2Cl_2$ (200 mL). The combined organic phases were washed with satd. NaCl (500 mL), dried over $Na_2SO_4$, filtered and concentrated on a rotary evaporator to afford 6a4 (88.0 g, 99%).

Ketone 6a4: TLC (3:1 hexanes/EtOAc): $R_f$=0.40; $^1$H NMR ($CDCl_3$, 300 MHz) δ 5.75 (ddd, J=17.0, 10.3, 6.6 Hz, 1H), 5.49-5.37 (m, 1H), 5.37-5.24 (m, 1H), 4.74 (q, J=6.9 Hz, 2H), 4.59 (d, J=6.6 Hz, 1H), 3.80-3.67 (m, 1H), 3.67-3.53 (m, 3H), 3.49 (t, J=4.6 Hz, 2H), 3.34 (s, 3H), 2.60 (td, J=7.2, 3.9 Hz, 2H), 1.74 (p, J=6.7 Hz, 2H), 0.85 (s, 9H), 0.01 (s, 6H); $^{13}$C NMR ($CDCl_3$, 75 MHz) δ 208.01, 132.56, 119.85, 93.63, 82.58, 71.63, 67.40, 61.95, 58.94, 34.63, 26.25, 25.87, 18.23, −5.39.

(8S,9R)-9,14,14,15,15-Pentamethyl-8-vinyl-2,5,7,13-tetraoxa-14-silahexadecan-9-ol (6a). MeMgBr (3 M solution in $Et_2O$, 462 mL, 1385.1 mmol) was added in a drop wise fashion to a solution of(S)-14,14,15,15-tetramethyl-8-vinyl-2,5,7,13-tetraoxa-14-silahexadecan-9-one (6a4) (160.0 g, 461.7 mmol) in anhydrous THF (1.5 L) at −85° C. The reaction mixture was stirred at −85° C. for 2 h, allowed to warm to rt and then stirred for an additional 16 h. After recooling to 0° C., a satd. $NH_4Cl$ (500 mL) was added to the mixture in a drop wise fashion. The mixture was diluted with $H_2O$ (1 L) and extracted with TBME (2×500 mL). The combined organic phases were washed with $H_2O$ (500 mL) and satd. NaCl (500 mL), dried over $Na_2SO_4$, filtered and concentrated on a rotary evaporator. Pure 6a (78.9 g, 47%) was obtained by flash chromatography eluting with a gradient of hexanes to EtOAc.

Component 6a: TLC (5:1 hexanes/EtOAc): $R_f$=0.30; $^1$H NMR ($CDCl_3$, 300 MHz) δ 5.74 (ddd, J=17.1, 10.6, 8.0 Hz, 1H), 5.31 (dd, J=1.9, 0.7 Hz, 1H), 5.32-5.19 (m, 1H), 4.75 (d, J=6.9 Hz, 1H), 4.67 (d, J=6.9 Hz, 1H), 3.94-3.71 (m, 2H), 3.68-3.57 (m, 1H), 3.63-3.51 (m, 2H), 3.57-3.44 (m, 2H), 3.36 (s, 3H), 2.66 (s, 1H), 1.76-1.51 (m, 3H), 1.56-1.32 (m, 1H), 1.14 (s, 3H), 0.87 (s, 9H), 0.02 (s, 6H); $^{13}$C NMR ($CDCl_3$, 75 MHz) δ 134.27, 120.02, 93.20, 84.42, 73.27, 71.74, 67.43, 63.77, 58.97, 33.77, 26.50, 25.92, 23.41, 18.30, −5.34.

C. Synthesis of auxilary 6b. A two-step sequence was developed to prepare component 6b beginning with commercially available 6b1 as shown in Scheme S2.

Scheme S2. Synthesis component 6b

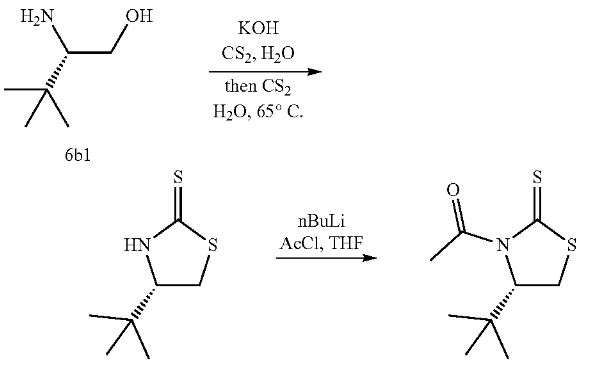

6b1 6b2 6b (S)-4-(tert-Butyl)thiazolidine-2-thione (6b2). KOH (2.63 kg, 46.9 mol) was dissolved in $H_2O$ (9 L) and stirred in a 20 L reactor equipped with a mechanical stirrer and two reflux condensers. (S)-2-Amino-3,3-dimethylbutan-1-ol (6b1) (250 g, 2.13 mol) was added followed by a drop wise addition of $CS_2$ (1.03 L, 17.1 mol) under $N_2$ atmosphere. The reaction mixture was heated at 95° C. for 16 h. After cooling the reaction mixture to 50° C., additional portion of $CS_2$ (1 L) was added in a drop wise fashion and the reaction mixture heated at 70° C. for 16 h. The reaction mixture was cooled to 50° C. again and additional portion of $CS_2$ (500 mL) was added in a drop wise fashion. The mixture was heated at 65° C. and stirred over the weekend. After cooling the reaction mixture to rt, the solids were collected by filtration and washed with $H_2O$. The white solids were dried at rt in the air. Pure 6b2 (175.7 g, 47%) was obtained by flash chromatography eluting with DCM.

Auxilary 6b2: TLC (100% DCM): $R_f$=0.7; $^1$H NMR ($CDCl_3$, 300 MHz) δ 7.58 (s, 1H), 4.01 (t, J=9.6, 8.5, 1.2 Hz, 1H), 3.50-3.32 (m, 2H), 1.01 (s, 9H); $^{13}$C NMR ($CDCl_3$, 75 MHz) δ 73.3, 34.5, 34.4, 25.9.

(S)-1-(4-(tert-Butyl)-2-thioxothiazolidin-3-yl)ethan-1-one (6b). To a cooled (−78° C.) solution of (S)-4-(tert-butyl)thiazolidine-2-thione (6b2) (181.83 g, 1.04 mol) in anhydrous THF (1.8 L), n-butyllithium (2.5 M in hexane, 0.46 L, 1.1 mol) was added in a drop wise fashion under $N_2$ atmosphere. The mixture was stirred at −78° C. for 30 min, acetyl chloride (82 mL, 1.2 mol) was added in a drop wise fashion and the mixture stirred in the above conditions for a further 1.5 h. After that time, the reaction mixture was warmed to rt, stirred for 1 h, cooled to 0° C. and quenched with satd. $NH_4Cl$ (800 mL). The phases were separated. The aqueous phase was extracted with DCM (2×200 mL). The combined organic phases were dried over $Na_2SO_4$, filtered and concentrated on rotary evaporator. Pure 6b3 (190.5 g, 85%) was obtained by flash chromatography eluting with a gradient of heptane to DCM.

Auxilary 6b: TLC (1:1 Heptane/DCM): $R_f$ 0.8; $^1H$ NMR ($CDCl_3$, 300 MHz) δ 5.30 (d, J=8.4, 0.9 Hz, 1H), 3.60-3.44 (m, 1H), 3.09 (d, J=11.8, 0.9 Hz, 1H), 2.77 (s, 3H), 1.03 (s, 9H); $^{13}C$ NMR ($CDCl_3$, 75 MHz) δ 205.3, 170.3, 72.0, 38.0, 30.4, 26.8, 26.8; LCMS (ES-API) $[M+1]^+$: 218.0.

D. Synthesis of component 6c. A seven-step sequence was developed to prepare component 6c beginning with commercially available 6c1 as shown in Schemes S3-S4.

Scheme S3. Synthesis of component 6c

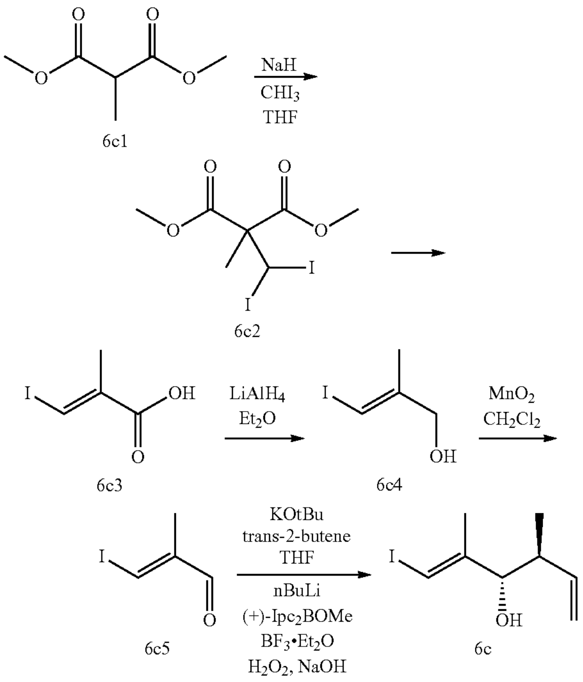

6c1
6c2
6c3
6c4
6c5
6c

Dimethyl 2-(diiodomethyl)-2-methylmalonate (6c2). A solution of dimethyl 2-methylmalonate (6ca) (310 mL, 2.33 mol) in THF (800 mL) was added in a drop wise fashion over the period of 20 min to a suspension of NaH (150 g, 3.8 mol) in THF (800 mL) under $N_2$ atmosphere. The reaction was stirred at reflux for 1.5 h. A solution of iodoform (801.9 g, 2.037 mol) in THF (2 L) was added in a drop wise fashion over the period of 40 min. The reaction mixture was cooled to 50° C. and stirred in these conditions for 16 h. After cooling to 0° C., 2 M HCl (1.5 L) was added to the reaction mixture. The phases were separated. The aqueous phase was extracted with EtOAc (2×300 mL). The combined organic phases were dried over $Na_2SO_4$, filtered and concentrated on a rotary evaporator to afford 6c2 (1008.8 g, quant. yield).

Diester 6c2: $^1H$ NMR ($CDCl_3$, 300 MHz) δ 3.77 (s, 6H), 3.22 (q, J=6.7 Hz, 1H), 1.81 (s, 3H), 0.85 (t, J=8.2 Hz, 7H); $^{13}C$ NMR ($CDCl_3$, 75 MHz) δ 166.6, 53.6, 52.6, 20.42, 9.0.

(E)-3-Iodo-2-methylacrylic acid (6c3). Dimethyl 2-(diiodomethyl)-2-methylmalonate (6c2) (1008.8 g, 2.45 mol) was dissolved in a mixture of EtOH (2 L) and $H_2O$ (500 mL). KOH (300 g, 4.5 mol) was added in a portion wise fashion. Due to a large exotherm the remaining KOH (400 g, 6.06 mol) was dissolved in $H_2O$ (300 mL) and added in a drop wise fashion over the period of 1 h. The reaction mixture was heated at reflux and stirred for 16 h. After cooling to rt, the mixture was concentrated on a rotary evaporator. The remaining material was acidified to pH 1 with conc. HCl. The solids formed were collected by filtration and washed with $CH_2Cl_2$. The organic phase was washed with $H_2O$ (1×1 L) and the aqueous phase was extracted with $CH_2Cl_2$ (3×600 mL). The combined organic phases were dried over $Na_2SO_4$, filtered and concentrated on a rotary evaporator to afford 6c3 (288.53 g, 65%).

Acid 6c3: $^1H$ NMR ($CDCl_3$, 300 MHz) δ 9.65 (bs, 1H), 8.02 (s, 1H), 2.06 (s, 3H); $^{13}C$ NMR ($CDCl_3$, 75 MHz) δ 168.9, 139.0, 101.8, 19.8.

(E)-3-Iodo-2-methylprop-2-en-1-ol (6c4). A solution of (E)-3-iodo-2-methylacrylic acid (6c3) (288.53 g, 1.3 mol) in $Et_2O$ (400 mL) was added in a drop wise fashion over 20 min to suspension of $LiAlH_4$ (76.4 g, 2.01 mol) in $Et_2O$ (800 mL) a cooled to −5° C.) under $N_2$ atmosphere. The reaction mixture was stirred at −5° C. for 1 h, warmed to rt and stirred for a further 2 h. After cooling the mixture to −78° C., acetone (200 mL) was added in a drop wise fashion over the period of 35 min, followed by a dropwise addition of 2 M HCl (750 mL) over the period of 1 h. The resulting mixture was filtered over a Büchner filter. The phases were separated and the aqueous phase was extracted with TBME (3×1 L). The combined organic phases were washed with satd. NaCl (3×500 mL), dried over $Na_2SO_4$, filtered and concentrated on a rotary evaporator. Pure 6c4 (146.4 g, 56%) was obtained by flash chromatography eluting with a gradient of heptane to $CH_2Cl_2$.

Alcohol 6c4: TLC (0:1 heptane/$CH_2Cl_2$): $R_f$=0.6; $^1H$ NMR ($CDCl_3$, 300 MHz) δ 6.24 (m, J=1.3 Hz, 1H), 4.12-4.04 (d, 2H), 2.43 (t, J=5.9 Hz, 1H), 1.82 (s, 3H). $^{13}C$ NMR ($CDCl_3$, 75 MHz) δ 147.2, 67.0, 21.4.

(E)-3-Iodo-2-methylacrylaldehyde (6c5). Activated $MnO_2$ (642.8 g, 7.394 mol) was added to a solution of (E)-3-iodo-2-methylprop-2-en-1-ol (6c4) (146.4 g, 739.4 mmol) in $CH_2Cl_2$ (1 L) under $N_2$ atmosphere. The reaction mixture was stirred at rt for 16 h. Pure 6c5 (142.4 g, 84%) was obtained after filtration over Celite and concentration on a rotary evaporator.

Aldehyde 6c5: $^1H$ NMR ($CDCl_3$, 300 MHz) δ 9.52 (s, 1H), 7.80 (d, J=1.3 Hz, 1H), 5.29 (s, 1H), 1.92 (d, J=1.2 Hz, 3H). $^{13}C$ NMR (CDCl3, 75 MHz) δ 189.4, 150.8, 109.4, 16.4.

(3S,4S,E)-1-Iodo-2,4-dimethylhexa-1,5-dien-3-ol (6c). (E)-But-2-ene (200 mL, 2 mol) was condensed and added to THF (1.5 L) at −78° C. under $N_2$ atmosphere. KOtBu (113.8 g, 1.014 mol) was added and the reaction mixture was stirred in the above conditions for 30 min. n-BuLi (2.5 M in hexane, 400 mL, 1.0 mol) was added in a drop wise fashion over the period of 15 min and the mixture was stirred at −78° C. for 30 min. A solution of methoxybis((1S,2R,3S,5S)-2,6,6-trimethylbicyclo[3.1.1]heptan-3-yl)borane (253 g, 800 mmol) in THF (1 L) was added in a drop wise fashion over the period of 15 min. After stirring the mixture for 30 min, $BF_3$. $Et_2O$ (170 mL, 1.34 mol) was added in a drop wise fashion over the period of 10 min and the mixture was stirred for 10 min. After cooling the reaction mixture to −94° C., a solution of (E)-3-iodo-2-methylacrylaldehyde (6c5) (121 g, 617 mmol) in THF (750 mL) was added in a drop wise fashion over the period of 45 min. After complete addition, the reaction mixture was allowed to warm to rt and stirred for 16 h. $H_2O$ (2 L) was added and the mixture was concentrated on a rotary evaporator. Component 6c (78 g, 50%) was obtained by flash chromatography eluting with $CH_2Cl_2$.

Intermediate 6c: $^1H$ NMR ($CDCl_3$, 300 MHz) δ 6.26 (s, 1H), 5.72 (ddd, J=17.8, 9.9, 8.1 Hz, 1H), 5.24-4.94 (m, 2H), 3.87 (dd, J=8.1, 2.3 Hz, 1H), 2.35 (q, J=7.4 Hz, 1H), 1.88-1.55 (s, 3H), 0.92 (d, J=6.8 Hz, 3H); $^{13}C$ NMR ($CDCl_3$, 75 MHz) δ 148.0, 139.9, 117.2, 80.1, 79.7, 42.2, 19.3, 16.5; chiral GC: 78.8% ee.

Scheme S4. Resolution and delivery of enantiopure 6c.

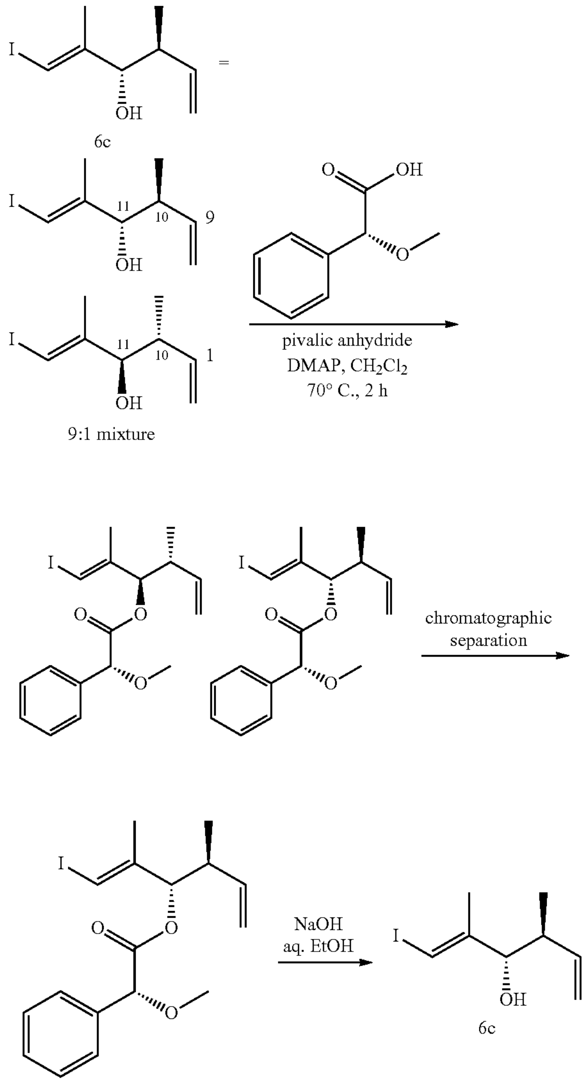

6c
9:1 mixture
6c (3S,4S,E)-1-iodo-2,4-dimethylhexa-1,5-dien-3-yl (R)-2-methoxy-2-phenylacetate. The mixture of 6c (9.3 g, 36.8 mmol) was added to a 100 mL pearl shaped round bottom flask and dried by toluene azeotrope (2×25 mL). Solid (R)-2-methoxy-2-phenylacetic acid (6.74 g, 40.6 mmol) and DMAP (678.0 mg, 5.5 mmol) were added followed by pivalic anhydride (15 mL). The mixture was heated to 70° C. in a 100 mL Heat-On attachment with a Hei-Tec stir plate. After 2 h the reaction was cooled, dried via rotary evaporation and airflow. The resulting crude wax was submitted to flash chromatography with a gradient of hexanes to 20:1 hexanes:$Et_2O$ to afford fractions of both pure major 6c6 (80±3%) and minor 6c7 (6±2%) and a mixed fraction (4±1%) which can be reused. The pure major isomer 6c6 was immediately subjected to following step.

Ester 6c6: $^1H$ NMR ($CDCl_3$, 300 MHz) δ 7.37 (m, 5H), 5.96 (s, 1H), 5.61 (ddd, J=7.9, 10.2, 18.1 Hz, 1H), 5.15 (d, J=7.9 Hz, 1H), 5.01 (dd, J=1.4, 17.1 Hz, 1H), 4.99 (d, J=9.7 Hz, 1H), 4.73 (s, 1H), 3.39 (s, 3H), 2.46 (dt, J=6.8, 7.3 Hz, 1H), 1.51 (d, J=1.5 Hz, 3H), 0.89 (d, J=6.9 Hz, 1H); $^{13}C$ NMR ($CDCl_3$, 75 MHz) δ 143.7, 138.9, 136.0, 129.0, 128.8, 127.4, 116.2, 82.4, 81.6, 81.0, 57.4, 40.0, 20.0, 16.5.

Enantiopure (3S,4S,E)-1-Iodo-2,4-dimethylhexa-1,5-dien-3-ol (6c). Pure 6d6 (12.2 g, 30.4 mmol) was dissolved in MeOH (400 mL) and $H_2O$ (~80 mL) until the solution became slightly cloudy. NaOH (1 M) was added in 50 mL portions until TLC analyses indicated complete hydrolysis (typically complete in 5-6 additions over 1.5 h). Once complete $H_2O$ (100 mL) was added and the resulting mixture was extracted with $CH_2Cl_2$ (3×300 mL), washed with brine (100 mL) and dried with $Na_2SO_4$. The resulting resolved 6c (7.4 g, 79%) was used as is.

Enantiopure 6c: $^1H$ NMR ($CDCl_3$, 300 MHz) δ 6.26 (s, 1H), 5.72 (ddd, J=17.8, 9.9, 8.1 Hz, 1H), 5.24-4.94 (m, 2H), 3.87 (dd, J=8.1, 2.3 Hz, 1H), 2.35 (q, J=7.4 Hz, 1H), 1.88-1.55 (s, 3H), 0.92 (d, J=6.8 Hz, 3H); $^{13}C$ NMR ($CDCl_3$, 75 MHz) δ 148.0, 139.9, 117.2, 80.1, 79.7, 42.2, 19.3, 16.5; chiral GC: 99% ee.

This procedure was repeated to deliver a total of >50 g of 6c over 5 batches.

E. Synthesis of component 6d. A seven-step sequence was developed to prepare component 6d beginning with commercially available 6d1 as shown in Scheme S5.

Scheme S5. Synthesis of component 6d

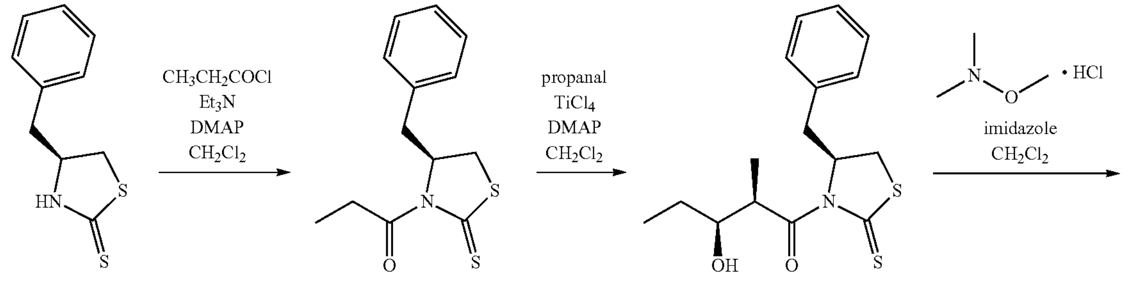

6d1
6d2
6d3

-continued

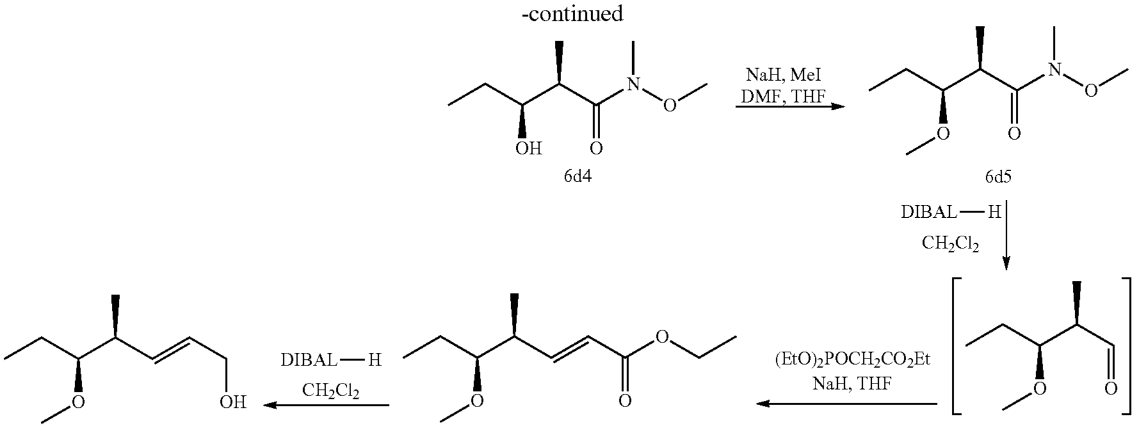

6d4 6d5 6d6 6d7 6d (R)-1-(4-Benzyl-2-thioxothiazolidin-3-yl)propan-1-one (6d2). Triethylamine (0.7 L, 5.2 mol) and N,N-dimethylpyridin-4-amine (105.1 g, 0.86 mol) were added at rt to a solution of (R)-4-benzylthiazolidine-2-thione (6d1) (891.8 g, 4.3 mol) in $CH_2Cl_2$ (9.0 L), The reaction mixture was cooled to 0° C. and a solution of propionyl chloride (490 mL, 5.61 mol) in $CH_2Cl_2$ (2.25 L) was added in a drop wise fashion over the period of 1.5 h while maintaining the temperature below 5° C. The reaction mixture was stirred at rt for 18 h. After that time, the mixture was cooled to 0° C. and satd. $NH_4Cl$ (5.8 L) was added in a drop wise fashion while keeping the temperature below 5° C. The mixture was extracted with DCM (3x2 L). The combined organic phases were washed with satd. $NaHCO_3$ (4 L) and satd. NaCl (4 L), dried over $Na_2SO_4$, filtered and concentrated on a rotary evaporator. This batch was combined with a smaller batch 6d2 (130 g). Pure 6d2 (950.1 g, 84%) was obtained by crystallization from MeCN.

Auxilary 6d2: $^1$H NMR ($CDCl_3$, 300 MHz) δ 7.40-7.21 (m, 5H), 5.38 (m, 1H), 3.52-3.40 (m, 1H), 3.40-3.32 (m, 1H), 3.28-2.96 (m, 3H), 2.88 (dd, J=11.5, 0.7 Hz, 1H), 1.19 (t, J=7.2 Hz, 3H); $^{13}$C NMR ($CDCl_3$, 75 MHz) δ 174.9, 136.6, 129.5, 128.9, 127.2, 68.7, 36.8, 32.3, 31.9, 8.82. LCMS (ES-API) $[M+1]^+$: 266.40.

(2R,3S)-1-((S)-4-Benzyl-2-thioxothiazolidin-3-yl)-3-hydroxy-2-methylpentan-1-one (6d3). (S)-1-(4-Benzyl-2-thioxothiazolidin-3-yl)propan-1-one (6d2) (235.3 g, 887 mmol) was dissolved in $CH_2Cl_2$ (7.05 L) with mechanical stirring. The reaction mixture was cooled below 0° C. $TiCl_4$ (1 M solution in $CH_2Cl_2$, 922 mL, 922 mmol) was added in a drop wise fashion over the period of 1 h, while maintaining the temperature below 0° C. $EtN(iPr)_2$ (168 mL, 966 mmol) was added in a drop wise fashion over the period of 30 min and the reaction mixture was stirred at 0° C. for 15 min. After cooling the reaction mixture below −82° C., a solution of propionaldehyde (71 mL, 984 mmol) in $CH_2Cl_2$ (350 mL) was added in a drop wise fashion over a period of 6 h while maintaining the temperature below −82° C. The reaction mixture was stirred in the above conditions for 30 min and slowly warmed to rt overnight. Satd. $NaHCO_3$ (1.67 L) was added in a drop wise fashion to the mixture. CAUTION: a large exotherm observed, temperature kept below 5° C. The phases were separated. The aqueous phase was extracted with $CH_2Cl_2$ (3x1 L). The combined organic phases were washed with satd. NaCl (2 L), dried over $Na_2SO_4$, filtered and concentrated on a rotary evaporator. Pure 6d3 (249.5 g, 87%) was obtained by flash chromatography eluting with a gradient of heptane to EtOAc.

Adduct 6d3: TLC (3:1 heptane/EtOAc): $R_f$=0.63; $^1$H NMR ($CDCl_3$, 300 MHz) δ 7.41-7.22 (m, 5H), 5.43-5.32 (m, 1H), 4.72 (dd, J=7.1, 2.3 Hz, 1H), 3.97 (tt, J=5.2, 2.6 Hz, 1H), 3.37 (ddd, J=11.5, 7.1, 1.0 Hz, 1H), 3.24 (dd, J=13.2, 4.1 Hz, 1H), 3.04 (dd, J=13.2, 10.4 Hz, 1H), 2.89 (dd, J=11.6, 0.8 Hz, 1H), 2.77 (dd, J=2.9, 0.9 Hz, 1H), 1.70-1.35 (m, 3H), 1.18 (d, J=7.1 Hz, 3H), 0.98 (t, J=7.4 Hz, 3H); $^{13}$C NMR ($CDCl_3$, 75 MHz) δ 201.6, 178.5, 136.4, 129.5, 128.9, 127.3, 72.5, 68.9, 42.3, 36.9, 31.8, 26.7, 10.5, 10.5; LCMS (ES-API) $[M+1]^+$: 324.40.

(2R,3S)-3-Hydroxy-N-methoxy-N,2-dimethylpentanamide (6d4). N,O-dimethylhydroxylamine hydrochloride (174.0 g, 1.78 mol) and imidazole (182.2 g, 2.68 mol) were successively added to a solution of (2R,3S)-1-((S)-4-benzyl-2-thioxothiazolidin-3-yl)-3-hydroxy-2-methylpentan-1-one (6d3) (288.5 g, 0.89 mol) in $CH_2Cl_2$ (12.5 L), at rt. The reaction mixture was stirred at rt for additional 16 h. $H_2O$ (3.0 L) was added and the aqueous phase (pH 7) was extracted with $CH_2Cl_2$ (3x2.5 L). The combined organic phases were washed with satd. NaCl (5.0 L), dried over $Na_2SO_4$, filtered, and concentrated on a rotary evaporator. to give a yellow oil (344.0 g). Pure 6d4 (155.0 g, 99%) was obtained by flash chromatography eluting with a gradient of heptane to EtOAc.

Amide 6d4 TLC (3:1 heptane/EtOAc): $R_f$=0.17; $^1$H NMR ($CDCl_3$, 300 MHz) δ 3.73 (ddd, J=8.1, 5.4, 2.9 Hz, 1H), 3.67 (s, 3H), 3.17 (s, 3H), 2.91-2.83 (br, 1H), 1.55 (dt, J=13.5, 7.5 Hz, 1H), 1.37 (ddd, J=11.8, 7.4, 5.4 Hz, 1H), 1.13 (d, J=7.1 Hz, 3H), 0.93 (t, J=7.4 Hz, 3H); $^{13}$C NMR ($CDCl_3$, 75 MHz) δ 178.5, 73.0, 61.5, 38.2, 31.8, 26.7, 10.4, 10.0; LCMS (ES-API) $[M+1]^+$: 176.40.

(2R,3S)—N,3-Dimethoxy-N,2-dimethylpentanamide (6d5). MeI (1.1 L, 18.0 mol) was added at rt to a solution of (2R,3S)-3-hydroxy-N-methoxy-N,2-dimethylpentanamide (6d4) (155.0 g, 0.89 mol) in a mixture of THF (6.1 L) and DMF (1.5 L), The reaction mixture was cooled to 0° C. and NaH (60% in a mineral oil, 88.5 g, 2.21 mol) was added in a portion wise fashion. The reaction mixture was slowly warmed to rt and stirred for 16 h. After cooling the reaction mixture to 0° C., a solution of phosphate buffered saline pH 7 (1.5 L) was added in a drop wise fashion. The volatiles were evaporated on a rotary evaporator. $H_2O$ (4.5 L) was added to the residue and the obtained mixture was extracted with TBME (3x3 L). The combined organic phases were washed with satd. NaCl (3 L), dried over $Na_2SO_4$, filtered and evaporated on a rotary evaporator. Pure 6d5 (152.3 g, 91%) was obtained by flash chromatography eluting with a gradient of heptane to EtOAc.

Amide 6d5: TLC (3:1 heptane/EtOAc): $R_f$=0.27; $^1H$ NMR ($CDCl_3$, 300 MHz) δ 3.59 (s, 3H), 3.30 (s, 3H), 3.28-3.14 (m, 1H), 3.08 (s, J=5.1 Hz, 3H), 2.98-2.87 (m, 1H), 1.49 (ddt, J=14.5, 7.4, 3.7 Hz, 1H), 1.33 (dt, J=14.2, 7.1 Hz, 1H), 1.11 (d, 3H), 0.83 (t, J=7.4, 6.1 Hz, 3H); $^{13}C$ NMR ($CDCl_3$, 75 MHz) δ 176.0, 171.0, 83.5, 61.1, 59.9, 58.0, 42.8, 39.1, 35.1, 26.1, 26.0, 24.7, 22.6, 20.6, 13.9, 9.2; LCMS (ES-API) $[M+1]^+$: 190.40.

Ethyl (4S,5S,E)-5-methoxy-4-methylhept-2-enoate (6d7). (2R,3S)—N,3-Dimethoxy-N,2-dimethylpentanamide (6d5) (107 g, 565 mmol) was dissolved in $CH_2Cl_2$ (2.14 L). The reaction mixture was cooled below −78° C. DIBAL-H (1.1 M in heptane, 0.8 L, 0.88 mol) was added in a drop wise fashion over the period of 45 min while maintaining the temperature below −78° C. The reaction mixture was stirred in the above conditions for 15 min. Acetone (64.1 mL, 0.88 mol) was added in a drop wise fashion over the period of 10 min. The reaction mixture was warmed to 0° C. Satd. Rochelle salt (1.75 L) was added over the period of 30 min and the mixture was stirred at rt for 1.5 h. The phases were separated. The aqueous phase was extracted with a mixture of $CH_2Cl_2$ (520 mL) and heptane (52 mL). The combined organic phases were dried over $Na_2SO_4$, filtered and concentrated on a rotary evaporator. The residue was co-evaporated with toluene (460 mL) to deliver aldehyde 6d6, which was used immediately after preparation.

Aldehyde 6d6: $^1H$ NMR ($CDCl_3$, 300 MHz) δ 9.77 (s, 1H), 3.56-3.48 (m, 1H), 3.35 (s, 3H), 2.58-2.48 (m, 1H), 1.73-1.45 (m, 2H), 1.10 (d, J=7.1 Hz, 3H), 0.94 (t, J=6.0, 3H).

A solution of ethyl 2-(diethoxyphosphoryl)acetate (572 mL, 2.88 mol) in anhydrous THF (400 mL) was added in a drop wise fashion over the period of 30 min to a cooled suspension of NaH (60% in mineral oil, 97.4 g, 2.44 mol) in anhydrous THF (1.0 L) cooled to 0° C. The reaction mixture was stirred at 0° C. for 15 min and a solution of 6d6 in anhydrous THF was added in a drop wise fashion over the period of 30 min. The reaction mixture was stirred at rt for 16 h, cooled to 0° C. and quenched with satd. $NH_4Cl$ (1.6 L). The volatiles were evaporated on a rotary evaporator and $H_2O$ (400 mL) was added. The mixture was extracted with EtOAc (2×1 L). The combined organic phases were dried over $Na_2SO_4$, filtered and concentrated on a rotary evaporator. Ester 6d7 was purified by flash chromatography eluting with a gradient of $CH_2Cl_2$ to EtOAc. Isolated 6d7 was further stirred in a mixture of satd. $NaHSO_3$ (500 mL), EtOAc (450 mL) and heptane (50 mL) for 40 min. $H_2O$ (250 mL) was added. The phases were separated. The aqueous phase was extracted with a mixture of EtOAc and heptane (3×250 mL, 9:1). The combined organic phases were dried over $Na_2SO_4$, filtered and concentrated on a rotary evaporator to afford 6d7 (57.9 g, 51%).

Ester 6d7: TLC (100% DCM): $R_f$=0.14; $^1H$ NMR ($CDCl_3$, 300 MHz) δ 6.95 (dd, J=15.8, 7.7 Hz, 1H), 5.82 (dd, J=15.8, 1.3 Hz, 1H), 4.18 (q, J=7.1 Hz, 2H), 3.37 (s, 3H), 3.01 (m, 1H), 2.57 (m, 1H), 1.62-1.28 (m, 2H), 1.29 (t, J=7.5 Hz, 3H), 1.07 (d, J=6.8 Hz, 3H), 0.91 (t, J=7.4 Hz, 3H); $^{13}C$ NMR ($CDCl_3$, 75 MHz) δ 166.5, 151.1, 120.9, 85.4, 60.0, 57.7, 39.1, 23.7, 14.6, 14.2, 9.7; LCMS (ES-API) $[M+NH_4]^+$: 218.6

(4S,5S,E)-5-Methoxy-4-methylhept-2-en-1-ol (6d). DIBAL-H (1.1 M in heptane, 0.77 L, 0.85 mol) was added in a drop wise fashion over a period of 60 min to a solution of ethyl (4S,5S,E)-5-methoxy-4-methylhept-2-enoate (6d7) (56.5 g, 282 mmol) in $CH_2Cl_2$ (1.5 L) cooled to −78° C. The reaction mixture was stirred in the above conditions for 1 h. Acetone (57 mL, 0.78 mol) was added in a drop wise fashion over the period of 25 min. The reaction mixture was warmed to 0° C. and satd. Rochelle salt (1030 mL) was added over the period of 40 min. The mixture was stirred at rt for 1 h and 45 min. The phases were separated. The aqueous phase was extracted with $CH_2Cl_2$ (3×500 mL). The combined organic phases were washed with satd. NaCl (250 mL), dried over $Na_2SO_4$, filtered and concentrated on a rotary evaporator. Pure 6d (39.0 g, 87%) was obtained by flash chromatography eluting with a gradient of heptane to EtOAc.

Intermediate 6d: TLC (3:1 heptane/EtOAc): $R_f$=0.26. $^1H$ NMR ($CDCl_3$, 300 MHz) δ 5.73-5.57 (m, 2H), 4.11 (m, 2H), 3.36 (s, 3H), 2.92 (ddd, J=7.4, 5.7, 4.3 Hz, 1H), 2.44 (m, 1H), 1.57-1.34 (m, 2H), 1.02 (d, J=6.8 Hz, 3H), 0.91 (t, J=7.4 Hz, 3H); $^{13}C$ NMR ($CDCl_3$, 75 MHz) δ 134.3, 129.2, 86.4, 63.2, 57.4, 38.8, 23.2, 15.8, 9.8; chiral GC: 98.4% e.e.

F. Synthesis of component 6e. A two-step sequence was developed to prepare component 6e beginning with commercially available 6e1 as shown in Scheme S6.

Scheme S6. Synthesis component 6e

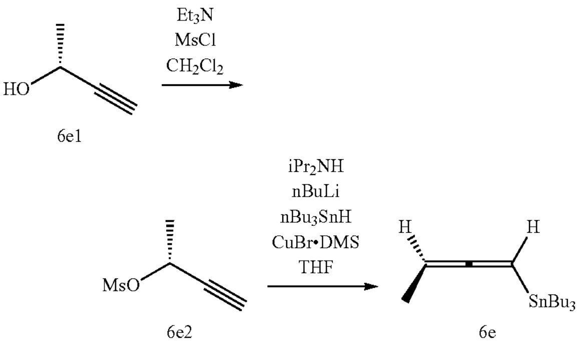

6e1

6e2

6e (R)-But-3-yn-2-yl methanesulfonate (6e2). $Et_3N$ (198 mL, 1.43 mol) was added in a drop wise fashion over a period of 15 min to a solution of (R)-but-3-yn-2-ol (6e1) (50.0 g, 713 mmol) in $CH_2Cl_2$ (750 mL) cooled to −78° C. After 10 min, MsCl (83.4 mL, 1.07 mol) was added in a drop wise fashion over a period of 2 h. The reaction mixture was stirred in the above conditions for 1 h. Satd. $NaHCO_3$ (750 mL) was added in a drop wise fashion over a period of 4 h. The reaction mixture was allowed to warm to rt. $H_2O$ (250 mL) was added and the phases separated. The aqueous phase was extracted with $CH_2Cl_2$ (250 mL). The combined organic phases were washed with satd. NaCl (250 mL), dried over $Na_2SO_4$, filtered and concentrated on a rotary evaporator. The impure product was partitioned between DCM (750 mL) and satd. $NaHCO_3$ (750 mL) and the mixture was stirred at rt for 2 h. The phases were separated. The organic phase was dried over $Na_2SO_4$, filtered, and concentrated on a rotary evaporator to afford 6e2 (21.1 g, 20.0%).

Mesylate 6e2: $^1H$ NMR ($CDCl_3$, 300 MHz) δ 5.29 (qd, J=6.7, 2.1 Hz, 1H), 3.12 (s, 3H), 2.70 (d, J=2.2 Hz, 1H), 1.66 (d, J=6.7 Hz, 3H); $^{13}C$ NMR ($CDCl_3$, 75 MHz) δ 80.1, 76.4, 67.5, 39.1, 22.4.

(S)-Buta-1,2-dien-1-yltributylstannane (6e). n-BuLi (2.5 M in hexane, 172 mL, 429 mmol) was added in a drop wise fashion to a solution of diisopropylamine (60.7 mL, 429 mmol) in THF (800 mL) at 0° C. over a period of 10 min. After 15 min, $nBu_3SnH$ (135 mL, 501 mmol) was added in a drop wise fashion over a period of 7 min and the reaction mixture was stirred at 0° C. for 2.5 h. After cooling the reaction mixture to −85° C. (LESS THAN −78), CuBr·DMS (88.2 g, 429 mmol) was added in a portion wise fashion over the period of 40 min. The mixture was stirred at −85° C. (or LESS THAN −78) for 30 min. (R)-But-3-yn-2-yl methanesulfonate (6e2) (53.0 g, 358 mmol) was added in a drop wise fashion over a period of 2 min and the mixture stirred for a further 8 min. The reaction mixture was poured into a mixture of TBME (1.75 L), 25% aqueous $NH_3$ (260 mL) and satd. $NH_4Cl$ (2.12 L) and stirred vigorously for 1 h. The phases were separated. The organic phase was dried over $Na_2SO_4$, filtered, and concentrated on a rotary evaporator. Component 6e (77.2 g, 62.9%) was obtained by falling-film distillation.

Intermediate 6e: $^1$H NMR ($CDCl_3$, 300 MHz) δ 5.08-4.88 (m, 1H), 4.56 (p, J=7.0 Hz, 1H), 1.74-1.41 (m, 12H), 1.31 (h, J=7.2 Hz, 6H), 0.92 (dt, J=11.6, 7.7 Hz, 12H); $^{13}$C NMR ($CDCl_3$, 75 MHz) δ 209.1, 75.2, 74.3, 30.6, 28.9, 13.7, 10.3; chiral GC: 94.2% e.e.

Derivatization of 6e for determination of enantiomeric excess: Isobutyraldehyde (40 μL, 0.44 mmol) in $CH_2Cl_2$ (4 mL) was added in a drop wise fashion to solution of (S)-buta-1,2-dien-1-yltributylstannane (6e) (200 mg, 583 μmol) and $BF_3$·$OEt_2$ (210 μL, 1.66 mmol) cooled to −78° C. After stirring at −78° C. for 1 h, the reaction was quenched with a satd. $NaHCO_3$ (4 mL). The mixture was allowed to warm to rt and the phases were separated. The organic phase was stirred with KF on Celite (50 w %, 100 mg) and $Na_2SO_4$ (100 mg). The solid was removed by filtration and an aliquot of the filtrate was used for chiral GC analysis indicating 96% ee.

G. Component assembly to 17S-FD-895 (1). The following procedures and spectral data were developed for the assembly of components 6a-6c to 2 and 6d-6e to 3 and the coupling of 2 and 3 to deliver 17S-FD-895 (1), as shown in Scheme 1.

3-((4R,5S)-2-(4-methoxyphenyl)-4-methyl-5-vinyl-1,3-dioxolan-4-yl)propan-1-ol (7). To a 3 L round bottom flask equipped with a magnetic stir bar was sequentially added alcohol 6a (15.0 g, 42.5 mmol), wet iPrOH (1.5 L), $CBr_4$ (19.9 g, 63.8 mmol) and imidazole (0.145 g, 2.1 mmol). The mixture was heated to reflux and stirred overnight at which point mixture turns into a clear light brown solution. Complete conversion of 6a to intermediate was determined by NMR. The mixture was quenched with 4 Å molecular sieves (200 g) and cooled to rt. Mixture was filtered through an oven-dried vacuum funnel into a flame dried 2 L flask and concentrated in vacuo to yield a dark brown oil. Crude was immediately taken up in dry $CH_2Cl_2$ (300 mL) and purged with Ar atmosphere. Anisaldehyde dimethyl acetal (14.5 mL, 85.1 mmol) was added in one aliquot and mixture turned purple after 10 min stirring at rt. Reaction was further stirred at rt for 2 h. Satd. aqueous $NaHCO_3$ (100 mL) was added and the mixture was extracted into $CH_2Cl_2$. Organics were combined and concentrated in vacuo to yield a brown oil. Pure 7 (7.7 g, 65%) was obtained as a mixture of 5:3 acetal diastereomers by flash chromatography eluting with a gradient of hexanes to 35% EtOAc/hexanes. Note 1: Formation of intermediate is typically quantitative as determined by NMR and in practice is sufficiently pure to carry forward. Note 2: Intermediate is somewhat unstable and optimum yields may be obtained when anisaldehyde dimethyl acetal is added as soon as possible.

Alcohols 8: TLC (1:1 hexanes/EtOAc): $R_f$=0.37; CAM stain; one spot; $^1$H NMR Major ($C_6D_6$, 500 MHz) δ 7.55 (d, J=8.7 Hz, 2H), 6.82 (d, J=8.7 Hz, 2H), 5.91 (s, 1H), 5.84-5.75 (m, 1H), 5.31 (dt, J=17.1, 1.3 Hz, 1H), 5.07 (dt, J=10.4, 1.2 Hz, 1H), 4.09 (dt, J=7.1, 1 Hz, 1H), 4.24 (dt, J=7.1, 1 Hz), 3.25 (s, 3H), 3.39 (dd, J=9.7, 5.6 Hz, 1H), 3.64-3.58 (m, 1H), 1.83-1.63 (m, 4H), 1.38 (s, 3H); Minor: δ 7.50 (d, J=8.7 Hz, 2H), 6.80 (d, J=8.6 Hz, 2H), 6.16 (s, 1H), 5.84-5.75 (m, 1H), 5.31 (dt, J=17.1, 1.3 Hz, 1H), 5.07 (dt, J=10.4, 1.2 Hz, 1H), 4.09 (dt, J=7.1, 1 Hz, 1H), 4.24 (dt, J=7.1, 1 Hz), 3.25 (s, 3H), 3.39 (dd, J=9.7, 5.6 Hz, 1H), 3.64-3.58 (m, 1H), 1.83-1.63 (m, 4H), 1.38 (s, 3H); $^{13}$C NMR (500 MHz) δ 160.4, 160.2, 133.5, 133.4, 132.5, 130.7, 128.2, 127.7, 117.6, 117.5, 113.6, 113.5, 102.2, 101.9, 87.6, 85.6, 83.2, 82.0, 62.7, 62.6, 54.4, 33.4, 32.3, 31.0, 29.5, 28.2, 27.1, 26.9, 26.7, 22.1, 21.7; FTIR (film) vmax 3421, 3080, 2938, 1718, 1614, 1516, 1932, 1303, 1249, 1170, 1032 $cm^{-1}$; HR-ESI-MS m/z calcd. for $C_{16}H_{22}O_4Na$ $[M+Na]^+$: 301.1410, found 301.1411.

3-((4R,5S)-2-(4-methoxyphenyl)-4-methyl-5-vinyl-1,3-dioxolan-4-yl)propanal (8). To a 2 L flask was sequentially added alcohols 7 (7.5 g, 26.9 mmol), DMSO (250 mL), and freshly prepared IBX (18.9 g, 67.4 mmol). Mixture was stirred at rt for 2 h at which point TLC indicated complete conversion. Mixture was diluted with 350 mL of EtOAc and washed with 150 mL of $H_2O$. Aqueous layer was back extracted with EtOAc (2×250 mL). Organic layers were combined and further washed with $H_2O$ (5×450 mL) and brine (250 mL). Organics were concentrated in vacuo and subsequent oil was filtered through a pad of Celite and eluted with EtOAc. Elutants were concentrated to yield 8 (6.70 g, 90%) as a yellow oil that was carried directly to the next reaction. Note: Aldehydes 9 are susceptible to rearrangement when purified over unbuffered silica gel. In practice this material was sufficiently clean to employ for the subsequent reaction without chromatography; however crude 9 may be purified over neutral silica gel eluting with a gradient of hexanes to 25% EtOAc/hexanes.

Aldehydes 9: $^1$H NMR ($C_6D_6$, 500 MHz) δ Major Isomer 9.26 (s, 1H), 7.44 (d, J=8.7 Hz, 2H), 6.76 (d, J=4.3 Hz, 2H), 5.80 (s, 1H), 5.67 (m, 1H), 5.25 (d, J=12.9 Hz, 1H), 5.01 (d, J=4.7 Hz, 1H), 3.99 (d, J=6.6 Hz, 1H), 3.23 (s, 3H), 2.17-2.28 (m, 1H), 1.93-2.07 (m, 2H), 1.80-1.87 (m, 1H), 1.34-1.41 (m, 1H), 1.20-1.25 (m, 1H), 0.96 (s, 3H); Minor Isomer 9.36 (s, 1H), 7.42 (d, J=8.7 Hz, 2H), 6.78 (d, J=4.3 Hz, 2H), 6.00 (s, 1H), 5.62 (m, 1H), 5.21 (d, J=12.9 Hz, 1H), 4.99 (d, J=4.7 Hz, 1H), 4.07 (d, J=6.6 Hz, 1H), 3.22 (s, 3H), 2.17-2.28 (m, 1H), 1.93-2.07 (m, 2H), 1.80-1.87 (m, 1H), 1.34-1.41 (m, 1H), 1.20-1.25 (m, 1H), 0.97 (s, 3H); $^{13}$C NMR ($C_6D_6$, 500 MHz) δ 200.2, 200.0, 160.5, 160.2, 132.8, 132.7, 132.3, 130.4, 117.82, 117.78, 113.64, 113.56, 102.2, 101.9, 87.2, 85.3, 82.4, 81.0, 54.4, 38.5, 38.1, 28.9, 25.3, 22.2, 21.5.

Hectogram Preparation of 2-iodoxybenzoic acid (IBX): To a 5 L flask equipped with a magnetic stir bar was added solid oxone and deionized $H_2O$. Mixture was stirred and heated to 75° C. After oxone fully dissolves 2-iodobenzoic acid was added as a solid and mixture was vigorously stirred at 75° C. for 4 h. After stirring is stopped a white precipitate (product) settles on the bottom of the flask. Mixture was vacuum filtered over a Büchner funnel and the isolated white powder was further washed with $H_2O$ (3×150 mL) and acetone (3×100 mL). IBX was obtained as a crystalline white powder and stored in −20° C. Characterization data matched literature values previously reported by Frigerio, M; et al.

(3R)-1-((R)-5-(tert-butyl)-2-thioxothiazolidin-3-yl)-3-hydroxy-5-((4R,5S)-2-(4-methoxy-phenyl)-4-methyl-5-vinyl-1,3-dioxolan-4-yl)pentan-1-one (9). To a flame dried 3 L flask equipped with a stir bar was added auxiliary 6b (13.76 g, 63.3 mmol) as a solid and taken up in anhydrous toluene. Solution was concentrated via rotary evaporation to remove trace amounts of moisture. Flask was then purged with argon and taken up in dry $CH_2Cl_2$ (600 mL). Dichlorophenylborane (8.22 mL, 63.3 mmol) was added at rt and stirred at rt for 15 min. (−)-Sparteine (29.1 mL, 126.7 mmol) was added neat at which point mixture turns cloudy but clears up upon further stirring. After stirring at rt for 30 min mixture was cooled to −78° C. and aldehydes 8 (14.0 g, 50.7 mmol) in a solution of dry DCM (75 mL) were added dropwise over 15 min. Mixture was stirred at −78° C. for 1 h and slowly warmed to 0° C. over 3 h at which point NMR indicated complete consumption of starting material. Mixture was quenched with satd. aqueous $NaHCO_3$ (200 mL) and the organic layer was separated. Aqueous layer was washed with $CH_2Cl_2$ (200 mL) and organic layers were combined, dried over $Na_2SO_4$, filtered, and concentrated in vacuo to yield crude 9 as a deep yellow oil. Material was then passed through a vacuum funnel plug (DCVC) of neutral silica gel eluting with a gradient of 50% EtOAc/hexanes into a 3 L flask. Mixture was concentrated and further dried via removal of toluene and carried directly to the next step. A small aliquot was purified via preparatory TLC for spectroscopy. Note 1: Selectivity of the acetate aldol reaction was obtained at a 10:1 ratio. Resolution of the unwanted diastereomer was achieved at the saponification step 2 steps further. Note 2: Aldol adduct 9 is susceptible to hydrolysis when purified on untreated silica gel. Flash chromatography on neutral silica gel (Silicycle) eluting with a gradient of hexanes to 50% EtOAc/hexanes can be used to obtain 9 in 95%+purity. In practice this material is sufficiently clean after passing it through a vacuum funnel plug of neutral silica as noted in the procedure. Note 3: (−)-sparteine can be recovered from the DCVC column.

Alcohol 9: TLC (25% EtOAc/Hex) $R_f$=0.23 $^1$H NMR ($C_6D_6$, 500 MHz) δ Major Isomer 7.49 (d, J=8.6 Hz, 2H), 6.77 (d, J=8.7 Hz, 2H), 6.23 (s, 1H), 5.83-5.76 (m, 1H), 5.31-5.25 (m, 1H), 5.08-5.00 (m, 2H), 4.18 (d, J=6.7 Hz, 1H), 3.64-3.57 (m, 1H), 3.24 (s, 3H), 2.46 (m, 2H), 2.02-1.94 (m, 2H), 1.93-1.85 (m, 1H), 1.66-1.50 (m, 3H), 1.20 (s, 3H), 0.71 (s, 9H); Minor Isomer δ 7.59 (d, J=8.7 Hz, 2H), 6.83 (d, J=8.8 Hz, 2H), 5.91 (s, 1H), 5.89-5.79 (m, 1H), 5.01 (dd, J=9.2, 0.8 Hz, 1H), 4.09 (d, J=6.8 Hz, 1H), 3.58 (m, 1H), 3.25 (s, 3H), 2.46 (m, 2H), 2.02-1.94 (m, 2H), 1.93-1.85 (m, 1H), 1.66-1.50 (m, 3H), 1.17 (s, 3H), 0.68 (s, 9H); $^{13}$C NMR ($C_6D_6$, 500 MHz) δ Major Isomer 204.8, 172.6, 160.2, 133.5, 132.6, 128.0, 117.6, 113.5, 102.0, 86.0, 83.1, 71.6, 68.4, 54.4, 45.5, 30.5, 29.4, 29.1, 21.8; Minor Isomer δ 204.8, 172.6, 160.4, 133.4, 130.8, 128.4, 117.7, 113.7, 102.4, 87.7, 81.9, 71.6, 68.4, 54.4, 45.5, 30.9, 29.4, 29.1, 22.4.

(3R)-1-((R)-5-(tert-butyl)-2-thioxothiazolidin-3-yl)-3-((tert-butyldimethylsilyl)oxy)-5-((4R,5S)-2-(4-methoxyphenyl)-4-methyl-5-vinyl-1,3-dioxolan-4-yl)pentan-1-one (10). To a 3 L flask charged with crude 9 was sequentially added $CH_2Cl_2$ (600 mL) and 2,6-lutidine (29.5 mL, 253.3 mmol). Mixture was purged with argon and cooled to 0° C. TBSOTf (34.9 mL, 152.0 mmol) was added dropwise and mixture was warmed to rt and stirred for 2 h at which point NMR indicated complete consumption of starting material. Solution was quenched with addition of solid sodium bicarbonate (20 g) and stirred for 15 min. Mixture was vacuum filtered through a DCVC pad of neutral silica gel eluting with $CH_2Cl_2$ (1.5 L) into a 3 L flask. Elutants were concentrated in vacuo to yield 10 as a deep yellow crude oil and was carried directly to the next reaction. A small aliquot was purified via prep TLC for spectroscopy.

Intermediate 10: TLC (100% $CH_2Cl_2$) $R_f$=0.40 $^1$H NMR ($C_6D_6$, 500 MHz) δ Major Isomer 7.61 (d, J=8.6 Hz, 2H), 6.89 (d, J=8.7 Hz, 2H), 5.94 (s, 1H), 5.85 (m, 1H), 5.34 (d, J=17.1 Hz, 2H), 5.11 (d, J=10.6 Hz, 2H), 5.03 (d, J=8.3 Hz, 1H), 4.46 (m, 1H), 4.14 (d, J=17.1, 1H), 3.85-3.55 (m, 2H), 3.31 (s, 3H), 2.57 (m, 2H), 2.03 (d, J=11.8 Hz, 2H), 1.91 (m, 2H), 1.26 (s, 3H), 1.00 (s, 9H), 0.77 (s, 9H), 0.19 (s, 3H), 0.14 (s, 3H). Minor Isomer 7.56 (d, J=8.6 Hz, 2H), 6.81 (d, J=8.7 Hz, 2H), 6.31 (s, 1H), 5.85 (m, 1H), 5.34 (d, J=17.1 Hz, 2H), 5.11 (d, J=10.6 Hz, 2H), 5.06 (d, J=8.3 Hz, 1H), 4.54 (m, 1H), 4.23 (d, J=17.1, 1H), 3.85-3.55 (m, 2H), 3.26 (s, 3H), 2.54 (m, 2H), 2.03 (d, J=11.8 Hz, 2H), 1.91 (m, 2H), 1.9 (s, 3H), 1.03 (s, 9H), 0.78 (s, 9H), 0.22 (s, 3H), 0.19 (s, 3H); $^{13}$C NMR ($C_6D_6$, 500 MHz) δ 204.7, 204.6, 170.5, 170.4, 160.4, 160.2, 133.3, 133.2, 132.6, 130.9, 128.3, 128.0, 127.8, 127.6, 117.6, 117.5, 113.7, 113.6, 102.4, 102.0, 87.6, 85.7, 83.1, 82.1, 81.1, 71.7, 69.1, 69.0, 54.4, 46.0, 45.7, 37.5, 32.4, 31.7, 31.2, 29.4, 28.5, 26.1, 25.9, 25.8, 25.5, 22.4, 21.8, 18.0. Note 1: 10 can be further purified (95%+) via flash chromatography on neutral silica gel eluting with a gradient of hexanes to $CH_2Cl_2$. In practice the material is sufficiently clean to proceed to the next step without chromatography.

(3R)-3-((tert-butyldimethylsilyl)oxy)-5-((4R,5S)-2-(4-methoxyphenyl)-4-methyl-5-vinyl-1,3-dioxolan-4-yl)pentanoic acid (4)

Lithium hydroxide monohydrate (6.38 g, 0.152 mmol) was added to a 3 L flask containing a solution of crude 10 in 4:1 $CH_3CN/H_2O$ (250 mL). Mixture was stirred at rt overnight at which point the deep yellow color dissipates into a light brown. The mixture was diluted with 200 mL of $H_2O$ and 200 mL of ether. The aqueous layer was collected and the organic layer was back extracted with $H_2O$ (2×100 mL). The aqueous layers were combined and carefully acidified to pH 6 with 1 M HCl. Mixture was extracted into EtOAc (3×500 mL) and organics were combined, dried over $Na_2SO_4$, filtered, and concentrated in vacuo to yield a clear brown oil. Material was purified over silica gel eluting with a gradient of hexanes to 30% EtOAc/hexanes to yield acids 4 (5.5 g, 50% over four steps) as a light brown oil. Note 1: Minor diastereomer obtained from the acetate aldol reaction is removed at this step following chromatography.

Acids 4: TLC (50% EtOAc/Hexanes) $R_f$=0.54; $^1$H NMR ($C_6D_6$, 500 MHz) δ Major Isomer 7.51 (d, J=8.7 Hz, 2H), 6.82 (d, J=8.7 Hz, 2H), 5.88 (s, 1H), 5.77 (m, 1H), 5.28 (d, J=10.5, 1H), 5.06 (d, J=10.5, 1H), 4.07 (m, 1H), 3.26 (s, 3H), 2.17-2.47 (m, 2H), 1.84 (m, 2H), 1.60 (m, 2H), 1.13 (s, 3H), 0.92 (s, 9H), 0.06 (s, 3H), 0.02 (s, 3H); Minor Isomer 7.50 (d, J=8.7 Hz, 2H), 6.78 (d, J=8.7 Hz, 2H), 6.16 (s, 1H), 5.77 (m, 1H), 5.28 (d, J=10.5, 1H), 5.06 (d, J=10.5, 1H), 4.15 (m, 1H), 3.23 (s, 3H), 2.17-2.47 (m, 2H), 1.84 (m, 2H), 1.60 (m, 2H), 1.16 (s, 3H), 0.95 (s, 9H), 0.10 (s, 3H), 0.07 (s, 3H); $^{13}$C NMR ($C_6D_6$, 500 MHz) δ

(3S,4S,E)-1-iodo-2,4-dimethylhexa-1,5-dien-3-yl-(3R)-3-((tert-butyldimethylsilyl)oxy)-5-((4R,5S)-2-(4-methoxyphenyl)-4-methyl-5-vinyl-1,3-dioxolan-4-yl)pentanoate (11)

Acids 4 (5.5 g, 12.2 mmol) and alcohol 6c (3.23 g, 12.8 mmol) were combined in a 250 mL round bottom and dried via removal of toluene prior to use. DMAP (0.150 g, 1.22 mmol) and pivalic anhydride (3.71 mL, 18.3 mmol) were added sequentially and the mixture was stirred neat at 50° C. for 5 h. Pivalic anhydride was then removed from the mixture under a constant stream of air overnight. Crude material was then loaded directly onto silica gel and eluted with a gradient of hexanes to 10% $Et_2O$/hexanes to yield esters 11 (6.7 g, 80%) as a clear oil. Note 1: Pivalic anhydride tends to streak and decrease resolution on silica gel. Maximum purification resolution is achieved when little to no pivalic anhydride is present in the crude mixture prior to chromatography. Note 2: A thin 1 cm stir bar is most effective for this reaction as it allows for vigorous stirring without splattering along the sides of the flask.

Esters 11: $^1H$ NMR ($C_6D_6$, 500 MHz) δ Major Isomer 7.54 (d, J=8.7 Hz, 2H), 6.83 (d, J=8.6 Hz, 2H), 6.16 (s, 1H), 5.90 (s, 1H), 5.84-5.76 (m, 1H), 5.66-5.56 (m, 1H), 5.30 (d, J=17.3 Hz, 1H), 5.13 (d, J=8.1 Hz, 1H), 5.07 (d, J=8.1 Hz, 2H) 4.99-4.87 (m, 2H), 4.09 (dt, J=6.5, 1.3 Hz, 1H), 3.27 (s, 3H), 2.40 (dd, J=15.1, 6.6 Hz, 1H), 2.19 (dd, J=15.0, 5.7 Hz, 1H), 1.89-1.80 (m, 2H), 1.75 (dd, J=12.9, 3.7 Hz, 1H), 1.66 (s, 3H), 1.65 (m, 2H), 1.19 (s, 3H), 0.95 (s, 9H), 0.66 (d, J=6.9 Hz, 3H), 0.09 (s, 2H), 0.07 (s, 2H). Minor Isomer δ 7.52 (d, J=8.7 Hz, 2H), 6.79 (d, J=8.6 Hz, 2H), 6.19 (s, 1H), 6.17 (s, 1H), 5.84-5.76 (m, 1H), 5.66-5.56 (m, 1H), 5.16 (d, J=8.1 Hz, 1H), 5.07 (d, J=8.1 Hz, 2H) 4.99-4.87 (m, 2H), 4.09 (dt, J=6.5, 1.3 Hz, 1H), 3.23 (s, 3H), 2.47 (dd, J=15.0, 6.3 Hz, 1H), 2.27 (m, 2H) 1.98-1.96 (m, 2H), 1.68 (s, 3H), 1.22 (s, 3H), 0.98 (s, 9H), 0.67 (d, J=6.9 Hz, 3H), 0.12 (s, 3H), 0.11 (s, 3H); $^{13}C$ NMR ($C_6D_6$, 500 MHz) δ Major Isomer 164.7, 160.4, 144.6, 139.3, 133.3, 130.9, 128.2, 128.0, 127.8, 127.6, 127.4, 127.2, 117.6, 115.4, 113.6, 102.3, 87.5, 81.7, 81.5, 80.0, 69.5, 54.4, 42.6, 42.3, 40.0, 32.5, 31.4, 25.7, 22.4, 20.0, 17.9, 16.0; Minor Isomer 169.6, 160.2, 144.5, 139.5, 133.2, 132.5, 128.2, 128.0, 127.8, 127.6, 127.4, 127.2, 117.5, 115.4, 113.5, 120.0, 85.6, 83.0, 81.6, 80.0, 69.4, 54.4, 40.0, 30.0 28.5, 25.7, 21.8, 20.0, 17.9, 16.1.

(3aS,6S,7S,11R,13aR,E)-11-((tert-butyldimethylsilyl) oxy)-7-((E)-1-iodoprop-1-en-2-yl)-2-(4-methoxyphenyl)-6, 13a-dimethyl-3a,6,7,10,11,12,13,13a-octahydro-9H-[1,3] dioxolo[4,5-f][1]oxacyclododecin-9-one (12). Esters 11 were dried via rotary evaporation of toluene in a 3 L flask and then charged with anhydrous toluene (700 mL). Mixture was purged with Ar and heated to reflux. Hoveyda-Grubbs $2^{nd}$ Gen. catalyst (0.520 mg, 0.830 mmol) was added dropwise as a solution in dry toluene (500 mL) via a 1 L addition funnel. After stirring for 20 min. mixture turns from a clear green color into a black solution and is further stirred at reflux for 5 h. Mixture is then cooled to rt and concentrated. Crude black semi-solid is suspended in hexanes and filtered through a pad of Celite eluting with hexanes. Elutants were concentrated to yield a green oil which was purified over silica gel eluting with a gradient of hexanes to 15% $Et_2O$/hexanes to yield macrocycles 12 (3.25 g, 51%) as an off-white solid.

Macrocycles 12: $^1H$ NMR (500 MHz, $C_6D_6$) Major δ 7.57 (d, J=8.7 Hz, 2H), 6.86 (d, J=8.7 Hz, 2H), 6.24 (s, 1H), 5.93 (s, 1H), 5.88-5.75 (m, 1H), 5.72-5.56 (m, 1H), 5.33 (d, J=17.2 Hz, 1H), 5.16 (d, J=8.1 Hz, 1H), 5.03-4.90 (m, 2H), 4.25-4.10 (m, 1H), 3.30 (s, 3H), 2.45 (d, J=6.6 Hz, 1H), 2.42 (d, J=6.6 Hz, 1H), 2.34-2.20 (m, 3H), 2.04-1.75 (m, 2H), 1.69 (s, 3H), 1.22 (s, 3H), 0.98 (s, 9H), 0.69 (d, J=6.9 Hz, 3H), 0.12 (s, 3H), 0.10 (s, 3H); Minor δ 7.55 (d, J=8.7 Hz, 2H), 6.83 (d, J=8.7 Hz, 2H), 6.22 (s, 1H), 6.19 (s, 1H), 5.88-5.75 (m, 1H), 5.72-5.56 (m, 1H), 5.19 (d, J=17.2 Hz, 1H), 5.10 (d, J=8.1 Hz, 1H), 5.03-4.90 (m, 2H), 4.25-4.10 (m, 1H), 3.27 (s, 3H), 2.51 (d, J=6.6 Hz, 1H), 2.49 (d, J=6.6 Hz, 1H), 2.34-2.20 (m, 3H), 2.04-1.75 (m, 2H), 1.71 (s, 3H), 1.25 (s, 3H), 1.01 (s, 9H), 0.71 (d, J=6.9 Hz, 3H), 0.15 (s, 3H), 0.14 (s, 3H); $^{13}C$ NMR (500 MHz, $C_6D_6$) δ

(4R,7R,8S,11S,12S,E)-4,7,8-trihydroxy-12-((E)-1-iodoprop-1-en-2-yl)-7,11-dimethyloxacyclododec-9-en-2-one (13). Lactone 12 (3.25 g, was dissolved in 5:1 $CH_2Cl_2$/MeOH (300 mL) and CSA (3.45 g, 14.9 mmol) was added as a solid. Mixture was stirred for 5 h at which point TLC indicated complete conversion of starting material. Satd. bicarbonate solution (50 mL) and mixture was extracted into $CH_2Cl_2$. Organics were collected and concentrated to a crude oil that was further purified on silica gel ($CH_2Cl_2$ to 35% Acetone/$CH_2Cl_2$) to yield pure 13 (1.10 g, 52%).

Triol 13: TLC (30% Ace/$CH_2Cl_2$) $R_f$=0.25; $^1H$ NMR ($CDCl_3$, 500 MHz) δ 6.49 (s, 1H), 5.76 (dd, J=15.2, 9.7 Hz, 1H), 5.40 (dd, J=15.2, 9.9 Hz, 1H), 5.31 (d, J=10.7 Hz, 1H), 3.82 (d, J=9.8 Hz, 1H), 3.77 (dt, J=11.3, 3.6 Hz, 1H), 2.69-2.46 (m, 3H), 1.84 (s, 3H), 1.70 (tt, J=13.1, 4.3 Hz, 1H), 1.52-1.36 (m, 2H), 1.32 (s, 3H), 1.25 (m, 1H), 0.93 (d, J=6.7 Hz, 3H).

(2S,3S,6S,7R,10R,E)-7,10-dihydroxy-2-((E)-1-iodoprop-1-en-2-yl)-3,7-dimethyl-12-oxooxacyclododec-4-en-6-yl acetate (2). Triol 13 (1.10 g, 2.6 mmol) and CSA (0.12 g, 0.52 mmol) were dissolved in $CH_2Cl_2$ (100 mL) and cooled to 0° C. Trimethyl orthoformate (0.40 mL, 3.1 mmol) in a solution of $CH_2Cl_2$ (20 mL) was added via addition funnel and mixture was stirred at 0° C. for 1 h at which point saturated aq. bicarb. (5 mL) was added. Mixture was extracted into $CH_2Cl_2$ and organics were concentrated to a crude oil, which was purified on silica gel ($CH_2Cl_2$ to 25% Acetone/$CH_2Cl_2$) to yield pure core 2 (980 mg, 81%) as an off-yellow semi-solid.

Core 2: TLC (3:1 hexanes/EtOAc): $R_f$=0.16; 1 H NMR ($CDCl_3$, 500 MHz) δ 6.47 (s, 1H), 5.67 (dd, J=15.2, 9.5 Hz, 1H), 5.57 (dd, J=15.2, 9.7 Hz, 1H), 5.29 (d, J=10.5 Hz, 1H), 5.05 (d, J=9.5 Hz, 1H), 3.75 (bs, 1H), 3.42 (d, J=11.1 Hz, 1H), 2.66-2.44 (m, 3H), 2.09 (s, 3H), 1.82 (s, 3H), 1.62-1.31 (m, 4H), 1.20 (s, 3H), 0.90 (d, J=6.7 Hz, 3H); $^{13}C$ NMR (CDCl3, 100 MHz) δ 172.0, 169.8, 143.5, 139.8, 126.3, 84.4, 80.4, 78.9, 73.5, 69.3, 41.1, 38.4, 35.3, 29.9, 24.8, 21.5, 19.2, 16.5; FTIR (film) vmax 3502, 3058, 2959, 2873, 1733, 1616, 1368, 1243, 1168, 1021 $cm^{-1}$; HR-ESI-MS m/z calcd. for $C_{18}H_{27}IO_6Na$ $[M+Na]^+$: 489.0745, found 489.0742.

((2R,3R)-3-((2R,3S)-3-methoxypentan-2-yl)oxiran-2-yl) methanol (14). Tert-butyl hydroperoxide in a 5.5 M solution in decane (46.0 mL, 253 mmol) was added to a 1 L round bottom flask containing a stirring solution of $Ti(O\text{-}iPr)_4$ (2.73 mL, 12.6 mmol), (−)-diethyl tartrate (2.2 mL, 12.6 mmol) and powdered 4 Å molecular sieves (2 g) in dry $CH_2Cl_2$ (300 mL). Mixture was cooled to −20° C. The resulting mixture was stirred at −20° C. for 30 min. A solution of alcohol 6d (20.0 g, 127 mmol) in $CH_2Cl_2$ (40 mL) was added dropwise. The reaction was warmed to −10° C. over 1 h and stirred at −10° C. for 2 h. The reaction was quenched via addition of 10% aqueous NaOH (25 mL). $MgSO_4$ (20 g) was added and mixture was filtered through a pad of Celite and elutants were concentrated. Crude product was purified on silica gel (hexanes to 50% EtOAc/Hexanes) to yield epoxyalcohol 14. Notes: Selectivity was obtained at a 11:1 ratio as determined by NMR. Diastereomers were not separable and carried on directly to the oxidation step.

Epoxyalcohol 14: TLC (2:1 hexanes/EtOAc): $R_f$=0.10; $^1H$ NMR ($C_6D_6$, 500 MHz) δ 3.56-3.48 (m, 1H), 3.33-3.26 (m, 1H), 3.17 (s, 3H), 3.07-3.03 (m, 1H), 2.86 (dd, J=7.7, 2.3 Hz, 1H), 2.78 (dd, J=7.2, 2.3 Hz, 1H), 2.59 (dt, J=4.9, 2.6 Hz, 1H), 1.62-1.49 (m, 1H), 1.41-1.29 (m, 3H), 0.99 (d, J=6.9 Hz, 1H), 0.84-0.79 (m, 3H). $^{13}C$ NMR ($C_6D_6$, 500 MHz) δ 83.4, 61.9, 57.6, 57.5, 57.4, 38.4, 23.6, 10.0, 9.78; FTIR (film) vmax 3422, 2972, 2930, 2879, 1468, 1103 $cm^{-1}$;

HR-ESI-MS m/z calcd. for $C_9H_{18}O_3$[M]$^+$: 174.1250, found 174.1249; $[\alpha]^{25}_D$=+4.0° (c=0.075, $CHCl_3$).

(2S,3R)-3-((2R,3S)-3-methoxypentan-2-yl)oxirane-2-carbaldehyde (15). To a 1 L round-bottom flask equipped with a magnetic stir bar was added epoxyalcohol 14 and DMSO (200 mL). Freshly prepared IBX was added as a solid and mixture was cooled to −20° C. in an ice salt bath. The oxidation reaction was stirred and warmed to rt over 2 h. Mixture was then diluted with EtOAc (500 mL) and $H_2O$ (250 mL) and extracted. The aqueous layer was back extracted with EtOAc (2×200 mL). The EtOAc layers were combined and washed with $H_2O$ (5×350 mL). The organic layer was then concentrated via rotary evaporation. The crude semisolid was then vacuum filtered through a plug of Celite and elutants were concentrated. Crude was purified over silica gel (hexanes to 30% EtOAc/Hex) to yield aldehyde 15 as a clear oil. Notes: Diastereomers in a 10:1 ratio were not separable at this step and carried on directly to the Marshall addition. Resolution was achieved after the stannylation of the allyne obtained in the next step.

Aldehyde 15: TLC (2:1 hexanes/EtOAc): $R_f$=0.55; $^1$H NMR ($C_6D_6$, 500 MHz) δ 8.68 (d, J=6.4 Hz, 1H), 3.10 (s, 3H), 2.91 (td, J=6.4, 4.0 Hz, 1H), 2.84 (dd, J=7.5, 2.0 Hz, 1H), 2.79 (dd, J=6.3, 2.0 Hz, 1H), 1.49-1.40 (m, 1H), 1.27-1.17 (m, 1H), 0.86-0.79 (m, 1H), 0.74 (t, J=7.4 Hz, 3H), 0.64 (d, J=7.0 Hz, 3H). $^{13}$C NMR ($C_6D_6$, 500 MHz) δ 197.3, 83.0, 59.0, 58.2, 57.4, 38.0, 23.4, 9.6, 9.4; FTIR (film) vmax 2972, 2930, 2879, 2828, 1732, 1468, 1103 cm 1; HR-ESI-MS m/z calcd. for $C_9H_{17}O_3$[M+H]$^+$: 173.1172, found 173.1174.

(1S,2R)-1-((2R,3R)-3-((2R,3S)-3-methoxypentan-2-yl) oxiran-2-yl)-2-methylbut-3-yn-1-ol (5). Aldehyde 15 (7.01 g, 40.8 mmol) and allenylstannane 6e (21.0 g, 61.0 mmol) were dried in a 500 mL round bottom flask prior to the reaction via azeotropic removal of toluene or benzene in vacuo. Cry $CH_2Cl_2$ (200 mL) was added to the flask and cooled to −78° C. $BF_3$ etherate (7.53 mL, 61.0 mmol) was added in a dropwise fashion over 5 min. The reaction was stirred for 1 h at −78° C. A mixture of MeOH (50 mL) and satd. $NaHCO_3$ (10 mL) was added and the mixture was warmed to rt. The layers were separated and the aqueous layer extracted with ether (3×20 mL). The organic layers were combined, washed with brine and dried with $Na_2SO_4$ and concentrated. Flash chromatography with a gradient from hexanes to 4:1 hexanes/EtOAc afforded alkyne 5 (80%) as a clear oil. Notes: Any minor diastereomers obtained from the Marshall addition are removed after chromatography. The remaining diastereomer from the Sharpless epoxidation was resolved after purification of the next step.

Alkyne 5: TLC (2:1 hexanes/EtOAc); $R_f$=0.50; CAM stain; one spot; $^1$H NMR ($CDCl_3$, 500 MHz) δ 3.58 (dd, J=4.4 Hz, 1H), 3.41 (s, 3H), 3.20 (td, J=6.4, 4.1 Hz, 1H), 3.06 (dd, J=8.1, 2.3 Hz, 1H), 2.91 (dd, J=4.5, 2.3 Hz, 1H), 2.81 (ddd, J=7.0, 4.3, 2.6 Hz, 1H), 2.17 (d, J=2.5 Hz, 1H), 2.05 (d, J=4.8 Hz, 1H), 1.67 (ddd, J=14.2, 7.6, 6.7 Hz, 1H), 1.53-1.44 (m, 2H), 1.31 (dd, J=7.1, 0.7 Hz, 3H), 0.97 (d, J=7.1 Hz, 3H), 0.90 (t, J=7.4 Hz, 3H); $^{13}$C NMR ($CDCl_3$, 500 MHz) δ 84.4, 83.8, 72.3, 71.4, 59.0, 58.3, 38.9, 30.4, 23.9, 17.0, 10.6, 10.1.

(1S,2R,E)-1-((2R,3R)-3-((2R,3S)-3-methoxypentan-2-yl) oxiran-2-yl)-2-methyl-4-(tributylstannyl)but-3-en-1-ol (3). To a solution of alkyne 5 in a 500 mL round bottom flask equipped with a magnetic bar was added freshly distilled THF over Na benzophenone (200 mL) and $PdCl_2(PPh_3)_2$. The mixture was cooled to −20° C. in ice salt bath. Tributyltin hydride was added dropwise at which point mixture gradually turns into a black solution. After mixture was stirred at −20° C. for 45 min the black solution was concentrated to yield a black crude oil. Material was taken up in hexanes, filtered through a pad of Celite and the elutant was concentrated. This process was repeated again to remove as much of the palladium catalyst as possible. The crude yellow-orange oil was purified over silica gel twice (hexanes to 5% $Et_2O$/hexanes) to yield vinylstannane 3 as a single diastereomer.

Vinylstannane 3: TLC (10:1 hexanes/$Et_2O$): $R_f$=; $^1$H NMR ($C_6D_6$, 500 MHz) δ 6.24 (dd, J=19.1, 6.8 Hz, 1H), 6.16 (d, J=6.8 Hz, 1H), 3.42 (td, J=4.9, 1.8 Hz, 1H), 3.20 (s, 3H), 3.13 (td, J=6.3, 4.2 Hz, 1H), 3.04 (dd, J=8.0, 2.3 Hz, 1H), 2.70 (dd, J=4.3, 2.3 Hz, 1H), 2.48 (td, J=6.9, 5.2 Hz, 1H), 1.58 (m, 6H), 1.45-1.29 (m, 7H), 1.16 (d, J=6.9 Hz, 3H), 0.99-0.89 (m, 19H), 0.83 (t, J=7.4 Hz, 3H); $^{13}$C NMR ($C_6D_6$, 500 MHz) δ 154.5, 150.5, 150.4, 150.4, 150.3, 83.8, 83.3, 72.8, 59.0, 57.5, 57.3, 57.2, 39.0, 39.0, 29.3, 27.4, 23.5, 15.9, 15.8, 13.4, 10.5, 9.63, 9.41.

Convergent Stille Coupling to 17S-FD-895 (1). Vinylstannane 5 (1.33 g, 2.57 mmol) and core macrolide 2 (1.00 g, 2.14 mmol) were combined in a 100 mL flask and dried via rotary evaporation of benzene. To the mixture was then sequentially added CuCl (0.425 g, 4.29 mmol), KF (0.249 g, 4.29 mmol) and XPhos Pd G2 (0.169 g, 0.214 mmol) and anhydrous t-butanol (25 mL). Reaction vessel was purged under Ar, heated to 50° C. and stirred overnight at which point solution turns into a gray cloudy mixture. Mixture was then directly filtered through a plug of celite and the plug was washed with acetone. Elutants were concentrated to yield a crude brown semi-solid, which was then purified over neutral silica gel eluting with a gradient of hexanes to 30% acetone/hexanes to yield 17S-FD-895 as a white semi-solid.

17S-FD-895 (1): Isomer 1SR: $^1$H NMR ($C_6D_6$, 400 MHz) δ 171.9, 168.7, 140.4, 138.1, 131.4, 131.3, 126.2, 125.8, 83.5, 82.4, 79.0, 73.1, 71.9, 69.1, 58.9, 57.4, 57.0, 41.6, 40.9, 38.9, 38.3, 35.6, 29.9, 24.5, 23.7, 20.5, 16.2, 16.1, 11.6, 10.6, 9.8; $^{13}$C NMR ($C_6D_6$, 100 MHz) δ 172.1, 169.0, 140.7, 137.9, 132.5, 132.4, 131.7, 131.3, 126.4, 126.4, 83.7, 82.6, 79.2, 73.3, 72.9, 69.3, 59.6, 57.7, 57.7, 41.5, 41.1, 39.3, 38.5, 35.8, 32.4, 30.3, 30.1, 29.8, 24.8, 23.9, 23.1, 20.7, 17.2, 16.4, 14.4, 11.9, 10.8, 10.0; FTIR (film) vmax 3447, 2963, 2930, 2875, 1739, 1457, 1374, 1239, 1176, 1089, 1021 cm$^{-1}$; [M+Na]$^+$; HR-ESI-MS m/z calcd. for $C_{31}H_{50}O_9Na_1$ [M+Na]$^+$: 589.3345, found 589.3347.

Example 3. Additional Synthetic Effort

Figure 9:
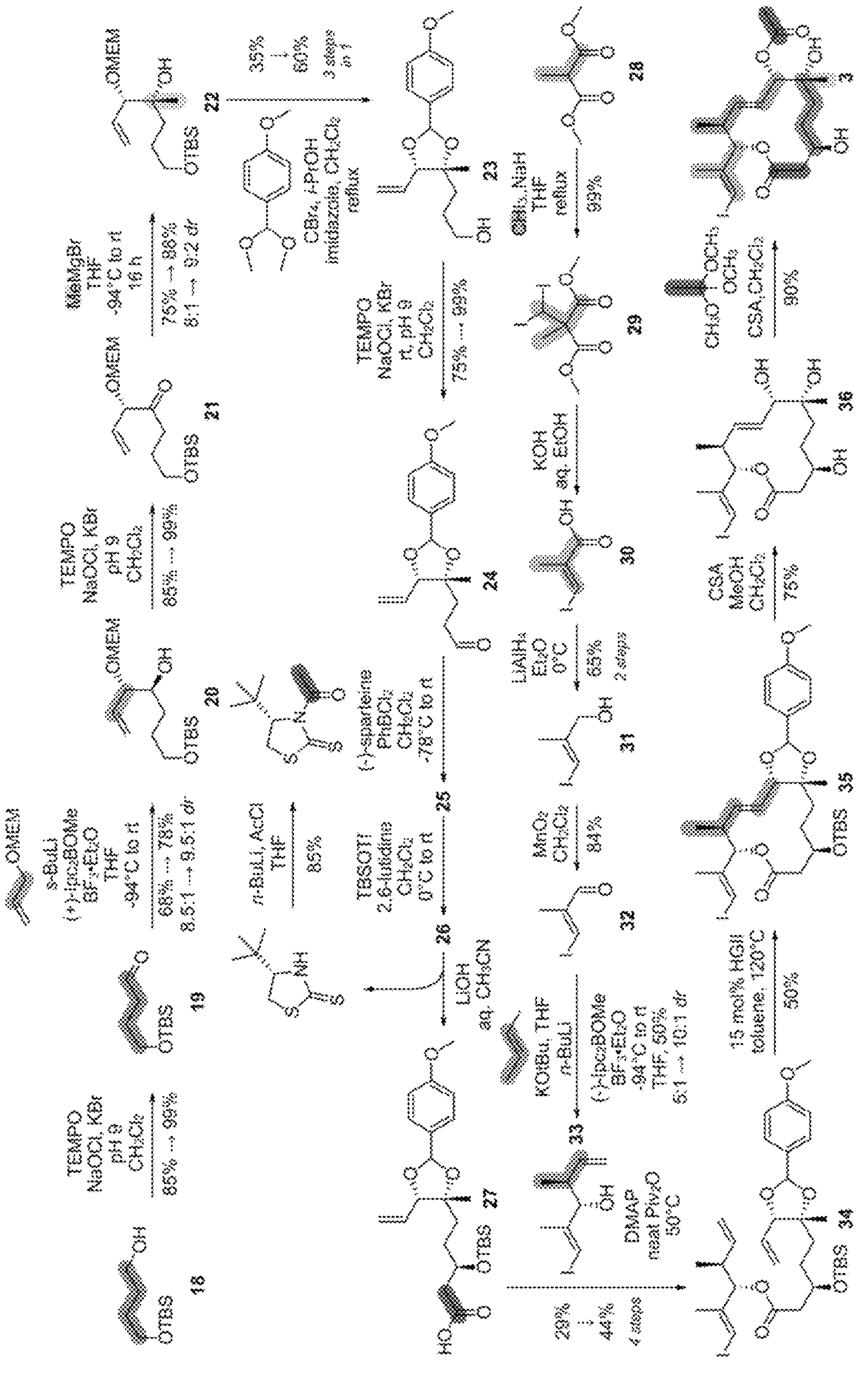
FIG. 9. Scheme A2. Synthesis of core 3 from mono-protected 1,4-butanediol 18. The yields and stereoselectivities indicated reflect the improvements made that enabled gram scale production. Abbreviations: Ipc, isopinocampheyl; Ph, phenyl; TBSOTf; tert-butyldimethylsilyl trifluoromethylsulfonyl; HGII, $2^{nd}$ generation Hoveyda-Grubbs catalyst; CSA, (1S)-(+)-10-camphorsulfonic acid.
Figure 10:
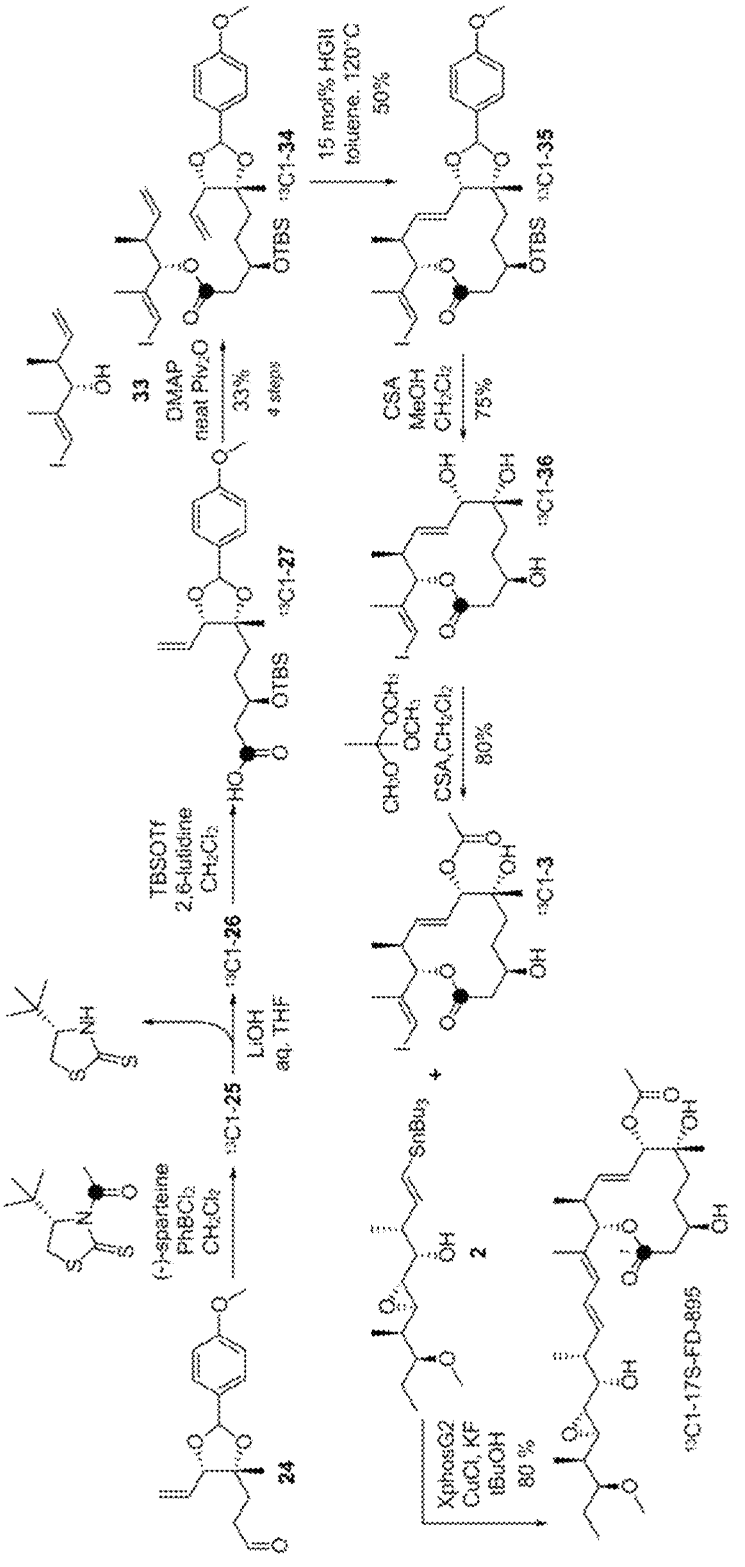
FIG. 10. Scheme AS1. Black sphere denotes position of $^{13}$C labeling.

The compound numbers used in Examples 3, 4, and 6 correspond to the compounds described in these examples, as well as the compounds described in FIGS. 3A-3B, FIGS. 4A-4F, FIGS. 5A-5H, FIG. 6, FIGS. 7A-7C, Scheme A1 (FIG. 8) and Scheme A2 (FIG. 9), Scheme AS1 (FIG. 10), Scheme AS2, Scheme AS3 (FIG. 11), Scheme AS4 (FIG. 12), Scheme AS5, and Tables S1-S3.

Since their first discovery in the mid-1990s, families of polyketide natural products, including FD-895, the pladienolides, the spliceostatins, herboxidiene, and the thailanstatins, have garnered interest due to selective antitumor activities (1-5). In recent years, two lead candidates, E7107 (6) and H3B-8800 (7), have advanced to Phase I clinical trials for solid tumors and leukemia. Mode of action studies indicate that they share similar abilities to modulate splicing (8-10) through interactions within the SF3B component of the spliceosome (11). First suggested as a consensus motif (12) and later validated by structural analyses (13), these small molecules uniquely position themselves at an interface between SF3B1, PHF5A, and SF3B3 (14), a hinge region involved in regulating the branch site adenosine-binding pocket (15,16). These splice modulators all possess a similar structural backbone containing a macrolactone ring linked by a diene to a side chain (17,18). Here, the importance and positioning of the stereochemical centers within these molecules clearly indicates a unique geometrical requirement for activity.

While many of these splice modulators display the necessary functional spatiality to enable facile binding to the SF3B pocket in vitro, the high density of their functional groups results in a low stability in biological media resulting in short half-lives ($t_{1/2}$≤30 min) (19). Recent studies now indicate that synthetic modifications along the side chain are not only tolerated, but allow for access to a three-dimensional arrangement that reduces the rate of degradation (19). These studies also indicate that synthetic analogs meet the requirements for active binding to the spliceosome pocket in vivo (13,14). This ultimately led to our identification of 17S-FD-895 (1) as a therapeutic lead (20).

While efforts have been developed to access gram scale quantities of pladienolides via fermentation (21), these approaches have been limited to the production of natural materials. To access the non-natural C17 stereocenter in 17S-FD-895, we focused on a synthetic approach. To date, reported gram scale synthesis has enabled access only to the less-complex herboxidiene (22). The synthetic challenges in facing gram scale preparation of 17S-FD-895 (1, FIG. 3A), include: 11 total stereocenters (6 contiguous), a substituted diene, remote functionality, a quaternary carbon and a 12-membered lactone. Our approach (FIG. 3A) expanded on prior milligram-scaled campaigns (FIG. 3B) (23-28) that identified the importance of component assembly. As 1 possesses potent biological activity, with a human maximum tolerated dose (MTD) estimated at 4 mg/m$^2$ (6), we opted for a route that avoided production of active materials until the final step. In general, we targeted a process that would be amenable for large-scale synthesis by reducing operations and chromatographic requirements.

We began by developing methods to prepare 20 g (0.039 mol) of side chain 2 (Scheme A1, FIG. 8) to secure over 15 g (0.027 mol) of 1. This started with optimization and preparation of Crimmins' auxiliary 7 on a kilogram scale (29). Diastereoselective aldol addition, followed by aminolysis and subsequent methylation, enabled the successful transition to 155 g (0.82 mol) of Weinreb amide 10 per batch from 235 g (0.94 mol) of 7 (23). Fortunately, we were able to recover 65±5% of 6. At this point, we encountered our first challenge: the high volatility of aldehyde 11. This was circumvented by a solvent change to 2-methyltetrahydrofuran, enabling reduction of 10 and homologation to 12 without isolation of 11. Next, DIBAL-H reduction afforded alcohol 13, which could be stored at 4° C. for over 2 years. Sharpless epoxidation of 13 provided 14 with a 6:1 dr (diastereomeric ratio), which was oxidized to 15 by use of TEMPO. As shown in Scheme A1 (FIG. 8), condensation of aldehyde 15 with Marshall allenylstannane 16 (30) provided allyne 17.

The next issue arose in the hydrostannylation of 17, where the use of a palladium catalyst generated only a 1:5 α:β regioselectivity. This led to contamination by traces of the undesired α-vinylstannane, which was reduced by use of Figueroa's molybdenum catalyst (31) (inset, Scheme A1) to a 1:10 dr favoring the desired β-stannane. Ultimately, effective chromatographic conditions assisted access to 2 with 95+% purity via LC/MS analysis. To date, we have stocked over 200 g (1.3 mol) of 13. Over multiple repetitions, we were able to synthesize 6.5±0.5 g (0.013 mol) of 2 from 25 g (0.16 mol) of 13 in a week.

Parallel efforts were also launched to produce 20 g (0.043 mol) of 3. We developed scalable methods to prepare intermediate 22 (23) in 300 g batches from mono-protected 18. To achieve this, TEMPO oxidations enabled scalable conversion of 18 to 19 and 20 to 21 without chromatography. Reducing the reaction temperature (−78° C. to −94° C.) improved the dr (85% to 95%) of the allylboration of aldehyde 19 to 20. Solvent change (THF to $Et_2O$) and reaction temperature optimization (−78° C. to −94° C.) improved the selectivity of the Grignard addition (85% to 90% dr) to 21 affording 22. This process currently requires a single chromatographic step (20, Scheme A2 (FIG. 9)). With a stability of over 4 years at −20° C., compound 22 provides an ideal storage point for batch preparation of core 3.

The conversion of 22 to 3 provided the most significant challenge. Previously established methods (23) to convert 22 to 23 relied on extremely pure $ZnBr_2$, whose hygroscopicity added complications when scaled. After reaction screening, we observed that the in situ decomposition of $CBr_4$ in i-PrOH (32) reproducibly returned 65±5% of 23, enabling three transformations in one step. The next challenge arose in the installation of the C1-C3 fragment. Upon oxidation to 24, we installed the remote C3 stereocenter in 9:1 dr using a chiral tert-leucine derived thiazolidinethione auxilary (29). Subsequent protection and saponification afforded acid 27, which was esterified with alcohol 33 (34) in neat pivalic anhydride (35) to afford 34. This 6-step sequence could be conducted in 3 days, accessing 10 g (0.015 mol) batches of 34 from 25 g (0.069 mol) of 22. At this point, we had installed the remaining 5 stereocenters required for 1 with 95+% purity in 34.

Next, we turned our attention to the challenging ring closing metathesis (Scheme A2 (FIG. 9)). Previously, the reaction had been performed at a maximum of 1 g (28) and suffered from allylic isomerization despite the use of additives (36). After screening catalysts and reaction conditions, we discovered that inverting the order of addition (a solution of $2^{nd}$ Hoveyda-Grubbs catalyst in toluene to 34 in refluxing toluene) provided acceptable yields of 35 on the 5-10 g scale. Subsequent global deprotection of 35 with mild acid, followed by selective acetylation of C7 in 36 via orthoester formation, yielded core 3. After optimization, we are now able to convert 30 g (0.083 mol) of 22 to 1.8±0.2 g (0.0039 mol) of 3 (95+% purity via LC/MS) in less than 2 weeks.

Figure 4A:
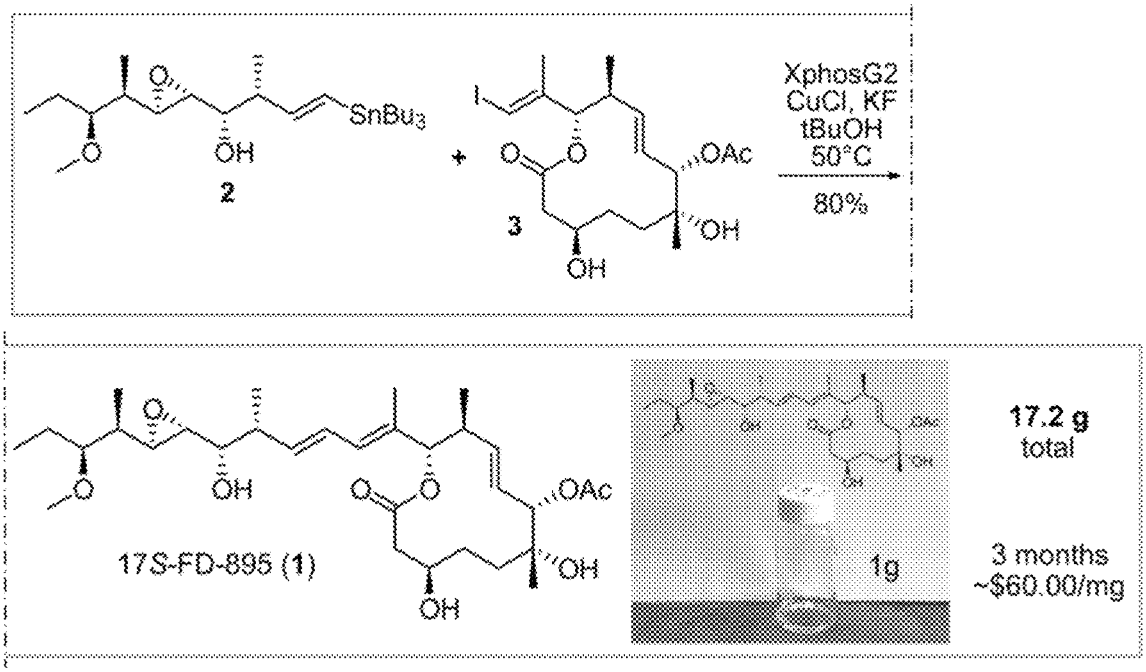
FIGS. 4A-4F. Synthesis of 17S-FD-895 (1), single-carbon isotopically-labeled materials and stereoisomeric analogues.

At this stage, we were set for the final step (FIG. 4A). We opted for an olefin cross-coupling at C13-C14, as alternate installation of the C14-C15 olefin by cross-metathesis or Julia-Kocienski olefination (FIG. 4B) (24,28,38) can be complicated by the formation of undesired cis-olefins. After parallelized-reaction screening, we settled on a Stille coupling using Buchwald's XPhos Pd G2 catalyst with CuCl and KF in anhydrous t-BuOH (39). Under Class III safety conditions, we prepared 1 in 80±2% yield, with a worker exposure of less than 3 h per 5 g batch. Fortunately, we were able to recover 16±3% of 3, which could be recycled, providing an effective mass balance in the conversion of 3 to 1. Side chain 2 was not recoverable.

Figure 4B:
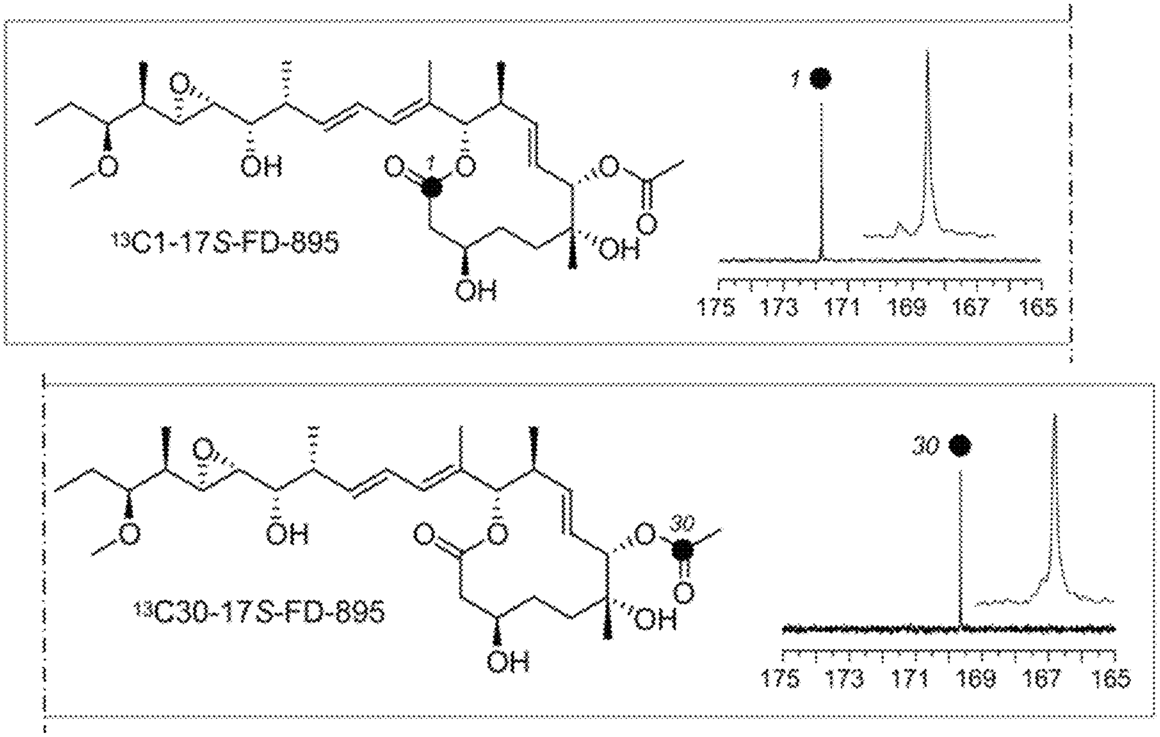
Figure 4C:
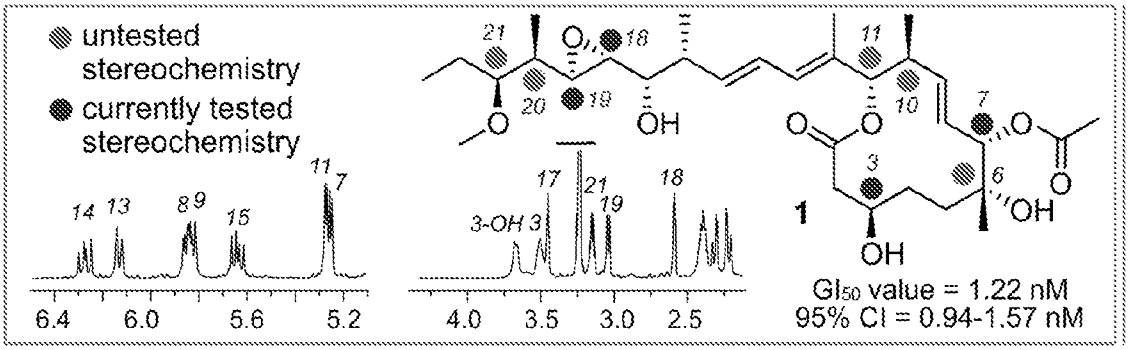
Figure 4D:
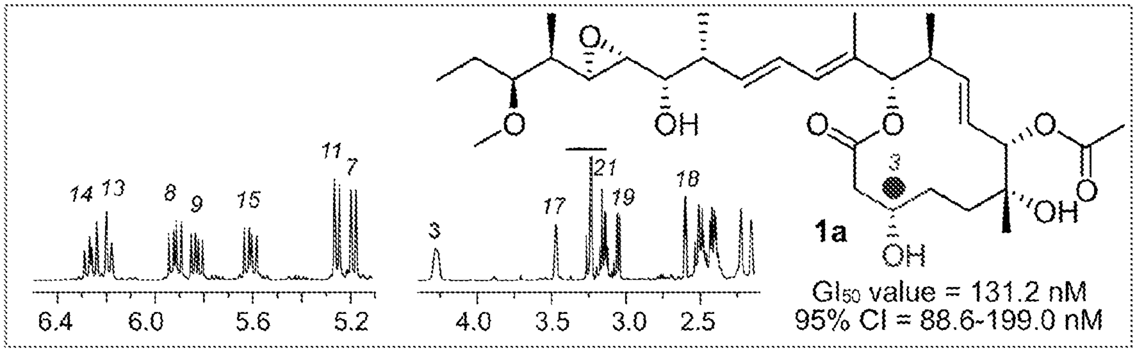
Figure 4E:
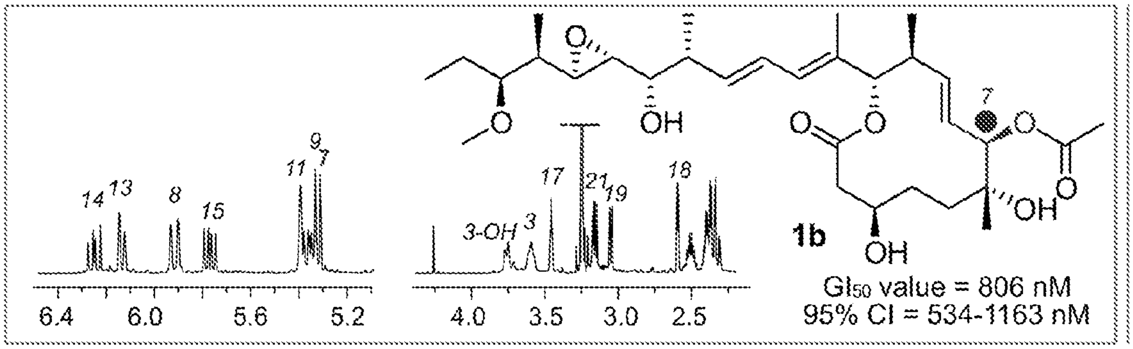
Figure 4F:
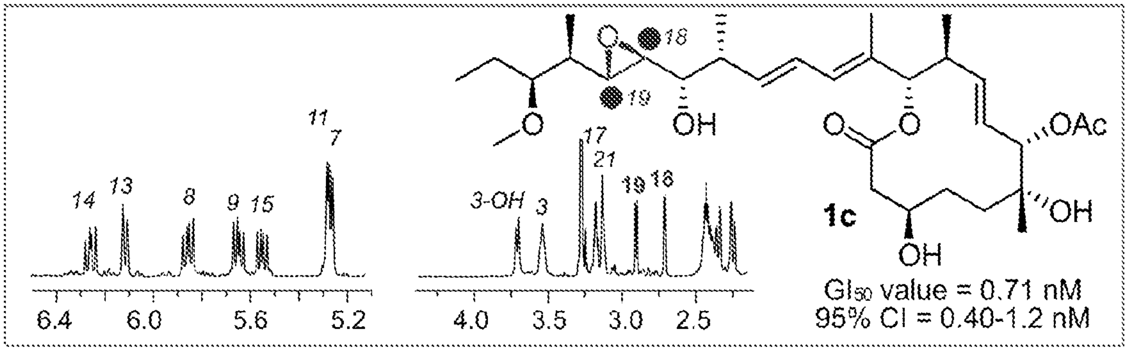
Figure 5A:
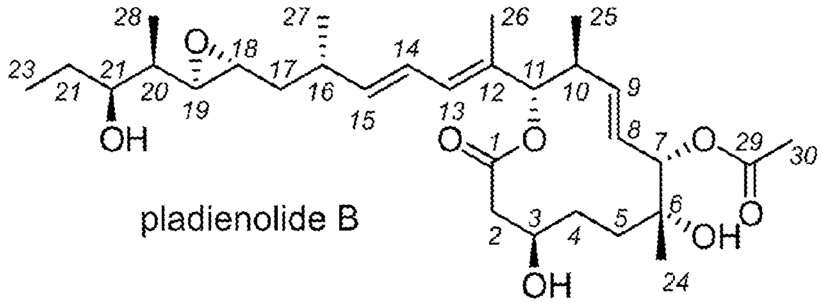
FIGS. 5A-5I. X-ray crystal structures depicting the binding of pladienolide B (PDB ID 6EN4), FD-895 (18) and CYP (18) within the SF3B core. Side-chains of residues observed within 6 Å from FIG. 5A: pladienolide B.
Figure 5A:
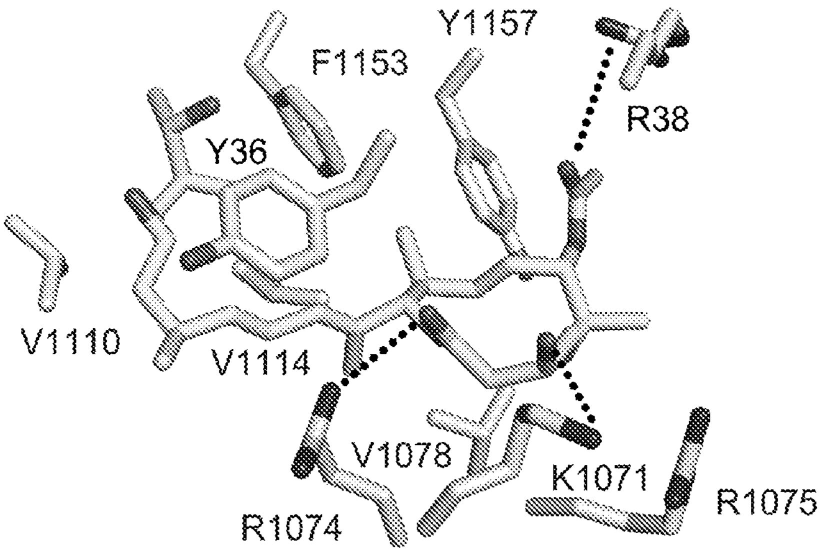
Figure 5B:
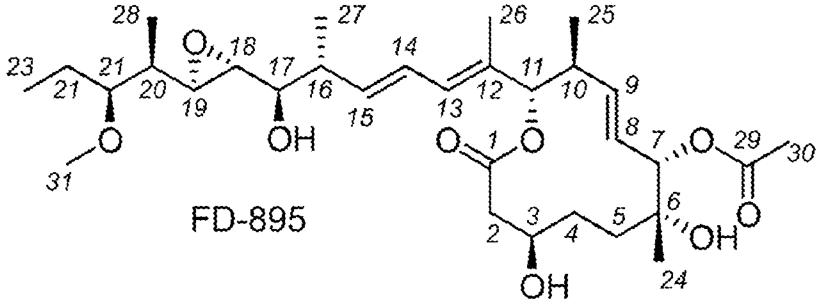
Figure 5B:
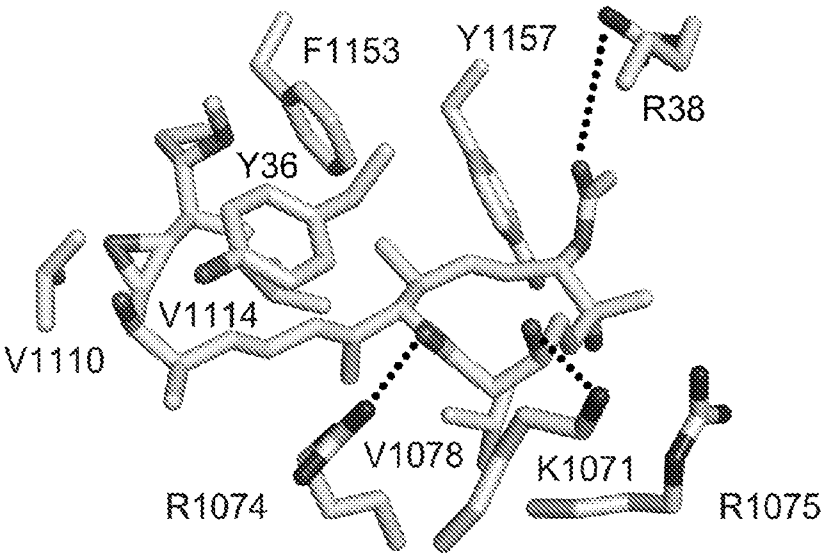
Figure 5C:
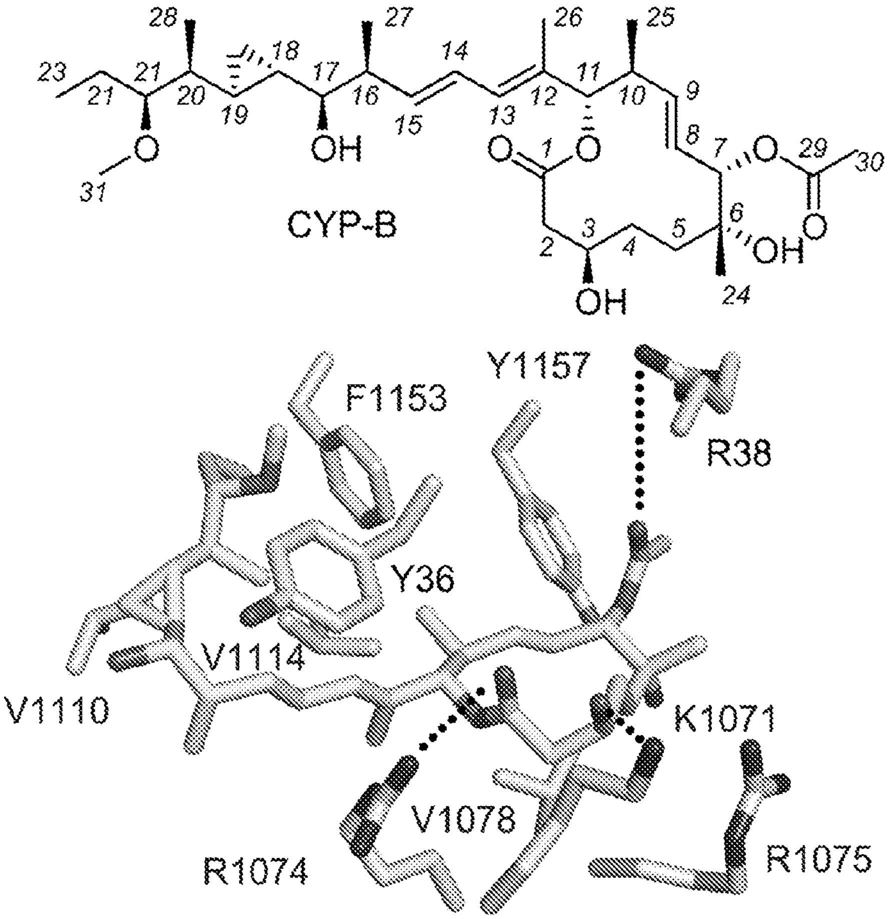
Figure 5D:
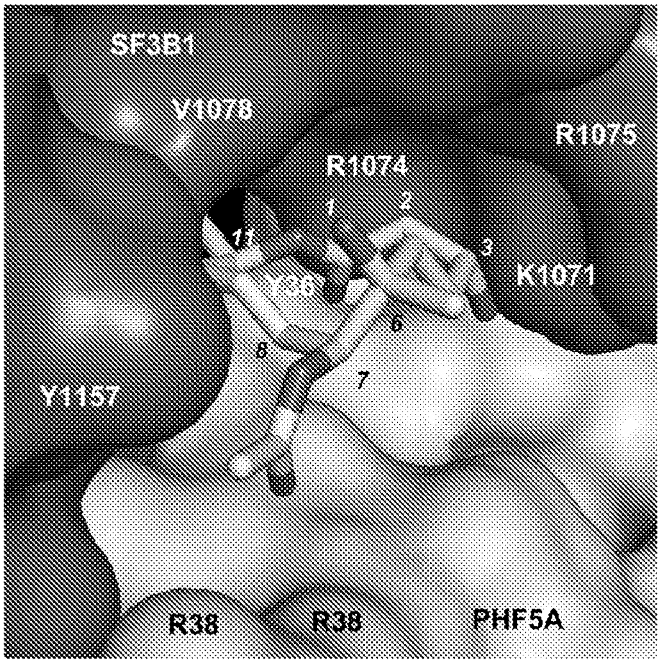
Figure 5E:
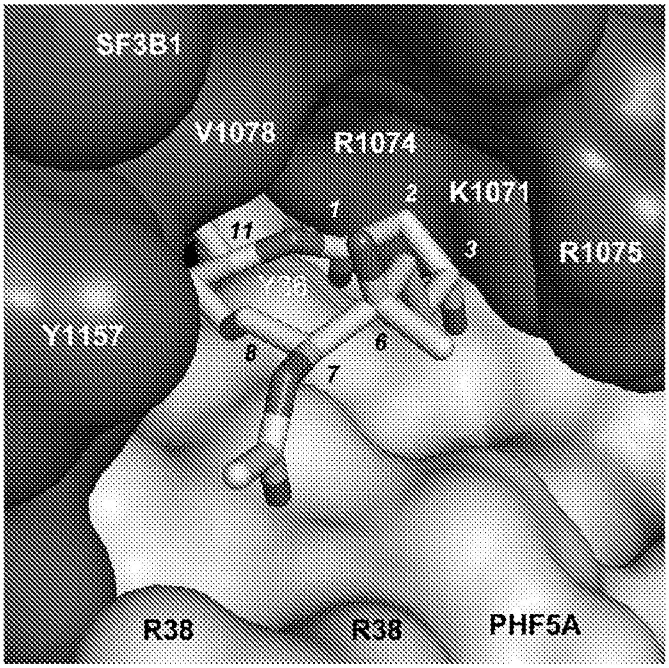
Figure 5F:
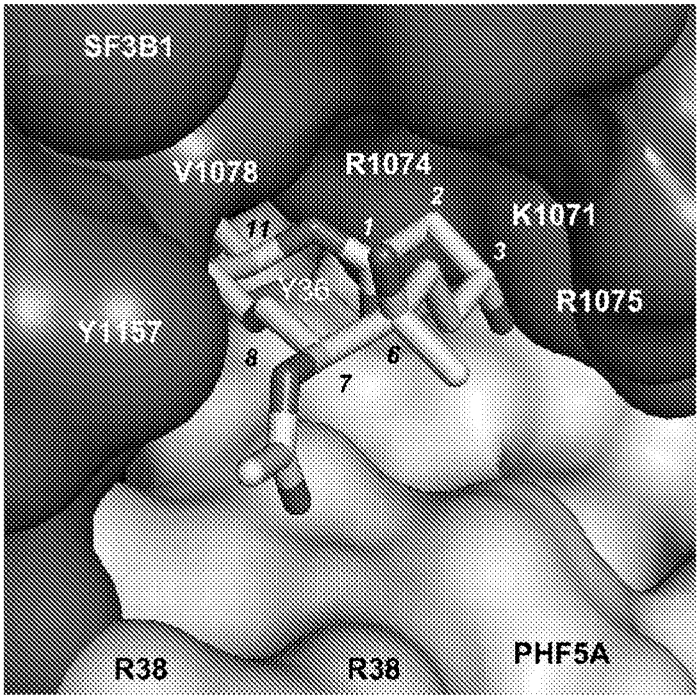
Figure 5G:
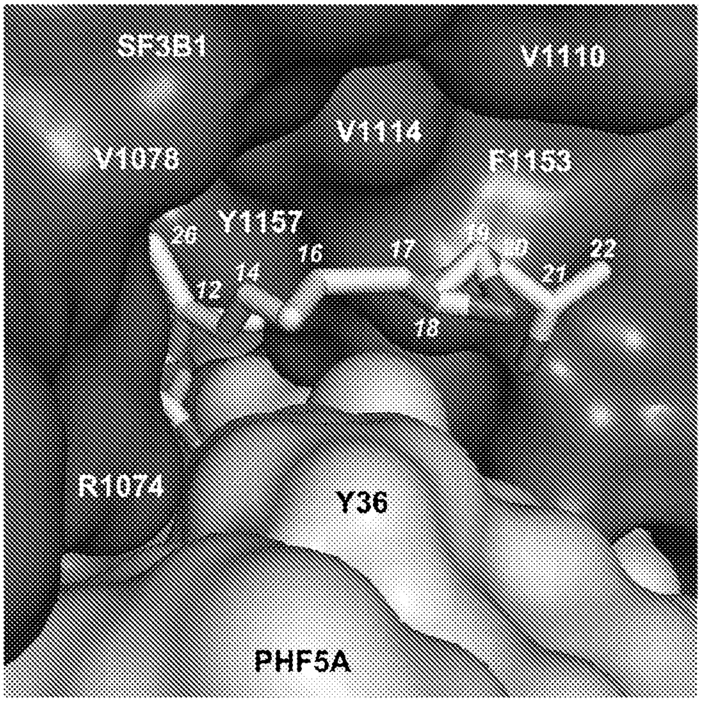
Figure 5H:
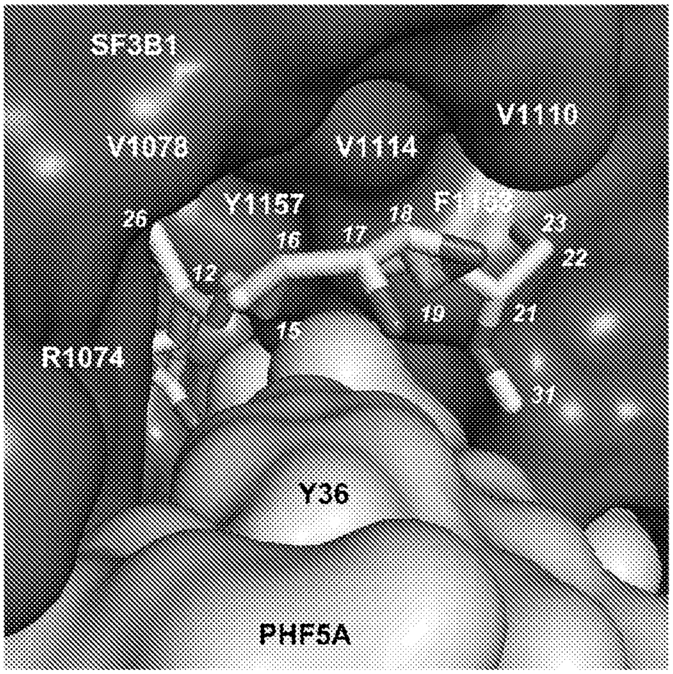
Figure 5I:
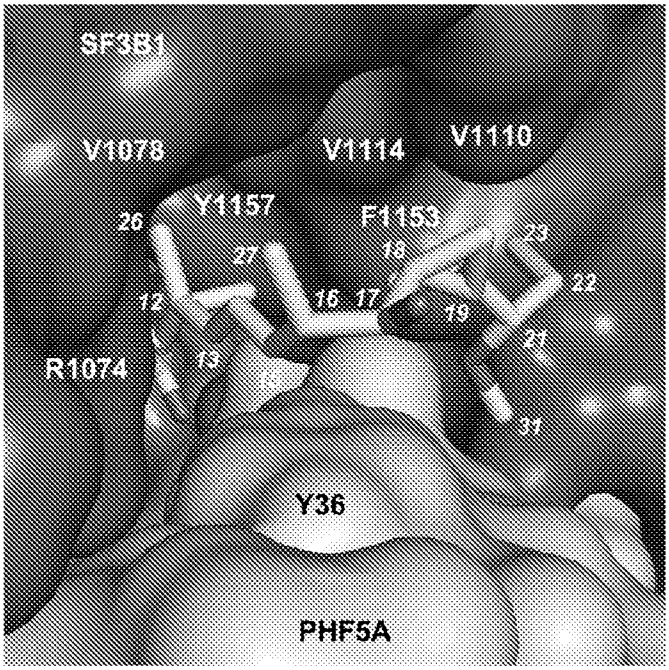
Figure 6:
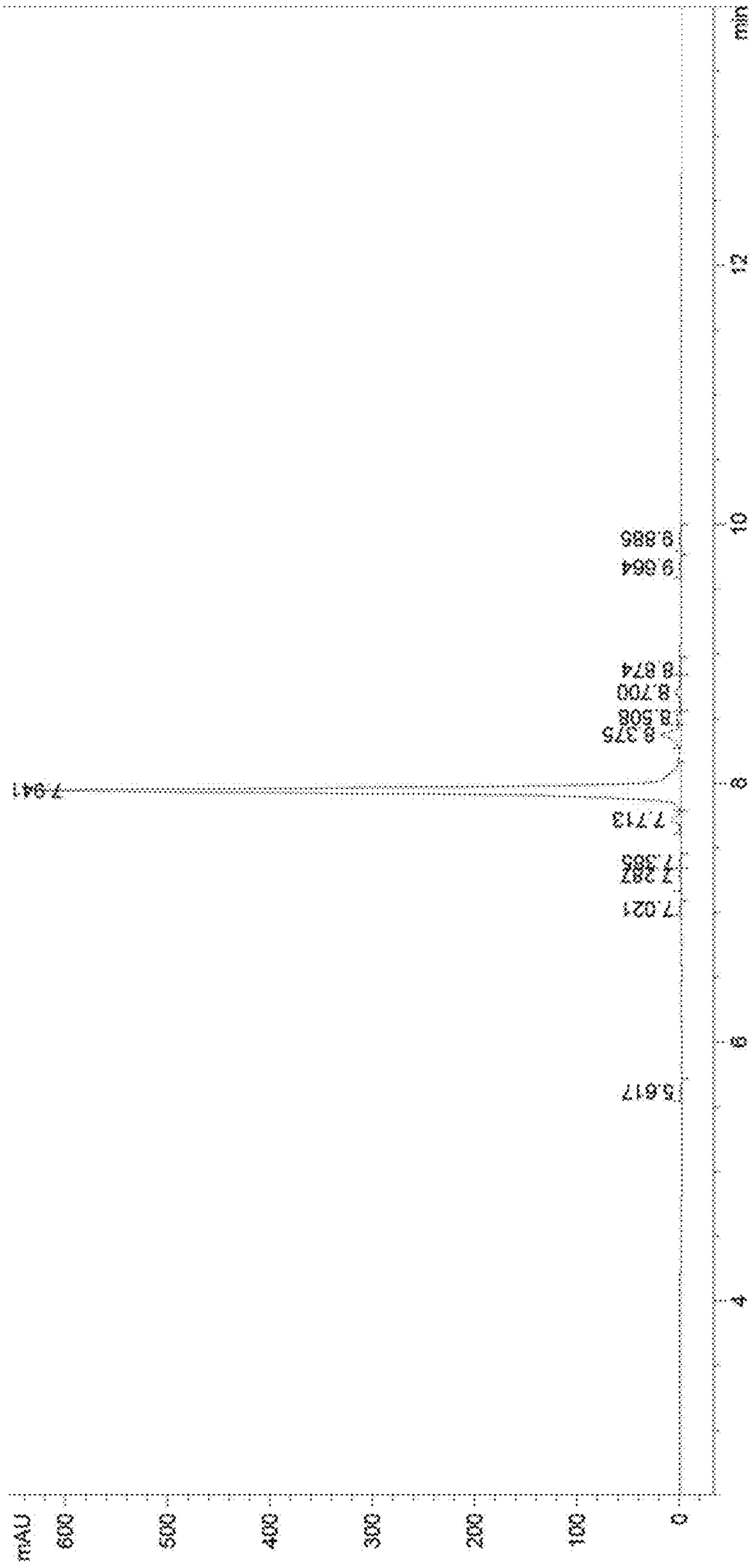
FIG. 6. LC-MS trace. A 20-40 μL sample prepared in EtOH or DMSO was injected into an Agilent 1260 liquid chromatograph (LC) system coupled with a Thermo LCQ-deca mass spectrometer (MS) using positive ion mode electrospray ionization (ESI) as the ion source. A Phenomenex Kinetex EVO C18 (ID 2.1 mm×length 50 mm, particle size 5.0 μm) was utilized for LC separation using water with 0.1% formic acid as the mobile phase A and acetonitrile with 0.1% formic acid as the mobile phase B. The LC flow rate was set at 0.30 mL/min. The LC gradient setting was as follows: 0 min: 5% mobile phase B; 10 min: 95% mobile phase B; 12 min: 95% mobile phase B; 13 min: 5% mobile phase B; and, 18 min: 5% mobile phase B. The total run time was 18 min. The UV detection wavelength was set at 254 nm (17S-FD-895 can be observed using detection at 254 nm). MS and HRMS is typically observed as the sodium ion in positive mode (HR-ESI-MS m/z calcd. for $C_{31}H_{50}O_9Na$ $[M+Na]^+$: 589.3345, found 589.3347).
Figure 7A:
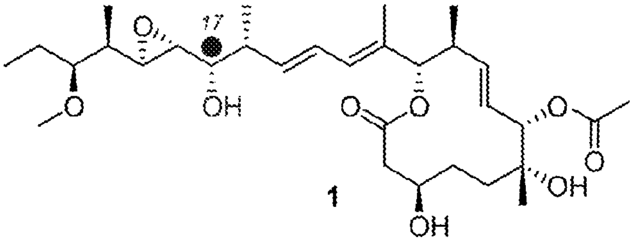
FIGS. 7A-7C. NMR comparison. Histograms depicting $^1$H (left) and $^{13}$C (right) chemical shifts differences between FD-895 (grey insert, upper right)
Figure 7A:
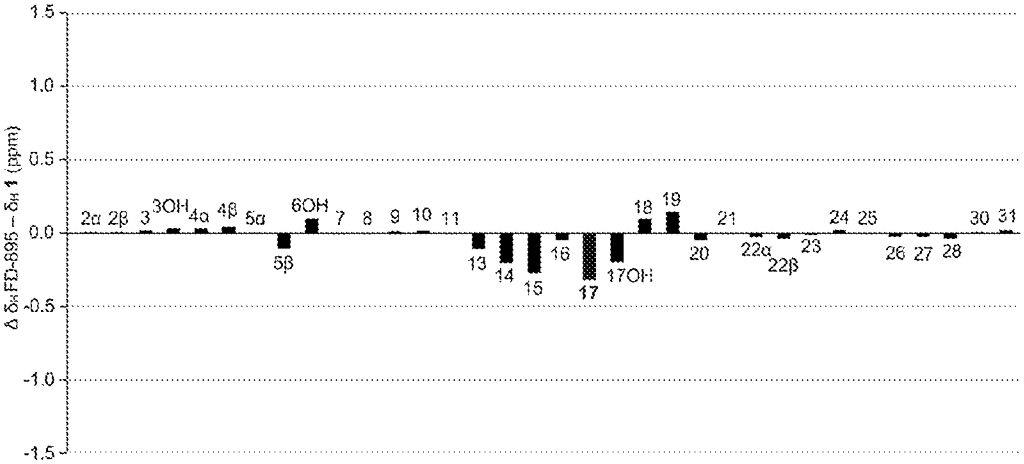
Figure 7A:
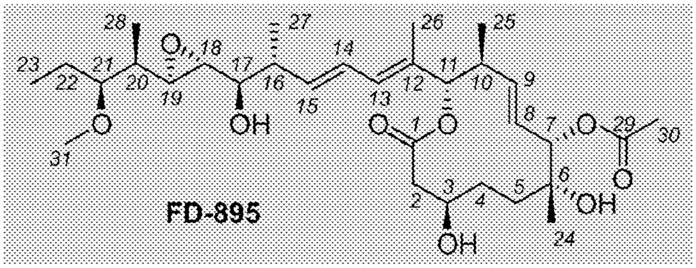
Figure 7A:
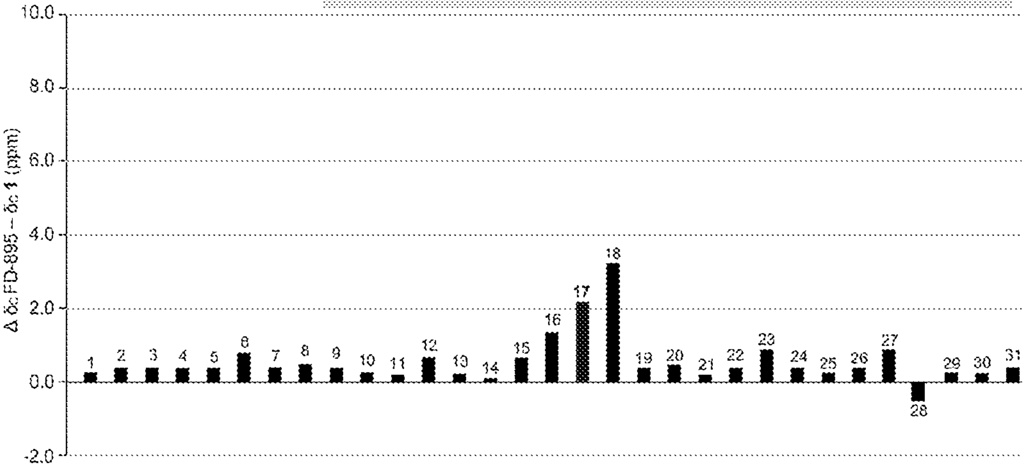
Figure 7B:
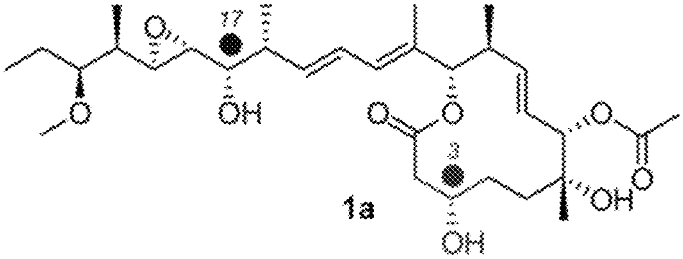
Figure 7B:
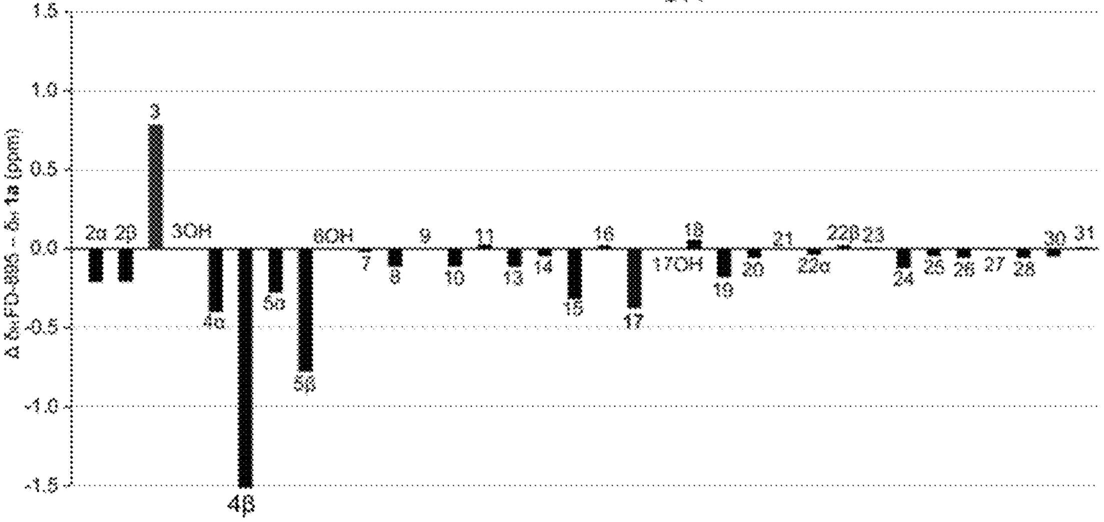
Figure 7B:
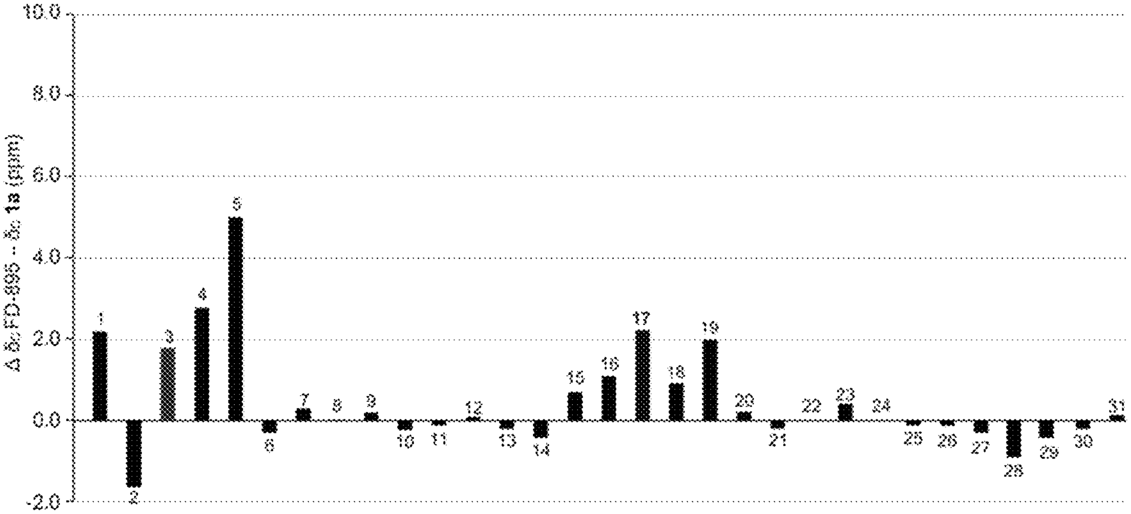
Figure 7C:
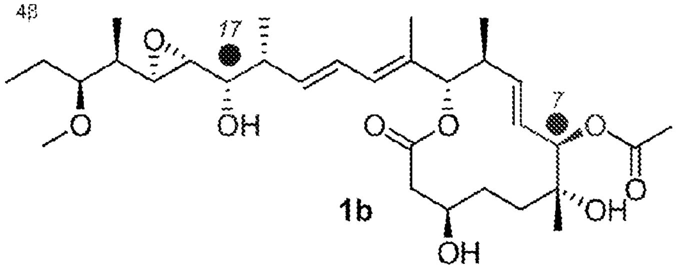
Figure 7C:
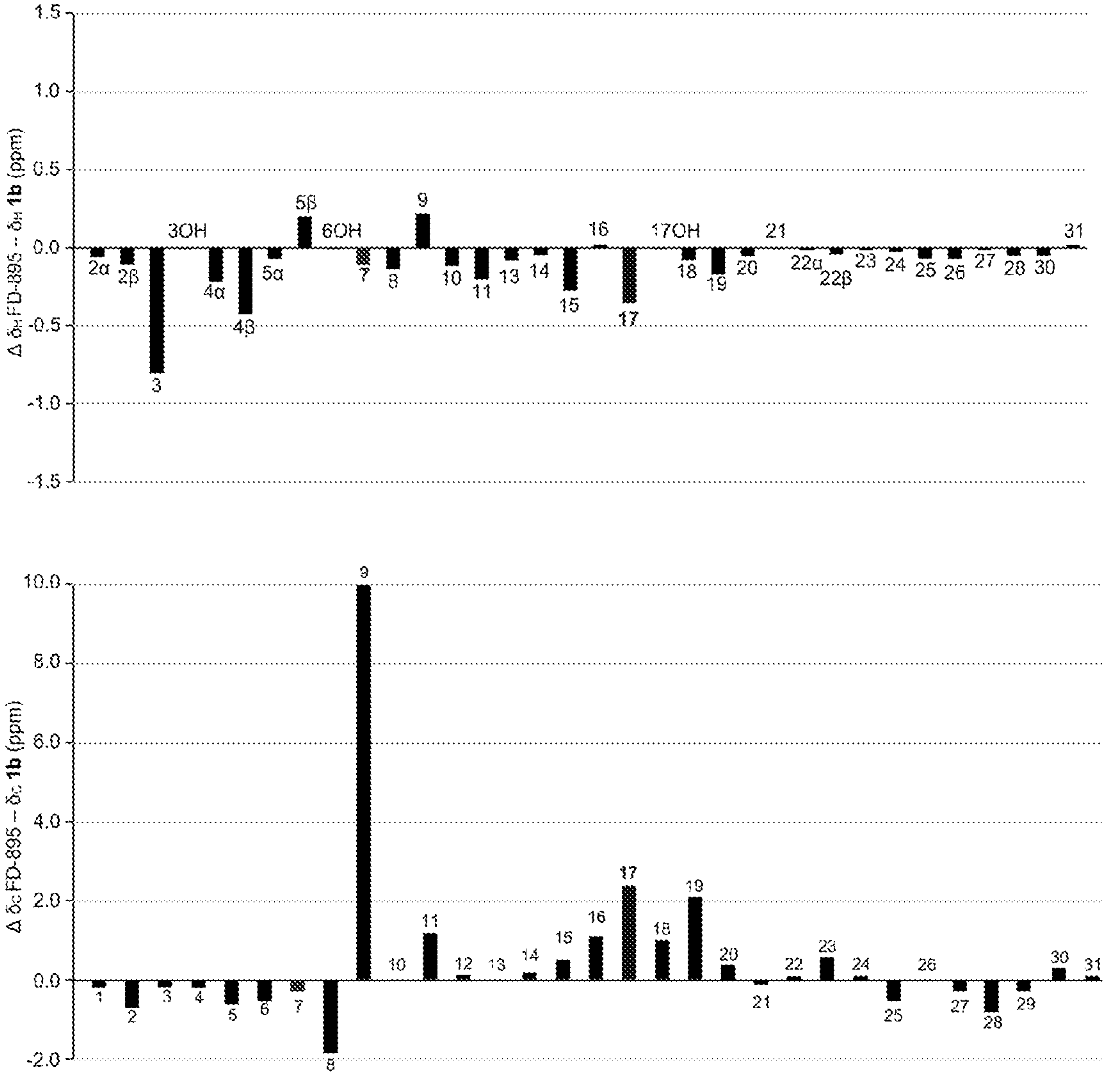

To further evaluate the route, we introduced $^{13}C$ labels in 1 independently at C1 and C30 (FIG. 4B). The $^{13}C$ isotopic tag at C1 was installed by preparing the Sammakia auxiliary with 1-$^{13}C$ acetyl chloride (Scheme AS1 (FIG. 10)), relaying it to the corresponding $^{13}C$1-labeled core 3, and coupling it with side chain 2 to afford 1 g of $^{13}C$1-17S-FD-895. The $^{13}C$ tag at C30 was introduced by selective acetylation of 36 with 1-$^{13}$C acetic anhydride (Scheme S2). The resulting $^{13}$C30-labeled 3 was coupled to 2 to prepare 100 mg of $^{13}$C30-17S-FD-895. $^{13}$C-NMR spectroscopy (FIG. 4B) confirmed that batches of $^{13}$C1-17S-FD-895 and $^{13}$C30-17S-FD-895 were a single compound with 98% purity. Overall, this improved route has produced over 17 g of 17S-FD-895 (1), with all 11 stereocenters installed in high selectivity and reproducibility. Furthermore, the ability to produce gram scale lots of stable, isotopically labeled material is especially advantageous for in vivo pharmacological assessments.

Next, we wanted to expand the structure activity relationship (SAR) profile of 1 (FIG. 4C) (2, 40-42) by utilizing this route to access non-natural analogs from late-stage intermediates. The C3-isomer 1a (FIG. 4D), C7-isomer 1b (FIG. 4E) and C18-C19 epoxide isomer 1c (FIG. 4F) were synthesized by changes in chiral reagents (1a, Scheme AS3 (FIG. 11) and 1b, Scheme AS4 (FIG. 12)) or by collection of minor isomeric byproducts (1c) generated during the synthesis of 1. Screening of 1a-1c in human colorectal tumor HCT-116 cells indicated that inverting the C3 or C7 stereocenters in 1a and 1b compromised activity, while the epoxide isomer 1c retained potency compared to 1.

These results were consistent with established X-ray crystal structure (FIG. 5) of the SF3B core complexed with pladienolide B (14). In this and related structures (18), inverting the C3 hydroxyl-group in 1a ablates its interaction with K1071 of the SF3B1 subunit (FIGS. 5A-5F). The lack in activity of the C7 isomer followed a similar reasoning, as inversion of the C7 acetate in 1b disrupts its interaction with R38 in PHF5A. These findings support a strict SAR within the 12-membered core, as it bridges the interface between SF3B1 and PHF5A. Tolerance for inversion of the C18-C19 epoxide in 1c, an isomer with comparable activity to 1 in HCT-116 cells, was also supported structurally. Rotational freedom within the side chain (FIGS. 5G-5H) permitted pladienolide B and associated analogues to adopt distinct conformations to access the same binding pocket. Overall, this synthesis has facilitated material access to complete preclinical evaluation, delivered isotopic materials, filled gaps in the SAR data, and contributed to an understanding of structural features required to engage small molecule splice modulation.

Example 4. General Experimental Methods

Chemical reagents were obtained from Acros Organics, Alfa Aesar, Chem-Impex Int., CreoSalus, Fischer Scientific, Fluka, Oakwood Chemical, Sigma-Aldrich, Spectrum Chemical Mfg. Corp., or TCI Chemicals. Deuterated NMR solvents were obtained from Cambridge Isotope Laboratories. All reactions were conducted with rigorously dried anhydrous solvents that were obtained by passing through a column composed of activated Al alumina or purchased as anhydrous. Anhydrous N,N-dimethylformamide was obtained by passage over activated 3 Å molecular sieves and a subsequent NaOCN column to remove traces of dimethylamine. Triethylamine ($Et_3N$) was dried over Na and freshly distilled. Ethyl-N,N-diisopropylamine (EtNi-$Pr_2$) was distilled from ninhydrin, then from KOH. Anhydrous $CH_3CN$ was obtained by distillation from $CaH_2$. All reactions were performed under positive pressure of Ar in oven-dried glassware sealed with septa, with stirring from a Teflon coated stir bars using an IKAMAG RCT-basic stirrer (IKA GmbH). Solutions were heated on adapters for IKAMAG RCT-basic stirrers. Analytical Thin Layer Chromatography (TLC) was performed on Silica Gel 60 F254 precoated glass plates (EM Sciences). Preparative TLC (pTLC) was conducted on Silica Gel 60 plates (EM Sciences). Visualization was achieved with UV light and/or an appropriate stain ($I_2$ on $SiO_2$, $KMnO_4$, bromocresol green, dinitrophenylhydrazine, ninhydrin, and ceric ammonium molybdate). Flash chromatography was carried out on Fischer Scientific Silica Gel, 230-400 mesh, grade 60 or SiliaFlash Irregular Silica Gel P60, 40-63 μm mesh, grade 60. Yields correspond to isolated, chromatographically and spectroscopically homogeneous materials. $^1$H NMR and $^{13}$C NMR spectra were recorded on a Varian VX500 spectrometer equipped with an Xsens Cold probe. Chemical shift δ values for $^1$H and $^{13}$C spectra are reported in parts per million (ppm) and multiplicities are abbreviated as s=singlet, d=doublet, t=triplet, q=quartet, m=multiplet, br=broad. All $^{13}$C NMR spectra were recorded with complete proton decoupling. FID files were processed using MestraNova 12.0.3. (MestreLab Research). Electrospray (ESI) mass spectrometric analyses were performed using a ThermoFinnigan LCQ Deca spectrometer, and high-resolution analyses were conducted using a ThermoFinnigan MAT900XL mass spectrometer with electron impact (EI) ionization. A Thermo Scientific LTQ Orbitrap XL mass spectrometer was used for high-resolution electrospray ionization mass spectrometry analysis (HR-ESI-MS). FTIR spectra were obtained on a Nicolet *magna* 550 series II spectrometer as thin films on either KBr or NaCl discs, and peaks are reported in wavenumbers ($cm^{-1}$). Optical rotations [α]D were measured using a Perkin-Elmer Model 241 polarimeter with the specified solvent and concentration and are quoted in units of deg $cm^2$ $g^{-1}$. Spectral data and procedures are provided for all new compounds and copies of select spectra have been provided.

Example 5. Experimental Data for Additional Synthetic Effort

Figure 8:
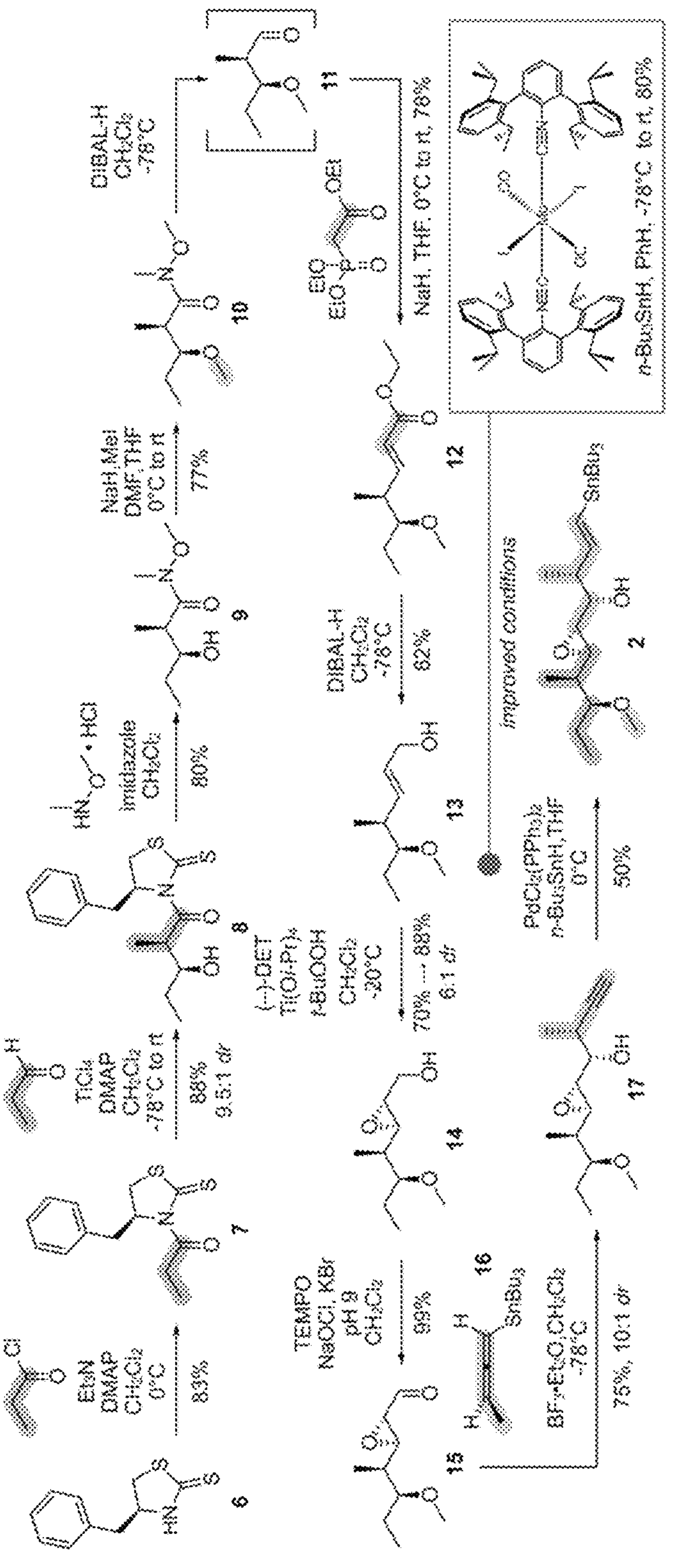
FIG. 8. Scheme A1. Side chain 2 was synthesized in 11 steps beginning from Crimmins auxilary 6. The yields and stereoselectivities indicated reflect the improvements made that enabled gram scale production. Compounds 6 and 7 were purified by recrystallization. Colored highlighting denotes carbons from sourced precursors (FIG. 1). Abbreviations: DMAP, dimethylaminopyridine; DIBAL-H, diisobutylaluminium hydride; DET, diethyltartrate; i-Pr, isopropyl; t-Bu, tert-butyl; TEMPO, 2,2,6,6-tetramethylpiperidine-N-oxyl; n-Bu, butyl.

Procedures for the synthesis of side chain 2 (FIG. 8, Scheme A1). An eleven step sequence was developed to prepare 20 g of component 2 beginning with auxiliary 6.

This procedure was optimized, in part, from published methods (19). Although the known compound 9 had been previously synthesized in decagram quantities (33), large amounts of toxic $AlMe_3$ were required to hydrolyze the oxazolidinone auxiliary. Switching to the more labile thiazolidinethione auxiliary allowed for mild hydrolysis and facilitated decagram production of alcohol 13 and subsequent gram scale production of vinylstannane 2. Each 25 g batch of 13 provided 6.5 g of 2 at 95% purity with a total of 20 g of 2 produced to date.

Synthesis of Auxiliary 7

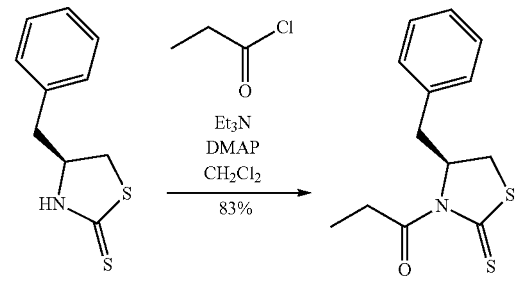

6 7

Reagents: $Et_3N$, 98% (Fischer Scientific): redistilled before use. DMAP, 98% (CreoSalus): used without further purification. Propionyl chloride, 98% (Sigma-Aldrich): freshly distilled before use.

(R)-1-(4-Benzyl-2-thioxothiazolidin-3-yl)propan-1-one (7). $Et_3N$ (700 mL, 5.20 mol) and DMAP (105 g, 862 mol) were added at rt to a 20 L reaction vessel containing a solution of 6 (892 g, 4.26 mol) in anhydrous $CH_2Cl_2$ (9 L). The mixture was cooled to 0° C., and propionyl chloride (490 mL, 5.61 mol) dissolved in $CH_2Cl_2$ (2.3 L) was added dropwise over 1.5 h while maintaining the temperature at 0° C. The mixture was then stirred at rt. After 18 h, the mixture was cooled to 0° C., and satd. $NH_4Cl$ (5.8 L) was added dropwise while keeping the temperature below 0° C. The mixture was extracted with $CH_2Cl_2$ (3×2 L). The combined organic phases were washed with satd. $NaHCO_3$ (4 L) and brine (4 L), dried over $Na_2SO_4$, filtered and concentrated on a rotary evaporator. Pure auxiliary 7 (950 g, 83%) was obtained by crystallization from $CH_3CN$. Characterization data matched literature values (43). $^1H$ NMR (500 MHz, $CDCl_3$) δ 7.30 (m, 3H), 7.24 (m, 2H), 5.34 (ddd, J=10.9, 7.2, 3.8 Hz, 1H), 3.36 (m, 2H), 3.17 (dd, J=13.2, 3.8 Hz, 1H), 3.05 (m, 2H), 2.84 (d, J=11.6, 1H), 1.15 (t, J=7.2 Hz, 3H); $^{13}C$ NMR (125 MHz, $CDCl_3$) δ 201.2, 175.0, 136.7, 129.6, 129.0, 127.3, 68.8, 36.8, 32.5, 32.0, 8.9; LCMS (ES-API) m/z calcd. for $C_{12}H_{13}NOS_2$ $[M+1]^+$: 266.40.

Synthesis of Adduct 8

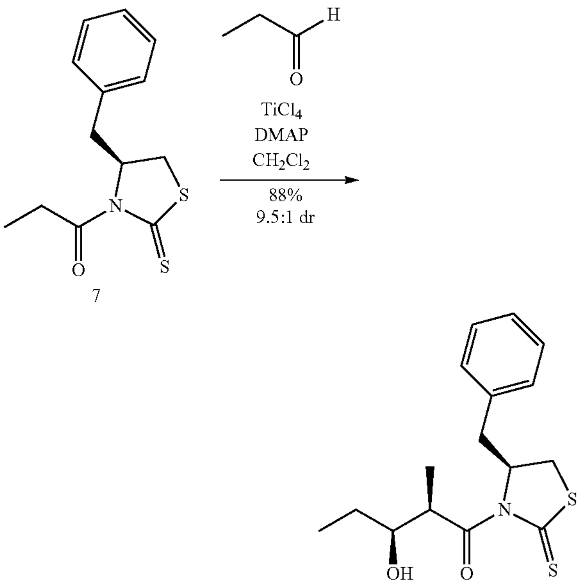

7

8

Reagents: Propionaldehyde, 98% (Alfa Aesar): redistilled before use. $EtN(i\text{-}Pr)_2$, 97% (Fisher Scientific): redistilled before use. $TiCl_4$, 98% (Alfa Aesar): used without further purification (2R,3S)-1-((S)-4-Benzyl-2-thioxothiazolidin-3-yl)-3-hydroxy-2-methylpentan-1-one (8). (S)-1-(4-Benzyl-2-thioxothiazolidin-3-yl)propan-1-one (7) (235 g, 887 mmol) was added to a 20 L reaction flask and dissolved in $CH_2Cl_2$ (7 L) with mechanical stirring. The mixture was cooled below 0° C. $TiCl_4$ (1 M solution in $CH_2Cl_2$, 922 mL, 922 mmol) was added dropwise over 1 h, while maintaining the temperature below 0° C., at which point the mixture turned orange. $EtN(i\text{-}Pr)_2$ (168 mL, 966 mmol) was added dropwise over 30 min, at which point the resulting black mixture was stirred at 0° C. for 15 min. After cooling the reaction to −94° C., a solution of propionaldehyde (71.0 mL, 984 mmol) in anhydrous $CH_2Cl_2$ (350 mL) was added dropwise over 6 h. The mixture was stirred at −94° C. for 30 min before being slowly warmed to rt overnight. The mixture was cooled to 0° C. and satd. $NaHCO_3$ (1.7 L) was slowly added. CAUTION RAPID HEATING. The phases were separated, and the aqueous phase was extracted with $CH_2Cl_2$ (3×1 L). The combined organic phases were washed with brine (2 L), dried over $Na_2SO_4$, filtered and concentrated on a rotary evaporator. Pure adduct 8 (250 g, 88%) was obtained in a 9.5:1 dr by flash chromatography, eluting with a gradient of heptane to 1:3 EtOAc/heptane.

Adduct 8: TLC (1:3 EtOAc/heptane): $R_f$=0.63 (CAM stain); $^1H$ NMR (500 MHz, $CDCl_3$) δ 7.34 (m, 2H), 7.29 (m, 3H), 5.37 (ddd, J=11.2, 7.1, 4.4 Hz, 1H), 4.73 (qd, J=7.1, 2.3 Hz, 1H), 3.97 (ddd, J=8.1, 5.3, 2.2 Hz, 1H), 3.38 (ddd, J=11.5, 7.2, 1.1 Hz, 1H), 3.25 (dd, J=13.2, 4.1 Hz, 1H), 3.05 (dd, J=13.2, 10.5 Hz, 1H), 2.89 (dd, J=11.6, 0.8 Hz, 1H), 2.77 (bs, 1H), 1.61 (m, 1H), 1.45 (m, 1H) 1.18 (d, J=7.1 Hz, 3H), 0.98 (t, J=7.5 Hz, 3H); $^{13}C$ NMR (125 MHz, $CDCl_3$) δ 201.7, 178.7, 136.5, 129.6, 129.1, 129.1, 127.4, 72.6, 69.1, 42.3, 37.1, 31.9, 26.7, 10.6, 10.5; FTIR (film) $\nu_{max}$ 3444, 3027, 2964, 2937, 2876, 1689, 1455, 1352, 1258, 1191, 1164, 1041, 1029, 960 $cm^{-1}$; LCMS (ES-API) m/z calcd. for $C_{15}H_{19}NO_2S_2$ $[M+1]^+$: 324.40; $[\alpha]^{25}_D$=199.5° (c=1.0 $CH_2Cl_2$).

Conversion of Alcohol 8 to Weinreb Amide 9

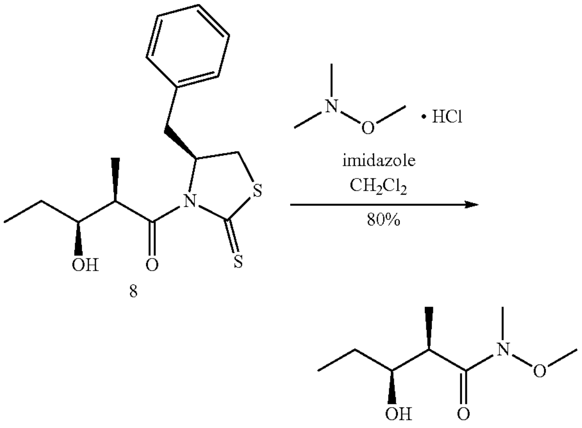

8

9

Reagents: N,O-Dimethylhydroxylamine hydrochloride, 99% (Alfa Aesar): used without further purification. Imidazole, 99% (Sigma-Aldrich): used without further purification.

(2R,3S)-3-Hydroxy-N-methoxy-N,2-dimethylpentanamide (9). N,O-Dimethylhydroxylamine hydrochloride (174 g, 1.78 mol) and imidazole (182 g, 2.68 mol) were added in succession to a solution of 8 (288 g, 892 mmol) in $CH_2Cl_2$ (13 L) in a 20 L reaction vessel at rt. The mixture was stirred at rt for an additional 16 h. $H_2O$ (3 L) was added, and the mixture was separated followed by extraction of the aqueous phase with $CH_2Cl_2$ (3×2.5 L). The combined organic phases were washed with brine (5 L), dried over $Na_2SO_4$, filtered and concentrated on a rotary evaporator to afford a yellow oil. Pure amide 9 (131 g, 80%) was obtained by flash chromatography, eluting with a gradient of heptane to 3:1 EtOAc/heptane. Note 1: 65±5% of auxiliary 6 was recovered after chromatography. Note 2: Rotational isomers were observed by NMR Amide 9: TLC (3:1 EtOAc/heptane): $R_f$=0.17 ($KMnO_4$); $^1$H NMR (500 MHz, $CDCl_3$) δ 3.79 (bs, 1H), 3.76 (td, J=5.4, 2.6 Hz, 1H), 3.69 (s, 3H), 3.17 (s, 3H), 2.90 (bs, 1H), 1.77 (bs, 1H), 1.57 (m, 1H), 1.39 (m, 1H), 1.15 (d, J=7.1 Hz, 3H), 0.95 (t, J=7.4 Hz, 3H); $^{13}$C NMR (125 MHz, $CDCl_3$) δ 178.5, 73.1, 61.7, 38.1, 32.0, 26.8, 10.5, 10.1; FTIR (film) $\nu_{max}$ 2969, 2917, 2855, 1719, 1449, 1265, 1178, 1108, 1020, 715 $cm^{-1}$; LCMS (ES-API) m/z calcd. for $C_8H_{17}NO_3$ $[M+1]^+$: 176.40; $[\alpha]^{25}_D$=11.3° (c=1.0, $CH_2Cl_2$).

Methylation of Amide 9 to 10

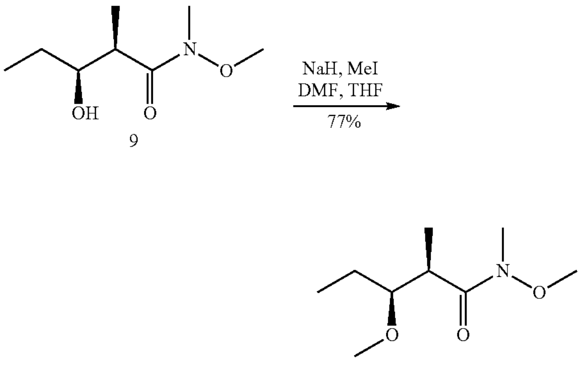

9

10

Reagents: NaH, 60% in mineral oil (Alfa Aesar): used without further purification. MeI, 98% (Sigma-Aldrich): used without further purification.

(2R,3S)—N,3-Dimethoxy-N,2-dimethylpentanamide (10). MeI (1.12 L, 18.0 mol) was added at rt to a solution of amide 9 (155 g, 886 mmol) in a mixture of anhydrous THF (6 L) and anhydrous DMF (1.5 L) in a 20 L reaction vessel. The mixture was cooled to 0° C. and NaH (60% in mineral oil, 88.5 g, 2.21 mol) was added in portions ensuring the mixture remained at 0° C. The mixture was slowly warmed to rt and stirred for 16 h. After cooling the mixture to 0° C., a solution of phosphate buffered saline pH 7 (1.5 L) was added dropwise. The volatiles were concentrated on a rotary evaporator. $H_2O$ (4.5 L) was added to the residue, and the obtained mixture was extracted with t-butyl methyl ether (3×3 L). The combined organic phases were washed with brine (3 L), dried over $Na_2SO_4$, filtered and concentrated on a rotary evaporator. Pure amide 10 (129 g, 77%) was obtained as a colorless oil by flash chromatography, eluting with a gradient of heptane to 1:1 EtOAc/heptane. Note 1: Rotational isomers are observed by NMR Amide 10: TLC (3:1 EtOAc/heptane): $R_f$=0.27 ($KMnO_4$); $^1$H NMR (500 MHz, $CDCl_3$) δ 3.68 (s, 3H), 3.41 (s, 3H), 3.30 (tdd, J=7.0, 4.0, 1.0 Hz, 1H), 3.18 (s, 3H), 3.03 (bs, 1H), 1.58 (dqd, J=14.9, 7.5, 3.9 Hz, 1H), 1.42 (dt, J=14.4, 7.2 Hz, 1H), 1.21 (d, J=6.9 Hz, 3H), 0.93 (t, J=7.4 Hz, 3H); $^{13}$C NMR (125 MHz, $CDCl_3$) δ 176.5, 83.9, 61.6, 58.7, 39.6, 32.2, 25.3, 14.5, 9.6; FTIR (film) $\nu_{max}$ 3581, 3502, 2969, 2934, 2882, 2820, 1658, 1457, 1379 $cm^{-1}$; LCMS (ES-API) m/z calcd. for $C_9H_{19}NO_3$ $[M+1]^+$: 190.40; $[\alpha]^{25}_D$=−13.0° (c=1.0 $CHCl_3$)

Conversion of 10 to Ester 12

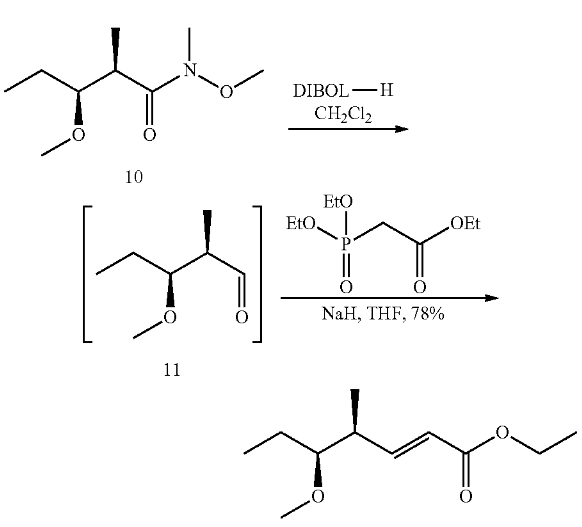

10

11

12

Reagents: DIBAL-H, 1.0 M in hexanes (Sigma-Aldrich): used without further purification. NaH, 60% in mineral oil, (Alfa Aesar): used without further purification. Triethyl phosphonoacetate, 99% (Oakwood Chemical): used without further purification.

Ethyl (4S,5S,E)-5-methoxy-4-methylhept-2-enoate (12) Amide 10 (107 g, 565 mmol) was dissolved in anhydrous $CH_2Cl_2$ (2 L) in a 5 L flask. The mixture was cooled to −78° C. DIBAL-H (1.0 M, 880 mL, 886 mol) was added dropwise over 45 min at −78° C. and stirred for 15 min. Acetone (100 mL) was added dropwise over 10 min, and the mixture was warmed to 0° C. Satd. Rochelle's salt (2 L) was added over 30 min, and the mixture was stirred at rt for 1.5 h. The phases were separated, and the aqueous phase was extracted with $CH_2Cl_2$ (3×500 mL). The combined organic phases were dried over $Na_2SO_4$, filtered and concentrated on a rotary evaporator. The residue was then dried via azeotropic removal of toluene to deliver aldehyde 11, which was used immediately after preparation. A solution of triethyl phosphonoacetate (572 mL, 2.88 mol) in anhydrous 2-methyltetrahydrofuran (400 mL) was added dropwise over 30 min to a 5 L reaction flask containing a suspension of NaH (60% in mineral oil, 97.4 g, 2.44 mol) in anhydrous 2-methyltetrahydrofuran (1 L) cooled to 0° C. CAUTION RAPID EVOLUTION OF $H_2$. The mixture was stirred at 0° C. for 15 min and a solution of 11 in anhydrous 2-methyltetrahydrofuran (1 L) was added dropwise over 30 min. The mixture was stirred at rt for 16 h, cooled to 0° C. and quenched with satd. $NH_4Cl$ (1.6 L). The organics were concentrated on a rotary evaporator. The mixture was extracted with EtOAc (2×1 L), and the combined organic phases were dried over $Na_2SO_4$, filtered and concentrated on a rotary evaporator. Pure ester 12 (88.3 g, 78% over two steps) was obtained as a colorless oil by flash chromatography, eluting with a gradient of $CH_2Cl_2$ to 1:10 EtOAc/$CH_2Cl_2$.

Ester 12: TLC ($CH_2Cl_2$): $R_f$=0.14 (CAM stain); $^1$H NMR (500 MHz, $CDCl_3$) δ 6.95 (dd, J=15.8, 7.7 Hz, 1H), 5.82 (dd, J=15.8, 1.3 Hz, 1H), 4.18 (q, J=7.1 Hz, 2H), 3.36 (s, 3H), 3.00 (ddd, J=7.4, 5.6, 4.4 Hz, 1H), 2.57 (m, 1H), 1.51 (m, 1H), 1.41 (m, 1H), 1.28 (t, J=7.1 Hz, 3H), 1.07 (d, J=6.8 Hz, 3H), 0.90 (t, J=7.4 Hz, 3H); $^{13}$C NMR (125 MHz, $CDCl_3$)

δ 166.8, 151.3, 121.1, 85.6, 60.4, 58.0, 39.3, 20.0, 14.9, 14.4, 10.0; FTIR (film) $\nu_{max}$ 2978, 2934, 2882, 2820, 1719, 1650, 1466 $cm^{-1}$; LCMS (ES-API) m/z calcd. for $C_{11}H_{20}O_3$ $[M+NH_4]^+$: 218.6; $[\alpha]^{25}_D$=−45.4° (c=1.0, $CH_2Cl_2$).

Reduction of 12 to Alcohol 13

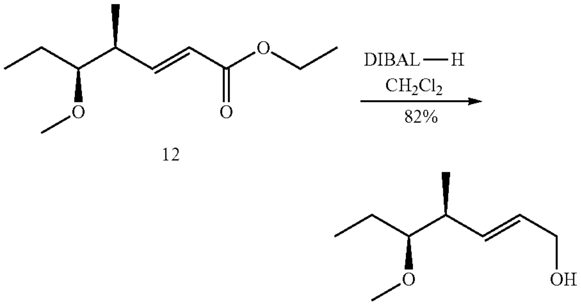

12

13

Reagents: DIBAL-H, 1.0 M in hexanes (Sigma-Aldrich): used without further purification.

(4S,5S,E)-5-Methoxy-4-methylhept-2-en-1-ol (13). DIBAL-H (1.0 M, 700 mL, 0.85 mol) was added dropwise over 60 min to a 5 L reaction flask containing a solution of ester 12 (56.5 g, 282 mmol) in anhydrous $CH_2Cl_2$ (1.5 L) cooled to −78° C. The mixture was stirred for 1 h at −78° C. Acetone (100 mL) was then added dropwise over 25 min. The mixture was warmed to 0° C., satd. Rochelle's salt (1 L) was added, and the mixture was stirred at rt for 2 h. The phases were separated, and the aqueous phase was extracted with $CH_2Cl_2$ (3×500 mL). The combined organic phases were washed with brine (250 mL), dried over $Na_2SO_4$, filtered and concentrated on a rotary evaporator. Pure alcohol 13 (36.5 g, 82%) was obtained by flash chromatography, eluting with a gradient of heptane to 1:1 EtOAc/heptane.

Alcohol 13: TLC (1:3 EtOAc/heptane): $R_f$=0.26 (CAM stain); $^1$H NMR (500 MHz, $CDCl_3$) δ 5.65 (m, 2H), 4.10 (bs, 2H), 3.36 (s, 3H), 2.92 (ddd, J=7.5, 5.7, 4.2 Hz, 1H), 2.44 (m, 1H), 1.52 (m, 1H), 1.40 (m, 1H), 1.01 (d, J=6.9 Hz, 3H), 0.90 (t, J=7.4 Hz, 3H); $^{13}$C NMR (125 MHz, $CDCl_3$) δ 135.2, 129.0, 86.4, 64.0, 57.7, 38.9, 23.5, 16.0, 10.0; FTIR (film) $\nu_{max}$ 3388, 2968, 2932, 2876, 2826, 1460, 1375 $cm^{-1}$; LCMS (ES-API) m/z calcd. for $C_9H_{18}O_2$ $[M+1]^+$: 158.20; $[\alpha]^{25}_D$=−34.5° (c=0.2, $CHCl_3$).

Epoxidation of Alcohol 13 to Epoxide 14

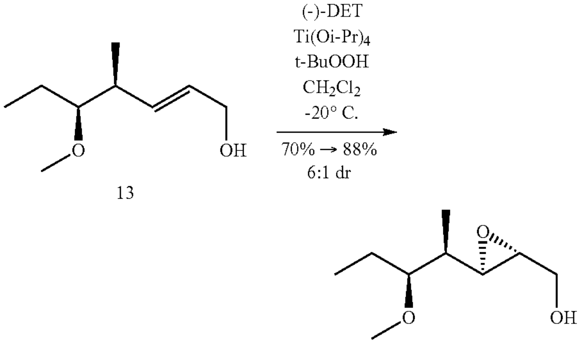

13

14

Reagents: Ti(Oi-Pr)$_4$, 97% (Sigma-Aldrich): vacuum distilled at 90° C., 5 mbar. (−)-Diethyltartrate, 99% (Alfa Aesar): used without further purification. t-Butylhydroperoxide, 3.3 M in toluene: dried from a 70% solution in water according to methods developed by the Sharpless laboratory (44).

((2R,3R)-3-((2R,3S)-3-Methoxypentan-2-yl)oxiran-2-yl)methanol (14). t-Butylhydroperoxide (3.3 M, 76.6 mL, 253 mmol) was added to a 1 L flask containing a stirring solution of Ti(Oi-Pr)$_4$ (2.73 mL, 12.6 mmol), (−)-diethyl tartrate (2.21 mL, 12.6 mmol) and powdered 4 Å molecular sieves (2 g) in anhydrous $CH_2Cl_2$ (400 mL). The mixture was cooled to −20° C. and stirred for 30 min. A solution of alcohol 13 (20.0 g, 127 mmol) in $CH_2Cl_2$ (50 mL) was added dropwise. The reaction was stirred at −20° C. for 4 h. The reaction was quenched via addition of 10% NaOH (25 mL). The mixture was then extracted into $CH_2Cl_2$ and concentrated on a rotary evaporator. Pure epoxyalcohol 14 (22.1 g, 88%) was obtained as a 6:1 mixture of diastereomers by flash chromatography, eluting with a gradient of hexanes to 1:1 EtOAc/hexanes. Note 1: Diastereomers were not separable and carried on directly to the next step.

Epoxyalcohol 14: TLC (1:2 EtOAc/hexanes): $R_f$=0.10 (CAM stain); $^1$H NMR (500 MHz, $C_6D_6$) δ 3.55 (m, 1H), 3.33 (m, 1H), 3.20 (s, 3H), 3.08 (td, J=6.3, 4.5 Hz, 1H), 2.89 (dd, J=7.6, 2.3 Hz, 1H), 2.63 (dt, J=4.9, 2.6 Hz, 1H), 1.59 (tt, J=13.9, 7.4 Hz, 1H), 1.41 (m, 1H), 1.35 (m, 1H), 1.02 (d, J=6.9 Hz, 1H), 0.85 (t, J=7.4 Hz, 3H), 0.84 (d, J=7.4 Hz, 3H); $^{13}$C NMR (125 MHz, $C_6D_6$) δ 83.8, 62.2, 58.0, 57.9, 57.7, 38.8, 24.0, 10.4, 10.1; FTIR (film) $\nu_{max}$ 3422, 2972, 2930, 2879, 1468, 1103 $cm^{-1}$; HR-ESI-MS m/z calcd. for $C_9H_{18}O_3[M]^+$: 174.1250, found 174.1249; $[\alpha]^{25}_D$=+182.4° (c=1.0, $CHCl_3$).

Oxidation of Epoxyalcohol 14 to Epoxyaldehyde 15

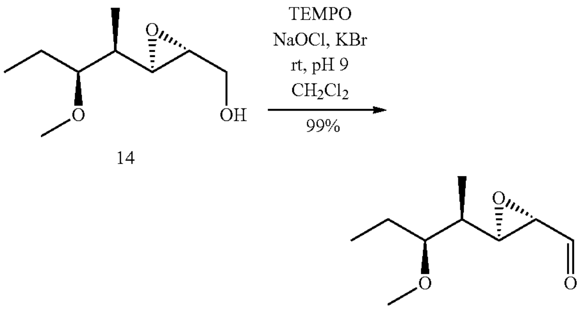

14

15

Reagents: TEMPO, 99% (Oakwood Chemical): used without further purification. KBr, (Spectrum Chemical Mfg. Corp.): used without further purification. NaOCl, 2 M, 10-15% active chlorine (Spectrum Chemical Mfg. Corp.): used without further purification.

(2S,3R)-3-((2R,3S)-3-Methoxypentan-2-yl)oxirane-2-carbaldehyde (15). A solution of KBr (1.21 g, 10.2 mmol) in $H_2O$ (50 mL), satd. $NaHCO_3$ (100 mL) and TEMPO (1.33 g, 8.50 mmol) were added sequentially to a 2 L flask containing a solution of epoxyalcohol 14 (22.1 g, 127 mmol) in $CH_2Cl_2$ (600 mL). The mixture was cooled to 0° C. and a solution of NaOCl (2 M, 85 mL, 170 mmol) and satd. $NaHCO_3$ (100 mL) were added dropwise via an addition funnel. The mixture was allowed to warm to rt and stirred for 2 h. The phases were separated, and the aqueous phase was extracted with $CH_2Cl_2$ (3×300 mL). The combined organic phases were washed with brine (500 mL), dried over $Na_2SO_4$, filtered and concentrated on a rotary evaporator.

Aldehyde 15 (21.8 g, 99%) was obtained without further purification and was carried on directly to the next step. Note 1: Diastereomers obtained from epoxidation were not separable at this step and thus carried forward.

Aldehyde 15: TLC (1:2 EtOAc/hexanes): $R_f$=0.55 (CAM stain); $^1$H NMR (500 MHz, $C_6D_6$) δ 8.67 (d, J=6.4 Hz, 1H), 3.10 (s, 3H), 2.90 (td, J=6.4, 4.0 Hz, 1H), 2.84 (dd, J=7.5, 2.0 Hz, 1H), 2.79 (dd, J=6.4, 2.0 Hz, 1H), 1.44 (m, 1H), 1.21 (m, 1H), 0.82 (m, 1H), 0.74 (t, J=7.4 Hz, 3H), 0.63 (d, J=7.0 Hz, 3H); $^{13}$C NMR (125 MHz, $C_6D_6$) δ 197.7, 83.4, 58.6, 58.5, 57.7, 38.3, 23.7, 10.0, 9.8; FTIR (film) $\nu_{max}$ 2972, 2930, 2879, 2828, 1732, 1468, 1103 $cm^{-1}$; HR-ESI-MS m/z calcd. for $C_9H_{16}O_3$[M+H]$^+$: 173.1172, found 173.1174; $[\alpha]^{25}_D$=−89.0° (c=1.0, $CH_2Cl_2$).

Synthesis of allenylstannane 16. A two-step sequence to prepare grams of allenylstannane 16 beginning with commercially available (R)-but-3-yn-2-ol (29).

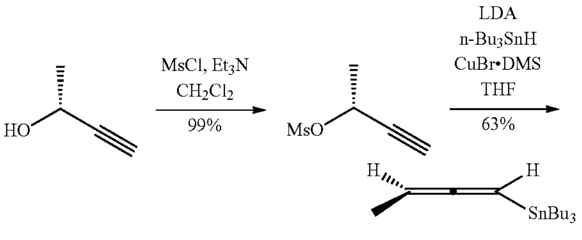

16

Reagents: $Et_3N$, 98% (Fischer Scientific): redistilled over $CaH_2$ before use. MsCl, 98% (Alfa Aesar): used without further purification.

(R)-But-3-yn-2-yl methanesulfonate. $Et_3N$ (198 mL, 1.43 mol) was added dropwise over 15 min to a 3 L three-necked flask containing a solution of (R)-but-3-yn-2-ol (50.0 g, 713 mmol) in $CH_2Cl_2$ (750 mL) cooled to −78° C. After 10 min, MsCl (83.4 mL, 1.07 mol) was added dropwise over 2 h. The mixture was stirred at −78° C. for 1 h, at which point satd. $NaHCO_3$ (500 mL) was added slowly. The mixture was warmed to rt, and the phases were separated. The aqueous phase was extracted with $CH_2Cl_2$ (3×500 mL). The combined organic phases were washed with brine (250 mL), dried over $Na_2SO_4$, filtered and concentrated on a rotary evaporator. The crude was passed through a plug of $SiO_2$, and the elutants were concentrated. (R)-But-3-yn-2-yl methanesulfonate (99%, 107.5 g) was obtained without further purification and was carried directly to the next step. Characterization data matched literature values.

(R)-But-3-yn-2-yl methanesulfonate: $^1$H NMR (500 MHz, $CDCl_3$) δ 5.27 (qd, J=6.7, 2.1 Hz, 1H), 3.11 (s, 3H), 2.71 (d, J=2.2 Hz, 1H), 1.65 (d, J=6.7 Hz, 3H); $^{13}$C NMR (125 MHz, $CDCl_3$) δ 80.2, 76.4, 67.6, 39.2, 22.5; LCMS (ES-API) m/z calcd. for $C_6H_8O_3S$ [M+1]$^+$: 148.08.

Conversion of (R)-but-3-yn-2-yl methanesulfonate to allenylstannane 16

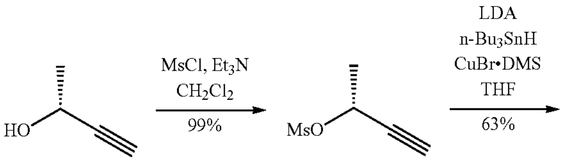

-continued

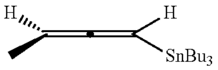

16

Reagents: n-BuLi, 2.5 M in hexanes (Acros Organics): used without further purification. $iPr_2NH$, 98% (Alfa Aesar): distilled over $CaH_2$. n-$Bu_3SnH$, 97% contains 0.05% BHT as stabilizer (Acros Organics): used without further purification. CuBr-DMS, 99% (Acros Organics): used without further purification.

(S)-Buta-1,2-dien-1-yltributylstannane (16). n-BuLi (2.5 M, 172 mL, 429 mmol) was added dropwise to a solution of $iPr_2NH$ (60.7 mL, 429 mmol) in anhydrous THF (800 mL) in a 5 L flask at 0° C. over 10 min. After 15 min, n-$Bu_3SnH$ (135 mL, 501 mmol) was added dropwise over 10 min, and the mixture was stirred at 0° C. for 2.5 h. After cooling the mixture to −85° C., CuBr-DMS (88.2 g, 429 mmol) was added in portions over 40 min. The mixture was stirred at for 30 min at −85° C. (R)-But-3-yn-2-yl methanesulfonate (53.0 g, 358 mmol) was added dropwise, and the mixture was stirred for 10 min. The mixture was poured into a mixture of t-butyl methyl ether (2 L), 25% aqueous $NH_3$ (260 mL) and satd. $NH_4Cl$ (2 L) and stirred vigorously for 1 h. The phases were separated, and the organics were dried over $Na_2SO_4$, filtered and concentrated on a rotary evaporator. Allenylstannane 16 (77.2 g, 63%) was obtained in 96% ee by vacuum distillation (1 mbar, 150° C.). Characterization data matched literature values. Note 1: This procedure was repeated to deliver a total over 500 g of 16.

Allenylstannane 16: $^1$H NMR (500 MHz, $CDCl_3$) δ 5.20 (dq, J=6.9, 4.0 Hz, 1H), 4.68 (p, J=6.9 Hz, 1H), 1.64 (dd, J=6.9, 1.4 Hz, 3H), 1.60 (m, 12H), 1.37 (m, 6H), 0.93 (t, J=7.4 Hz, 9H); $^{13}$C NMR (125 MHz, $CDCl_3$) δ 210.0, 75.6, 74.9, 29.4, 27.6, 14.0, 10.6; LCMS (ES-API) m/z calcd. for $C_{13}H_{32}Sn$ [M+1]$^+$: 345.15.

Derivatization of 16 for determination of enantiomeric excess.

Reagents: Isobutyraldehyde (Alfa Aesar): used without further purification. $BF_3$. $Et_2O$, 46.5% $BF_3$ (Alfa Aesar): used without further purification Isobutyraldehyde (40 μL, 0.44 mmol) in $CH_2Cl_2$ (4 mL) was added dropwise to a solution of allenylstannane 16 (200 mg, 583 μmol) and $BF_3$—$OEt_2$ (210 μL, 1.66 mmol) cooled to −78° C. After stirring at −78° C. for 1 h, the reaction was quenched with a satd. $NaHCO_3$ (4 mL). The mixture was allowed to warm to rt, and the phases were separated. The organic phase was stirred with KF on Celite (50 wt %, 100 mg) and $Na_2SO_4$ (100 mg). The solid was removed by filtration and an aliquot of the filtrate was used for chiral GC analysis indicating 96% ee.

Marshall Addition of Allenylstannane 16 to Aldehyde 15

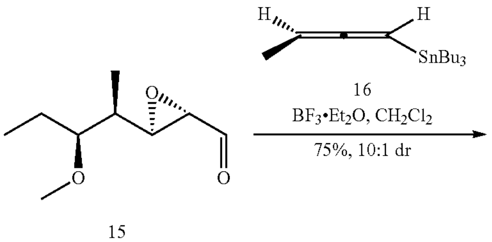

15

-continued

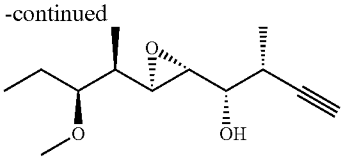

17

Reagents: $BF_3 \cdot Et_2O$, 46.5% $BF_3$ (Alfa Aesar): used without further purification.

(1S,2R)-1-((2R,3R)-3-((2R,3S)-3-Methoxypentan-2-yl)oxiran-2-yl)-2-methylbut-3-yn-1-ol (5). Aldehyde 15 (7.01 g, 40.8 mmol) and allenylstannane 16 (21.0 g, 61.0 mmol) in a 1 L flask were dissolved in anhydrous $CH_2Cl_2$ (400 mL) and purged with an Ar atmosphere. The mixture was cooled to −78° C. and $BF_3$. $Et_2O$ (7.53 mL, 61.0 mmol) was added dropwise over 5 min. The reaction was stirred for 1 h at −78° C. A mixture of MeOH (50 mL) and satd. $NaHCO_3$ (10 mL) was added, and the solution was warmed to rt. The phases were separated, and the aqueous phases were extracted with $Et_2O$ (3×400 mL). The organic phases were combined, dried with $Na_2SO_4$ and concentrated on a rotary evaporator. Alkyne 17 (6.92 g, 75%) was obtained in a 10:1 dr as a colorless oil by flash chromatography, eluting with a gradient of hexanes to 1:3 $Et_2O$/hexanes. Note 1: Minor C16-C17 Marshall diastereomers were removed chromatographically. Note 2: The remaining C18-C19 epoxide diastereomer from the Sharpless epoxidation was resolved after purification of the next step.

Alkyne 17: TLC (1:2 EtOAc/hexanes); $R_f$=0.50 (CAM stain); $^1H$ NMR (500 MHz, $CDCl_3$) δ 3.58 (dd, J=4.4, 4.4 Hz, 1H), 3.41 (s, 3H), 3.20 (td, J=6.5, 4.1 Hz, 1H), 3.06 (dd, J=8.1, 2.3 Hz, 1H), 2.91 (dd, J=4.5, 2.3 Hz, 1H), 2.81 (qdd, J=7.0, 4.7, 2.4 Hz, 1H), 2.17 (d, J=2.6 Hz, 1H), 2.05 (d, J=4.8 Hz, 1H), 1.67 (ddd, J=14.2, 7.6, 6.7 Hz, 1H), 1.48 (m, 2H), 1.31 (dd, J=7.2, 0.7 Hz, 3H), 0.97 (d, J=7.1 Hz, 3H), 0.90 (t, J=7.4 Hz, 3H); $^{13}C$ NMR (125 MHz, $CDCl_3$) δ 84.4, 83.8, 72.3, 71.4, 58.9, 58.3, 38.9, 30.4, 23.9, 17.1, 10.6, 10.1; FTIR (film) $\nu_{max}$ 3438, 3310, 2973, 2937, 2879, 1457, 1090 $cm^{-1}$; HR-ESI-MS m/z calcd. for $C_{13}H_{22}O_3$ $[M+H]^+$ 226.1642, found 226.1641; $[\alpha]^{25}_D$=+45.4° (c=1.0, $CH_2Cl_2$).

Hydrostannylation of 17

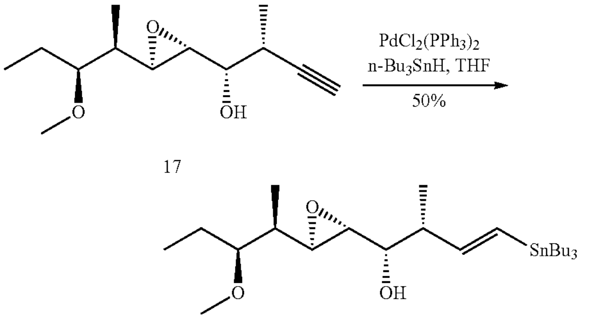

17

2

Reagents: n-$Bu_3SnH$, 97% contains 0.05% BHT as stabilizer (Acros Organics): used without further purification. $PdCl_2(PPh_3)_2$ (Oakwood Chemical): dried via azeotropic distillation of benzene.

(1S,2R,E)-1-((2R,3R)-3-((2R,3S)-3-Methoxypentan-2-yl)oxiran-2-yl)-2-methyl-4-(tributylstannyl)but-3-en-1-ol (2). $PdCl_2(PPh_3)_2$ (1.55 g, 2.21 mmol) was added to a solution of alkyne 17 (5.01 g, 22.1 mmol) in a 500 mL flask in anhydrous THF (200 mL). The mixture was cooled to 0° C. and n-$Bu_3SnH$ (17.9 mL, 66.3 mmol) was added dropwise. The mixture was stirred for 45 min at 0° C., at which point the resulting mixture was concentrated to yield a black crude oil. The material was extracted into hexanes, filtered through a pad of Celite and was eluted with hexanes. The elutant was concentrated on a rotary evaporator, and this process was repeated twice until a clear black solution was achieved. Pure vinylstannane 2 (5.72 g, 50%) was obtained as a mixture of 1:5 α:β regioisomers by flash chromatography, eluting with a gradient of hexanes to $CH_2Cl_2$ to 1:20 $Et_2O/CH_2Cl_2$. The desired regioisomer can be obtained in 95+% purity by additional flash chromatography, eluting with a gradient of hexanes to $CH_2Cl_2$ to 1:20 $Et_2O/CH_2Cl_2$.

Alternate Procedure Using Figueroa's Catalyst.

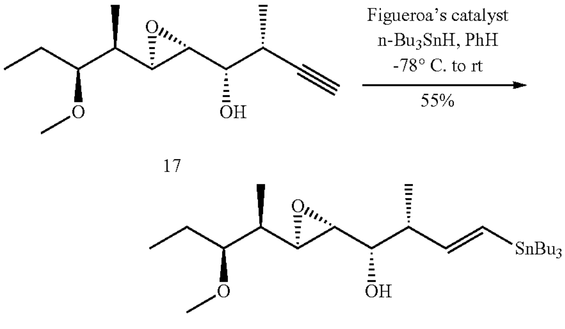

17

2

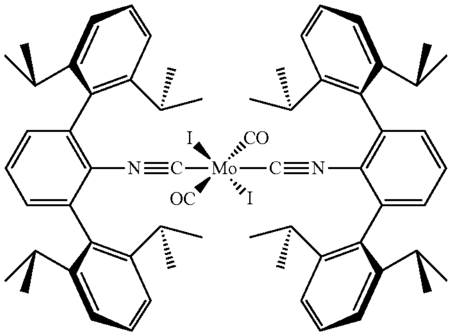

Figueroa's catalyst

Alkyne 17 (5.01 g, 22.1 mmol) in a 500 mL flask was dissolved in benzene (200 mL) and cooled to −78° C. n-$Bu_3SnH$ (17.9 mL, 66.3 mmol) was added dropwise. Figueroa's catalyst ($MoI_2(CO)_2(CNAr^{Dipp2})_2$) (31) was added as a solid. The resulting frozen red mixture was slowly thawed with stirring to rt over 4 h. The mixture was concentrated on a rotary evaporator. Pure vinylstannane 2 (11.3 g, 55%) was obtained as a 1:10 α:β regioisomers by flash chromatography, eluting with a gradient of hexanes to $CH_2Cl_2$ to 1:20 $Et_2O/CH_2Cl_2$. Note 1: The unwanted epoxide diastereomer byproduct is also removed by chromatography.

Vinylstannane 2: TLC (1:10 $Et_2O$/hexanes): $R_f$=0.28 (CAM stain); $^1H$ NMR (500 MHz, $C_6D_6$) δ 6.27 (dd, J=19.1, 6.8 Hz, 1H), 6.19 (d, J=19.1 Hz, 1H), 3.45 (m, 1H), 3.23 (s, 3H), 3.16 (m, 1H), 3.07 (dd, J=8.0, 2.3 Hz, 1H), 2.73 (dd, J=4.4, 2.3 Hz, 1H), 2.51 (td, J=6.9, 5.2 Hz, 1H), 1.61 (m, 8H), 1.39 (m, 8H), 1.19 (d, J=6.9 Hz, 3H), 1.01 (d, J=7.1 Hz, 3H), 1.00 (d, J=8.1 Hz, 3H), 0.95 (t, J=7.4 Hz, 12H), 0.86 (t, J=7.4 Hz, 3H); $^{13}C$ NMR (125 MHz, $C_6D_6$) δ 150.8, 129.0, 83.7, 73.1, 59.3, 57.8, 57.7, 46.1, 39.3, 29.6, 27.7, 23.9, 16.2, 14.0, 10.9, 10.0, 9.8; FTIR (film) $\nu_{max}$ 3454, 3310, 2973, 2937, 2890, 1459, 1101, 840 $cm^{-1}$; HR-ESI-MS m/z calcd. for $C_{25}H_{50}O_3Sn$ $[M+H]^+$ 519.2843, found 519.2839; $[\alpha]^{25}_D$=+12.3° (c=1.0, $CH_2Cl_2$).

Procedures for the synthesis of core 3. A twelve step sequence optimized from published methods (1) was developed to prepare 3 at gram scale, beginning with commercially available 18 (Scheme A2 (FIG. 9)) and shown below.

Alcohol 22 was prepared in hectogram quantities. Each 20 g batch of alcohol 22 produced 6 g of 27 with a total of 90 g of 27 synthesized to date. Each 6 g batch of acid 27 then yielded 1.1 g of core 3 with a total of 18 g of 3 synthesized to date.

Oxidation of 18 to Aldehyde 19

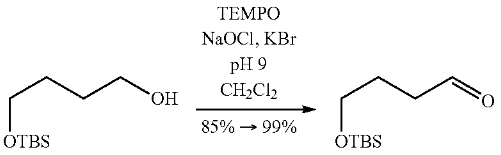

18 19

Reagents: TEMPO, 99% (Oakwood Chemical): used without further purification. KBr (Spectrum Chemical Mfg. Corp.): used without further purification. NaOCl 2 M, 10-15% active chlorine (Spectrum Chemical Mfg. Corp.): used without further purification.

4-((tert-Butyldimethylsilyl)oxy)butanal (19). A solution of KBr (6.99 g, 58.7 mmol) in $H_2O$ (60 mL) was added to a 3 L flask containing a solution of 18 (100 g, 489 mmol) in $CH_2Cl_2$ (1 L) followed by satd. $NaHCO_3$ (100 mL) and TEMPO (2.29 g, 14.7 mmol). The mixture was cooled to 0° C. and a mixture of NaOCl (2 M, 318 mL, 636 mmol) and satd. $NaHCO_3$ (300 mL) was added in portions via a dropping funnel. The mixture was allowed to warm to rt and stirred for 3 h. The mixture was extracted with $CH_2Cl_2$ (3×250 mL). The combined organic phases were washed with $H_2O$ (500 mL), brine (500 mL), dried over $Na_2SO_4$, filtered and concentrated on a rotary evaporator. Aldehyde 19 (100 g, 99%) was obtained as a clear oil without further purification. Characterization data matched literature values.

Aldehyde 19: TLC (1:10 EtOAc/hexanes): $R_f$ 0.20 ($KMnO_4$); $^1H$ NMR (500 MHz, $CDCl_3$) δ 9.79 (t, J=1.7 Hz, 1H), 3.65 (t, J=6.0 Hz, 2H), 2.50 (td, J=7.1, 1.7 Hz, 2H), 1.86 (tt, J=7.1, 5.9 Hz, 2H), 0.90 (m, 9H), 0.04 (s, 6H); $^{13}C$ NMR (125 MHz, $CDCl_3$) δ 202.5, 62.1, 40.8, 25.9, 25.5, 18.2, −5.4; LCMS (ES-API) m/z calcd. for $C_{10}H_{22}O_2Si$ $[M+1]^+$: 203.14.

Brown Addition to Aldehyde 19

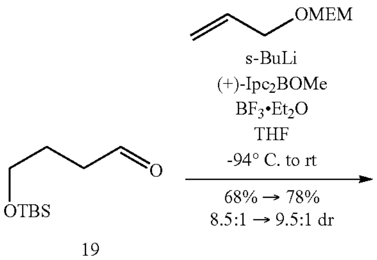

19

-continued

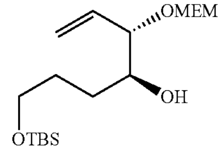

20

Reagents: s-BuLi, 1.4 M in cyclohexane (Sigma-Aldrich): used without further purification. (+)-B-Methoxydiisopinocampheylborane, 99% (Sigma-Aldrich): used without further purification. $BF_3$·$Et_2O$, 46.5% $BF_3$ (Alfa Aesar): used without further purification.

(8S,9S)-14,14,15,15-Tetramethyl-8-vinyl-2,5,7,13-tetraoxa-14-silahexadecan-9-ol (20). A solution of s-BuLi (1.4 M, 353 mL, 494 mmol) was added dropwise over 30 min to a 3 L three-necked flask containing a solution of MEM-protected allyl alcohol (86.7 g, 593 mmol) in anhydrous THF (1 L) cooled to −78° C. The resulting solution was stirred at −78° C. for 1 h followed by addition of a solution of (+)-B-methoxydiisopinocampheylborane (156 g, 494 mmol) in anhydrous THF (500 mL). The resulting clear mixture was stirred again at −78° C. for 1 h. $BF_3$. $Et_2O$ (79.3 mL, 642 mmol) was added followed by an addition of a solution of 4-((t-butyldimethylsilyl)oxy)butanal (19) (100 g, 494 mmol) in anhydrous THF (200 mL). The mixture was stirred at −78° C. for 3 h and then warmed to rt overnight. After cooling to 0° C., satd. $NH_4Cl$ (500 mL) was added to the mixture, which was extracted with $CH_2Cl_2$ (3×250 mL). The combined organic phases were washed with $H_2O$ (500 mL), brine (500 mL), dried over $Na_2SO_4$, filtered and concentrated on a rotary evaporator. Pure alcohol 20 (134 g, 78%) was obtained in 90.5% dr as determined by chiral HPLC by flash chromatography, eluting with a gradient of heptane to 1:1 EtOAc/heptane.

Alcohol 20: TLC (1:5 EtOAc/hexanes): $R_f$=0.25 (CAM stain); $^1H$ NMR (500 MHz, $CDCl_3$) δ 5.68 (ddd, J=17.3, 10.5, 8.0 Hz, 1H), 5.32 (m, 2H), 4.79 (d, J=7.0 Hz, 1H), 4.70 (d, J=7.0 Hz, 1H), 3.91 (t, J=7.9 Hz, 1H), 3.83 (ddd, J=10.9, 5.3, 3.5 Hz, 1H), 3.64 (m, 3H), 3.55 (ddd, J=5.3, 3.6, 1.9 Hz, 2H), 3.39 (s, 3H), 2.98 (bs, J=3.5 Hz, 1H), 1.71 (m, 1H), 1.63 (m, 2H), 1.40 (m, 1H), 0.88 (s, 9H), 0.04 (s, 6H); $^{13}C$ NMR (125 MHz, $CDCl_3$) δ 134.9, 120.0, 93.1, 81.6, 73.3, 71.7, 67.5, 63.3, 59.2, 29.5, 29.0, 26.1, 18.5, −5.2; FTIR (film) $\nu_{max}$ 3347, 2927, 2856, 1616, 1250, 1021 $cm^{-1}$; HR-ESI-MS m/z calcd. for $C_{17}H_{36}O_5SiNa$ $[M+Na]^+$: 371.2224, found 371.2223; $[\alpha]^{25}_D$=+51.5° (c=1.0, $CH_2Cl_2$).

Oxidation of 20 to Ketone 21

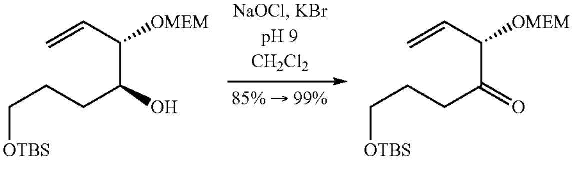

20 21

Reagents: TEMPO, 99% (Oakwood Chemical): used without further purification; KBr (Spectrum Chemical Mfg. Corp.): used without further purification; NaOCl 2 M, 10-15% active chlorine (Spectrum Chemical Mfg. Corp.): used without further purification.

(S)-14,14,15,15-Tetramethyl-8-vinyl-2,5,7,13-tetraoxa-14-silahexadecan-9-one (21). A solution of KBr (3.65 g, 30.6 mmol) in $H_2O$ (100 mL), satd. $NaHCO_3$ (250 mL) and TEMPO (3.99 g, 25.5 mmol) were added sequentially to a 2 L flask containing a solution of 20 (89.0 g, 255 mmol) in $CH_2Cl_2$ (400 mL). The mixture was cooled to 0° C. and a solution of NaOCl (2 M, 255 mL, 511 mmol) and satd. $NaHCO_3$ (300 mL) were added in portions (20 mL at a time) while maintaining the temperature below 0° C. The mixture was warmed to rt and stirred for 2 h. The phases were separated, and the aqueous phase was extracted with $CH_2Cl_2$ (2×200 mL). The combined organic phases were washed with brine (500 mL), dried over $Na_2SO_4$, filtered and concentrated on a rotary evaporator. Ketone 21 (88.0 g, 99%) was obtained without further purification.

Ketone 21: TLC (1:3 EtOAc/hexanes): $R_f$=0.40 (CAM stain); $^1H$ NMR (500 MHz, $CDCl_3$) δ 5.77 (ddd, J=17.2, 10.4, 6.8 Hz, 1H), 5.46 (dt, J=17.2, 1.3 Hz, 1H), 5.36 (dt, J=10.4, 1.0 Hz, 1H), 4.80 (d, J=7.0 Hz, 1H), 4.74 (d, J=7.0 Hz, 1H), 4.62 (dt, J=6.7, 1.2 Hz, 1H), 3.76 (dt, J=11.0, 4.4 Hz, 1H), 3.67 (m, 1H), 3.59 (t, J=6.1 Hz, 2H), 3.52 (t, J=4.6 Hz, 2H), 3.37 (s, 3H), 2.62 (m, 2H), 1.76 (m, 2H), 0.87 (s, 9H), 0.02 (s, 6H); $^{13}C$ NMR (125 MHz, $CDCl_3$) δ 208.2, 132.6, 120.2, 93.7, 82.7, 71.8, 67.5, 62.1, 59.2, 34.8, 26.4, 26.0, 18.4, −5.2; FTIR (film) $\nu_{max}$ 2954, 2929, 2857, 1720, 1472, 1256, 1101 $cm^{-1}$; HR-ESI-MS m/z calcd. for $C_{17}H_{34}O_5SiNa$ $[M+Na]^+$: 369.2068, found 369.2067; $[\alpha]^{25}_D$=+22.0° (c=1.0, $CH_2Cl_2$).

Stereoselective Grignard Addition to Ketone 21

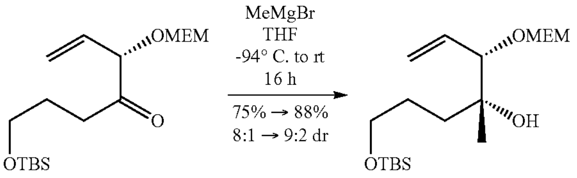

21 22

Reagents: MeMgBr, 3 M solution in $Et_2O$ (Sigma-Aldrich): used without further purification.

(8S,9R)-9,14,14,15,15-Pentamethyl-8-vinyl-2,5,7,13-tetraoxa-14-silahexadecan-9-ol (22). MeMgBr (3 M, 462 mL, 1.39 mmol) was added dropwise to a 5 L reaction flask containing a solution of ketone 21 (160 g, 462 mmol) in anhydrous THF (1.5 L) at −94° C. The mixture was stirred at −94° C. for 2 h, allowed to warm to rt and then stirred for an additional 16 h. After recooling to −78° C., satd. $NH_4Cl$ (500 mL) was added to the mixture dropwise. The mixture was diluted with $H_2O$ (1 L) and extracted with t-butyl methyl ether (2×500 mL). The combined organic phases were washed with $H_2O$ (500 mL) and brine (500 mL), dried over $Na_2SO_4$, filtered and concentrated on a rotary evaporator. The crude was filtered through a pad of Celite eluting with EtOAc, and the elutants were concentrated on a rotary evaporator. Alcohol 22 (155 g, 88%) was obtained in a 90% dr as determined by chiral HPLC without further purification. Note 1: Average batches of crude 22 contained <5% of starting material 21. Note 2: Solutions of MeMgBr in $Et_2O$ gave better yields and selectivity as compared to that in THF (≤70% yield, ≤90% de).

Alcohol 22: TLC (1:5 EtOAc/hexanes): $R_f$=0.30 (CAM stain); $^1H$ NMR (500 MHz, $CDCl_3$) δ 5.73 (ddd, J=17.2, 10.5, 8.1 Hz, 1H), 5.29 (ddd, J=14.7, 1.9, 0.8 Hz, 1H), 5.26 (ddd, J=21.6, 1.9, 0.8 Hz, 1H), 4.75 (d, J=7.0 Hz, 1H), 4.70 (d, J=7.0 Hz, 1H), 3.86 (d, J=8.0 Hz, 1H), 3.82 (dd J=5.2, 3.7 Hz, 1H), 3.80 (dd, J=5.5, 3.4 Hz, 1H), 3.61 (m, 3H), 3.53 (dd, J=3.3, 2.3 Hz 1H), 3.52 (dd, J=3.3, 1.9 Hz, 1H), 3.36 (s, 3H), 2.69 (s, 1H), 1.64 (m, 1H), 1.59 (m, 2H), 1.42 (m, 1H), 1.14 (s, 3H), 0.87 (s, 9H), 0.02 (s, 6H); $^{13}C$ NMR (125 MHz, $CDCl_3$) δ 134.3, 120.3, 93.3, 87.5, 73.4, 71.8, 67.5, 63.9, 59.1, 33.9, 26.6, 26.1, 23.6, 18.5, −5.2; FTIR (film) $\nu_{max}$ 2954, 2929, 2857, 2359, 1472, 1255, 1097, 1037 $cm^{-1}$; HR-ESI-MS m/z calcd. for $C_{18}H_{38}O_5SiNa$ $[M+Na]^+$: 385.2401, found 385.2403; $[\alpha]^{25}_D$=+57.3° (c=1.0, $CH_2Cl_2$).

Conversion of 22 to Alcohol 23

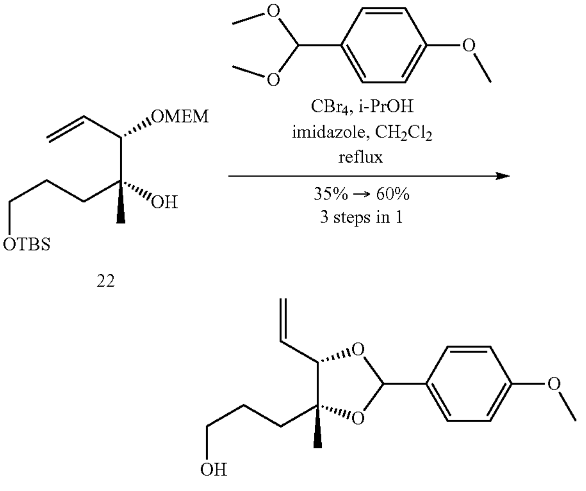

22

23

Reagents: $CBr_4$, 99% (TCI Chemicals): used without purification. Imidazole, 99% (Sigma-Aldrich): used without purification.

p-Anisaldehyde dimethyl acetal, 98% (Acros Organics): used without further purification. i-PrOH, 99% (Fischer Scientific): used as provided without further drying 3-((4R,5S)-2-(4-Methoxyphenyl)-4-methyl-5-vinyl-1,3-dioxolan-4-yl)propan-1-ol (23). $CBr_4$ (27.7 g, 63.8 mmol) and imidazole (500 mg, 7.34 mmol) were added to a solution of alcohol 22 (20.0 g, 55.2 mmol) in i-PrOH (2 L). The mixture was heated to reflux and stirred overnight at 100° C., at which point an orange color appeared, and NMR analyses indicated complete consumption of starting material. The mixture was cooled to rt and concentrated on a rotary evaporator. The resulting brown crude oil was immediately taken up in anhydrous $CH_2Cl_2$ (700 mL) and purged with Ar. Anisaldehyde dimethyl acetal (20.0 mL, 117 mmol) was added in one aliquot, and the mixture turned purple after 10 min of stirring at rt. The reaction was stirred overnight. Satd. $NaHCO_3$ (100 mL) was added, and the mixture was extracted with $CH_2Cl_2$ (2×500 mL). The organics were combined and concentrated on a rotary evaporator to yield a brown oil. Pure alcohols 23 (9.21 g, 60%) was obtained by flash chromatography, eluting with a gradient of hexanes to 1:3 EtOAc/hexanes. Note 1: Batches of 23 were obtained in an inconsequential mixture of acetal diastereomers, as noted in its structure.

Alcohols 23: TLC (1:1 EtOAc/hexanes): $R_f$=0.37 (CAM stain); $^1H$ NMR (500 MHz, $C_6D_6$) δ 7.55 (d, J=8.6 Hz, 2H), 7.50 (d, J=8.7 Hz, 2H), 6.82 (d, J=8.7 Hz, 2H), 6.81 (d, J=8.6 Hz, 2H), 6.16 (s, 1H), 5.91 (s, 1H), 5.79 (m, 1H), 5.71 (m, 1H), 5.30 (dt, J=3.5, 1.6 Hz, 1H), 5.27 (dt, J=3.5, 1.6 Hz, 1H), 5.07 (dd, J=1.7, 1.7 Hz, 1H), 5.05 (dd, J=1.7, 1.7 Hz, 1H), 4.17 (dt, J=6.7, 1.2 Hz, 1H), 4.09 (dt, J=6.7, 1.2 Hz, 1H), 3.42 (m, 2H), 3.38 (m, 2H), 3.27 (s, 3H), 3.26 (s, 3H), 1.73 (m, 2H) 1.53 (m, 2H), 1.33 (m, 1H) 1.19 (s, 3H) 1.17 (s, 3H); $^{13}C$ NMR (125 MHz, $C_6D_6$) δ 160.8, 160.6, 133.9, 133.8, 133.8, 133.7, 132.8, 131.1, 128.5, 128.3, 117.9, 117.9, 117.8, 117.6, 114.0, 113.9, 107.7, 102.5, 102.2, 96.3, 88.0, 86.5, 86.2, 86.2, 83.6, 82.5, 82.4, 81.8, 63.1, 63.0, 63.0, 58.4, 58.4, 33.8, 32.7, 31.3, 29.9, 28.6, 27.5, 27.3, 27.2, 27.1, 22.9, 22.5, 22.0, 21.8; FTIR (film) vmax 3421, 3080, 2938, 1718, 1614, 1516, 1932, 1303, 1249, 1170, 1032 $cm^{-1}$; HR-ESI-MS m/z calcd. for $C_{16}H_{22}O_4Na$ $[M+Na]^+$: 301.1410, found 301.1411; $[\alpha]^{25}_D$=+14.8° (c=0.4, $CH_2Cl_2$).

Oxidation of 23 to Aldehyde 24

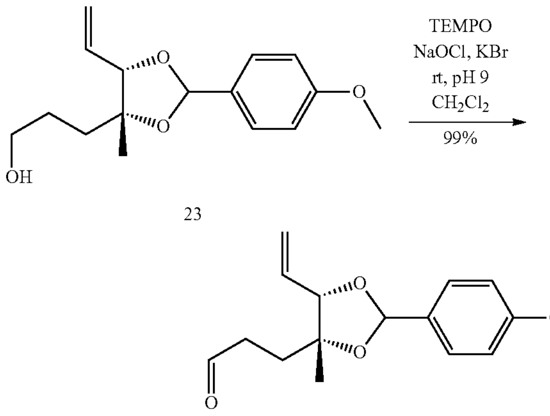

23

24

Reagents: TEMPO, 99% (Oakwood Chemical): used without further purification; KBr (Spectrum Chemical Mfg. Corp.): used without further purification; NaOCl, 2 M, 10-15% active chlorine (Spectrum Chemical Mfg. Corp.): used without further purification.

3-((4R,5S)-2-(4-Methoxyphenyl)-4-methyl-5-vinyl-1,3-dioxolan-4-yl)propanal (24). A solution of KBr (0.699 g, 5.87 mmol) in $H_2O$ (60.0 mL) was added to a 2 L flask containing a solution of alcohol 23 (11.2 g, 40.2 mmol) in $CH_2Cl_2$ (750 mL) followed by satd. $NaHCO_3$ (75 mL) and TEMPO (229 mg, 1.47 mmol). The mixture was cooled to 0° C., and a mixture of NaOCl (2 M, 32.0 mL, 63.6 mmol) and satd. $NaHCO_3$ (50 mL) was added in portions (20 mL). The mixture was allowed to warm to rt. After stirring at rt for 3 h, the mixture was extracted with $CH_2Cl_2$ (3×250 mL). The combined organic phases were washed with $H_2O$ (500 mL) and brine (500 mL), dried over $Na_2SO_4$, filtered and concentrated on a rotary evaporator. Aldehyde 24 (11 g, 99%) was used without further purification. Note 1: Aldehydes 24 are susceptible to rearrangement when purified over unbuffered silica gel.

Aldehydes 24: TLC (1:1 EtOAc/hexanes): $R_f$=0.70 (CAM stain); $^1H$ NMR (500 MHz, $C_6D_6$) δ 9.39 (s, 1H), 9.29 (s, 1H), 7.47 (d, J=8.7 Hz, 2H), 7.45 (d, J=8.7 Hz, 2H), 6.81 (d, J=4.3 Hz, 2H), 6.79 (d, J=4.3 Hz, 2H), 6.02 (s, 1H), 5.83 (s, 1H), 5.70 (m, 1H), 5.65 (m, 1H), 5.28 (dt, J=13.0, 1.6 Hz, 1H), 5.24 (dt, J=12.8, 1.8 Hz, 1H), 5.04 (dt, J=4.7, 1.5 Hz, 1H), 5.02 (dt, J 4.6, 1.4 Hz, 1H), 4.10 (dt, J=6.6, 1.3 Hz, 1H), 4.02 (dt, J=6.6, 1.2 Hz, 1H), 3.27 (s, 3H), 3.25 (s, 3H), 2.26 (m, 2H), 2.04 (m, 3H), 1.87 (ddd, J=13.0, 9.8, 5.5 Hz, 1H), 1.41 (ddd J=14.3, 9.7, 5.5 Hz, 1H), 1.00 (s, 3H), 0.99 (s, 3H); $^{13}C$ NMR (125 MHz, $C_6D_6$) δ 200.5, 200.4, 160.8, 160.6, 133.2, 133.1, 132.7, 130.8, 128.4, 128.4, 118.2, 118.2, 114.0, 113.9, 102.5, 102.2, 87.6, 87.5, 82.7, 81.4, 54.8, 38.9, 38.4, 29.3, 25.7, 22.6, 21.9; FTIR (film) vmax 2935, 2838, 2730, 1724, 1612, 1515, 1392, 1257, 1249, 1172, 1114, 1033, 1006 $cm^{-1}$; HR-ESI-MS m/z calcd. for $C_{16}H_{20}O_4Na$ $[M+Na]^+$: 299.3181, found 299.3175; $[\alpha]^{25}_D$=+35.7° (c=1.0, $CH_2Cl_2$).

Synthesis of auxiliary 39. A two-step sequence to prepare auxiliary (S)-1-(4-(tert-Butyl)-2-thioxothiazolidin-3-yl) ethan-1-one beginning with commercially available (S)-4-(tert-Butyl)thiazolidine-2-thione, was optimized from developed methods (32).

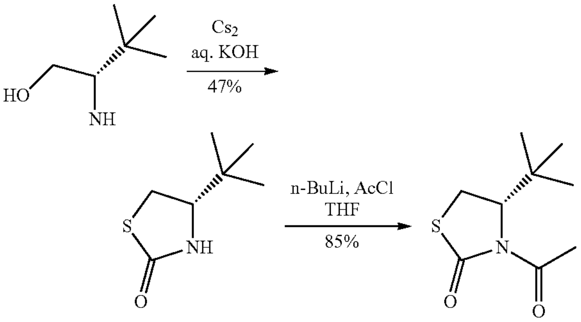

Reagents: KOH, 99% (Fischer Scientific): used without further purification. $CS_2$, 98% (Alfa Aesar): used without further purification.

Preparation of (S)-4-(tert-butyl)thiazolidine-2-thione (S)-4-(tert-Butyl)thiazolidine-2-thione. KOH (2.63 kg, 46.9 mol) was dissolved in $H_2O$ (9 L) and stirred in a 20 L reactor equipped with a mechanical stirrer and two reflux condensers. (S)-2-Amino-3,3-dimethylbutan-1-ol (250 g, 2.13 mol) was added followed by dropwise addition of $CS_2$ (1.03 L, 17.1 mol). The mixture was heated at 95° C. for 16 h. After cooling to 50° C., an additional portion of $CS_2$ (1.03 L, 17.1 mol) was added dropwise, and the mixture was heated at 70° C. for 16 h. The mixture was cooled to 50° C., and a third portion of $CS_2$ (500 mL) was added dropwise. The mixture was heated to 65° C. and stirred for 48 h. After cooling the mixture to rt, the solids were collected by filtration and washed with $H_2O$ (2 L). The white solids were dried at rt by airflow. Pure (S)-4-(tert-butyl)thiazolidine-2-thione (176 g, 47%) was obtained by flash chromatography, eluting with $CH_2Cl_2$.

(S)-4-(tert-Butyl)thiazolidine-2-thione: TLC ($CH_2Cl_2$): $R_f$=0.70, UV; $^1H$ NMR (500 MHz, $CDCl_3$) δ 7.58 (s, 1H), 4.01 (t, J=9.6, 8.5, 1.2 Hz, 1H), 3.41 (m, 2H), 1.01 (s, 9H); $^{13}C$ NMR (125 MHz, $CDCl_3$) δ 73.3, 34.5, 34.4, 25.9; LCMS (ES-API) m/z calcd. for $C_7H_{13}NS_2$ $[M+1]^+$: 176.05.

Acetylation of (S)-4-(tert-butyl)thiazolidine-2-thione

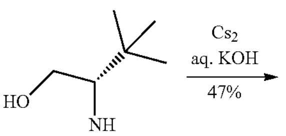

-continued

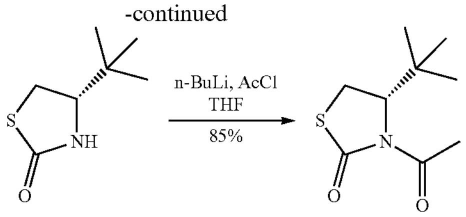

Reagents: n-BuLi, 2.5 M in hexane (Acros Organics): used without further purification. Acetyl chloride, 98% (Sigma-Aldrich): used without further purification (S)-1-(4-(tert-Butyl)-2-thioxothiazolidin-3-yl)ethan-1-one. n-BuLi (2.5 M, 460 mL, 1.15 mol) was added dropwise to a 5 L flask containing a solution of (S)-4-(tert-butyl) thiazolidine-2-thione (182 g, 1.04 mol) in anhydrous THF (1.8 L) at −78° C. The mixture was stirred at −78° C. for 30 min. Acetyl chloride (89.0 mL, 1.25 mol) was added dropwise, and the mixture was stirred at −78° C. for 1.5 h. The mixture was then warmed to rt, stirred for 1 h, recooled to 0° C. and quenched with satd. $NH_4Cl$ (800 mL). The phases were separated, and the aqueous phase was extracted with $CH_2Cl_2$ (2×200 mL). The combined organic phases were dried over $Na_2SO_4$, filtered and concentrated on a rotary evaporator. Pure (S)-1-(4-(tert-butyl)-2-thioxothiazolidin-3-yl)ethan-1-one (191 g, 85%) was obtained by flash chromatography, eluting with a gradient of heptane to $CH_2Cl_2$. Note 1: This procedure was repeated to deliver a total of 186 g of (S)-1-(4-(tert-butyl)-2-thioxothiazolidin-3-yl)ethan-1-one, which was routinely recycled throughout this program.

(S)-1-(4-(tert-Butyl)-2-thioxothiazolidin-3-yl)ethan-1-one: TLC (1:1 $CH_2Cl_2$/heptane): $R_f$=0.80, UV; $^1H$ NMR (500 MHz, $CDCl_3$) δ 5.28 (dd, J=8.4, 1.0 Hz, 1H), 3.51 (dd, J=11.8, 8.5 Hz, 1H), 3.08 (d, J=11.0 Hz, 1H), 2.77 (s, 3H), 1.03 (s, 9H); $^{13}C$ NMR (125 MHz, $CDCl_3$) δ 205.3, 170.3, 72.0, 38.0, 30.5, 26.9, 26.8; LCMS (ES-API) m/z calcd. for $C_9H_{15}NS_2$ $[M+1]^+$: 217.06.

Stereoselective Aldol Addition of 24 to 25

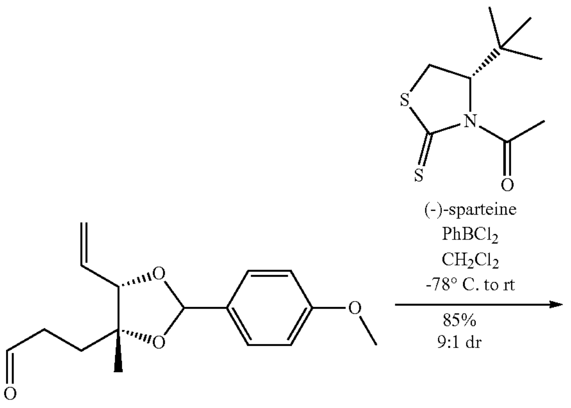

24

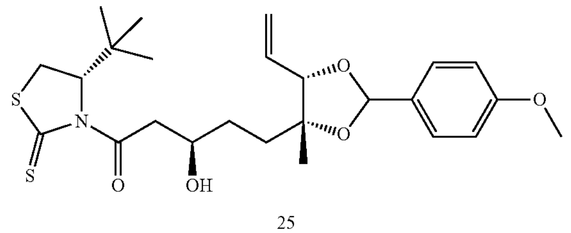

25

Reagents: Dichlorophenylborane, 97% (Acros Organics): used without further purification. (−)-Sparteine, 98% (TCI Chemicals), S0461: used without further purification. (S)-1-(4-(tert-butyl)-2-thioxothiazolidin-3-yl)ethan-1-one: dried via azeotropic removal of toluene by rotary evaporation (3R)-1-((R)-5-(tert-Butyl)-2-thioxothiazolidin-3-yl)-3-hydroxy-5-((4R,5S)-2-(4-methoxy-phenyl)-4-methyl-5-vinyl-1,3-dioxolan-4-yl)pentan-1-one (25). (S)-1-(4-(tert-Butyl)-2-thioxothiazolidin-3-yl)ethan-1-one (11.7 g, 53.7 mmol) was added to a 3 L flask and dissolved in anhydrous $CH_2Cl_2$ (800 mL). An Ar atmosphere was introduced, and dichlorophenylborane (6.20 mL, 47.8 mmol) was added at rt and stirred for 15 min. (−)-Sparteine (21.9 mL, 95.5 mmol) was added neat, at which point the mixture appeared cloudy but became homogeneous upon further stirring within 1 min. After stirring at rt for 30 min the mixture was cooled to −78° C., and aldehyde 24 (11.0 g, 39.8 mmol) in a solution of anhydrous $CH_2Cl_2$ (80 mL) was added dropwise over 15 min. The mixture was stirred at −78° C. for 1 h and slowly warmed to 0° C. over 3 h, at which point NMR analyses indicated complete consumption of starting material. The mixture was quenched with satd. $NaHCO_3$ (200 mL), and the organic phase was separated. The aqueous phase was washed with $CH_2Cl_2$ (200 mL), and the organic phases were combined, dried over $Na_2SO_4$, filtered and concentrated on a rotary evaporator. Alcohol 25 (16.7 g, 85%) was obtained in a 9:1 dr as a yellow oil by vacuum filtration over neutral silica gel eluting with $CH_2Cl_2$ (1.5 L, elution of unreacted auxiliary) and 1:1 EtOAc/hexanes (1.5 L, elution of product). Note 1: Aldol adduct 25 was susceptible to hydrolysis when purified on untreated silica gel. Flash chromatography on neutral silica gel eluting with a gradient of hexanes to 1:1 EtOAc/hexanes can be used to obtain 25 in 95%+ purity. In practice this material is sufficiently clean after passing it through a vacuum funnel plug of neutral silica. Note 2: Minor unwanted C3 isomers were observable by NMR and carried forward.

Alcohols 25: TLC (1:3 EtOAc/hexanes): $R_f$=0.23 (CAM stain); $^1H$ NMR (500 MHz, $C_6D_6$) δ 7.62 (d, J=8.6 Hz, 2H), 7.52 (d, J=8.6 Hz, 2H), 7.34 (m, minor), 6.86 (d, J=8.7 Hz, 2H), 6.81 (d, J=8.7 Hz, 2H), 6.78 (d, J=8.8 Hz, minor), 6.26 (s, 1H), 5.94 (s, 1H), 5.84 (m, 2H), 5.76 (m, minor), 5.33 (dt, J=2.0, 1.0 Hz, 1H), 5.29 (dt, J=2.0, 1.0 Hz, 1H), 5.27 (dd, J=1.9, 1.3 Hz, 1H, minor), 5.23 (dd, J=1.9, 1.3 Hz, minor), 5.10 (dt, J=2.0, 1.2 Hz, 1H), 5.07 (dt, J=2.1, 1.2 Hz, 1H), 5.06 (dd, J=1.9, 1.2 Hz, minor), 5.05 (d, J=0.8 Hz, 1H), 5.04 (dd, J=1.9, 1.2 Hz, minor), 5.03 (d, J=7.6 Hz, 1H), 4.98 (d, J=7.6 Hz, 1H), 4.87 (d, J=0.8 Hz, 1H), 4.21 (dt, J=6.7, 1.3 Hz, 1H), 4.12 (d, J=6.7, 1.2 Hz 1H), 4.09 (m, 2H), 4.02 (d, J=9.4 Hz, minor), 3.99 (d, J=9.4 Hz, minor), 3.87 (t, J=1.2 Hz, minor), 3.85 (t, J=1.2 Hz, minor), 3.61 (m, 2H), 3.30 (d, J=2.9 Hz, minor) 3.29 (s, minor), 3.28 (s, 3H), 3.27 (s, 3H), 3.23 (d, J=2.6 Hz, minor) 3.19 (d, J=2.6 Hz, minor), 2.49 (m, 2H), 2.45 (m, minor), 2.27 (ddd, J=13.9, 11.8, 4.4 Hz, 1H), 2.21 (ddd, J=13.5, 11.8, 4.6 Hz, 1H), 2.01 (m, 2H), 1.93 (m, 1H), 1.89 (m, minor), 1.83 (m, minor), 1.63 (m, 2H), 1.44 (ddd, J=13.5, 11.5, 4.8 Hz, 1H), 1.31 (m, 1H), 1.23 (s, 3H), 1.20 (s, 3H), 1.10 (s, minor) 0.74 (s, 3H), 0.73 (s, minor), 0.71 (s, 3H); $^{13}C$ NMR (125 MHz, $C_6D_6$) δ 205.2, 205.2, 173.0, 173.0, 172.4, 172.0, 160.8, 160.6, 159.6, 135.8, 133.9, 133.8, 133.8, 133.0, 131.2, 128.7, 128.4, 128.2, 128.1, 127.6, 118.1, 118.0, 117.9, 114.2, 114.1, 113.9, 113.5, 102.8, 102.3, 93.7, 88.0, 86.5, 86.3, 83.4, 82.3, 81.8, 72.1 72.0, 72.0, 70.6, 68.8, 68.8, 68.8, 54.8, 54.8, 47.3, 45.8, 45.7, 45.5, 37.9, 37.9, 33.2, 31.3, 31.1, 30.9, 30.8, 29.8, 29.8, 29.4, 26.7, 22.8, 22.2, 22.0; FTIR (film) $\nu_{max}$ 3640, 3427, 2966, 2877, 1685, 1594, 1501, 1452, 1352, 1338, 1320, 1248, 1155, 1140, 1075, 1024 $cm^{-1}$; HR-ESI-MS m/z calcd. for $C_{25}H_{35}NO_5S_2Na$ $[M+Na]^+$: 516.6689, found 516.6694; $[\alpha]^{25}{}_D$=+245° (c=1.0, $CH_2Cl_2$).

TBS Protection of 25 to Adduct 26

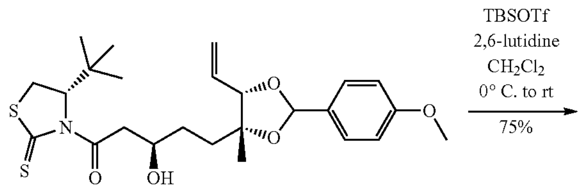

25

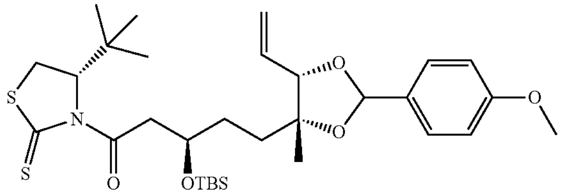

26

Reagents: 2,6-Lutidine, redistilled, 99% (Chem-Impex Int.): used without further purification. TBSOTf, 99% (Chem-Impex Int.): used without further purification.

(3R)-1-((R)-5-(tert-Butyl)-2-thioxothiazolidin-3-yl)-3-((tert-butyldimethylsilyl)oxy)-5-((4R,5S)-2-(4-methoxyphenyl)-4-methyl-5-vinyl-1,3-dioxolan-4-yl)pentan-1-one (26). Alcohol 25 (15.0 g, 30.4 mmol) was dissolved in anhydrous $CH_2Cl_2$ (600 mL) in a 2 L flask followed by addition of 2,6-lutidine (18.54 mL, 159 mmol). The mixture was purged with Ar and cooled to 0° C. TBSOTf (27.4 mL, 119 mmol) was added dropwise, and the mixture was warmed to rt and stirred overnight, at which point NMR analyses indicated complete consumption of starting material. The solution was quenched with addition of solid $NaHCO_3$ (5 g) and stirred for 15 min. The mixture was concentrated to 50 mL under rotary evaporation. Adduct 26 (13.9 g, 75%) was obtained as a yellow oil by vacuum filtration over neutral silica gel eluting with $CH_2Cl_2$. Note 1: 26 can be further purified (95+%) via flash chromatography on neutral silica gel eluting with a gradient of hexanes to 1:10 EtOAc/hexanes. In practice the material is sufficiently clean to proceed to the next step without chromatography. Note 2: Minor unwanted $C_3$ isomers were carried forward.

Adducts 26: TLC ($CH_2Cl_2$): $R_f$=0.40 (CAM stain); $^1$H NMR (500 MHz, $C_6D_6$) δ 7.61 (d, J=8.6 Hz, 2H), 7.56 (d, J=8.6 Hz, 2H), 6.89 (d, J=8.8 Hz, 2H), 6.81 (d, J=8.7 Hz, 2H), 6.31 (s, 1H), 5.94 (s, 1H), 5.87 (m, 2H), 5.36 (dt, J=3.1, 1.6 Hz, 1H), 5.33 (dt, J=2.9, 1.5 Hz, 1H), 5.14 (m, minor), 5.12 (t, J=1.5 Hz, 1H), 5.11 (t, J=1.5 Hz, 1H), 5.10 (t, J=1.4 Hz, 1H), 5.09 (t, J=1.5 Hz, 1H), 5.06 (d, J=7.9 Hz, 1H), 5.03 (d, J=7.6 Hz, 1H), 4.97 (d, J=8.1 Hz, minor), 4.54 (m, 1H), 4.46 (m, 1H), 4.23 (dt, J=6.4, 1.3 Hz, 1H), 4.14 (dt, J=6.5, 1.3 Hz, 1H), 3.80 (dd, J=17.2, 5.9 Hz, 1H), 3.76 (m, minor), 3.73 (m, 1H), 3.69 (m, 1H), 3.66 (m, minor), 3.61 (dd, J=17.3, 5.3 Hz, 1H), 3.31 (s, 3H), 3.30 (s, minor), 3.26 (s, 3H), 2.56 (ddd, J=11.8, 10.9, 8.3 Hz, 1H), 2.54 (m, minor), 2.17 (m, 1H), 2.03 (m, 1H), 1.93 (m, 2H), 1.90 (m, minor), 1.50 (m, 1H), 1.41 (ddd, J=13.5, 11.4, 5.1 Hz, 1H), 1.28 (s, 3H), 1.26 (s, minor), 1.26 (s, 3H), 1.23 (s, minor), 1.03 (s, 3H), 1.03 (s, minor), 1.00 (s, 9H), 0.99 (s, minor), 0.78 (s, minor), 0.77 (s, 9H), 0.27 (s, minor), 0.22 (s, 3H), 0.21 (s, minor), 0.19 (s, 3H), 0.19 (s, 3H), 0.16 (s, minor), 0.14 (s, 3H); $^{13}$C NMR (125 MHz, $C_6D_6$) δ 205.1, 205.0, 170.9, 170.9, 170.8, 160.8, 160.6, 133.9, 133.7, 133.6, 133.0, 131.3, 128.7, 128.4, 128.2, 127.9, 127.7, 127.5, 118.0, 117.9, 114.1, 113.9, 102.7, 102.4, 88.0, 87.9, 86.1, 83.6, 83.5, 82.4, 82.2, 72.2, 72.1, 70.3, 69.5, 69.4, 54.8, 54.8, 53.3, 46.4, 46.1, 37.9, 37.8, 34.0, 32.8, 32.0, 31.5, 29.9, 29.8, 28.9, 26.8, 26.2, 26.2, 25.9, 22.7, 22.2, 18.4, 18.3, −3.4, −4.2, −4.2, −4.3, −4.3; FTIR (film) $\nu_{max}$ 2966, 2858, 1697, 1369, 1319, 1265, 1261, 1195, 1037, 1029 $cm^{-1}$; HR-ESI-MS m/z calcd. for $C_{31}H_{49}NO_5S_2SiNa$ $[M+Na]^+$: 630.2689, found 630.2691; $[\alpha]^{25}{}_D$=+210° (c=1.0, $CH_2Cl_2$).

Saponification of Adduct 26 to Acid 27

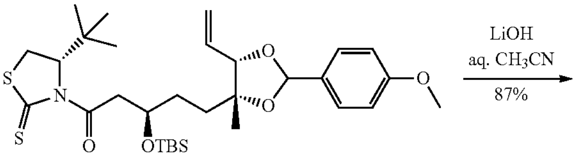

26

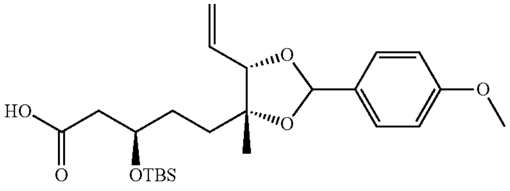

27

Reagents: LiOH—$H_2O$, 98% (Alfa Aesar): used without further purification.

(3R)-3-((tert-Butyldimethylsilyl)oxy)-5-((4R,5S)-2-(4-methoxyphenyl)-4-methyl-5-vinyl-1,3-dioxolan-4-yl)pentanoic acid (27). LiOH—$H_2O$ (5.01 g, 119 mmol) was added to a 3 L flask containing a solution of 26 (13.5 g, 22.2 mmol) in 20% aq $CH_3CN$ (500 mL). The mixture was stirred at rt overnight, at which point the deep yellow color dissipated into a light brown solution. The mixture was diluted with $H_2O$ (500 mL) and $Et_2O$ (600 mL). The aqueous phase was collected, and the organic phase was extracted with $H_2O$ (2×400 mL). The aqueous phases were combined, and the pH was adjusted to 6.5 with 1 M HCl. The mixture was extracted into EtOAc (3×700 mL), and the organics were combined, dried over $Na_2SO_4$, filtered and concentrated by rotary evaporation. Acid 27 (8.76 g, 87%) was obtained as a colorless oil by vacuum filtration over silica gel eluting with $CH_2Cl_2$ (elution of auxiliary) and 1:5 EtOAc/hexanes (elution of product).

Acids 27: TLC (1:1 EtOAc/hexanes): $R_f$=0.54 (CAM stain); $^1$H NMR (500 MHz, $C_6D_6$) δ 7.55 (d, J=8.8 Hz, 2H), 7.53 (d, J=8.7 Hz, 2H), 6.86 (d, J=8.7 Hz, 2H), 6.82 (d, J=8.7 Hz, 2H), 6.20 (s, 1H), 5.92 (s, 1H), 5.81 (ddd, J=17.4, 10.7, 6.6 Hz, 1H), 5.78 (ddd, J=17.4, 10.7, 6.6 Hz, 1H), 5.71 (m, minor), 5.35 (dd, J=1.5, 1.5 Hz, 1H), 5.31 (dd, J=1.5, 1.5 Hz, 1H), 5.29 (m, minor), 5.25 (m, minor), 5.11 (dt, J=3.4, 1.5 Hz, 1H), 5.09 (dt, J=3.3, 1.4 Hz, 1H), 5.08 (m, minor), 5.06 (m, minor), 4.19 (m, 1H), 4.11 (m, 1H) 3.31 (s, 3H), 3.27 (s, 3H), 2.47 (dd, J=15.0, 7.2 Hz, 1H), 2.39 (dd, J=15.0, 7.4 Hz, 1H), 2.31 (dd, J=15.0, 5.0 Hz, 1H), 2.31 (dd, J=15.0, 4.7 Hz, 1H), 1.89 (m, 2H), 1.66 (m, 2H), 1.22 (m, 1H), 1.17 (s, 3H), 1.06 (s, 9H), 0.97 (s, minor), 0.96 (s, 9H), 0.15 (s, 3H), 0.12 (s, minor), 0.11 (s, 3H), 0.08 (s, minor) 0.06 (s, 3H); $^{13}$C NMR (125 MHz, $C_6D_6$) δ 177.4, 177.4, 160.8, 160.6, 133.6, 133.5, 132.9, 131.2, 128.5, 128.4, 128.2, 128.0, 127.7, 127.7, 127.6, 118.0, 117.9, 114.0, 114.0, 93.7, 87.9, 86.3, 86.0, 83.3, 82.0, 81.6, 70.0, 69.9, 54.8, 54.8, 32.6, 31.8, 31.4, 30.2, 28.8, 26.6, 26.1, 26.0, 22.6, 22.1, 21.9, 18.3, 18.2, −4.3, −4.4, −4.4, −4.6, −4.6, −4.7; FTIR (film) $\nu_{max}$ 3683, 2958, 2931, 2858, 1731, 1612, 1265, 1250, 1072 $cm^{-1}$; HR-ESI-MS m/z calcd. for $C_{24}H_{38}O_6SiNa$ $[M+Na]^+$: 473.2287, found 473.2290; $[\alpha]^{25}_D$=+11.95° (c=0.8, $CH_2Cl_2$).

Synthesis of intermediate 33. A four step sequence was optimized from developed methods (45) to prepare aldehyde 32 at multi-gram scale. Conversion of 32 to 33 produced a dr of 91%.

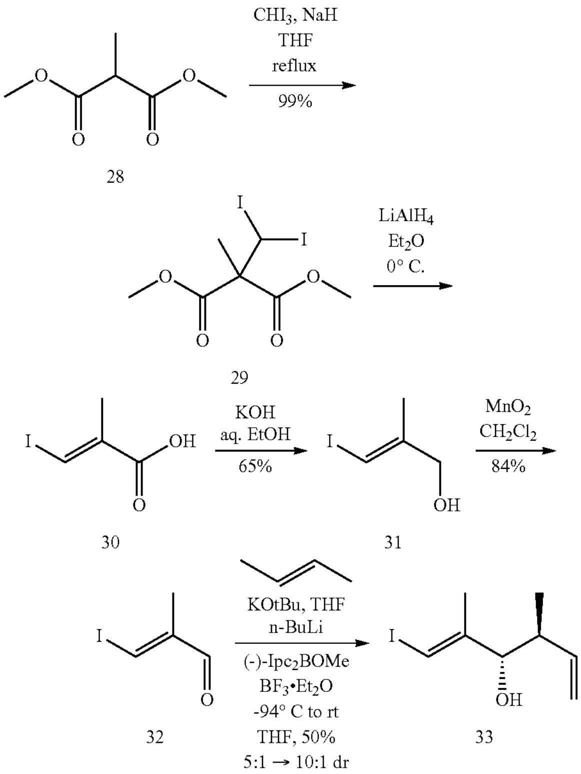

28 29 30 31 32 33

Reagents: Dimethyl 2-methylmalonate, 97% (Sigma-Aldrich): used without further purification; NaH, 60% dispersion in mineral oil, (Alfa Aesar): used without further purification; $CHI_3$, 98% (Oakwood Chemicals): used without further purification; KOH, 99% (Fischer Scientific): used without further purification; $LiAlH_4$, 99%. (Sigma-Aldrich): used without further purification.

(E)-3-Iodo-2-methylprop-2-en-1-ol (31). The conversion of 28 to alcohol 31 was completed without purification of 29 and 30. A solution of dimethyl 2-methylmalonate (28) (310 mL, 2.33 mol) in anhydrous THF (800 mL) was added dropwise over 20 min to a suspension of NaH (60% in a mineral oil, 150 g, 3.75 mol) in anhydrous THF (800 mL) in a 10 L reaction vessel. The reaction was stirred at reflux for 1.5 h. A solution of $CHI_3$ (802 g, 2.04 mol) in anhydrous THF (2 L) was added dropwise over 40 min. The mixture was cooled to 50° C. and stirred for 16 h. After cooling to 0° C., 2 M HCl (1.5 L) was slowly added to the mixture. The phases were separated, and the aqueous phase was extracted with EtOAc (2×300 mL). The combined organic phases were dried over $Na_2SO_4$, filtered and concentrated on a rotary evaporator to yield diester 29 (1.01 kg, 99%), which was then dissolved in 80% EtOH (2.5 L) in a 5 L flask. KOH (700 g, 12.5 mol) was added dropwise as a solution in $H_2O$ (1 L) over 1 h. The mixture was heated at reflux and stirred for 16 h. After cooling to rt, the mixture was concentrated on a rotary evaporator. The resulting crude material was acidified to pH 1 with conc. HCl and extracted into $CH_2Cl_2$ (1 L). The organic phase was washed with $H_2O$ (1 L), and the aqueous phase was extracted with $CH_2Cl_2$ (3×600 mL). The combined organic phases were dried over $Na_2SO_4$, filtered and concentrated on a rotary evaporator. The resulting crude acid 30 (289 g, 1.36 mol) was dissolved in anhydrous $Et_2O$ (400 mL) and added dropwise over 20 min to a 3 L three-necked flask containing a suspension of $LiAlH_4$ (76.4 g, 2.01 mol) in anhydrous $Et_2O$ (800 mL) cooled to −20° C. The mixture was stirred at −20° C. for 1 h, warmed to rt and stirred for a further 2 h. After cooling the mixture to −78° C., acetone (200 mL) was added dropwise over 30 min, followed by a dropwise addition of 2 M HCl (800 mL) over 1 h. The resulting mixture was filtered through a Büchner filter fitted with Whatman filter paper #1. The phases were separated, and the aqueous phase was extracted with t-butyl methyl ether (3×1 L). The combined organic phases were washed with brine (3×500 mL), dried over $Na_2SO_4$, filtered and concentrated on a rotary evaporator. Pure alcohol 31 (146 g, 65% over two steps) was obtained by flash chromatography, eluting with a gradient of heptane to $CH_2Cl_2$ in incremental increases of 1:5 $CH_2Cl_2$/heptane. Characterization data matched literature values.

Alcohol 31: TLC (1:1 $CH_2Cl_2$/heptane): $R_f$=0.60 ($KMnO_4$); $^1$H NMR (500 MHz, $CDCl_3$) δ 6.27 (h, J=1.2 Hz, 1H), 4.11 (bs, 2H), 1.83 (bs, 3H); $^{13}$C NMR (125 MHz, $CDCl_3$) δ 147.3, 67.2, 21.5; HR-ES-MS m/z calcd. for $C_4H_7IONa$ $[M+Na]^+$: 220.9498, found 220.9499.

(3S,4S,E)-1-Iodo-2,4-dimethylhexa-1,5-dien-3-ol (33). The conversion of alcohol 31 to vinyl iodide 33 was completed without purification of aldehyde 32. Activated $MnO_2$ (643 g, 7.39 mol) was added to a 2 L three-necked flask containing a solution of 31 (146 g, 739 mmol) in anhydrous $CH_2Cl_2$ (1 L). The mixture was stirred vigorously at rt for 16 h. The mixture was then passed through a pad of Celite, followed by concentration on a rotary evaporator, to yield crude aldehyde 32 (142.4 g, 84%). (E)-But-2-ene (200 mL, 2.00 mol) was condensed and added to a 10 L reaction flask containing anhydrous THF (1.5 L) at −78° C. KOt-Bu (114 g, 1.01 mol) was added, and the mixture was stirred at −78° C. for 30 min. n-BuLi (2.5 M in hexane, 400 mL, 1.00 mol) was added dropwise over 15 min, and the resulting yellow mixture was stirred at −78° C. for an additional 30 min. A solution of (−)-B-methoxydiisopinocampheylborane (253 g, 800 mmol) in anhydrous THF (1 L) was added dropwise over 15 min, and the mixture turned clear. After stirring the mixture for 30 min, $BF_3$. $Et_2O$ (170 mL, 1.34 mol) was added dropwise over 10 min, and the mixture was stirred for an additional 10 min. After cooling the mixture to −94° C., a solution of 32 (121 g, 617 mmol) in anhydrous THF (750 mL) was added dropwise over 45 min. The mixture was allowed to warm to rt and stirred for 16 h. $H_2O$ (2 L) was added, and the mixture was concentrated on a rotary evaporator. Vinyl iodide 33 (78.0 g, 50%) was obtained at a 10:1 dr by flash chromatography, eluting with $CH_2Cl_2$. Note 1: Efficacy of $MnO_2$ may vary depending on supplier. An alternative procedure involving stirring alcohol 31 with 2 eq. of IBX in DMSO at rt for 30 min will also produce comparable yields of aldehyde 32. Note 2: Aldehyde 32 is volatile and will evaporate upon exposure to high vacuum.

Vinyl iodide 33: TLC ($CH_2C_2$): $R_f$=0.40 ($KMnO_4$); $^1$H NMR (500 MHz, $CDCl_3$) δ 6.26 (s, 1H), 5.72 (m, 1H), 5.18

(d, J=16.0 Hz, 1H), 5.18 (d, J=11.3 Hz, 1H), 3.87 (dd, J=8.1, 2.9 Hz, 1H), 2.36 (h, J=7.4 Hz, 1H), 1.88 (d, J=2.9 Hz, 1H), 1.82 (bs, 3H), 0.92 (d, J=6.8 Hz, 3H); $^{13}C$ NMR (125 MHz, $CDCl_3$) δ 148.1, 140.0, 117.4, 80.2, 80.0, 42.4, 19.4, 16.6; HR-ES-MS m/z calcd. for $C_8H_{13}IONa$ $[M+Na]^+$: 274.9998, found 274.9997; $[\alpha]^{25}_D$=−23.6° (c=1.0, $CH_2Cl_2$).

Esterification of Acids 27 with Alcohol 33 to Afford 34

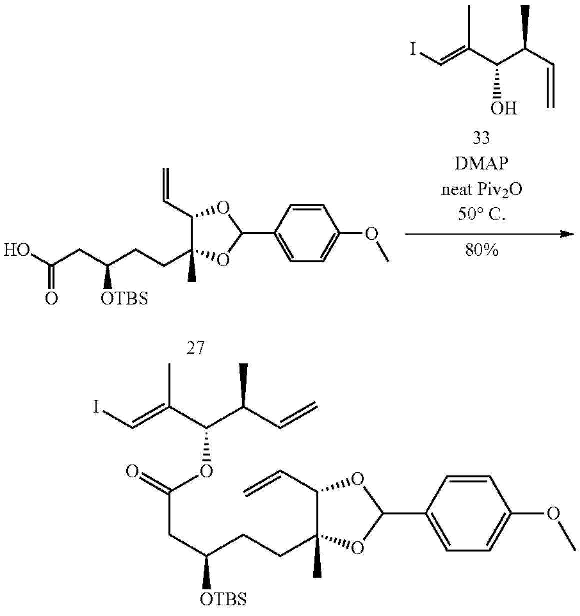

33

27

34

Reagents: DMAP, 98% (Sigma-Aldrich): used without further purification; Pivalic anhydride, 99% (Alfa Aesar): used without further purification.

(3S,4S,E)-1-Iodo-2,4-dimethylhexa-1,5-dien-3-yl-(3R)-3-((tert-butyldimethylsilyl)oxy)-5-((4R,5S)-2-(4-methoxyphenyl)-4-methyl-5-vinyl-1,3-dioxolan-4-yl)pentanoate (34). DMAP (150 mg, 1.22 mmol) and pivalic anhydride (3.71 mL, 18.3 mmol) were added sequentially to a 250 mL flask containing 27 (5.51 g, 12.2 mmol) and alcohol 33 (3.23 g, 12.8 mmol). The mixture was purged with Ar and stirred neat at 50° C. for 8 h. Pivalic anhydride was removed from the mixture under airflow. Crude material was then loaded directly onto silica gel in hexanes and eluted with a gradient of hexanes to 1:10 $Et_2O$/hexanes. Pure esters 34 (6.72 g, 80%) were obtained as a clear oil. Note 1: The removal of pivalic anhydride led to improved chromatographic conditions. Note 2: $C_3$ isomers were also removed after chromatography Esters 34: TLC (1:4 $Et_2O$/hexanes): $R_f$=0.40 and 0.38 (CAM stain); $^1H$ NMR (500 MHz, $C_6D_6$) δ 7.57 (d, J=8.7 Hz, 2H), 7.55 (d, J=8.7 Hz, 2H), 6.86 (d, J=8.6 Hz, 2H), 6.82 (d, J=8.6 Hz, 2H), 6.24 (s, 1H), 6.22 (s, 1H), 6.19 (s, 1H), 5.93 (s, 1H), 5.83 (m, 1H), 5.80 (m, 2H), 5.65 (m, 1H), 5.63 (m, 1H), 5.33 (dt, J=17.2, 1.6 Hz, 1H), 5.19 (d, J=8.1 Hz, 1H), 5.16 (d, J=8.1 Hz, 1H), 5.10 (dq, J=10.4, 1.4 Hz, 1H), 4.96 (m, 2H), 4.21 (m, 1H), 4.16 (p, J=5.8 Hz, 1H), 4.12 (dt, J=6.6, 1.3 Hz, 1H), 3.30 (s, 3H), 3.26 (s, 3H), 2.50 (dd, J=15.0, 6.3 Hz, 1H), 2.43 (dd, J=15.0, 6.6 Hz, 1H), 2.30 (dd, J=15.0, 5.6 Hz, 1H), 2.26 (m, 1H), 2.22 (dd, J=15.0, 5.7 Hz, 1H), 1.99 (dt, J=13.0, 4.0 Hz, 1H), 1.87 (m, 1H), 1.79 (m, 1H), 1.71 (d, J=1.1 Hz, 3H), 1.69 (d, J=1.1 Hz, 3H), 1.67 (m, 1H), 1.25 (s, 3H), 1.24 (m, 2H), 1.22 (s, 3H), 1.01 (s, 9H), 0.98 (s, 9H), 0.71 (d, J=5.3 Hz, 3H), 0.69 (d, J=5.3 Hz, 3H), 0.15 (s, 3H), 0.14 (s, 3H), 0.12 (s, 3H), 0.10 (s, 3H); $^{13}C$ NMR (125 MHz, $C_6D_6$) δ 170.0, 170.0, 160.8, 160.6, 144.9, 144.9, 139.7, 137.7, 137.6, 132.9, 131.3, 128.6, 128.4, 128.2, 128.1, 127.6, 118.0, 117.9, 115.8, 115.8, 114.0, 114.0, 102.7, 102.3, 87.9, 86.0, 83.3, 82.1, 82.0, 81.9, 80.4, 80.4, 69.9, 69.7, 54.8, 54.8, 42.9, 42.7, 40.4, 40.4, 32.9, 31.8, 31.3, 29.0, 26.2, 26.1, 22.8, 22.2, 20.3, 18.3, 18.3, 16.4, 16.4, −4.4, −4.4, −4.4, −4.5; FTIR (film) $\nu_{max}$ 2956, 2929, 2856, 1739, 1616, 1517, 1378, 1249, 1170, 1070 $cm^{-1}$; HR-ES-MS m/z calcd. for $C_{32}H_{49}NO_5S2SiNa$ $[M+Na]^+$: 707.2203, found 707.2199; $[\alpha]^{25}_D$=13.1° (c=1.0, $CH_2C_2$).

Ring-Closing Metathesis of 34 to Lactone 35

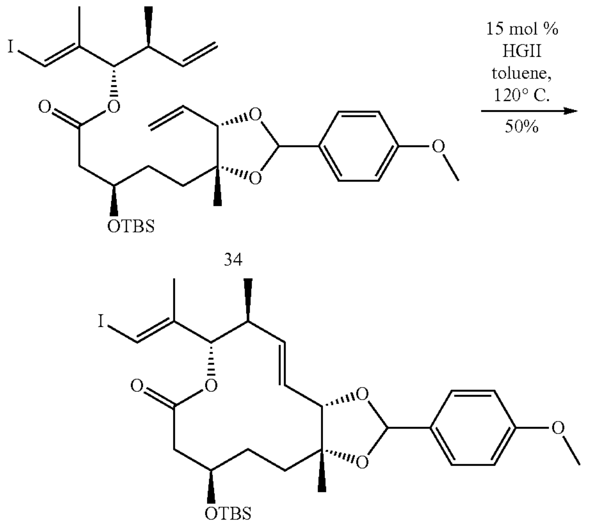

34

35

Reagents: 2$^{nd}$ Generation Hoveyda Grubbs catalyst, 97% (Sigma-Aldrich): used without further purification (3aS,6S,7S,11R,13aR,E)-11-((tert-Butyldimethylsilyl)oxy)-7-((E)-1-iodoprop-1-en-2-yl)-2-(4-methoxyphenyl)-6,13a-dimethyl-3a,6,7,10,11,12,13,13a-octahydro-9H-[1,3]dioxolo[4,5-f][1]oxacyclododecin-9-one (35). Esters 34 (5.15 g, 7.52 mmol) in a two-necked 3 L flask equipped with a 1 L addition funnel were dissolved into anhydrous, degassed toluene (700 mL). The mixture was purged with Ar and heated to reflux. 2$^{nd}$ Generation Hoveyda-Grubbs catalyst (706 mg, 1.13 mmol) in anhydrous, degassed toluene (700 mL) purged under Ar was dropwise added to the solution of 34 in boiling toluene. After stirring for 20 min the mixture turned from a clear green color into a black solution and was further stirred at reflux for 5 h. The mixture was then cooled to rt and concentrated by a rotary evaporator. The crude black semi-solid was then suspended in hexanes and filtered through a pad of Celite and eluted with hexanes. The elutants were concentrated on a rotary evaporator to yield a crude green oil. Pure lactones 35 (2.47 g, 50%) was obtained as a white solid by flash chromatography, eluting with a gradient of hexanes to 1:10 $Et_2O$/hexanes. Note 1: Allylic isomerization is the main byproduct of this reaction. Although literature suggests certain additives (i.e. hydroquinone) may inhibit such competing reactions, no improvements in yields were observed with 34 or similar analogues (i.e. other protecting groups) as the substrate. Note 2: The acetal diastereomers were separable by chromatography, and their spectroscopic data are recorded individually below.

Lactones 35: TLC (1:2 $Et_2O$/hexanes): $R_f$=0.38, 0.35 (CAM stain); $^1H$ NMR (500 MHz, $C_6D_6$) Isomer A δ 7.61 (d, J=8.8 Hz, 2H), 6.82 (d, J=8.7 Hz, 2H), 6.29 (d, J=1.2 Hz, 1H), 6.03 (s, 1H), 5.66 (dd, J=15.2, 9.4 Hz, 1H), 5.00 (d, J=10.6 Hz, 1H), 4.99 (dd, J=15.2, 9.6 Hz, 1H), 4.07 (d, J=9.6, 1H), 3.93 (ddt, J=9.2, 7.4, 4.3 Hz, 1H), 3.24 (s, 3H), 2.36 (dd, J=14.4, 4.5 Hz, 1H), 2.31 (dd, 14.4, 9.4 Hz, 1H), 2.18 (m, 2H), 1.80 (m, 1H), 1.66 (d, J=1.1 Hz, 3H), 1.41 (m, 2H), 1.20 (s, 3H), 1.01 (m, 1H), 0.95 (s, 9H), 0.49 (d, J=6.8 Hz, 3H), 0.05 (s, 3H), 0.00 (s, 3H); Isomer B δ 7.60 (d, J=8.8 Hz, 2H), 6.82 (d, J=8.7 Hz, 2H), 6.32 (s, 1H), 5.75 (dd, J=15.1, 9.9 Hz, 1H), 5.00 (d, J=10.6 Hz, 1H), 4.98 (dd, J=15.1, 9.6 Hz, 1H), 4.20 (d, J=9.9 Hz, 1H), 3.93 (ddt, J=9.1, 7.7, 3.9 Hz, 1H), 3.26 (s, 3H), 2.36 (dd, J=14.3, 4.3 Hz, 1H), 2.30 (dd, J=14.3, 9.3 Hz, 1H), 2.23 (m, 1H), 2.16 (dt, J=12.9, 7.0 Hz, 1H), 1.81 (m, 1H), 1.72 (d, J=1.2 Hz, 3H), 1.42 (m, 1H), 1.34 (m, 1H), 1.27 (s, 3H), 1.03 (m, 1H), 0.97 (s, 9H), 0.55 (d, J=6.8 Hz, 3H), 0.09 (s, 3H), 0.03 (s, 3H); $^{13}C$ NMR (125 MHz, $C_6D_6$) Isomer A δ 168.2, 160.6, 144.3, 137.2, 132.4, 128.4, 128.1, 128.0, 127.7, 127.6, 114.0, 102.7, 86.0, 84.0, 83.6, 80.0, 72.2, 54.8, 43.7, 40.6, 35.0, 32.5, 26.2, 26.0, 19.0, 18.2, 16.4, −4.5, −4.5; Isomer B δ 168.2, 160.8, 144.3, 136.4, 131.5, 131.2, 128.4, 128.4, 128.2, 128.0, 127.7, 127.5, 114.0, 101.6, 85.2, 84.0, 83.6, 80.0, 72.1, 54.8, 43.9, 40.4, 35.1, 31.9, 26.0, 22.8, 19.0, 18.2, 16.4, −4.5; FTIR (film) $\nu_{max}$ 2948, 2915, 2899, 1741, 1625, 1500, 1381, 1263, 1171, 1071 $cm^{-1}$; HR-ES-MS m/z calcd. for $C_{30}H_{45}IO_6SiNa$ $[M+Na]^+$: 679.1902, found 679.1899; $[\alpha]^{25}_D$=−10.3° (c=0.5, $CH_2Cl_2$).

Deprotection of 35 to Triol 36

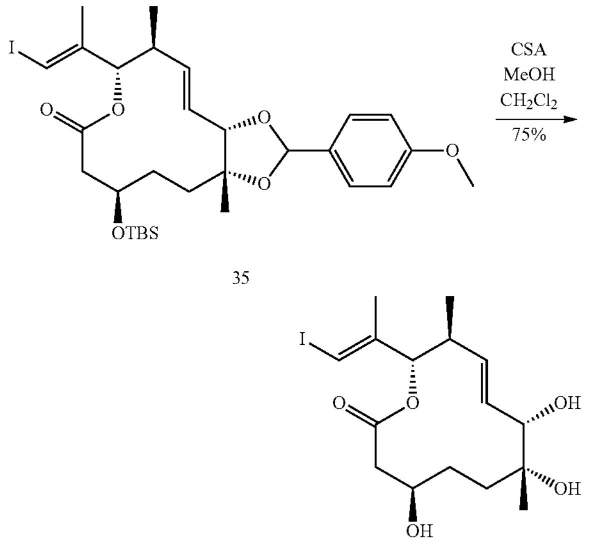

35

36

Reagents: (1S)-(+)-10-Camphorsulfonic acid, 98% (TCI Chemicals): used without further purification.

(4R,7R,8S,11S,12S,E)-4,7,8-Trihydroxy-12-((E)-1-iodoprop-1-en-2-yl)-7,11-dimethyloxacyclododec-9-en-2-one (36). Lactones 35 (2.47 g, 3.77 mmol) were dissolved in 1:3 MeOH/$CH_2Cl_2$ (300 mL) in a 1 L flask. (1S)-(+)-10-Camphorsulfonic acid (3.45 g, 14.9 mmol) was added as a solid in one portion. The mixture was stirred for 5 h, at which point TLC analyses indicated complete conversion of starting material. Satd. $NaHCO_3$ (50 mL) was added, and the mixture was extracted into $CH_2Cl_2$ (3×200 mL). The organics were collected and concentrated on a rotary evaporator to a crude oil. Pure triol 36 (1.19 g, 75%) was obtained as a white solid by flash chromatography, eluting with a gradient of $CH_2Cl_2$ to 1:2 acetone/$CH_2Cl_2$.

Triol 36: TLC (1:2 acetone/$CH_2Cl_2$): $R_f$=0.25 (CAM stain); $^1H$ NMR (500 MHz, $C_6D_6$) δ 6.18 (bs, 1H), 5.56 (dd, J=15.2, 9.7 Hz, 1H), 5.16 (d, J=10.7 Hz, 1H), 4.95 (dd, J=15.2, 9.8 Hz, 1H), 3.54 (d, J=11.0 Hz, 1H), 3.46 (ddq, J=10.7, 7.1, 3.4 Hz, 1H), 3.41 (dd, J=9.7, 4.4 Hz, 1H), 2.20 (dd, J=14.9, 4.0 Hz, 1H), 2.13 (m, 1H), 2.08 (dd, J=15.0, 2.8 Hz, 1H), 1.65 (d, J=1.1 Hz, 3H), 1.55 (m, 1H), 1.30 (m, 2H), 1.14 (s, 3H), 1.10 (m, 1H), 0.56 (d, J=6.8 Hz, 3H); $^{13}C$ NMR (125 MHz, $C_6D_6$) δ 171.6, 143.6, 135.4, 131.2, 127.2, 83.9, 79.7, 76.7, 72.9, 69.0, 40.6, 37.9, 35.7, 30.0, 24.3, 16.0; FTIR (film) $\nu_{max}$ 3683, 3602, 3552, 2977, 2958, 2935, 1708, 1616, 1365, 1284, 1172 $cm^{-1}$; HR-ES-MS m/z calcd. for $C_{16}H_{25}IO_5Na$ $[M+Na]^+$: 447.0601, found 447.0606; $[\alpha]^{25}_D$=57.0° (c=1.0, $CH_2Cl_2$).

Selective Acetylation of Triol 36 to Core 3

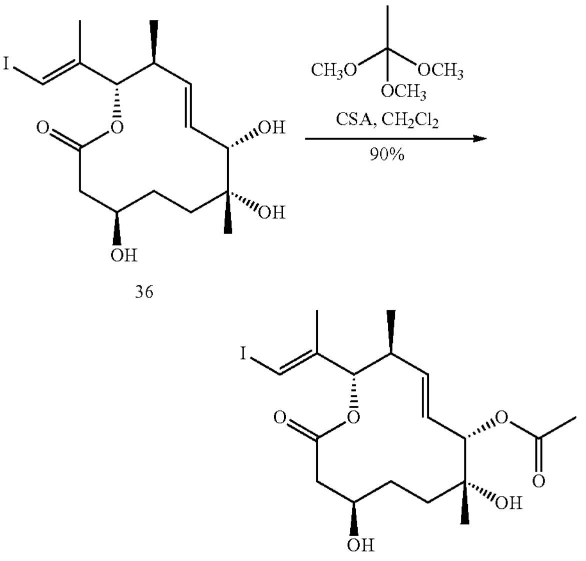

36

3

Reagents: (1S)-(+)-10-Camphorsulfonic acid, 98% (TCI Chemicals): used without further purification; Trimethyl orthoformate, 99% (Sigma-Aldrich): used without further purification.

(2S,3S,6S,7R,10R,E)-7,10-Dihydroxy-2-((E)-1-iodoprop-1-en-2-yl)-3,7-dimethyl-12-oxooxacyclododec-4-en-6-yl acetate (3). Triol 36 (1.10 g, 2.59 mmol) and (1S)-(+)-10-camphorsulfonic acid (120 mg, 0.259 mmol) were dissolved in anhydrous $CH_2Cl_2$ (100 mL) in a 100 mL flask and cooled to 0° C. Trimethyl orthoformate (400 μL, 3.13 mmol) was added dropwise as a solution of $CH_2Cl_2$ (20 mL), and the mixture was stirred at 0° C. for 1 h, at which point satd. $NH_4Cl$ (5 mL) was added. The mixture was stirred for 20 min and extracted into $CH_2Cl_2$ (150 mL). The organics were concentrated on a rotary evaporator. Pure core 3 (1.09 g, 90%) was obtained as a white semi-solid by flash chromatography, eluting with a gradient of $CH_2Cl_2$ to 1:3 acetone/$CH_2Cl_2$. Note 1: TLC analyses of the mixture taken prior to quench with aq. $NH_4Cl$ indicates two spots with $R_f$ values of 0.30 and 0.65. The higher $R_f$ spot corresponds to the unstable cyclic acetal that rearranges to the desired $C_7$ acetate upon exposure to aq. $NH_4Cl$.

Core 3: TLC (1:8 acetone/$CH_2Cl_2$): $R_f$=0.30 (CAM stain); $^1H$ NMR (500 MHz, $C_6D_6$) δ 6.12 (s, 1H), 5.74 (dd, J=15.3, 9.8 Hz, 1H), 5.47 (dd, J=15.3, 10.1 Hz, 1H), 5.18 (d, J=9.8 Hz, 1H), 5.13 (d, J=10.6 Hz, 1H), 3.46 (bs, 1H), 2.20 (d, J=14.9, 1H), 2.15 (m, 1H), 2.08 (d, J=14.9 Hz, 1H), 1.78 (bs, 1H), 1.64 (m, 1H), 1.61 (s, 3H), 1.60 (d, J=1.1 Hz, 3H), 1.55 (m, 1H), 1.44 (m, 1H), 1.16 (m, 2H), 0.98 (s, 3H), 0.51 (d, J=6.7 Hz, 3H); $^{13}C$ NMR (125 MHz, $C_6D_6$) δ 171.7, 169.0, 143.8, 139.8, 126.9, 84.4, 80.0, 79.0, 73.2, 69.3, 41.1, 38.4, 35.8, 30.2, 24.7, 20.8, 19.1, 16.1; FTIR (film) $\nu_{max}$ 3502, 3058, 2959, 2873, 1733, 1616, 1368, 1243, 1168, 1021 $cm^{-1}$; HR-ESI-MS m/z calcd. for $C_{18}H_{27}IO_6Na$ $[M+Na]^+$: 489.0745, found 489.0742; $[\alpha]^{25}_D$=67.5° (c=1.0, $CH_2Cl_2$).

Procedures for the Stille coupling of vinylstannane 2 to core 3 to deliver 17S-FD-895 (1). This procedure was optimized from El Marrouni and co-workers (36).

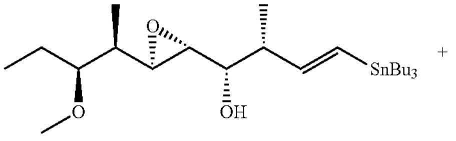

2

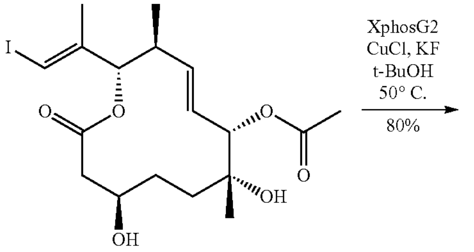

3

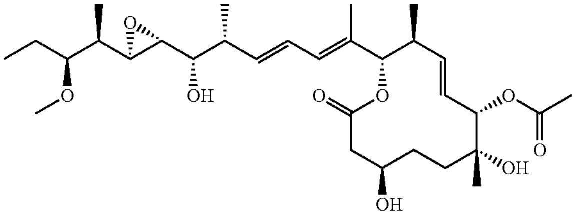

17S-FD-895 (1)

Reagents: CuCl, anhydrous, beads, 99.99% (Sigma-Aldrich): beads were powdered prior to addition; KF, anhydrous, powder, 99.9% (Sigma-Aldrich): used without further purification; XPhos Pd G2 (Sigma-Aldrich): used without further purification; t-BuOH, anhydrous, 99.5% (Sigma-Aldrich): used without further purification 17S-FD-895 (1). Vinylstannane 2 (1.33 g, 2.57 mmol) and core 3 (1.00 g, 2.14 mmol) were combined in a 100 mL flask and dried via rotary evaporation of benzene. To the mixture was then sequentially added CuCl (0.425 g, 4.29 mmol), KF (0.249 g, 4.29 mmol) and XPhos Pd G2 (0.169 g, 0.214 mmol) and anhydrous t-BuOH (25 mL). The reaction vessel was purged under Ar, heated to 50° C. and stirred overnight, at which point solution turns into a gray cloudy mixture. The mixture was then filtered through a plug of Celite and eluted with acetone (200 mL). The elutants were concentrated on a rotary evaporator to yield a crude brown semi-solid. Pure 17S-FD-895 (1) (1.21 g, 80%) was obtained as a white semi-solid by flash chromatography over neutral silica gel, eluting with a gradient of hexanes to 1:3 acetone/hexanes.

Note 1: An additional chromatographic step on mixed fractions may be needed to maximize yield. Note 2: This reaction was performed on a MAXIMUM of 1 g of core 3 due to toxicity.

17S-FD-895 (1): TLC (1:3 acetone/$CH_2Cl_2$): $R_f$=0.28 (CAM stain); NMR data provided in Table S1; FTIR (film) $\nu_{max}$ 3447, 2963, 2930, 2875, 1739, 1457, 1374, 1239, 1176, 1089, 1021 $cm^{-1}$; HR-ESI-MS m/z calcd. for $C_{31}H_{50}IO_9Na$ $[M+Na]^+$: 589.3345, found 589.3347; $[\alpha]^{25}_D$=+8.8° (c=1.0, $CH_2Cl_2$).

TABLE S1

NMR data for 17S-FD-895 (1) in $C_6D_6$

| Position | $\delta_C$ | $\delta_H$, mult (J in Hz) |
|---|---|---|
| 1 | 171.8 | |
| 2α | 38.2 | 2.29, dd (14.8, 3.9) |
| 2β | | 2.19, dd (14.8, 3.0) |
| 3 | 69.0 | 3.49, td (11.1, 3.5) |
| 3-OH | | 3.63, d (11.2) |
| 4α | 30.0 | 1.56, m |
| 4β | | 1.23, dt (19.1, 10.3) |
| 5α | 35.5 | 1.55, m |
| 5β | | 1.22, dt (19.1, 10.3) |
| 6 | 72.5 | |
| 6-OH | | 1.75, s |
| 7 | 78.8 | 5.26, d (1.5) |
| 8 | 140.3 | 5.62, dd (15.2, 10.0) |
| 9 | 126.0 | 5.83, dd (10.5, 9.1) |
| 10 | 40.8 | 2.39, dd (10.4, 6.8) |
| 11 | 82.2 | 5.24, d (2.4) |
| 12 | 131.0 | |
| 13 | 131.4 | 6.11, d (10.2) |
| 14 | 126.1 | 6.26, dd (15.2, 10.8) |
| 15 | 137.6 | 5.80, dd (10.5, 9.1) |
| 16 | 41.2 | 2.35, m |
| 17 | 73.0 | 3.42, q (3.7) |
| 17-OH | | 1.55, bs |
| 18 | 57.3 | 2.56, dd (3.8, 2.2) |
| 19 | 59.3 | 3.01, dd (8.3, 2.3) |
| 20 | 38.9 | 1.33, m |
| 21 | 83.4 | 3.15, m |
| 22α | 23.5 | 1.63, m |
| 22β | | 1.40, dt (14.0, 6.9) |
| 23 | 9.7 | 0.85, t (7.5) |
| 24 | 24.4 | 1.00, s |
| 25 | 16.1 | 0.70, d (6.7) |
| 26 | 11.5 | 1.59, d (1.3) |
| 27 | 16.9 | 1.12, d (7.0) |
| 28 | 10.5 | 0.88, d (6.9) |
| 29 | 168.7 | |
| 30 | 20.4 | 1.61, s |
| 31 | 57.4 | 3.23, s |

Procedures for the synthesis of $^{13}C1$-17S-FD-895. The following procedures are modified to deliver 1 g of $^{13}C1$-17S-FD-895 (Scheme AS1 (FIG. 10)). $^{13}C$ NMR spectra and HR-ES-MS data are provided for all isotopically-labeled compounds.

Synthesis of $^{13}C1$-(S)-1-(4-(tert-butyl)-2-thioxothiazolidin-3-yl)ethan-1-one

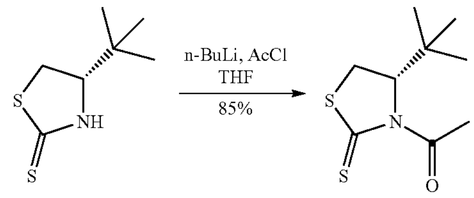

Reagents: n-BuLi, 2.5 M in hexanes (Acros Organics): used without further purification; Acetyl chloride (1-$^{13}$C, 99% $^{13}$C): used without further purification.

$^{13}$C1-(S)-1-(4-(tert-Butyl)-2-thioxothiazolidin-3-yl) ethan-1-one. n-BuLi (2.5 M, 9.77 mL, 24.4 mol) was added dropwise to a 500 mL flask containing a solution of (S)-4-(tert-butyl)thiazolidine-2-thione (4.44, 24.3 mol) in anhydrous THF (180 mL) at −78° C. The mixture was stirred at −78° C. for 30 min. Acetyl chloride (1-$^{13}$C, 99% $^{13}$C) (1.89 mL, 25.5 mol) was added dropwise, and the mixture was stirred at −78° C. for 1.5 h. The mixture was then warmed to rt, stirred for 1 h, re-cooled to 0° C. and quenched with satd. $NH_4Cl$ (10 mL). The phases were separated, and the aqueous phase was extracted with $CH_2Cl_2$ (2×200 mL). The combined organic phases were dried over $Na_2SO_4$, filtered and concentrated on a rotary evaporator. Pure $^{13}$C1-(S)-1-(4-(tert-butyl)-2-thioxothiazolidin-3-yl)ethan-1-one (4.01 g, 85%) was obtained by flash chromatography, eluting with a gradient of heptane to $CH_2Cl_2$.

$^{13}$C1-(S)-1-(4-(tert-Butyl)-2-thioxothiazolidin-3-yl) ethan-1-one: $^{13}$C NMR ($CDCl_3$, 125 MHz) δ 205.3, 170.3*, 72.0, 38.0, 30.4, 26.8, 26.8; LC-MS [M+1]$^+$: 219.1. * denotes $^{13}$C-labeled carbon.

Synthesis of $^{13}$C1-25

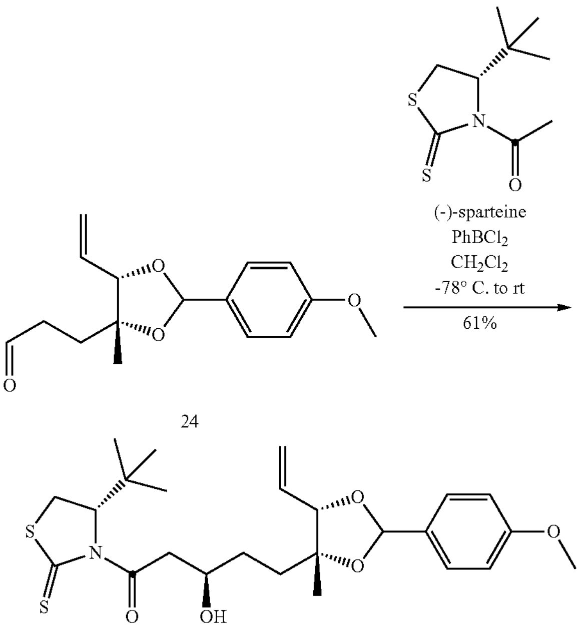

24

$^{13}$C1-25

Reagents: Dichlorophenylborane, 97% (Acros Organics): used without further purification; (−)-Sparteine, 98% (TCI Chemicals), S0461: used without further purification; (S)-1-(4-(tert-Butyl)-2-thioxothiazolidin-3-yl)ethan-1-one: dried via azeotropic removal of toluene by rotary evaporation.

$^{13}$C1-(3R)-1-((R)-5-(tert-Butyl)-2-thioxothiazolidin-3-yl)-3-hydroxy-5-((4R,5S)-2-(4-methoxy-phenyl)-4-methyl-5-vinyl-1,3-dioxolan-4-yl)pentan-1-one ($^{13}$C1-25). $^{13}$C1-(S)-1-(4-(tert-Butyl)-2-thioxothiazolidin-3-yl)ethan-1-one (3.89 g, 17.9 mmol) was added to a flame dried 2 L flask and dissolved in anhydrous $CH_2Cl_2$ (300 mL). An Ar atmosphere was introduced and dichlorophenylborane (2.00 mL, 15.9 mmol) was added at rt and stirred for 15 min. (−)-Sparteine (7.30 mL, 31.8 mmol) was added neat, at which point the mixture turns cloudy but clears up upon further stirring. After stirring at rt for 30 min the mixture was cooled to −78° C., and aldehyde 24 (3.66 g, 13.3 mmol) in a solution of anhydrous $CH_2Cl_2$ (30 mL) was added dropwise over 15 min. The mixture was stirred at −78° C. for 1 h and slowly warmed to 0° C. over 3 h, at which point NMR analyses indicated complete consumption of starting material. The mixture was quenched with satd. $NaHCO_3$ (65 mL), and the organic phase was separated. The aqueous phase was washed with $CH_2Cl_2$ (100 mL), and the organic phases were combined, dried over $Na_2SO_4$, filtered and concentrated on a rotary evaporator to yield a crude oil. Pure $^{13}$C1-25 (4.27 g, 61%) was obtained as a yellow oil by flash chromatography over neutral silica gel, eluting with a gradient of hexanes to 1:2 EtOAc/hexanes.

$^{13}$C1-25: $^{13}$C NMR (125 MHz, $C_6D_6$) δ 205.2, 205.2, 173.0*, 173.0*, 172.4, 172.0, 160.8, 160.6, 159.6, 135.8, 133.9, 133.8, 133.8, 133.0, 131.2, 128.7, 128.4, 128.2, 128.1, 127.6, 118.1, 118.0, 117.9, 114.2, 114.1, 113.9, 113.5, 102.8, 102.3, 93.7, 88.0, 86.5, 86.3, 83.4, 82.3, 81.8, 72.1, 72.0, 72.0, 70.6, 68.8, 68.8, 68.8, 54.8, 54.8, 47.3, 45.8, 45.7, 45.5, 37.9, 37.9, 33.2, 31.3, 31.1, 30.9, 30.8, 29.8, 29.8, 29.4, 26.7, 22.8, 22.2, 22.0; HR-ESI-MS m/z calcd. for $C_{25}H_{35}NO_5S_2Na$ [M+Na]$^+$: 517.5412, found 517.5415. * denotes $^{13}$C-labeled carbons.

TBS protection of $^{13}$C1-25 to $^{13}$C1-26

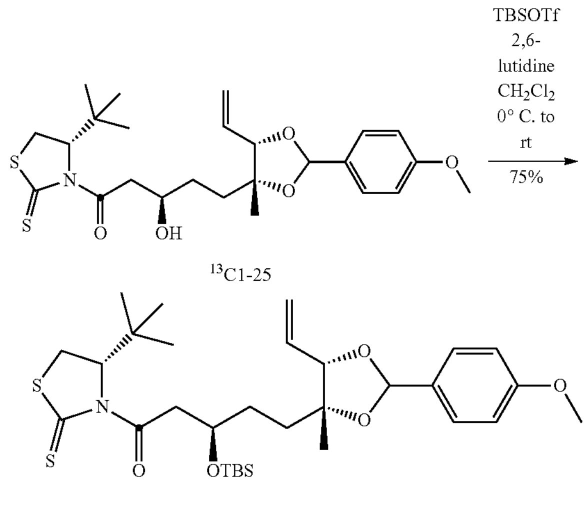

$^{13}$C1-25

$^{13}$C1-26

Reagents: 2,6-Lutidine, redistilled, 99% (Chem-Impex Int.): used without further purification. TBSOTf, 99% (Chem-Impex Int.): used without further purification.

$^{13}$C1-(3S)-1-((R)-5-(tert-Butyl)-2-thioxothiazolidin-3-yl)-3-((tert-butyldimethylsilyl)oxy)-5-((4R,5S)-2-(4-methoxyphenyl)-4-methyl-5-vinyl-1,3-dioxolan-4-yl)pentan-1-one ($^{13}$C1-26).

$^{13}$C1-25 (4.00 g, 8.12 mmol) was dissolved in anhydrous $CH_2Cl_2$ (300 mL) followed by addition of 2,6-lutidine (5.12 mL, 40.8 mmol). The mixture was purged with Ar and cooled to 0° C. TBSOTf (6.52 mL, 28.4 mmol) was added dropwise, and the mixture was warmed to rt and stirred overnight, at which point NMR analyses indicated complete consumption of starting material. The reaction was quenched with addition of solid $NaHCO_3$ (2 g) and stirred for 15 min. The mixture was filtered and concentrated under rotary evaporation to yield a yellow crude oil. Pure $^{13}$C1-26 (3.64 g, 75%) was obtained as a yellow oil by flash chromatography, eluting with a gradient of hexanes to 1:9 EtOAc/hexanes.

$^{13}$C1-26: $^{13}$C NMR (125 MHz, $C_6D_6$) δ 205.1, 205.0, 170.9*, 170.9*, 170.8, 160.8, 160.6, 133.9, 133.7, 133.6, 133.0, 131.3, 128.7, 128.4, 128.2, 127.9, 127.7, 127.5, 118.0, 117.9, 114.1, 113.9, 102.7, 102.4, 88.0, 87.9, 86.1, 83.6, 83.5, 82.4, 82.2, 72.2, 72.1, 70.3, 69.5, 69.4, 54.8, 54.8, 53.3, 46.4, 46.1, 37.9, 37.8, 34.0, 32.8, 32.0, 31.5, 29.9, 29.8, 28.9, 26.8, 26.2, 26.2, 25.9, 22.7, 22.2, 18.4, 18.3, -3.4, -4.2, -4.2, -4.3, -4.3; HR-ESI-MS m/z calcd. for $C_{31}H_{49}NO_5S2SiNa$ $[M+Na]^+$: 631.2612, found 630.2611. * denotes $^{13}$C-labeled carbons.

Saponification of $^{13}$C1-26 to $^{13}$C1-27

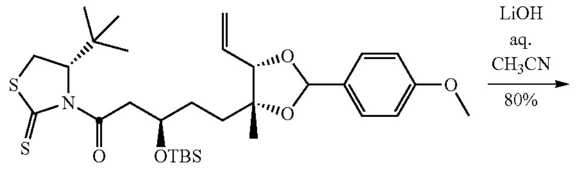

$^{13}$C1-26

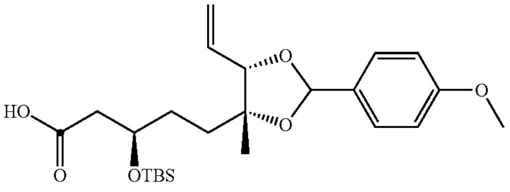

$^{13}$C1-27

Reagents: $LiOH \cdot H_2O$, 98% (Alfa Aesar): used without further purification.

$^{13}$C1-(3S)-3-((tert-Butyldimethylsilyl)oxy)-5-((4R,5S)-2-(4-methoxyphenyl)-4-methyl-5-vinyl-1,3-dioxolan-4-yl) pentanoic acid ($^{13}$C1-27) $LiOH \cdot H_2O$ (424 mg, 17.8 mmol) was added to a solution of $^{13}$C1-26 (3.60 g, 5.92 mmol) in 20% aq. $CH_3CN$ (500 mL). The mixture was stirred at rt overnight, at which point the deep yellow color dissipates into a light brown solution. The mixture was diluted with $H_2O$ (500 mL) and $Et_2O$ (500 mL). The aqueous phase was collected, and the organic phase was back extracted with $H_2O$ (2x500 mL). The aqueous phases were combined, and the pH was adjusted to 6.5 with 1 M HCl. The mixture was extracted into EtOAc (3x700 mL), and the organics were combined, dried over $Na_2SO_4$, filtered and concentrated by rotary evaporation. Pure $^{13}$C1-27 (2.13 g, 80%) was obtained as a colorless oil by flash chromatography, eluting with a gradient of hexanes to 1:2 EtOAc/hexanes.

$^{13}$C1-27: $^{13}$C NMR (125 MHz, $C_6D_6$) δ 177.4*, 177.4*, 160.8, 160.6, 133.6, 133.5, 132.9, 131.2, 128.5, 128.4, 128.2, 128.0, 127.7, 127.7, 127.6, 118.0, 117.9, 114.0, 114.0, 93.7, 87.9, 86.3, 86.0, 83.3, 82.0, 81.6, 70.0, 69.9, 54.8, 54.8, 32.6, 31.8, 31.4, 30.2, 28.8, 26.6, 26.1, 26.0, 22.6, 22.1, 21.9, 18.3, 18.2, -4.3, -4.4, -4.4, -4.6, -4.6, -4.7; HR-ESI-MS m/z calcd. for $C_{24}H_{38}O_6SiNa$ $[M+Na]^+$: 474.2254, found 474.2257. * denotes $^{13}$C-labeled carbons.

Esterification of $^{13}$C1-27 and Alcohol 33 to $^{13}$C1-34

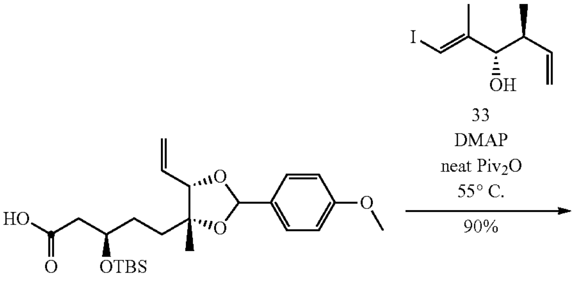

33

$^{13}$C1-27

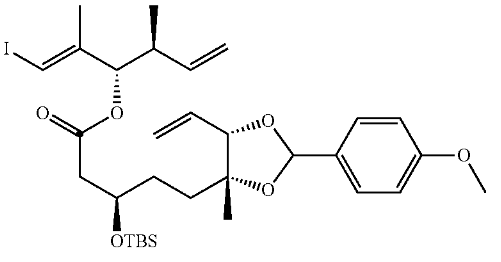

$^{13}$C1-34

Reagents: DMAP, 98% (Sigma-Aldrich): used without further purification; Pivalic anhydride, 99% (Alfa Aesar): used without further purification.

$^{13}$C1-(3S,4S,E)-1-Iodo-2,4-dimethylhexa-1,5-dien-3-yl-(3R)-3-((tert-butyldimethylsilyl)oxy)-5-((4R,5S)-2-(4-methoxyphenyl)-4-methyl-5-vinyl-1,3-dioxolan-4-yl)pentanoate ($^{13}$C1-34). DMAP (54.4 mg, 0.444 mmol) and pivalic anhydride (2.25 mL, 11.1 mmol) were sequentially added to acid $^{13}$C1-27 (2.00 g, 4.44 mmol) and alcohol 33 (1.23 g, 4.88 mmol). The mixture was purged with Ar and stirred neat at 50° C. for 8 h. Pivalic anhydride was removed from the mixture under airflow. The crude material in hexanes was then loaded directly onto silica gel and eluted with a gradient of hexanes to 1:9 $Et_2O$/hexanes. Pure $^{13}$C1-34 (2.73 g, 90%) was obtained as a clear oil.

$^{13}$C1-34: $^{13}$C NMR (125 MHz, $C_6D_6$) δ 170.0*, 170.0*, 160.8, 160.6, 144.9, 144.9, 139.7, 137.7, 137.6, 132.9, 131.3, 128.6, 128.4, 128.2, 128.1, 127.6, 118.0, 117.9, 115.8, 115.8, 114.0, 114.0, 102.7, 102.3, 87.9, 86.0, 83.3, 82.1, 82.0, 81.9, 80.4, 80.4, 69.9, 69.7, 54.8, 54.8, 42.9, 42.7, 40.4, 40.4, 32.9, 31.8, 31.3, 29.0, 26.2, 26.1, 22.8, 22.2, 20.3, 18.3, 18.3, 16.4, 16.4, -4.4, -4.4, -4.4, -4.5; HR-ES-MS m/z calcd. for $C_{32}H_{49}NO_5S_2SiNa$ $[M+Na]^+$: 708.2203, found 708.2199. * denotes $^{13}$C-labeled carbons.

Ring-Closing Metathesis of $^{13}$C1-34 to $^{13}$C1-35

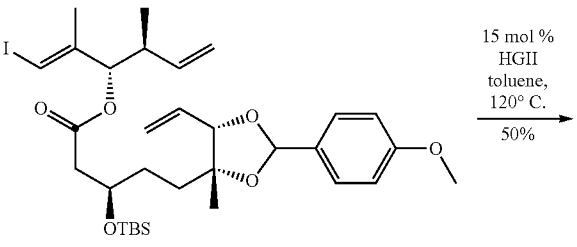

$^{13}$C1-34

-continued

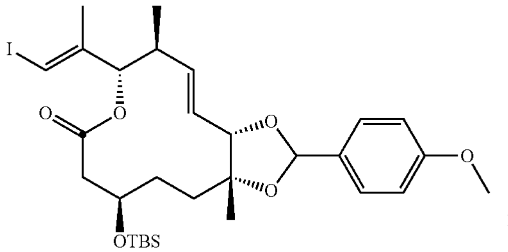

$^{13}$C1-35

Reagents: 2$^{nd}$ Generation Hoveyda Grubbs catalyst, 97% (Sigma-Aldrich): used without further purification.

$^{13}$C1-(3aS,6S,7S,11R,13aR,E)-11-((tert-Butyldimethylsilyl)oxy)-7-((E)-1-iodoprop-1-en-2-yl)-2-(4-methoxyphenyl)-6,13a-dimethyl-3a,6,7,10,11,12,13,13a-octahydro-9H-[1,3]dioxolo[4,5-f][1]oxacyclododecin-9-one ($^{13}$C1-35). Ester $^{13}$C1-34 (2.50 g, 3.65 mmol) was dissolved into anhydrous degassed toluene (280 mL). The mixture was purged with Ar and heated to reflux. 2$^{nd}$ Generation Hoveyda Grubbs catalyst (282 mg, 0.452 mmol) as an Ar purged solution in anhydrous degassed toluene (280 mL) was dropwise added to the solution of boiling toluene. After stirring for 20 min the mixture turned from a clear green color into a black solution and was further stirred at reflux for 5 h. The mixture was then cooled to rt and concentrated on a rotary evaporator. The crude black semi-solid was then suspended in hexanes and filtered through a pad of Celite eluting with hexanes. The elutants were concentrated on a rotary evaporator. Pure $^{13}$C1-35 (1.20 g, 50%) was obtained as an off-white semi-solid by flash chromatography, eluting with a gradient of hexanes to 1:6 $Et_2O$/hexanes.

$^{13}$C1-35: $^{13}$C NMR (125 MHz, $C_6D_6$) Isomer A δ 168.2*, 160.8, 144.3, 136.4, 131.5, 131.2, 128.4, 128.4, 128.2, 128.0, 127.7, 127.5, 114.0, 101.6, 85.2, 84.0, 83.6, 80.0, 72.1, 54.8, 43.9, 40.4, 35.1, 31.9, 26.0, 22.8, 19.0, 18.2, 16.4, −4.5; Isomer B δ 168.2*, 160.6, 144.3, 137.2, 132.4, 128.4, 128.1, 128.0, 127.7, 127.6, 114.0, 102.7, 86.0, 84.0, 83.6, 80.0, 72.2, 54.8, 43.7, 40.6, 35.0, 32.5, 26.2, 26.0, 19.0, 18.2, 16.4, −4.5, −4.5; HR-ES-MS m/z calcd. for $C_{30}H_{45}IO_6SiNa$ $[M+Na]^+$: 680.1902, found 680.1899. * denotes $^{13}$C-labeled carbon.

Deprotection of $^{13}$C1-35 to $^{13}$C1-36

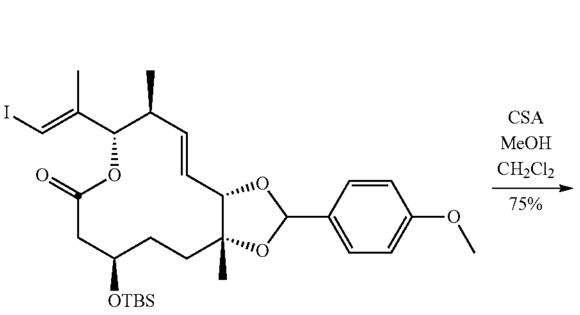

$^{13}$C1-35

-continued

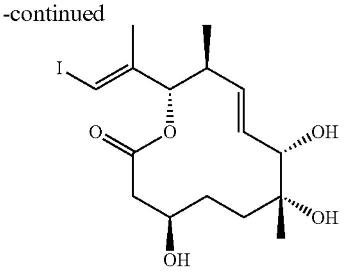

$^{13}$C1-36

Reagents: (1S)-(+)-10-Camphorsulfonic acid, 98% (TCI Chemicals): used without further purification.

(4R,7R,8S,11S,12S,E)-4,7,8-Trihydroxy-12-((E)-1-iodoprop-1-en-2-yl)-7,11-dimethyloxacyclododec-9-en-2-one ($^{13}$C1-36). $^{13}$C1-35 (1.20 g, 1.83 mmol) were dissolved in 1:3 MeOH/$CH_2Cl_2$ (50 mL) in a 250 mL flask and (1S)-(+)-10-camphorsulfonic acid (1.10 mg, 4.72 mmol) was added as a solid in one portion. The mixture was stirred for 5 h, at which point TLC indicated complete conversion of starting material. Satd. $NaHCO_3$ solution (50 mL) was added, and the mixture was extracted into $CH_2Cl_2$ (3×200 mL). The organics were collected and concentrated on a rotary evaporator. Pure $^{13}$C1-36 (628 mg, 75%) was obtained as a white solid by flash chromatography, eluting with a gradient of $CH_2Cl_2$ to 1:2 acetone/$CH_2Cl_2$.

$^{13}$C1-36: $^{13}$C NMR (125 MHz, $C_6D_6$) δ 171.6*, 143.6, 135.4, 131.2, 127.2, 83.9, 79.7, 76.7, 72.9, 69.0, 40.6, 37.9, 35.7, 30.0, 24.3, 16.0; HR-ES-MS m/z calcd. for $C_{16}H_{25}IO_5Na$ $[M+Na]^+$: 448.0586, found 448.0589. * denotes $^{13}$C-labeled carbon.

Selective Acetylation of $^{13}$C1-36 to $^{13}$C1-3

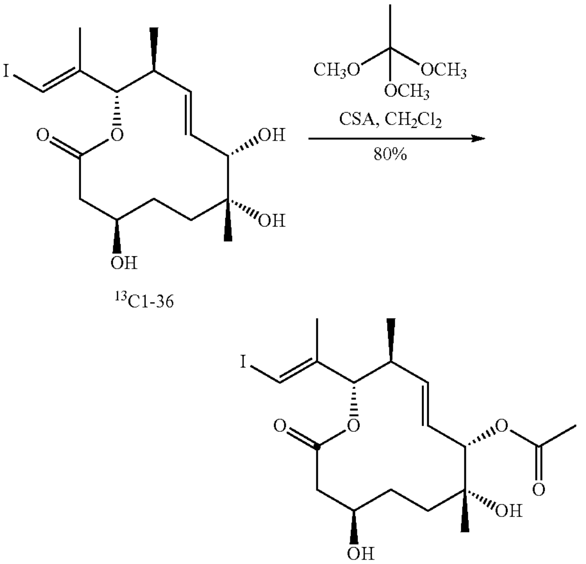

$^{13}$C1-36

$^{13}$C1-3

Reagents: (1S)-(+)-10-Camphorsulfonic acid, 98% (TCI Chemicals): used without further purification; Trimethyl orthoformate, 99% (Sigma-Aldrich): used without further purification.

$^{13}$C1-(2S,3S,6S,7R,10R,E)-7,10-Dihydroxy-2-((E)-1-iodoprop-1-en-2-yl)-3,7-dimethyl-12-oxooxacyclododec-4- en-6-yl acetate ($^{13}$C1-3). Triol $^{13}$C1-36 (700 mg, 1.65 mmol) and (1S)-(+)-10-camphorsulfonic acid (1.91 g, 8.25 mmol) were dissolved in anhydrous $CH_2Cl_2$ (5 mL) in a 20 mL scintillation vial and cooled to 0° C. Trimethyl orthoformate (1.54 mL, 0.626 mmol) was added neat to the mixture and stirred at 0° C. for 1 h, at which point satd. $NH_4Cl$ (5 mL) was added. The mixture was extracted into $CH_2Cl_2$ (150 mL), and the organics were concentrated on a rotary evaporator. Pure core $^{13}$C1-3 (701 mg, 80%) was obtained as a white semi-solid by flash chromatography, eluting with a gradient of $CH_2Cl_2$ to 1:3 acetone/$CH_2Cl_2$.

$^{13}$C1-3: $^{13}$C NMR (125 MHz, $C_6D_6$) δ 171.7*, 169.0, 143.8, 139.8, 126.9, 84.4, 80.0, 79.0, 73.2, 69.3, 41.1, 38.4, 35.8, 30.2, 24.7, 20.8, 19.1, 16.1; HR-ESI-MS m/z calcd. for $C_{18}H_{27}IO_6Na$ [M+Na]$^+$: 490.0712, found 490.0713. * denotes $^{13}$C-labeled carbon.

Synthesis of $^{13}$C1-17S-FD-895 by Stille Coupling of Core $^{13}$C1-3 to 2

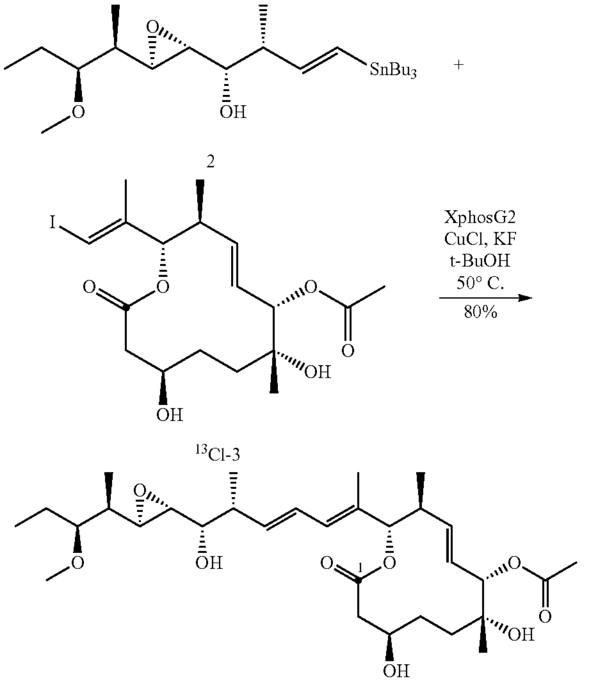

2

$^{13}$C1-3

$^{13}$C1-17S-FD-895

Reagents: CuCl, anhydrous, beads, 99.99% (Sigma-Aldrich): used without further purification' KF, anhydrous, powder, 99.9% (Sigma-Aldrich): used without further purification; XPhos Pd G2 (Sigma-Aldrich): used without further purification; t-BuOH, anhydrous, 99.5% (Sigma-Aldrich): used without further purification.

$^{13}$C1-17S-FD-895. Vinylstannane 2 (1.27 g, 2.25 mmol) and core $^{13}$C1-3 (700 mg, 1.50 mmol) were combined in a 100 mL flask and dried via rotary evaporation of benzene. To the mixture was then sequentially added CuCl (150 mg, 0.150 mmol), KF (89.2 mg, 0.150 mmol) and XPhos Pd G2 (126 mg, 0.160 mmol) and anhydrous t-BuOH (50 mL). The reaction vessel was purged under Ar, heated to 50° C. and stirred overnight, at which point the solution turns into a gray cloudy mixture. The mixture was then filtered through a plug of Celite and eluted with acetone (50 mL). The elutants were concentrated on a rotary evaporator. Pure $^{13}$C1-17S-FD-895 (680 mg, 80%) was obtained as a white semi-solid by flash chromatography over neutral silica gel eluting with a gradient of hexanes to 1:2 acetone/hexanes.

$^{13}$C1-17S-FD-895: $^{13}$C NMR (125 MHz, $C_6D_6$) δ 171.7*, 168.7, 140.3, 137.5, 131.3, 131.0, 126.0, 126.0, 83.3, 82.2, 78.8, 73.0, 72.5, 69.0, 59.3, 57.4, 57.3, 41.1, 40.8, 38.9, 38.2, 35.5, 30.0, 24.4, 23.5, 20.4, 16.9, 16.1, 11.5, 10.5, 9.7; HR-ESI-MS m/z calcd. for $C_{18}H_{27}IO_6Na$ [M+Na]$^+$: 590.3401, found 590.3403. * denotes $^{13}$C-labeled carbon.

Procedures for the synthesis of $^{13}$C30-17S-FD-895. A two-step procedure was used to convert triol 36 and side chain 2 to $^{13}$C30-17S-FD-895.

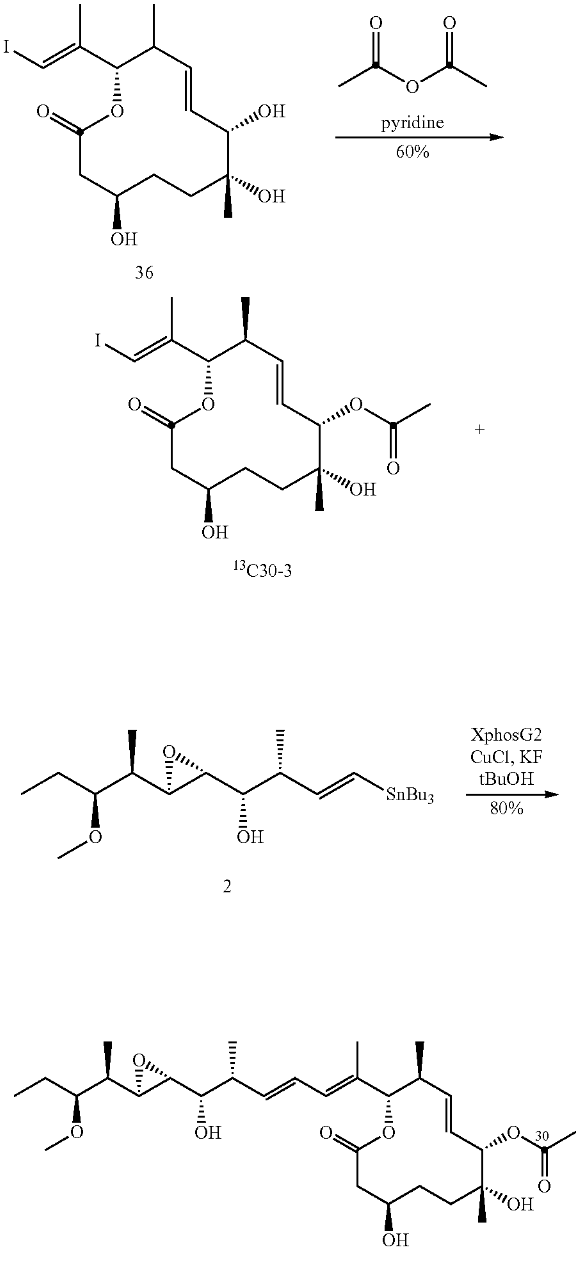

36

$^{13}$C30-3

2

$^{13}$C30-17S-FD-895

Scheme AS2. Black sphere denotes position of $^{13}C$ labeling.

Selective Acetate Isotopic Labeling of Triol 36 to $^{13}C30$-3

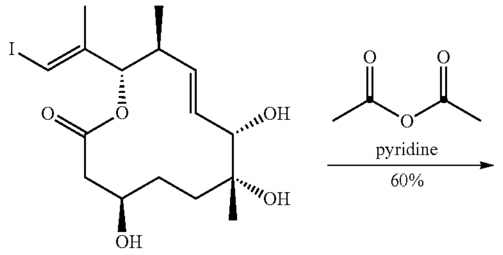

36

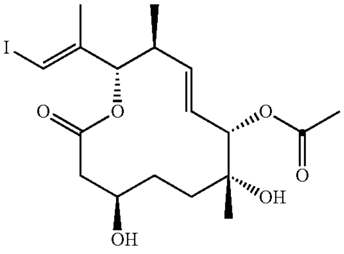

$^{13}C30$-3

Reagents: Acetic anhydride (1,1 $^{13}C2$, 99%) (Cambridge Isotopes): used without further purification; Pyridine, 99% (Fischer Scientific): freshly distilled over $CaH_2$.

$^{13}C30$-(2S,3S,6S,7R,10R,E)-7,10-Dihydroxy-2-((E)-1-iodoprop-1-en-2-yl)-3,7-dimethyl-12-oxooxacyclododec-4-en-6-yl acetate ($^{13}C30$-3). Triol 36 (150 mg, 0.354 mmol) was dissolved in pyridine (2 mL). Acetic anhydride (1,1 $^{13}C2$, 99%) (334 μL, 3.54 mmol) was added neat, and the mixture was stirred for 3 h. Satd. $NaHCO_3$ (1 mL) was added. $Na_2SO_4$ was added, and the organics were filtered and concentrated on a rotary evaporator. Pure $^{13}C30$-3 (97.7 mg, 60%) was obtained as a white semi-solid by flash chromatography, eluting with a gradient of $CH_2Cl_2$ to 1:3 acetone/$CH_2Cl_2$.

$^{13}C30$-3: $^{13}C$ NMR (125 MHz, $C_6D_6$) δ 171.7, 169.0*, 143.8, 139.8, 126.9, 84.4, 80.0, 79.0, 73.2, 69.3, 41.1, 38.4, 35.8, 30.2, 24.7, 20.8, 19.1, 16.1; HR-ESI-MS m/z calcd. for $C_{18}H_{27}IO_6Na$ $[M+Na]^+$: 489.0745, found 489.0742; $[\alpha]^{25}_D$=−67.5° (c=1.0, $CH_2Cl_2$). * denotes $^{13}C$-labeled carbon.

Synthesis of $^{13}C30$-17S-FD-895 by Stille Coupling of Core $^{13}C30$-3 to 2

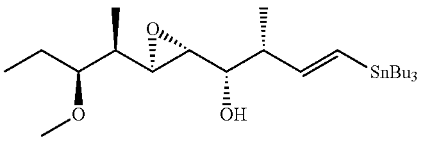

+

2

-continued

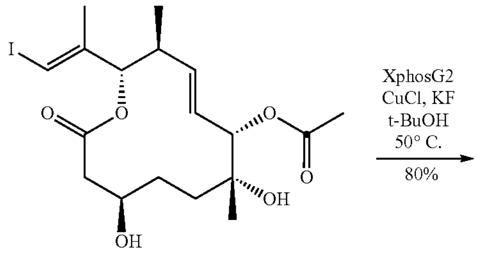

$^{13}C30$-3

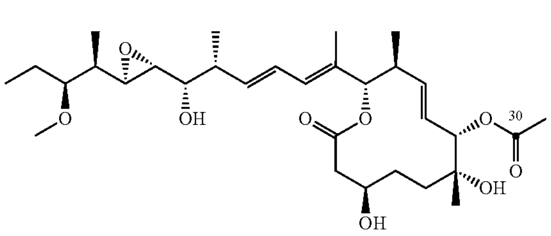

$^{13}C30$-17S-FD-895

Reagents: CuCl, anhydrous, beads, 99.99% (Sigma-Aldrich): used without further purification; KF, anhydrous, powder, 99.9% (Sigma-Aldrich): used without further purification; XPhos Pd G2 (Sigma-Aldrich): used without further purification; t-BuOH, anhydrous, 99.5% (Sigma-Aldrich): used without further purification.

$^{13}C30$-17S-FD-895. Vinylstannane 2 (0.127 g, 0.225 mmol) and core $^{13}C30$-3 (70.0 mg, 0.150 mmol) were combined in a 100 mL flask and dried via rotary evaporation of benzene. To the mixture was then sequentially added CuCl (15.0 mg, 0.150 mmol), KF (8.92 mg, 0.150 mmol) and XPhos Pd G2 (12.6 mg, 0.0160 mmol) and anhydrous t-BuOH (5 mL). The reaction vessel was purged under Ar, heated to 50° C. and stirred overnight, at which point the solution turns into a gray cloudy mixture. The mixture was then filtered through a plug of Celite and eluted with acetone (20 mL). The elutants were concentrated on a rotary evaporator. Pure $^{13}C30$-17S-FD-895 (68.0 mg, 80%) was obtained as a white semi-solid by flash chromatography over neutral silica gel eluting with a gradient of hexanes to 1:2 acetone/hexanes.

$^{13}C30$-17S-FD-895: $^{13}C$ NMR (125 MHz, $C_6D_6$) δ 171.7, 168.7*, 140.3, 137.5, 131.3, 131.0, 126.0, 126.0, 83.3, 82.2, 78.8, 73.0, 72.5, 69.0, 59.3, 57.4, 57.3, 41.1, 40.8, 38.9, 38.2, 35.5, 30.0, 24.4, 23.5, 20.4, 16.9, 16.1, 11.5, 10.5, 9.7; HR-ESI-MS m/z calcd. for $C_{18}H_{27}IO_6Na$ $[M+Na]^+$: 590.3401, found 590.3400. * denotes $^{13}C$-labeled carbon.

Figure 11:
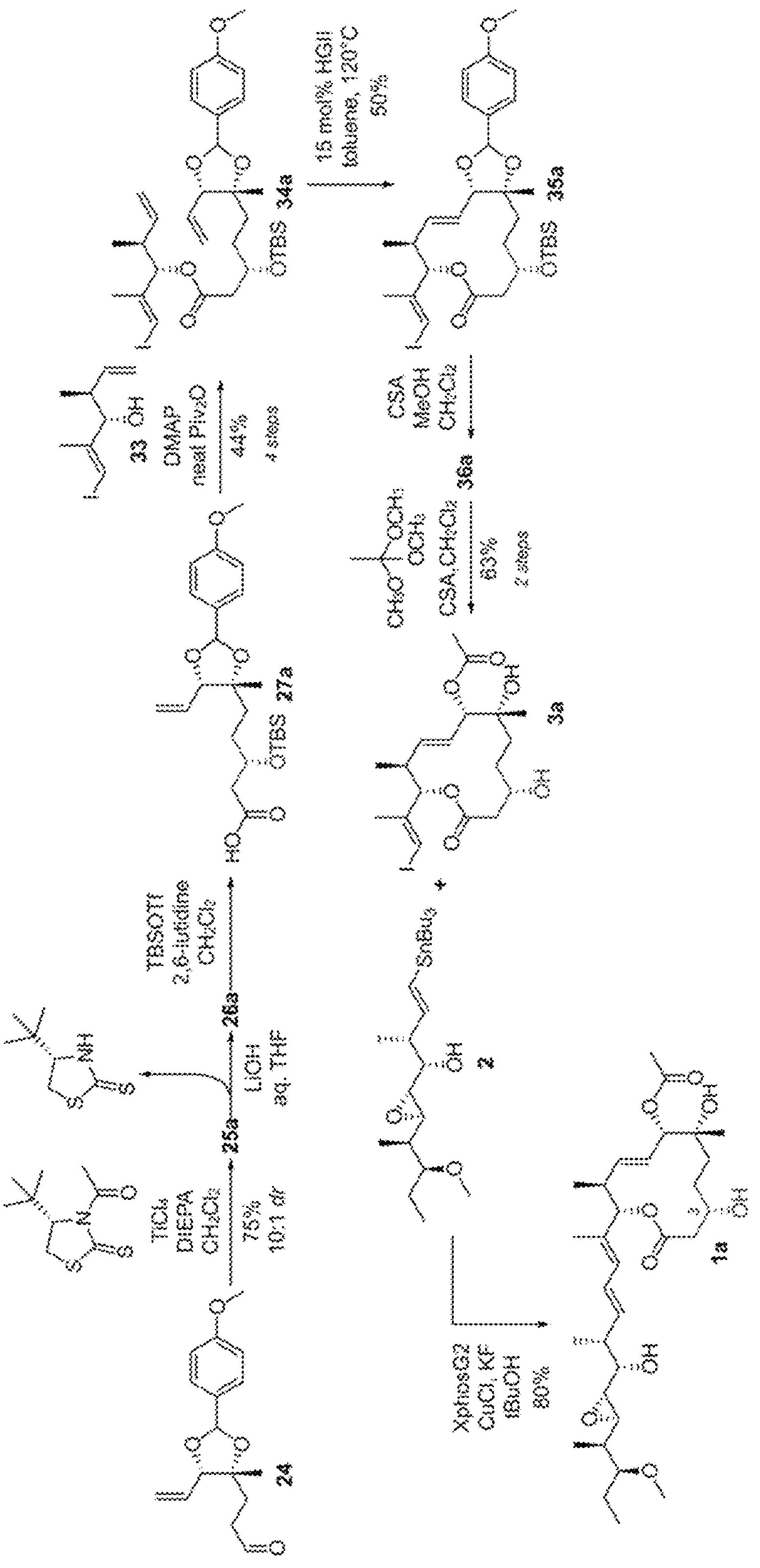
FIG. 11. Scheme AS3. The carbon attached to the –OTBS group and the carbon atom on either side of that carbon include the region of isomer installation.
Figure 12:
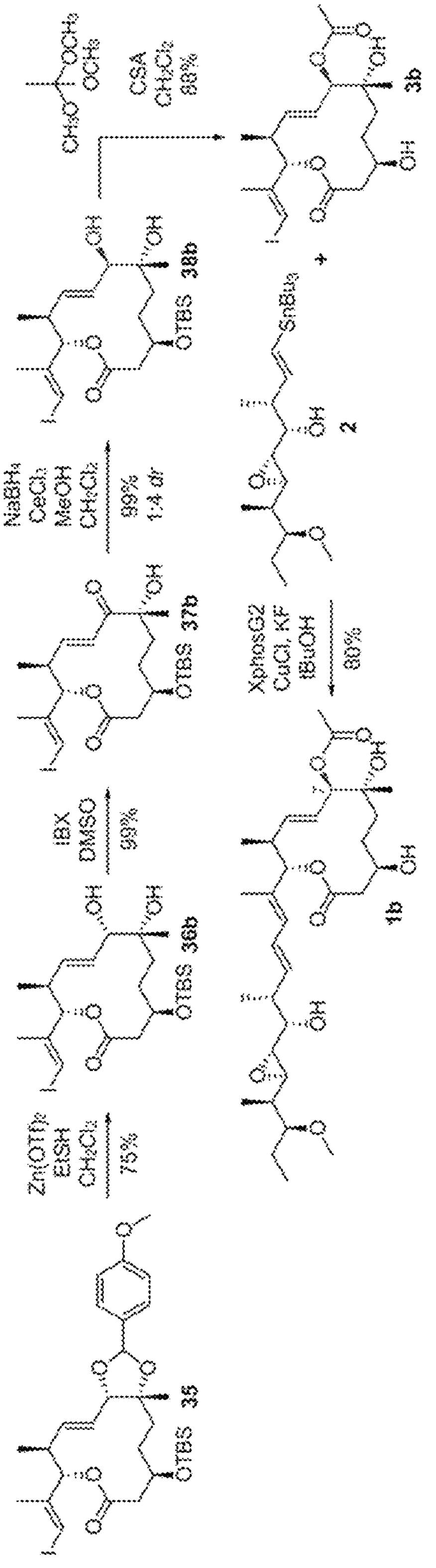
FIG. 12. Scheme AS4. Carbon 7 and the two adjacent carbons include the region of isomer installation.

Procedures for the synthesis of 3S, 17S-FD-895 (1a, FIG. 11). An eight step sequence was used to prepare 3S, 17S-FD-895 from aldehyde 24 and side chain 2.

Synthesis of Alcohol 25a

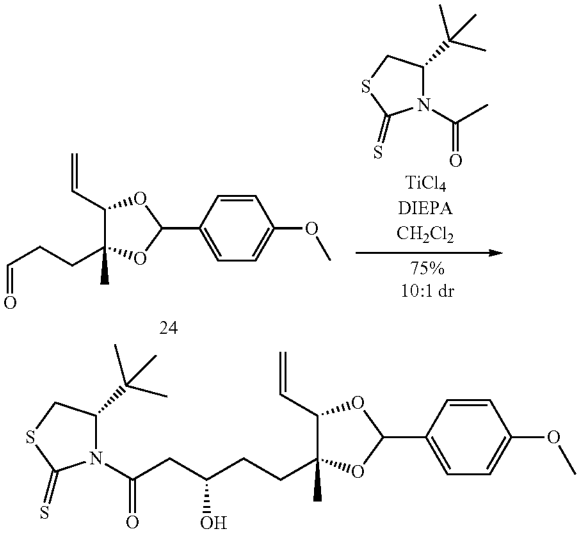

24

25a

Reagents: $TiCl_4$, 97% (Alfa Aesar): used without further purification; $Et_2$i-PrN, 95% (Fischer Scientific): redistilled over $CaH_2$; (S)-1-(4-(tert-Butyl)-2-thioxothiazolidin-3-yl) ethan-1-one: dried via azeotropic removal of toluene by rotary evaporation.

(3S)-1-((R)-5-(tert-Butyl)-2-thioxothiazolidin-3-yl)-3-hydroxy-5-((4R,5S)-2-(4-methoxyphenyl)-4-methyl-5-vinyl-1,3-dioxolan-4-yl)pentan-1-one (25a). (S)-1-(4-(tert-Butyl)-2-thioxothiazolidin-3-yl)ethan-1-one (1.17 g, 5.37 mmol) was dissolved in dry $CH_2Cl_2$ (80 mL) and purged with an Ar atmosphere. $TiCl_4$ (525 μL, 4.78 mmol) was added at rt and stirred for 15 min, at which point the mixture turns cloudy orange. $Et_2$i-PrN (862 μL, 4.95 mmol) was added neat, and the mixture turns black. After stirring at rt for 30 min, the mixture was cooled to −78° C. and 24 (1.10 g, 3.98 mmol) in a solution of anhydrous $CH_2Cl_2$ (10 mL) was added dropwise over 15 min. The mixture was stirred at −78° C. for 1 h and slowly warmed to 0° C. over 3 h, at which point NMR analyses indicated complete consumption of starting material. The mixture was quenched with satd. $NaHCO_3$ (10 mL), and the organic phase was separated. The aqueous phase was washed with $CH_2Cl_2$ (100 mL), and the combined organic phases were dried over $Na_2SO_4$, filtered and concentrated on a rotary evaporator to yield a crude yellow oil. Pure alcohol 25a (1.47 g, 75%) was obtained as a yellow oil by flash chromatography over neutral silica gel eluting with a gradient of hexanes to 1:2 EtOAc/hexanes.

Alcohol 25a: TLC (1:3 EtOAc/hexanes): $R_f$=0.23 (CAM stain); $^1$H NMR (500 MHz, $C_6D_6$) δ 8.10 (d, J=9.0 Hz, 2H), 7.60 (d, J=8.7 Hz, 1H), 7.55 (d, J=8.7 Hz, 1H), 6.84 (d, J=8.7 Hz, 1H), 6.82 (d, J=8.7 Hz, 1H), 6.60 (d, J=8.9 Hz, 2H), 6.25 (s, 1H), 5.94 (s, 1H), 5.85 (m, 1H), 5.66 (ddd, J=16.9, 10.5, 6.3 Hz, 1H), 5.85 (dt, J=6.3, 1.2 Hz, 1H), 5.32 (ddt, J=17.2, 3.0, 1.6 Hz, 1H), 5.25 (dt, J=17.1, 1.4 Hz, 1H), 5.09 (ddt, J=10.4, 5.7, 1.5 Hz, 1H), 5.00 (dt, J=10.5, 1.3 Hz, 1H), 4.92 (m, 1H), 4.21 (dt, J=6.6, 1.3 Hz, 1H), 4.15 (m, 1H), 4.12 (dt, J=6.7, 1.3 Hz, 1H), 3.69 (dd, J=17.5, 2.6 Hz, 1H), 3.61 (dd, J=17.3, 2.8 Hz, 1H), 3.27 (m, 2H), 3.15 (s, 3H), 2.37 (ddd, J=14.0, 10.2, 7.4 Hz, 1H), 2.13 (ddd, J=17.6, 10.5, 6.8 Hz, 1H), 1.95 (m, 2H), 1.83 (m, 1H), 1.70 (m, 2H), 1.23 (s, 3H), 1.20 (s, 3H), 1.08 (m, 2H), 1.01 (s, 9H), 0.75 (s, 3H), 0.72 (s, 3H); $^{13}$C NMR (125 MHz, $C_6D_6$) δ 205.2, 205.1, 174.9, 172.8, 172.6, 164.9, 164.0, 160.8, 160.6, 133.9, 133.8, 132.0, 132.1, 126.8, 127.7, 127.5, 122.6, 120.0, 118.0, 117.9, 114.2, 114.0, 113.9, 102.6, 102.4, 88.0, 86.3, 84.7, 83.7, 82.5, 77.9, 71.9, 68.8, 54.9, 54.8, 37.8, 37.8, 33.7, 31.2, 30.7, 29.8, 29.5, 28.5, 26.7, 23.2, 22.5; HR-ESI-MS m/z calcd. for $C_{25}H_{35}NO_5S_2Na$ $[M+Na]^+$: 516.6689, found 516.6690; $[\alpha]^{25}_D$=+37.2° (c=1.0, $CH_2Cl_2$).

TBS Protection of 25a to 26a

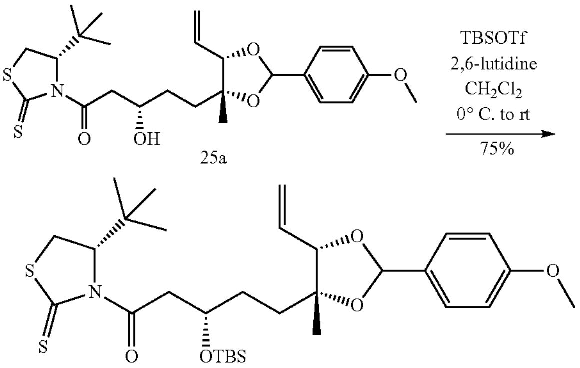

25a

26a

Reagents: 2,6-Lutidine, redistilled, 99% (Chem-Impex Int.): used without further purification; TBSOTf, 99% (Chem-Impex Int.): used without further purification.

(3S)-1-((R)-5-(tert-butyl)-2-thioxothiazolidin-3-yl)-3-((tert-butyldimethylsilyl)oxy)-5-((4R,5S)-2-(4-methoxyphenyl)-4-methyl-5-vinyl-1,3-dioxolan-4-yl)pentan-1-one (26a). Adduct 25a (1.00 g, 2.03 mmol) was dissolved in anhydrous $CH_2Cl_2$ (75 mL) followed by addition of 2,6-lutidine (1.28 mL, 10.2 mmol). The mixture was purged with Ar and cooled to 0° C. TBSOTf (1.63 mL, 7.10 mmol) was added dropwise, and the mixture was warmed to rt and stirred overnight, at which point NMR analyses indicated complete consumption of starting material. The reaction was quenched with addition of solid $NaHCO_3$ (1 g) and stirred for 15 min. The mixture was filtered and concentrated under rotary evaporation to yield a yellow crude oil. Pure adducts 26a (910 mg, 75%) was obtained as a yellow oil by flash chromatography, eluting with a gradient of hexanes to 1:9 EtOAc/hexanes.

Adducts 26a: TLC ($CH_2Cl_2$): $R_f$=0.40 (CAM stain); $^1$H NMR (500 MHz, $C_6D_6$) δ 7.61 (d, J=8.9 Hz, 2H), 7.55 (d, J=8.6 Hz, 2H), 6.89 (d, J=8.7 Hz, 2H), 6.82 (d, J=8.7 Hz, 2H) 6.29 (s, 1H), 5.94 (s, 1H), 5.90 (m, 1H), 5.86 (m, 1H), 5.32 (dt, J=17.1, 1.6 Hz, 2H), 5.12 (dt, J=10.6, 1.5 Hz, 1H), 5.10 (d, J=10.5, 1.5 Hz, 2H), 5.09 (d, J=7.9 Hz, 1H), 5.06 (d, J=7.9 Hz, 1H), 4.59 (tt, J=6.7, 4.4 Hz, 1H), 4.49 (tt, J=6.4, 4.9 Hz, 1H), 4.22 (dt, J=6.4, 1.2 1H), 4.13 (dt, J=6.4, 1.2 Hz, 1H), 4.04 (dd, J=17.2, 6.7 Hz, 1H), 4.01 (dd, J=17.2, 6.8 Hz, 1H), 3.44 (dd, J=11.9, 5.2 Hz, 1H), 3.40 (dd, J=11.9, 5.2 Hz, 1H), 3.30 (s, 3H), 3.28 (d, J=1.4 Hz, 1H), 3.26 (s, 3H), 3.25 (d, J=2.8 Hz, 1H), 2.64 (dd, J=12.6, 7.6 Hz, 1H), 2.62 (dd, J=13.2, 8.3 Hz, 1H), 2.05 (ddd, J=11.8, 5.4, 0.8 Hz, 2H), 2.00 (m, 1H), 1.79 (m, 1H), 1.64 (m, 1H), 1.54 (m, 1H), 1.24 (s, 3H), 1.21 (s, 3H), 1.02 (s, 9H), 0.99 (s, 9H), 0.77 (s, 9H), 0.75 (s, 9H), 0.21 (s, 3H), 0.17 (s, 3H), 0.15 (s, 3H); $^{13}$C NMR (125 MHz, $C_6D_6$) δ 205.3, 205.2, 171.2, 171.2, 160.8, 160.6, 134.0, 133.8, 133.0, 131.9, 131.3, 128.6, 128.4, 128.2, 127.5, 118.0, 117.9, 114.0, 113.9, 102.6, 102.3, 87.9, 86.2, 83.6, 82.4, 72.2, 72.2, 70.1, 69.9, 58.4, 58.4, 46.2, 46.0, 37.9, 37.9, 33.8, 33.7, 33.6, 32.2, 31.6, 30.1, 30.1, 29.4, 26.8, 26.2, 26.1, 25.2, 22.7, 22.2, 18.4, 18.4, −4.1, −4.2, −4.3, −4.3; HR-ESI-MS m/z calcd. for $C_{31}H_{49}NO_5S_2SiNa$ $[M+Na]^+$: 630.2689, found 630.2688; $[\alpha]^{25}_{D}$=+49.4° (c=1.0, $CH_2Cl_2$).

Saponification of 26a to 27a

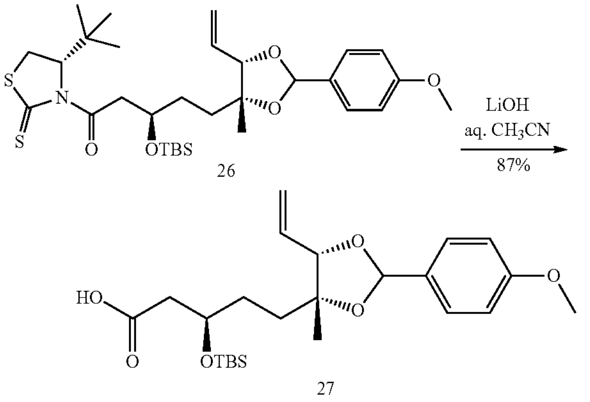

Reagents: $LiOH{\cdot}H_2O$, 98% (Alfa Aesar): used without further purification (3S)-3-((tert-Butyldimethylsilyl)oxy)-5-((4R,5S)-2-(4-methoxyphenyl)-4-methyl-5-vinyl-1,3-dioxolan-4-yl)pentanoic acid (27a) $LiOH{\cdot}H_2O$ (106 mg, 4.45 mmol) was added to a solution of 26a (900 mg, 1.48 mmol) in 20% aq. $CH_3CN$ (50 mL). The mixture was stirred at rt overnight, at which point the deep yellow color dissipates into a light brown solution. The mixture was diluted with $H_2O$ (50 mL) and $Et_2O$ (50 mL). The aqueous phase was collected, and the organic phase was back extracted with $H_2O$ (2×50 mL). The aqueous phases were combined, and the pH was adjusted to 6.5 with 1 M HCl. The mixture was extracted into EtOAc (3×100 mL), and the organics were combined, dried over $Na_2SO_4$, filtered and concentrated by rotary evaporation. Pure acid 27a (533 mg, 87%) was obtained as a colorless oil by flash chromatography, eluting with a gradient of hexanes to 1:2 EtOAc/hexanes. Note 1: NMR spectral data was complicated due to the presence of minor amounts of carboxylate salts.

Acid 27a: TLC (1:1 EtOAc/hexanes): $R_f$=0.54 (CAM stain); $^1H$ NMR (500 MHz, $C_6D_6$) δ 7.58 (d, J=8.8 Hz, 2H), 7.55 (d, J=8.8 Hz, 2H), 7.11 (d, J=8.6, 6.7 Hz, minor), 6.87 (d, J=8.7 Hz, 2H), 6.83 (d, J=8.7 Hz, 2H), 6.24 (s, 1H), 6.20 (s, minor), 5.95 (s, 1H), 5.93 (s, minor), 5.82 (m, 1H), 5.32 (ddt, J=17.1, 5.3, 1.6 Hz, 1H), 5.18 (m, minor), 5.12 (ddd, J=7.6, 2.0, 1.3 Hz, 1H), 5.10 (m, 1H), 5.08 (m, minor), 4.20 (dt, J=6.6, 1.3 Hz, 1H), 4.16 (dt, J=6.5, 1.3 Hz, minor), 4.11 (dt, J=6.7, 1.1 Hz, 1H), 4.08 (m, minor), 3.30 (s, 3H), 3.27 (s, 3H), 3.26 (m, minor), 2.78 (dd, J=15.0, 9.5 Hz, minor), 2.47 (dd, J=14.9, 7.6 Hz, 1H), 2.39 (dd, J=15.0, 7.2 Hz, 1H), 2.31 (dd, J=15.0, 5.8 Hz, minor), 2.27 (dd, J=13.3, 4.9 Hz, 1H), 2.24 (dd, J=13.5, 5.0 Hz, 1H), 1.85 (m, 2H), 1.63 (m, 2H), 1.49 (s, minor), 1.34 (s, minor), 1.20 (s, 3H), 1.18 (s, 3H), 1.02 (s, 9H), 0.99 (s, minor), 0.98 (s, minor), 0.97 (s, 9H), 0.16 (s, minor), 0.15 (s, 3H), 0.13 (s, minor), 0.11 (s, 3H), 0.10 (s, 3H), 0.09 (s, minor), 0.05 (s, 3H); $^{13}C$ NMR (125 MHz, $C_6D_6$) δ 178.2, 177.8, 160.8, 160.6, 160.4, 159.7, 136.1, 133.9, 133.7, 132.9, 131.3, 128.4, 128.2, 128.0, 127.6, 127.4, 118.0, 117.7, 114.1, 114.0, 114.0, 107.8, 102.3, 87.7, 86.1, 83.4, 82.4, 82.3, 70.2, 70.1, 69.8, 54.8, 54.8, 54.7, 42.8, 42.7, 42.6, 33.3, 32.1, 32.0, 31.7, 31.4, 29.0, 28.8, 27.3, 26.1, 26.1, 23.1, 22.6, 21.1, 18.4, 18.3, 18.3, −4.3, −4.4, −4.6; HR-ESI-MS m/z calcd. for $C_{24}H_{38}O_6SiNa$ $[M+Na]^+$: 473.2287, found 473.22889; $[\alpha]^{25}_{D}$=+10.0° (c=0.8, $CH_2Cl_2$).

Esterification of 27a and Alcohol 33 to 34a

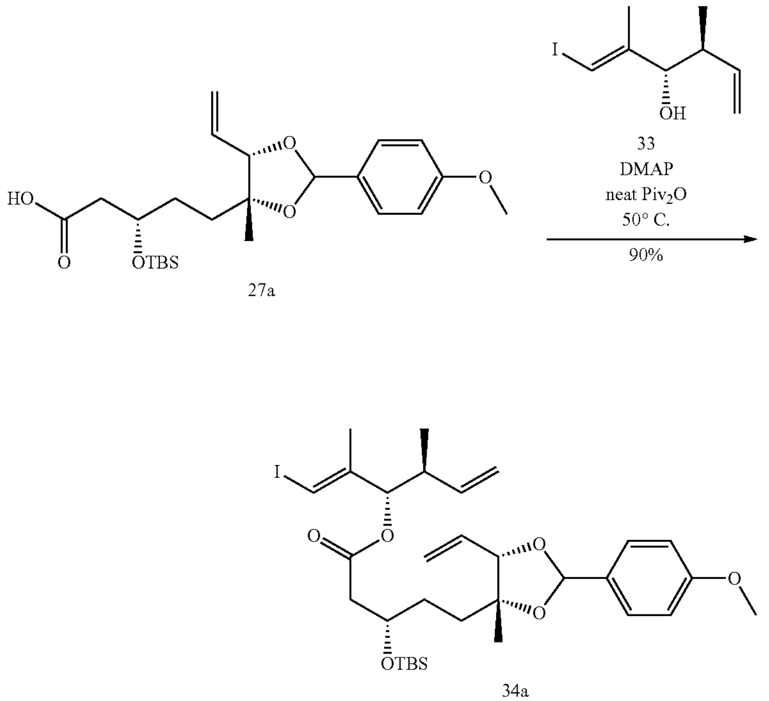

34a

Reagents: DMAP, 98% (Sigma-Aldrich): used without further purification; Pivalic anhydride, 99% (Alfa Aesar): used without further purification.

(3S,4S,E)-1-iodo-2,4-dimethylhexa-1,5-dien-3-yl-(3R)-3-((tert-butyldimethylsilyl)oxy)-5-((4R,5S)-2-(4-methoxyphenyl)-4-methyl-5-vinyl-1,3-dioxolan-4-yl)pentanoate (34a). DMAP (13.6 mg, 0.111 mmol) and pivalic anhydride (563 μL, 2.78 mmol) were sequentially added to acid 27a (500 mg, 4.44 mmol) and alcohol 33 (308 mg, 1.22 mmol). The mixture was purged with Ar and stirred neat at 50° C. for 8 h. Pivalic anhydride was removed from the mixture under airflow. The crude material in hexanes was then loaded directly onto silica gel and eluted with a gradient of hexanes to 1:9 $Et_2O$/hexanes. Pure esters 34a (683 mg, 90%) were obtained as a clear oil.

Esters 34a: TLC (1:4 $Et_2O$/hexanes): $R_f$=0.40, 0.38 (CAM stain); $^1H$ NMR (500 MHz, $C_6D_6$) δ 7.58 (d, J=8.5 Hz, 2H), 7.57 (d, J=8.5 Hz, 2H), 6.86 (d, J=8.7 Hz, 2H), 6.83 (d, J=8.7 Hz, 2H), 6.27 (s, 1H), 6.23 (d, J=0.9 Hz, 1H), 6.21 (d, J=0.9 Hz, 1H), 5.94 (s, 1H), 5.84 (m, 1H), 5.80 (m, 1H), 5.65 (m, 1H), 5.58 (ddd, J=17.0, 10.3, 8.1 Hz, 1H), 5.32 (dt, J=17.2, 1.6 Hz, 1H), 5.20 (dd, J=18.8, 8.9 Hz, 1H), 5.10 (m, 1H), 4.96 (m, 2H), 4.20 (m, 1H), 4.12 (m, 1H), 3.27 (s, 3H), 3.26 (s, 3H), 2.51 (dd, J=15.3, 6.9 Hz, 1H), 2.43 (dd, J=15.3, 6.7 Hz, 1H), 2.36 (m, 1H), 2.33 (dd, J=15.3, 5.7 Hz, 1H), 2.23 (m, 1H), 1.89 (m, 2H), 1.72 (d, J=1.2 Hz, 3H), 1.70 (d, J=1.2 Hz, 3H), 1.67 (m, 1H), 1.51 (m, 1H) 1.69 (s, 3H), 1.23 (s, 3H), 1.21 (s, 3H), 1.01 (s, 9H), 0.98 (s, 9H), 0.66 (d, J=6.7 Hz, 3H), 0.65 (d, J=6.8 Hz, 3H), 0.14 (s, 3H), 0.14 (s, 3H), 0.10 (s, 3H), 0.08 (s, 3H); $^{13}C$ NMR (125 MHz, $C_6D_6$) δ 170.2, 160.8, 160.6, 144.8, 144.7, 139.9, 139.8, 134.0, 134.0, 132.9, 131.1, 128.4, 128.2, 128.0, 127.7, 127.6, 115.9, 114.0, 114.0, 102.5, 102.5, 87.9, 87.8, 83.5, 82.3, 54.8, 43.0, 40.6, 33.6, 32.1, 26.2, 22.6, 20.0, 18.3, 118.3, 16.4, 16.4, −4.4, −4.4; HR-ES-MS m/z calcd. for $C_{32}H_{49}NO_5S_2SiNa$ $[M+Na]^+$: 707.2203, found 707.2201; $[\alpha]^{25}_D$=−38.1° (c=1.0, $CH_2Cl_2$).

Ring Closing Metathesis of 34a to 35a

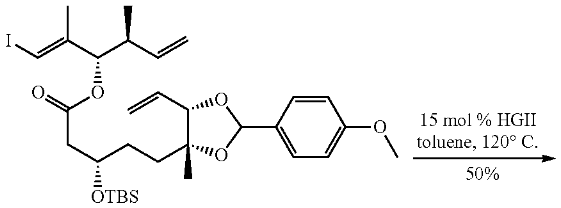

34a

-continued

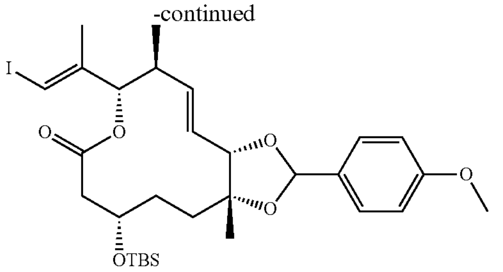

35a

Reagents: 2nd Generation Hoveyda Grubbs catalyst, 97% (Sigma-Aldrich): used without further purification (3aS,6S,7S,11R,13aR,E-11)-((tert-Butyldimethylsilyl)oxy)-7-((E)-1-iodoprop-1-en-2-yl)-2-(4-methoxyphenyl)-6,13a-dimethyl-3a,6,7,10,11,12,13,13a-octahydro-9H-[1,3]dioxolo[4,5-f][1]oxacyclododecin-9-one (35a). Ester 34a (625 mg, 913 mmol) was dissolved into anhydrous degassed toluene (70 mL). The mixture was purged with Ar and heated to reflux. 2nd Generation Hoveyda Grubbs catalyst (70.5 mg, 0.113 mmol) as an Ar purged solution in anhydrous degassed toluene (70 mL) was dropwise added to the solution of 34a in boiling toluene. After stirring for 20 min the mixture turned from a clear green into a black solution and was stirred at reflux for 5 h. The mixture was then cooled to rt and concentrated on a rotary evaporator. The crude black solid was then suspended in hexanes and filtered through a pad of Celite eluting with hexanes. The elutants were concentrated on a rotary evaporator. Pure lactones 35a (300 mg, 50%) were obtained as a white solid by flash chromatography, eluting with a gradient of hexanes to 1:6 $Et_2O$/hexanes. Note 1: NMR spectra data reflect the predominant acetal diastereomer.

Lactones 35a: TLC (1:2 $Et_2O$/hexanes): $R_f$=0.38 (CAM stain); $^1H$ NMR (500 MHz, $C_6D_6$) δ 7.65 (d, J=8.7 Hz, 2H), 6.83 (d, J=8.7 Hz, 2H), 6.25 (d, J=1.3 Hz, 1H), 6.21 (s, 1H), 5.71 (dd, J=15.2, 9.7 Hz, 1H), 4.97 (d, J=10.7 Hz, 1H), 4.90 (dd, J=15.2, 9.6 Hz, 1H), 4.42 (p, J=5.2 Hz, 1H), 4.12 (d, J=9.8 Hz, 1H), 3.23 (s, 3H), 2.40 (dd, J=13.6, 11.2 Hz, 1H), 2.20 (dd, J=12.6, 5.0 Hz, 1H), 2.16 (m, 1H), 1.95 (td, J=13.6, 3.1 Hz, 1H), 1.61 (d, J=1.2 Hz, 3H), 1.53 (m, 2H), 1.31 (s, 3H), 1.24 (m, 2H), 0.92 (s, 9H), 0.49 (d, J=6.8 Hz, 3H), 0.02 (s, 3H), −0.02 (s, 3H); $^{13}C$ NMR (125 MHz, $C_6D_6$) δ 169.5, 160.6, 144.3, 132.6, 128.4, 128.2 128.0, 127.7, 127.5, 114.0, 84.3, 68.5, 54.8, 40.7, 40.4, 28.9, 27.5, 25.9, 21.5, 19.0, 18.2, 15.8, −4.9; HR-ES-MS m/z calcd. for $C_{30}H_{45}IO_6SiNa$ $[M+Na]^+$: 679.1902, found 679.1903; $[\alpha]^{25}_D$=−12.7° (c=0.5, $CH_2Cl_2$).

Two Step Conversion of 35a to Core 3a.

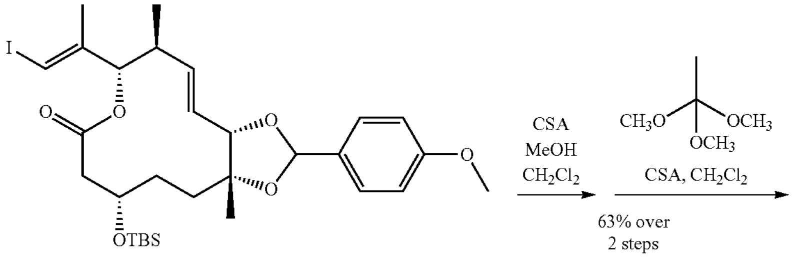

35a

-continued

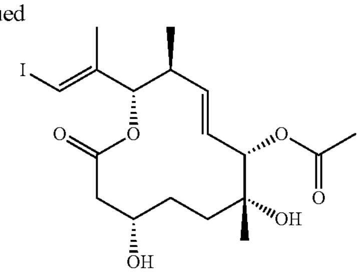

3a

Reagents: (1S)-(+)-10-Camphorsulfonic acid, 98% (TCI Chemicals): used without further purification; Trimethyl orthoformate, 99% (Sigma-Aldrich): used without further purification.

(2S,3S,6S,7R,10R,E)-7,10-Dihydroxy-2-((E)-1-iodoprop-1-en-2-yl)-3,7-dimethyl-12-oxooxacyclododec-4-en-6-yl acetate (3a). Macrocycles 35a (247 mg, 0.377 mmol) were dissolved in 1:3 $MeOH/CH_2Cl_2$ (30 mL) in a 1 L flask and (1S)-(+)-10-camphorsulfonic acid (345 mg, 1.49 mmol) was added as a solid in one portion. The mixture was stirred for 5 h, at which point TLC analyses indicated complete conversion of starting material. The solvent was removed under rotary evaporation, and the resulting crude was taken up in anhydrous $CH_2Cl_2$ (50 mL) in a 100 mL flask and cooled to 0° C. Trimethyl orthoformate (40.0 µL, 0.313 mmol) was added neat, and the mixture was stirred at 0° C. for 1 h, at which point satd. $NaHCO_3$ (1 mL) was added. The mixture was extracted into $CH_2Cl_2$ (15 mL), and the organics were concentrated on a rotary evaporator. Pure core 3a (89.0 mg, 63% over two steps) was obtained as a film by flash chromatography, eluting with a gradient of $CH_2Cl_2$ to 1:3 acetone/$CH_2Cl_2$.

Core 3a: TLC (1:8 acetone/$CH_2Cl_2$): $R_f$=0.30 (CAM stain); $^1$H NMR (500 MHz, $C_6D_6$) δ 6.22 (d, J=1.4 Hz, 1H), 5.85 (dd, J=15.2, 9.9 Hz, 1H), 5.47 (dd, J=15.2, 10.0 Hz, 1H), 5.20 (d, J=9.8 Hz, 1H), 5.11 (d, J=10.6 Hz, 1H), 4.22 (m, 1H), 2.39 (dd, J=13.4, 11.2 Hz, 1H), 2.30 (dd, J=13.4, 5.4 Hz, 3H), 2.42 (m, 1H), 2.12 (bs, 1H), 1.80 (t, J=9.1 Hz, 2H), 1.67 (m, 1H), 1.65 (s, 3H), 1.62 (d, J=1.1 Hz, 3H), 1.30 (m, 1H), 1.09 (s, 3H), 0.53 (d, J=6.7 Hz, 3H); $^{13}$C NMR (125 MHz, $C_6D_6$) δ 169.4, 169.2, 144.1, 139.6, 139.5, 126.9, 84.2, 84.0, 79.7, 79.0, 73.4, 67.5, 41.2, 39.8, 30.6, 27.4, 24.8, 20.7, 19.0, 16.1; HR-ESI-MS m/z calcd. for $C_{18}H_{27}IO_6Na$ $[M+Na]^+$: 489.0745, found 489.0742; $[\alpha]^{25}_D$=−31.6° (c=1.0, $CH_2Cl_2$).

Synthesis of 3S,17S-FD-895 (1a) by Stille Coupling of Core 3a to 2

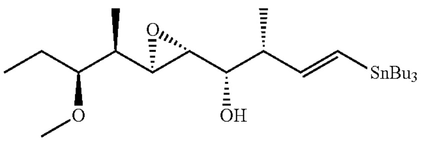

2

+

-continued

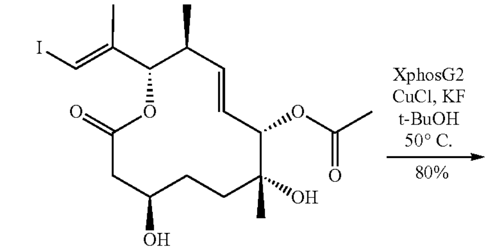

3a

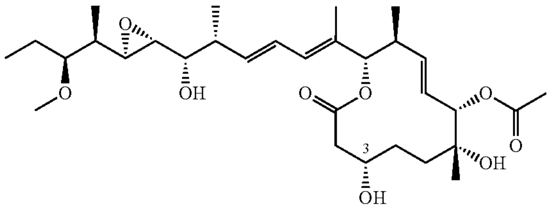

1a

Reagents: CuCl, anhydrous, beads, 99.99% (Sigma-Aldrich): used without further purification; KF, anhydrous, powder, 99.9% (Sigma-Aldrich): used without further purification; XPhos Pd G2 (Sigma-Aldrich): used without further purification; t-BuOH, anhydrous, 99.5% (Sigma-Aldrich): used without further purification.

3S,17S-FD-895 (1a). Vinylstannane 2 (127 mg, 0.225 mmol) and core 3a (70.0 mg, 0.150 mmol) were combined in a 100 mL flask and dried via rotary evaporation of benzene. To the mixture was then sequentially added CuCl (15.0 mg, 0.0150 mmol), KF (8.92 mg, 0.0150 mmol) and XPhos Pd G2 (12.6 mg, 0.0160 mmol) and anhydrous t-BuOH (15 mL). The reaction vessel was purged under Ar, heated to 50° C. and stirred overnight, at which point the solution turns into a gray cloudy mixture. The mixture was then filtered through a plug of Celite and eluted with acetone (20 mL). The elutants were concentrated on a rotary evaporator. Pure 3S-17S-FD-895 (1a) (68.0 mg, 80%) was obtained as a white semi-solid by flash chromatography over neutral silica gel eluting with a gradient of hexanes to 1:3 acetone/hexanes.

3S,17S-FD-895 (1a): TLC (1:3 acetone/$CH_2Cl_2$): $R_f$=0.20 (CAM stain); NMR data provided in Table $S_2$; HR-ESI-MS m/z calcd. for $C_{30}H_{50}O_9Na$ $[M+Na]^+$: 589.3441, found 589.3440; $[\alpha]^{25}_D$=+12.4° (c=1.0, $CH_2Cl_2$).

TABLE S2

| NMR data for 3S,17S-FD-895 (1a) in $C_6D_6$ | | |
|---|---|---|
| Position | $\delta_C$, Type | $\delta_H$, mult (J in Hz) |
| 1 | 169.9 | |
| 2α | 40.2 | 2.51, dd (13.3, 11.3) |
| 2β | | 2.41, dd (13.4, 5.4) |
| 3 | 67.8 | 4.30, m |
| 4α | 27.6 | 1.63, m |
| 4β | | 1.43, m |
| 5α | 30.9 | 1.82, m |
| 5β | | 1.89, m |
| 6 | 73.6 | |
| 7 | 79.3 | 5.28, d (9.7) |
| 8 | 126.5 | 5.94, dd (15.1, 9.7) |
| 9 | 140.5 | 5.63, dd (15.2, 10.0) |
| 10 | 41.3 | 2.48, m |
| 11 | 82.3 | 5.21, d (10.6) |
| 12 | 131.6 | |
| 13 | 131.8 | 6.21, d (10.8) |
| 14 | 126.6 | 6.29, dd (14.9, 10.8) |
| 15 | 137.6 | 5.85, dd (14.8, 8.4) |
| 16 | 41.5 | 2.38, m |
| 17 | 73.0 | 3.48, q (3.7) |
| 18 | 59.7 | 2.60, dd (3.8, 2.2) |
| 19 | 57.7 | 3.05, dd (8.2, 2.2) |
| 20 | 39.2 | 1.34, m |
| 21 | 83.8 | 3.15, m |
| 22α | 23.9 | 1.65, m |
| 22β | | 1.38, m |
| 23 | 10.2 | 0.86, t (7.4) |
| 24 | 24.8 | 1.14, s |
| 25 | 16.5 | 0.75, d (6.7) |
| 26 | 12.0 | 1.63, d (1.2) |
| 27 | 17.3 | 1.15, d (7.0) |
| 28 | 10.9 | 0.90, d (7.0) |
| 29 | 169.4 | |
| 30 | 20.9 | 1.67, s |
| 31 | 57.7 | 3.24, s |

Procedures for the synthesis of 7R,17S-FD-895 (1b, FIG. 11). A five step sequence was used to convert lactone 35 to core 3b containing inversion at C7 and coupling it to side chain 2 to afford 1b.

Conversion of 35 to Diol 36b

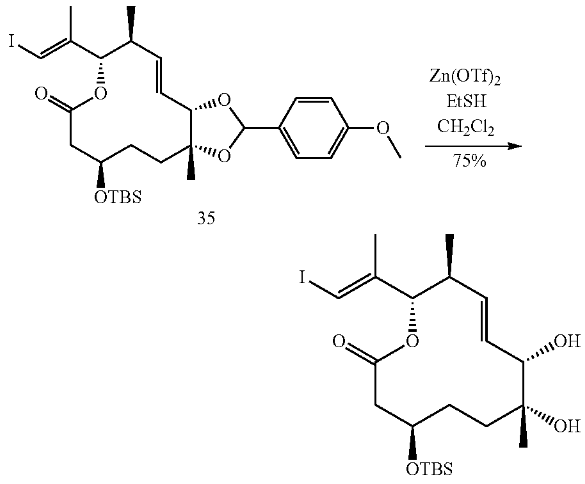

35

36b

Reagents: $Zn(OTf)_2$, 97% (Alfa Aesar): used without further purification; EtSH, 99% (Alfa Aesar): used without further purification; $NaHCO_3$, 98% (Fischer Scientific): used without further purification.

(3R,6R,7S)-(3S,4S,E)-1-iodo-2,4-dimethylhexa-1,5-dien-3-yl-3-((tert-butyldimethyl-silyl)oxy)-6,7-dihydroxy-6-methylnon-8-enoate (36b). Zinc triflate (1.60 g, 4.41 mmol) and EtSH (0.950 mL, 13.2 mmol) was added to a solution of 35 (500 mg, 0.882 mmol) in $CH_2Cl_2$ (50 mL) at 0° C. The reaction was warmed to rt. After 4 h satd. $NaHCO_3$ (10 mL) was added. The phases were separated, and the organic phases were dried with $Na_2SO_4$ and concentrated by a rotary evaporator. Pure diol 36b (356 mg, 75%) was obtained as colorless oil by flash chromatography, eluting with a gradient from hexanes to 1:4 EtOAc/hexanes.

Diol 36b: TLC (1:4 EtOAc/hexanes): $R_f$=0.30 (CAM stain); $^1$H NMR (500 MHz, $CDCl_3$) δ 6.35 (d, J=1.3 Hz, 1H), 5.62 (dd, J=15.1, 9.7 Hz, 1H), 5.33 (dd, J=15.2, 9.9 Hz, 1H), 5.01 (d, J=10.7 Hz, 1H), 3.72 (m, 1H), 3.69 (d, J=9.8 Hz, 1H), 2.40 (m, 1H), 2.38 (dd, J=13.8, 3.3 Hz, 1H), 2.30 (dd, J=13.8, 4.8 Hz, 1H), 1.81 (s, 3H), 1.68 (d, J=1.2 Hz, 3H), 1.50 (m, 2H), 1.29 (m, 2H), 1.20 (s, 3H), 1.15 (bs, 1H), 0.81 (d, J=6.9 Hz, 3H), 0.80 (s, 9H), −0.02 (s, 3H), −0.04 (s, 3H); $^{13}$C NMR (125 MHz, $CDCl_3$) δ 168.8, 143.9, 137.1, 130.2, 128.5, 83.9, 80.6, 73.7, 70.6, 40.6, 36.1 30.4, 29.8, 24.8, 25.9, 18.3, 16.6, −4.6, −4.7; HR-ESI-MS m/z calcd. for $C_{24}H_{43}IO_5SiNa$ $[M+Na]^+$: 561.1817, found 561.1819; $[\alpha]^{25}_D$=−28.1° (c=1.0, $CH_2Cl_2$).

Oxidation of Diol 36b to Ketone 37b

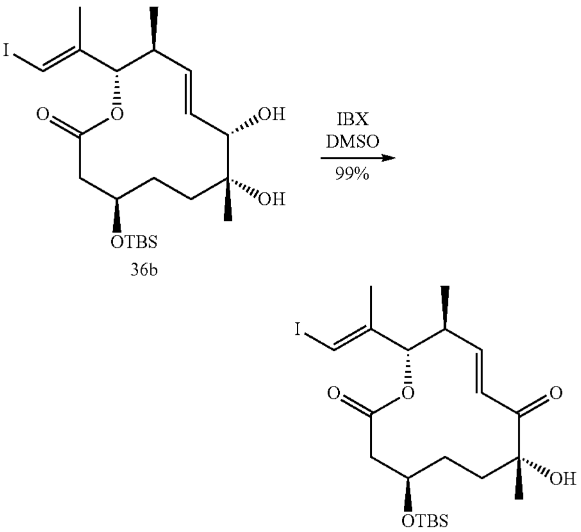

36b

37b

Reagents: IBX, 95%: synthesized from 2-iodobenzoic acid and oxone(46).

(4R,7R,11S,12S,E)-4-((tert-Butyldimethylsilyl)oxy)-7-hydroxy-12-((E)-1-iodoprop-1-en-2-yl)-7,11-dimethyloxa-cyclododec-9-ene-2,8-dione (37b) Diol 36b (300 mg, 0.558 mmol) was dissolved in DMSO (3 mL) in a scintillation vial and IBX (389 mg, 1.39 mmol) was added in one portion. The mixture was stirred at rt for 3 hr. EtOAc (50 mL) and $H_2O$ (50 mL) were added, and the phases were separated. The organic phase was washed with $H_2O$ (3×25 mL), dried over $Na_2SO_4$ and concentrated by a rotary evaporator. Pure ketone 37b (290 mg, 99%) was obtained as a colorless oil by flash chromatography, eluting with a gradient of hexanes to 1:4 EtOAc/hexanes.

Ketone 37b: TLC (1:4 EtOAc/hexanes): $R_f$=0.40 (CAM stain); $^1$H NMR (500 MHz, $C_6D_6$) δ 6.87 (d, J=15.6 Hz, 1H), 6.37 (dd, J=15.6, 9.7 Hz, 1H), 6.19 (d, J=1.2 Hz, 1H), 5.02

(d, J=10.4 Hz, 1H), 4.25 (tt, J=8.3, 4.1 Hz, 1H), 2.34 (dd, J=12.8, 3.6 Hz, 1H), 2.20 (m, 1H), 2.15 (dd, J=12.8, 9.1 Hz, 1H), 1.88 (bs, 1H), 1.79 (ddd, J=14.0, 9.2, 6.5 Hz, 1H), 1.65 (m, 1H), 1.63 (d, J=1.7 Hz, 3H), 1.52 (m, 1H), 1.44 (m, 1H), 1.23 (s, 3H), 0.96 (s, 9H), 0.46 (d, J=6.7 Hz, 3H), 0.10 (s, 3H), 0.05 (s, 3H); $^{13}C$ NMR (125 MHz, $C_6D_6$) δ 202.3, 168.4, 146.7, 143.7, 129.3, 84.3, 79.5, 79.0, 69.0, 44.3, 40.3, 36.9, 32.6, 26.1, 19.1, 18.3, 15.5, −4.3, −4.4; HR-ESI-MS m/z calcd. for $C_{24}H_{41}IO_5SiNa$ [M+Na]$^+$: 559.1442, found 559.1441; $[\alpha]^{25}_D$=−46.8° (c=1.0, $CH_2Cl_2$).

Reduction of Ketone 37b to Alcohol 38b

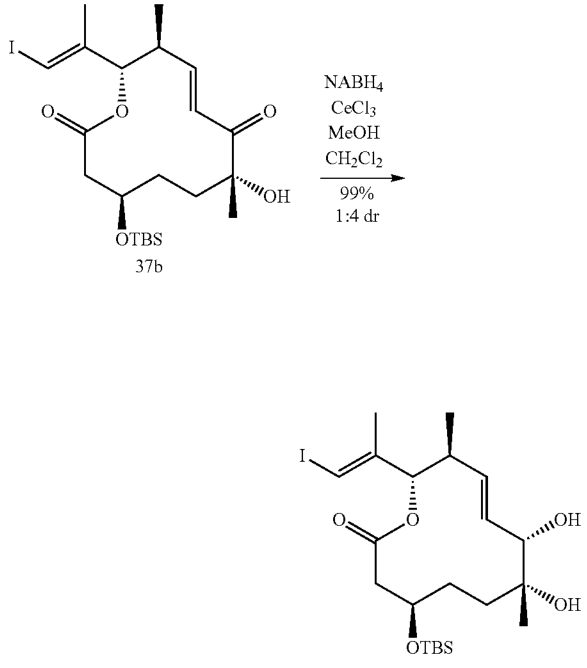

37b

38b

Reagents: $CeCl_3 \cdot 7H_2O$, 99% (Acros Organics): used without further purification; $NaBH_4$ 98%, (Acros Organics): used without further purification.

(4R,7R,8R,11S,12S,E)-4-((tert-Butyldimethylsilyl)oxy)-7,8-dihydroxy-12-((E)-1-iodoprop-1-en-2-yl)-7,11-dimethyloxacyclododec-9-en-2-one (38b) $CeCl_3 \cdot 7H_2O$ (274 mg, 1.11 mmol) was added to a solution of 37b (215 mg, 0.743 mmol) in MeOH (5 mL) and cooled to −20° C. $NaBH_4$ (0.817 mmol, 30.8 mg) was added in one portion, and the mixture was stirred for 5 min. The reaction was quenched with satd. $NaHCO_3$ (1 mL), dried over $NaSO_4$, and concentrated by a rotary evaporator. Pure diol 38b (54.8 mg, 99%) was obtained in a 1:4 dr by flash chromatography, eluting with a gradient of hexanes to 1:3 EtOAc/hexanes. Note 1: Diol 36b was the major diastereomeric product and was recycled by oxidation to 37b and reduction to provide additional 38b.

Diol 38b: TLC (1:4 EtOAc/hexanes): $R_f$=0.28 (CAM stain); $^1H$ NMR (500 MHz, $C_6D_6$) δ 6.36 (s, 1H), 5.93 (dd, J=15.6, 2.9 Hz, 1H), 5.30 (dd, J=15.6, 9.3 Hz, 1H), 5.01 (d, J=10.1 Hz, 1H), 3.79 (m, 1H), 3.75 (m, 1H), 2.31 (m, 1H), 2.26 (m, 2H), 1.83 (m, 1H), 1.72 (s, 3H), 1.60 (m, 2H), 1.43 (d, J=5.2 Hz, 1H), 1.29 (m, 1H), 1.18 (s, 3H), 1.01 (s, 9H), 0.65 (d, J=6.7 Hz, 3H), 0.08 (s, 3H), 0.07 (s, 3H); $^{13}C$ NMR (125 MHz, $C_6D_6$) δ 168.4, 144.8, 132.2, 130.0, 128.6, 83.4, 80.7, 78.3, 74.7, 71.0, 41.7, 40.3, 36.1, 31.6, 26.1, 19.5, 18.4, 16.6, −4.5; HR-ESI-MS m/z calcd. for $C_{24}H_{43}IO_5SiNa$ [M+Na]$^+$: 561.1817, found 561.1819; $[\alpha]^{25}_D$=+2.5° (c=1.0, $CH_2Cl_2$).

Two-Step Conversion of 38b to Core 3b

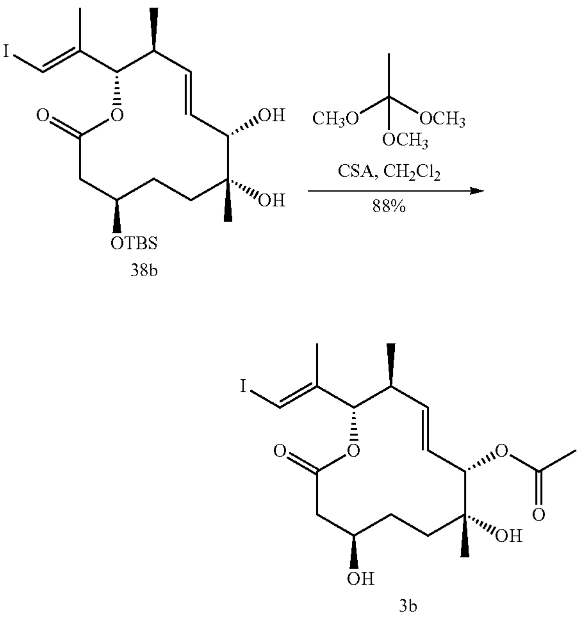

38b

3b

Reagents: (1S)-(+)-10-Camphorsulfonic acid, 98% (TCI Chemicals): used without further purification; Trimethyl orthoformate, 99% (Sigma-Aldrich): used without further purification (2S,3S,6R,7R,10R,E)-7,10-Dihydroxy-2-((E)-1-iodoprop-1-en-2-yl)-3,7-dimethyl-12-oxooxacyclododec-4-en-6-yl acetate (3b) Diol 38b (41.1 mg, 0.0638 mmol) was dissolved in 1:3 $MeOH/CH_2Cl_2$ (10 mL) in a 20 mL scintillation vial and (1S)-(+)-10-camphorsulfonic acid (57.5 mg, 0.248 mmol) was added as a solid in one portion. The mixture was stirred for 5 h, at which point TLC analyses indicated complete conversion of starting material. The solvent was removed under rotary evaporation, and the resulting crude was taken up in anhydrous $CH_2Cl_2$ (10 mL) in a 20 mL scintillation vial and cooled to 0° C. Trimethyl orthoformate (10.0 μL, 0.0783 mmol) was added neat, and the mixture was stirred at 0° C. for 1 h, at which point satd. $NaHCO_3$ (1 mL) was added. The mixture was extracted into $CH_2Cl_2$ (15 mL), and the organics were concentrated on a rotary evaporator. Pure core 3b (38.9 mg, 88%) was obtained as a colorless wax by flash chromatography, eluting with a gradient of $CH_2Cl_2$ to 1:3 acetone/$CH_2Cl_2$.

Core 3b: TLC (1:8 acetone/$CH_2Cl_2$): $R_f$=0.27 (CAM stain); $^1H$ NMR (500 MHz, $C_6D_6$) δ 6.19 (d, J=1.3 Hz, 1H), 5.87 (dd, J=15.4, 2.4 Hz, 1H), 5.39 (q, J=1.9 Hz, 1H), 5.24 (d, J=10.5 Hz, 1H), 5.24 (m, 1H), 3.54 (bs, 1H), 2.25 (m, 2H), 2.19 (d, J=14.0 Hz, 1H), 1.71 (m, 1H), 1.66 (s, 3H), 1.65 (d, J=1.7 Hz, 3H), 1.61 (m, 1H), 1.50 (m, 1H), 1.17 (bs, 1H), 1.01 (s, 3H), 0.96 (m, 1H), 0.56 (d, J=6.7 Hz, 3H); $^{13}C$ NMR (125 MHz, $C_6D_6$) δ 171.9, 169.2, 144.1, 129.8, 84.2, 80.0, 77.8, 73.7, 69.5, 41.0, 38.8, 36.4, 30.5, 24.7, 20.3, 19.1, 16.5; HR-ESI-MS m/z calcd. for $C_{18}H_{27}IO_6Na$ [M+Na]$^+$: 489.0745, found 489.0744; $[\alpha]^{25}_D$=−14.8° (c=1.0, $CH_2Cl_2$).

Synthesis of 7R,17S-FD-895 (1b) by Stille Coupling of Core 3b to 2

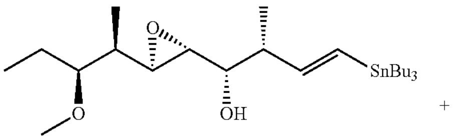

2

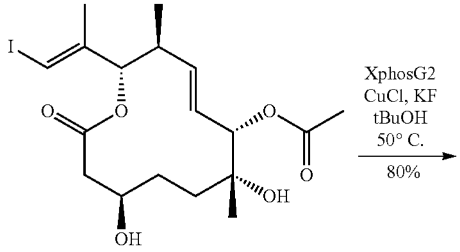

3b

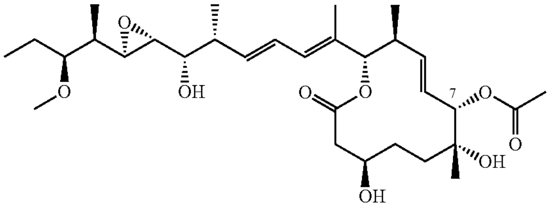

1b

Reagents: CuCl, anhydrous, beads, 99.99% (Sigma-Aldrich): used without further purification; KF, anhydrous, powder, 99.9% (Sigma-Aldrich): used without further purification; XPhos Pd G2 (Sigma-Aldrich): used without further purification; t-BuOH, anhydrous, 99.5% (Sigma-Aldrich): used without further purification.

7R,17S-FD-895 (1b). Vinylstannane 2 (42.3 mg, 0.0750 mmol) and core 3b (23.3 mg, 0.0500 mmol) were combined in a 20 mL scintillation vial and dried via rotary evaporation of benzene. To the mixture was then sequentially added CuCl (5.00 mg, 0.0500 mmol), KF (2.97 mg, 0.0500 mmol) and XPhos Pd G2 (4.20 mg, 0.00533 mmol) and anhydrous t-BuOH (5 mL). The reaction vessel was purged under Ar, heated to 50° C. and stirred overnight, at which point the solution turns into a gray cloudy mixture. The mixture was then filtered through a plug of Celite and eluted with acetone (20 mL). The elutants were concentrated on a rotary evaporator. Pure 7R-17S-FD-895 (1b) (13.6 mg, 80%) was obtained as a white semi-solid by flash chromatography over neutral silica gel eluting with a gradient of hexanes to 1:4 acetone/hexanes.

7R,17S-FD-895 (1b): TLC (1:8 acetone/$CH_2Cl_2$): $R_f$=0.28 (CAM stain); NMR data provided in Table S3; HR-ESI-MS m/z calcd. for $C_{30}H_{50}O_9Na$ $[M+Na]^+$: 589.3441, found 589.3440; $[\alpha]^{25}_D$=+22.1° (c=1.0, $CH_2Cl_2$).

TABLE S3

NMR data for 7R,17S-FD-895 (1b) in $C_6D_6$.

| Position | $\delta_C$ | $\delta_H$, mult (J in Hz) |
|---|---|---|
| 1 | 172.3 | 4.65, d (9.3) |
| 2α | 39.3 | 2.30, dd (14.7, 3.2) |
| 2β | | 2.36, dd (14.5, 4.2) |
| 3 | 69.6 | 3.59, m |
| 3-OH | | 3.76, d (10.6) |
| 4α | 30.6 | 1.80, m |
| 4β | | 1.69, m |
| 5α | 36.5 | 1.62, m |
| 5β | | 1.00, m |
| 6 | 73.8 | |
| 6-OH | | 1.97, bs |
| 7 | 82.9 | 5.36, d (10.5) |
| 8 | 128.3 | 5.96, dd (15.4, 2.4) |
| 9 | 130.7 | 5.40, ddd (9.8, 5.5, 2.2) |
| 10 | 41.1 | 2.48, tq (10.2, 6.7) |
| 11 | 78.0 | 5.44, m |
| 12 | 131.6 | |
| 13 | 131.6 | 6.18, dd (10.9, 1.5) |
| 14 | 126.4 | 6.29, dd (15.2, 10.9) |
| 15 | 137.8 | 5.81, dd (15.1, 8.5) |
| 16 | 41.5 | 2.38, m |
| 17 | 72.8 | 3.45, t (4.2) |
| 17-OH | | 1.82, bs |
| 18 | 59.6 | 2.58, dd (3.8, 2.3) |
| 19 | 57.6 | 3.04, dd (8.2, 2.2) |
| 20 | 39.0 | 1.33, m |
| 21 | 83.7 | 3.15, m |
| 22α | 23.8 | 1.62, m |
| 22β[1] | | 1.40, dt (13.9, 7.0) |
| | | 1.26, m |
| 23 | 10.0 | 0.85, t (7.4) |
| | | 0.86, t (7.4)[1] |
| 24 | 24.7 | 1.04, s |
| 25 | 16.9 | 0.77, d (6.8) |
| 26 | 11.9 | 1.64, d (1.2) |
| 27 | 17.3 | 1.13, d (7.0) |
| | | 1.13, d (10.6)[1] |
| 28 | 10.8 | 0.89, d (7.0) |
| 29 | 169.3 | |
| 30 | 20.4 | 1.67, s |
| 31 | 57.7 | 3.23, s |

[1]Rotational isomers were observed by $^{1}H$ NMR

Cell culture. The HCT-116 cell line was cultured in McCoy's 5a (Life Technologies) supplemented with 10% fetal bovine serum (FBS), 2 mM L-glutamine, and 100 U $mL^{-1}$ of penicillin and 100 μg $mL^{-1}$ of streptomycin at 37° C. in an atmosphere of 5% $CO_2$. Both the HeLa and Caov3 cell lines were maintained in DMEM (Life Technologies) supplemented with 10% FBS, 2 mM L-glutamine, and 100 U $mL^{-1}$ of penicillin and 100 μg $mL^{-1}$ of streptomycin at 37° C. in an atmosphere of 5% $CO_2$.

Cellular drug treatments. Compounds were dissolved in DMSO (MilliporeSigma). Cells were treated with 1a, 2a, 2b, or 3a in media with ≥0.5% DMSO for 24-72 h.

Cell viability assays for 2a, 2b, or 3a. HCT-116 cells were plated at $5\times10^3$ cells/well in McCoy's 5a containing 10% FBS. Cell were cultured for 24 h and then pre-treated with 1a for 24 h, then washed twice with 100 μL PBS. Next, cells were treated with cell cycle inhibitors ranging from 0-10 μM of 2a, 2b, or 3a for 72 h. Then, the cells were washed twice with 100 μL PBS, and 100 μL of media was added to each well, followed by 20 μL of CellTiter Aqueous One Solution (Promega). After 2 h at 37° C., absorbance readings were taken at 490 nm (test wavelength) and 690 nm (reference wavelength). $GI_{50}$ values were calculated in Prism (GraphPad) using at ≥3 biological replicates.

Cell Viability Assays for 1a-1c. HCT-116 cells were cultured in McCoy's 5a (Life Technologies) supplemented with 10% fetal bovine serum (FBS), 2 mM L-glutamine, 100 U $mL^{-1}$ penicillin and 100 μg $mL^{-1}$ streptomycin at 37° C. in an atmosphere of 5% $CO_2$. HCT-116 cells were plated at 5×10 cells/well in McCoy's 5a containing 10% FBS. Cells were cultured for 24 h, pretreated with 1 or 1a-1c in DMSO ranging from 0 to 1000 nM for 72 h (cell media contained <0.5% DMSO), and then washed with PBS (2×100 μL). 100 μL of PBS was added to each well, followed by 20 μL of CellTiter Aqueous One Solution (Promega). After 2 h at 37° C., absorbance readings were taken at 490 nm (test wavelength) and 690 nm (reference wavelength). $GI_{50}$ values were calculated in Prism (GraphPad) using at least three biological replicates.

Example 6. EE Separation Conditions

Scheme AS5. Resolution and delivery of enantiopure 33.

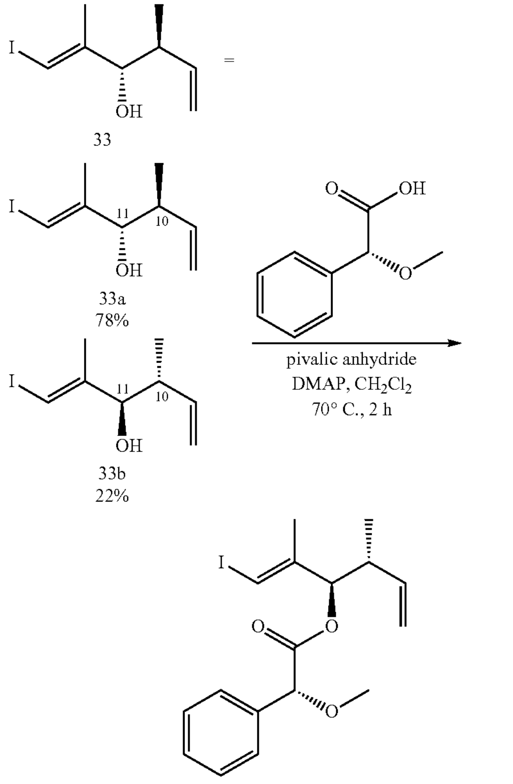

33

33a
78%

33b
22%

40b

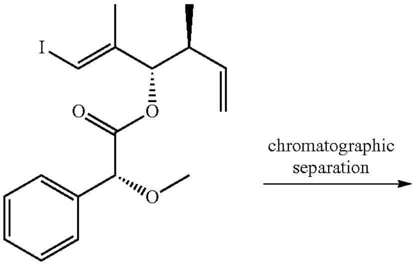

40a

-continued

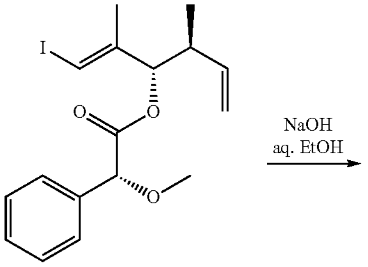

40a

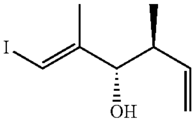

33

(3S,4S,E)-1-iodo-2,4-dimethylhexa-1,5-dien-3-yl (R)-2-methoxy-2-phenylacetate. Vinyl iodide 33 (9.3 g, 36.8 mmol), (R)-2-methoxy-2-phenylacetic acid (6.74 g, 40.6 mmol) and DMAP (678 mg, 5.50 mmol) were combined in a 100 mL flask and taken up in neat pivalic anhydride (15.0 mL). The mixture was heated to 70° C. and stirred for 2 h at which point the reaction was cooled to rt and satd. $NaHCO_3$ (5 mL) was added. The mixture was stirred for 2 h and extracted into $CH_2Cl_2$ (3×300 mL). The organics were washed with brine, dried over $Na_2SO_4$ and concentrated on a rotary evaporator. Pure 40a (16.0 g, 99%) was obtained by flash chromatography with a gradient of hexanes to 5% $Et_2O$/hexanes.

Ester 40a: TLC (5% $Et_2O$/hexanes): $R_f$=0.37 ($KMnO_4$ stain); $^1H$ NMR ($CDCl_3$, 300 MHz) δ 7.37 (m, 5H), 5.96 (s, 1H), 5.61 (ddd, J=7.9, 10.2, 18.1 Hz, 1H), 5.15 (d, J=7.9 Hz, 1H), 5.01 (dd, J=1.4, 17.1 Hz, 1H), 4.99 (d, J=9.7 Hz, 1H), 4.73 (s, 1H), 3.39 (s, 3H), 2.46 (dt, J=6.8, 7.3 Hz, 1H), 1.51 (d, J=1.5 Hz, 3H), 0.89 (d, J=6.9 Hz, 1H); $^{13}C$ NMR ($CDCl_3$, 75 MHz) δ 143.7, 138.9, 136.0, 129.0, 128.8, 127.4, 116.2, 82.4, 81.6, 81.0, 57.4, 40.0, 20.0, 16.5.

Enantiopure (3S,4S,E)-1-Iodo-2,4-dimethylhexa-1,5-dien-3-ol (6c). Pure 40a (12.2 g, 30.4 mmol) was dissolved in 80% MeOH (500 mL). NaOH (1 M) was added in 50 mL portions until TLC analyses indicated complete hydrolysis (typically complete in 5-6 additions over 1.5 h). $H_2O$ (100 mL) was added and the resulting mixture was extracted with $CH_2Cl_2$ (3×300 mL), washed with brine (100 mL) and dried with $Na_2SO_4$. The organics were concentrated on a rotary evaporator. Enantiopure 33 (7.40 g, 79%) was obtained without further purification.

Enantiopure 33: TLC (100% $CH_2Cl_2$): $R_f$=0.40 ($KMnO_4$ stain) $^1H$ NMR ($CDCl_3$, 300 MHz) δ 6.26 (s, 1H), 5.72 (ddd, J=17.8, 9.9, 8.1 Hz, 1H), 5.24-4.94 (m, 2H), 3.87 (dd, J=8.1, 2.3 Hz, 1H), 2.35 (q, J=7.4 Hz, 1H), 1.88-1.55 (s, 3H), 0.92 (d, J=6.8 Hz, 3H); $^{13}C$ NMR ($CDCl_3$, 75 MHz) δ 148.0, 139.9, 117.2, 80.1, 79.7, 42.2, 19.3, 16.5.

Example 7. Additional Enantiomers

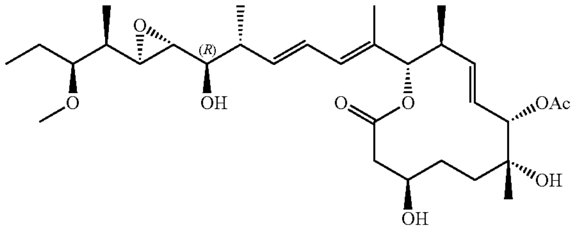

FD-895 (natural product), IC50: 0.8-1.0 nM

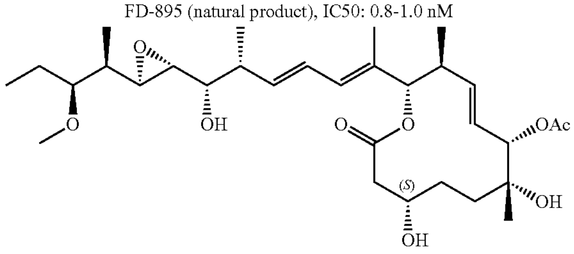

3S,17S-FD-895, IC50: 150 nM

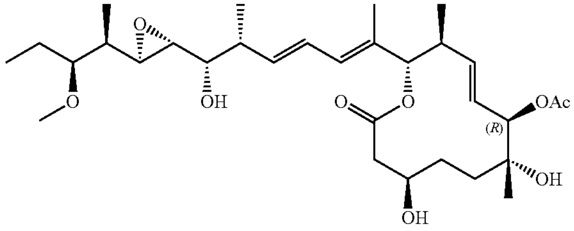

7R,17S-FD-895, IC50: > 1 μM

REFERENCES

Lagisetti C, Yermolina M V, Sharma L K, Palacios G, Prigaro B J, Webb T R. Pre-mRNA splicing-modulatory pharmacophores: the total synthesis of herboxidiene, a pladienolide-herboxidiene hybrid analog and related derivatives. ACS Chem Biol. 2014 Mar. 21; 9(3):643-8.

Gundluru M K, Pourpak A, Cui X, Morris S W, Webb T R. Design, synthesis and initial biological evaluation of a novel pladienolide analog scaffold. MedChemComm. 2011 Jan. 1; 2(9):904-908.

Fan L, Lagisetti C, Edwards C C, Webb T R, Potter P M. Sudemycins, novel small molecule analogues of FR901464, induce alternative gene splicing. ACS Chem Biol. 2011 Jun. 17; 6(6):582-9.

Lagisetti C, Pourpak A, Jiang Q, Cui X, Goronga T, Morris S W, Webb T R. Antitumor compounds based on a natural product consensus pharmacophore. J Med Chem. 2008 Oct. 9; 51(19):6220-4.

Trieger K, La Clair J, Burkart M. Splice Modulation Synergizes Cell Cycle Inhibition. ACS Chem. Biol. 2020, 15, 669-674.

(1) S. Bonnal, L. Vigevani, J. Valcarcel, *Nat. Rev. Drug. Discov.* 11, 847-859 (2012).

(2) B. León et al., *Angew. Chemie. Int. Ed.* 56, 12052-12063 (2017).

(3) E. G. Folco, K. E. Coil, R. Reed, *Genes Dev.* 25, 440-444 (2011).

(4) D. Pham, K. Koide, *Nat. Prod. Rep.* 33, 637-647 (2016).

(5) M. Kashyap, et al., *Haematologica,* 100, 945-954 (2015).

(6) F. A. L. M. Eskens, et al., *Clin. Cancer Res.* 19, 6296-6305 (2013).

(7) D. P. Steensma, et al., *Blood,* 134 Suppl. 1, 673 (2019).

(8) D. Kaida, et al., *Nat. Chem. Biol.* 3, 576-583 (2007).

(9) Y. Kotake, et al., *Nat. Chem. Biol.* 3, 570-575 (2007).

(10) M. Hasegawa, et al., *ACS Chem. Biol.* 6, 229-233 (2011).

(11) A. G. Matera, Z. Wang, *Nat. Rev. Mol. Cell Biol.* 15, 108-121 (2014).

(12) C. Lagisetti, G. Palacios, T. Goronga, B. Freeman, W. Caufield, T. R. Webb, *J. Med. Chem.* 56, 10033-10044 (2013).

(13) M. Seiler, et al., *Nat. Med.* 4, 497-504 (2018).

(14) C. Cretu, et al., *Mol. Cell* 2, 265-273 (2018).

(15) C. Cretu, et al., *Mol. Cell* 2, 307-319 (2016).

(16) M. Schellenberg, E. L. Dul, A. M. Macmillan, *RNA,* 17, 155-165 (2010).

(17) C. Lagisetti, G. Palacios, T. Goronga, B. Freeman, W. Caufield, T. R. Webb, *J. Med. Chem.* 56, 10033-10044 (2013).

(18) W. C. Chan, et al., ACS Med. *Chem. Lett.* 9, 1070-1072 (2018).

(19) R. Villa, M. K. Kashyap, D. Kumar, T. J. Kipps, J. E. Castro, J. J. La Clair, M. D. Burkart, *J. Med. Chem.* 56, 6576-6582 (2013).

(20) R. Villa, A. L. Mandel, B. D. Jones, J. J. La Clair, M. D. Burkart, *Org. Lett.* 14, 5396-5399 (2012).

(21) K. Machida, Y. Aritoku, T. Tsuchida, *J. Biosci. Bioeng.* 107, 596-598 (2009).

(22) L. A. Crews, et al., *Cell Stem Cell.* 19, 599-612 (2016).

(23) F. Meng, K. P. McGrath, A. H. Hoveyda, *Nature* 513, 367-374 (2014).

(24) A. K. Ghosh, D. D. Anderson, *Org. Lett.* 14, 4730-4733 (2012).

(25) P. R. Skaanderup, T. Jensen, *Org. Lett.* 10, 2821-2824 (2008).

(26) S. Miller, T. Mayer, F. Sasse, M. E. Maier, *Org. Lett.* 13, 3940-3943 (2011).

(27) V. P. Kumar, S. Chandrasekhar, *Org. Lett.* 15, 3610-3613 (2013).

(28) R. M. Kanada, et al., *Angew. Chemie. Int. Ed.* 46, 4350-4355 (2007).

(29) D. Delaunay, L. Toupet, M. Le Corre, *J. Org. Chem.* 60, 6604-6607 (1995).

(30) J. A. Marshall, Z. H. Lu, B. A. Johns, *J. Org. Chem.* 63, 817-823 (1998).

(31) K. A. Mandla, C. E. Moore, A. L. Rheingold, J. S. Figueroa, *Angew. Chemie. Int. Ed.* 57, 6853-6857 (2018).

(32) A. S.-Y. Lee, Y.-J. Hu, S.-F. Chu, *Tetrahedron* 57, 2121 (2001).

(33) Y. Zhang, A. J. Phillips, T. Sammakia, *Org. Lett.* 6, 23-25 (2004).

(34) A. L. Mandel, B. D. Jones, J. J. La Clair, M. D. Burkart, *Bioorg. Med. Chem. Lett.* 17, 5159-5164 (2007).

(35) A. Sakakura, K. Kawajiri, T. Ohlkubo, Y. Kosugi, K. Ishihara, *J. Am. Chem. Soc.* 129, 14775-14779 (2007).

(36) S. H. Hong, D. P. Sanders, C. W. Lee, R. H. Grubbs, *J. Am. Chem. Soc.* 127, 17160-17161 (2005).

(37) A. Elmarrouni, M. Campbell, J. J. Perkins, A. Converso, *Org. Lett.* 19, 3071-3074 (2017).

(38) S. Dhar, et al., *J. Am. Chem. Soc.* 138, 5063-5068 (2016).

(39) K. A. Effenberger, V. K. Urabe, M. S. Jurica, *Wiley Interdiscip. Rev. RNA* 8, e138, (2017).

(40) K. A. Effenberger, V. K. Urabe, B. E. Prichard, A. K. Ghosh, M. S. Jurica, *RNA* 22, 350-359 (2016).

(41) D. Kumar et al., *ACS Chem. Biol.* 11, 2716-2723 (2016).

(42) Y. Gao, et al., *ACS Chem. Biol.* 8, 895-900 (2013).

(43) Crimmins, M. T. & Chaudhary, K. (2000) Titanium enolates of thiazolidinethione chiral auxiliaries: Versatile tools for asymmetric aldol additions *Org. Lett.* 2, 775-777.

(44) Hill, J. H., Sharpless, K. B., Exon, C. M., and Regenye, R. (1985). Enantioselective epoxidation of allylic alcohols: (2S,3S)-3-propyloxiranemethanol. *Org. Synth.* 63, 66.

(45) Yang, Z., Xu, X., Yang. C.-H., Tian, Y., Chen. X., Lian, L., Pan, W., Su, X., Zhang, W. and Chen, Y. (2016). Total Synthesis of Nannocystin A. Org. Lett. 18, 5768-5770.

(46) Frigerio, M., Santagostino, M., and Sputore, S. (1999). A user-friendly entry to 2-iodoxybenzoic acid (IBX). J. Org. Chem. 64, 4537-4538.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A composition comprising a compound having the formula:

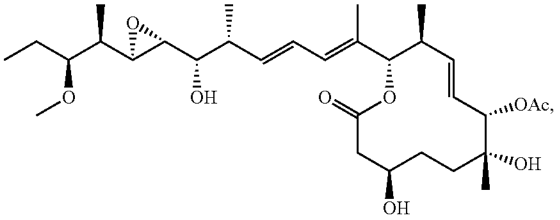

wherein, the composition comprises an enantiomeric purity of the compound of at least 95%.

2. The composition of claim 1, comprising at least 5 grams of the compound with or without a pharmaceutically acceptable excipient.

3. The composition of claim 1, further comprising a pharmaceutically acceptable excipient, wherein the composition comprises an enantiomeric purity of the compound of at least 98%.

4. The composition of claim 1, prepared by a method of making the composition, comprising a method of making a compound having the formula:

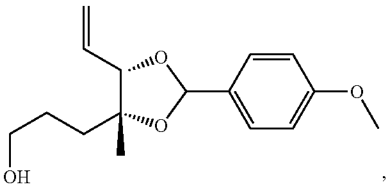

, comprising reacting a compound having the formula:

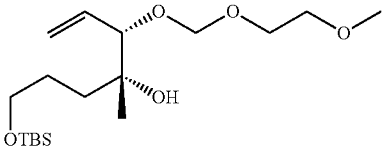 [SMILES: C=C[C@H](OCOCCOC)[C@](C)(O)CCCO[Si](C)(C)C(C)(C)C]

with 1-(dimethoxymethyl)-4-methoxybenzene in the presence of $CBr_4$, an alcohol, a base, and one or more organic solvents.

5. The composition of claim 1, prepared by a method of making the composition, comprising a method of making a compound having the formula:

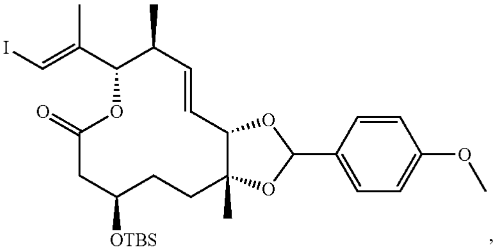

, comprising reacting a compound having the formula:

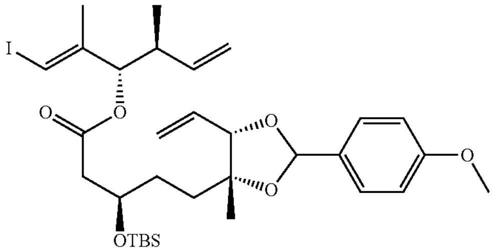

with a transition metal catalyst for olefin metathesis in the presence of one or more organic solvents.

6. The composition of claim 1, prepared by a method of making the composition, comprising a method of making a compound having the formula:

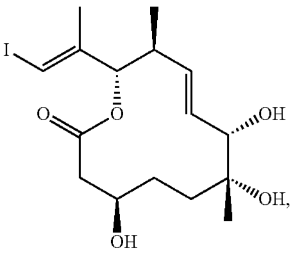 [SMILES: C/C(=C\I)[C@H]1OC(=O)C[C@H](O)CC[C@@](C)(O)[C@@H](O)/C=C/[C@@H]1C]

comprising reacting a compound having the formula:

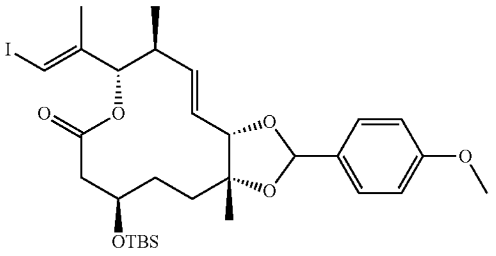

with a strong acid, in the presence of an alcohol and one or more organic solvents.

7. The composition of claim 1, prepared by a method of making the composition, comprising a method of making a compound having the formula:

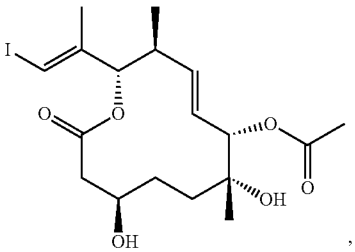 [SMILES: CC(=O)O[C@H]1/C=C/[C@H](C)[C@@H](/C(C)=C/I)OC(=O)C[C@H](O)CC[C@@]1(C)O]

, comprising reacting a compound having the formula:

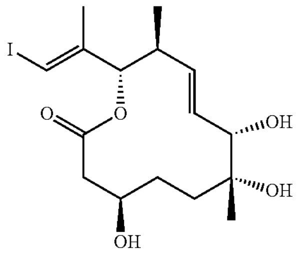 [SMILES: C/C(=C\I)[C@H]1OC(=O)C[C@H](O)CC[C@@](C)(O)[C@@H](O)/C=C/[C@@H]1C]

with an acetylating agent in the presence of a strong acid and one or more organic solvents.

8. The composition of claim 1, prepared by a method of making the composition, comprising a synthetic step comprising a reaction mixture, the reaction mixture comprising a reactant compound having the formula:

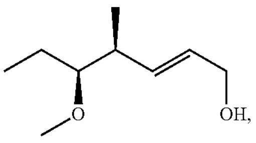

wherein the reaction mixture comprises an enantiomeric purity of the reactant compound of at least 95%.

9. The composition of claim 8, wherein the reaction mixture comprises an enantiomeric purity of the reactant compound of at least 98%.

10. The composition of claim 1, prepared by a method of making the composition, comprising a synthetic step comprising a reaction mixture, the reaction mixture comprising a reactant compound having the formula:

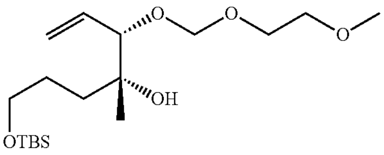

wherein the reaction mixture comprises an enantiomeric purity of the reactant compound of at least 95%.

11. The composition of claim 10, wherein the reaction mixture comprises an enantiomeric purity of the reactant compound of at least 98%.

12. The composition of claim 1, prepared by a method of making the composition, comprising a synthetic step comprising a reaction mixture, the reaction mixture comprising a reactant compound having the formula:

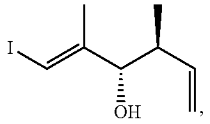

wherein the reaction mixture comprises an enantiomeric purity of the reactant compound of at least 95%.

13. The composition of claim 12, wherein the reaction mixture comprises an enantiomeric purity of the reactant compound of at least 98%.

14. The composition of claim 1, prepared by a method of making the composition, comprising a synthetic step comprising a reaction mixture, the reaction mixture comprising a reactant compound having the formula:

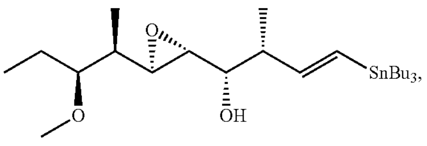

wherein the reaction mixture comprises an enantiomeric purity of the reactant compound of at least 95%.

15. The composition of claim 14, wherein the reaction mixture comprises an enantiomeric purity of the reactant compound of at least 98%.

16. The composition of claim 1, prepared by a method of making the composition, comprising a synthetic step comprising a reaction mixture, the reaction mixture comprising a reactant compound having the formula:

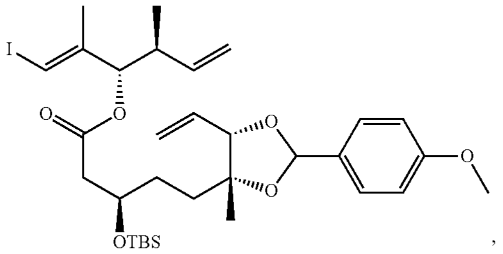

, wherein the reaction mixture comprises an enantiomeric purity of the reactant compound of at least 95%.

17. The composition of claim 16, wherein the reaction mixture comprises an enantiomeric purity of the reactant compound of at least 98%.

18. The composition of claim 1, prepared by a method of making the composition, comprising a synthetic step comprising a reaction mixture, the reaction mixture comprising a reactant compound having the formula:

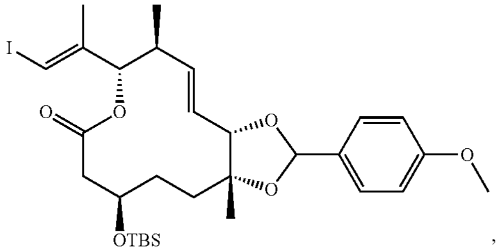

, wherein the reaction mixture comprises an enantiomeric purity of the reactant compound of at least 95%.

19. The composition of claim 1, prepared by a method of making the composition, comprising a synthetic step comprising a reaction mixture, the reaction mixture comprising a reactant compound having the formula:

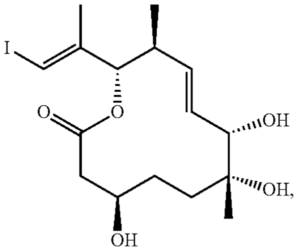 [SMILES: C/C(=C\I)[C@H]1OC(=O)C[C@H](O)CC[C@@](C)(O)[C@@H](O)/C=C/[C@@H]1C]

wherein the reaction mixture comprises an enantiomeric purity of the reactant compound of at least 95%.

20. The composition of claim 1, prepared by a method of making the composition, comprising a synthetic step comprising a reaction mixture, the reaction mixture comprising a reactant compound having the formula:

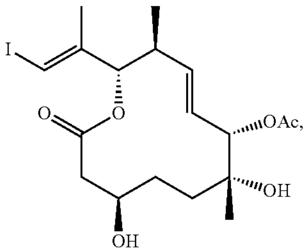 [SMILES: CC(=O)O[C@H]1/C=C/[C@H](C)[C@@H](/C(C)=C/I)OC(=O)C[C@H](O)CC[C@@]1(C)O]

wherein the reaction mixture comprises an enantiomeric purity of the reactant compound of at least 95%.

21. A pharmaceutical composition comprising the composition of claim 1 and a pharmaceutically acceptable excipient.

* * * * *